(12) United States Patent
Murillo et al.

(10) Patent No.: US 11,744,575 B2
(45) Date of Patent: Sep. 5, 2023

(54) SUTURE PASSER DEVICES AND METHODS

(71) Applicant: CETERIX ORTHOPAEDICS, INC., Fremont, CA (US)

(72) Inventors: Michael Murillo, Menlo Park, CA (US); Christopher P. Bender, Oakland, CA (US); Mark Y. Hirotsuka, San Jose, CA (US); Michael J. Hendricksen, Redwood City, CA (US); Justin D. Saliman, Beverly Hills, CA (US); John G. McCutcheon, Menlo Park, CA (US)

(73) Assignee: Ceterix Orthopaedics, Inc., Memphis, TN (US)

( * ) Notice: Subject to any disclaimer, the term of this patent is extended or adjusted under 35 U.S.C. 154(b) by 246 days.

(21) Appl. No.: 16/017,902

(22) Filed: Jun. 25, 2018

(65) Prior Publication Data
US 2018/0303476 A1 Oct. 25, 2018

Related U.S. Application Data

(63) Continuation-in-part of application No. 15/012,790, filed on Feb. 1, 2016, now Pat. No. 10,188,382, which
(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/0483* (2013.01);
(Continued)

(58) Field of Classification Search
CPC ............ A61B 17/0469; A61B 17/0482; A61B 17/0483; A61B 17/0625;
(Continued)

(56) References Cited

U.S. PATENT DOCUMENTS

| 1,037,864 A | 9/1912 | Carlson et al. |
| 1,815,725 A | 7/1931 | Pilling et al. |
(Continued)

FOREIGN PATENT DOCUMENTS

| CN | 201263696 Y | 7/2009 |
| CN | 101961256 A | 2/2011 |
(Continued)

OTHER PUBLICATIONS

Japanese Notice of Reasons for Rejection—Application No. 2015-092876 dated Feb. 19, 2019.
(Continued)

*Primary Examiner* — Jing Rui Ou
(74) *Attorney, Agent, or Firm* — Norman F. Hainer, Jr.; Kate Ryland Tetzlaff

(57) ABSTRACT

Devices, systems and methods for passing a suture. In general, described herein are suturing devices, such as suture passers, as well as methods of suturing tissue. These suture passing devices may include dual deployment suture passers in which a first distal jaw member is moveable at an angle with respect to the longitudinal axis of the elongate body of the device and the second distal jaw member is retractable proximally to the distal end region of the elongate body and/or the first jaw member.

3 Claims, 90 Drawing Sheets

Related U.S. Application Data is a continuation of application No. 13/893,154, filed on May 13, 2013, now Pat. No. 9,247,934, which is a continuation of application No. 13/462,773, filed on May 2, 2012, now Pat. No. 8,465,505, which is a continuation-in-part of application No. 13/323,391, filed on Dec. 12, 2011, now Pat. No. 9,700,299, application No. 16/017,902 is a continuation-in-part of application No. 15/853,531, filed on Dec. 22, 2017, now Pat. No. 10,987,095, which is a continuation of application No. 14/292,695, filed on May 30, 2014, now Pat. No. 9,848,868, which is a continuation-in-part of application No. 13/893,209, filed on May 13, 2013, now Pat. No. 8,888,848, which is a continuation of application No. 13/347,184, filed on Jan. 10, 2012, now Pat. No. 8,500,809, application No. 16/017,902 is a continuation-in-part of application No. 15/054,072, filed on Feb. 25, 2016, now Pat. No. 10,004,492, which is a continuation of application No. 14/659,471, filed on Mar. 16, 2015, now abandoned, which is a continuation of application No. 14/265,848, filed on Apr. 30, 2014, now Pat. No. 9,011,454, which is a continuation-in-part of application No. 13/873,841, filed on Apr. 30, 2013, now Pat. No. 8,808,299, which is a continuation of application No. 13/462,728, filed on May 2, 2012, now Pat. No. 8,449,533, which is a continuation of application No. 12/942,803, filed on Nov. 9, 2010, now Pat. No. 8,562,631, said application No. 14/265,848 is a continuation-in-part of application No. 13/893,154, filed on May 13, 2013, now Pat. No. 9,247,934, which is a continuation of application No. 13/462,773, filed on May 2, 2012, now Pat. No. 8,465,505, which is a continuation-in-part of application No. 13/323,391, filed on Dec. 12, 2011, now Pat. No. 9,700,299, said application No. 14/265,848 is a continuation-in-part of application No. PCT/US2014/030137, filed on Mar. 17, 2014.

(60) Provisional application No. 61/483,200, filed on May 6, 2011, provisional application No. 61/511,922, filed on Jul. 26, 2011, provisional application No. 61/431,293, filed on Jan. 10, 2011, provisional application No. 61/829,169, filed on May 30, 2013, provisional application No. 61/259,572, filed on Nov. 9, 2009, provisional application No. 61/295,354, filed on Jan. 15, 2010, provisional application No. 61/318,215, filed on Mar. 26, 2010.

(51) Int. Cl.
*A61B 17/064* (2006.01)
*A61B 17/06* (2006.01)
*A61B 17/00* (2006.01)

(52) U.S. Cl.
CPC .. *A61B 17/0625* (2013.01); *A61B 2017/0042* (2013.01); *A61B 2017/00371* (2013.01); *A61B 2017/00858* (2013.01); *A61B 2017/047* (2013.01); *A61B 2017/0475* (2013.01); *A61B 2017/0477* (2013.01); *A61B 2017/06042* (2013.01); *A61B 2017/0646* (2013.01); *A61B 2017/06047* (2013.01); *A61B 2017/06095* (2013.01)

(58) Field of Classification Search
CPC .. A61B 2017/00371; A61B 2017/0042; A61B 2017/06095; A61B 2017/00858; A61B 2017/047; A61B 2017/0475; A61B 2017/0477; A61B 2017/06042; A61B 2017/06047; A61B 2017/0646
See application file for complete search history.

(56) References Cited

U.S. PATENT DOCUMENTS

| | | |
|---|---|---|
| 2,738,790 A | 3/1956 | Todt, Sr. et al. |
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,484,580 A | 11/1984 | Nomoto et al. |
| 4,553,543 A | 11/1985 | Amarasinghe |
| 4,605,002 A | 8/1986 | Rebuffat |
| 4,621,640 A | 11/1986 | Mulhollan et al. |
| 4,706,666 A | 11/1987 | Sheets |
| 4,836,205 A | 6/1989 | Barrett |
| 4,890,615 A * | 1/1990 | Caspari ............... A61B 17/0469 606/139 |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,211,650 A | 5/1993 | Noda |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,254,126 A | 10/1993 | Filipi et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |

(56) References Cited

U.S. PATENT DOCUMENTS

| | | |
|---|---|---|
| 5,522,820 A | 6/1996 | Caspari et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,748 A | 5/1997 | Beck et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A | 9/1998 | Schulze et al. |
| 5,824,009 A | 10/1998 | Fukuda et al. |
| 5,827,300 A | 10/1998 | Fleega |
| 5,843,100 A | 12/1998 | Meade |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagodas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,099,568 A | 8/2000 | Simonian et al. |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,217,592 B1 | 4/2001 | Freda et al. |
| 6,221,085 B1 | 4/2001 | Djurovic |
| 6,231,606 B1 | 5/2001 | Graf et al. |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,332,889 B1 | 12/2001 | Sancoff et al. |
| 6,355,050 B1 | 3/2002 | Andreas et al. |
| 6,368,334 B1 | 4/2002 | Sauer |
| 6,368,343 B1 | 4/2002 | Bonutti et al. |
| 6,443,963 B1 | 9/2002 | Baldwin et al. |
| 6,454,778 B2 | 9/2002 | Kortenbach |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,605,096 B1 | 8/2003 | Ritchart |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,764 B1 | 4/2004 | Gellman et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,833,005 B1 | 12/2004 | Mantas |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,153,312 B1 | 12/2006 | Torrie et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,442,198 B2 | 10/2008 | Gellman et al. |
| 7,481,817 B2 | 1/2009 | Sauer |
| 7,481,826 B2 | 1/2009 | Cichocki |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,608,084 B2 | 10/2009 | Oren et al. |
| 7,632,284 B2 | 12/2009 | Martinek et al. |
| 7,674,276 B2 | 3/2010 | Stone et al. |
| 7,717,927 B2 | 5/2010 | Hahn et al. |
| 7,722,630 B2 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,938,839 B2 | 5/2011 | DiFrancesco et al. |

(56) References Cited

U.S. PATENT DOCUMENTS

| | | |
|---|---|---|
| 7,951,147 B2 | 5/2011 | Privitera et al. |
| 7,951,157 B2 | 5/2011 | Gambale |
| 7,951,159 B2 | 5/2011 | Stokes et al. |
| 7,972,344 B2 | 7/2011 | Murray et al. |
| 8,298,230 B2 | 10/2012 | Sutter et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murillo et al. |
| 8,500,809 B2 | 8/2013 | Saliman |
| 8,562,631 B2 | 10/2013 | Saliman |
| 8,632,563 B2 | 1/2014 | Nagase et al. |
| 8,647,354 B2 | 2/2014 | Domingo |
| 8,663,253 B2 | 3/2014 | Saliman |
| 8,702,731 B2 | 4/2014 | Saliman |
| 8,808,299 B2 | 8/2014 | Saliman et al. |
| 8,821,518 B2 | 9/2014 | Saliman |
| 8,888,848 B2 | 11/2014 | Saliman et al. |
| 8,911,456 B2 | 12/2014 | McCutcheon et al. |
| 8,920,441 B2 | 12/2014 | Saliman et al. |
| 9,011,454 B2 | 4/2015 | Hendricksen et al. |
| 9,211,119 B2 | 12/2015 | Hendricksen et al. |
| 9,247,934 B2 | 2/2016 | Murillo et al. |
| 9,247,935 B2 | 2/2016 | George et al. |
| 9,314,234 B2 | 4/2016 | Hirotsuka et al. |
| 9,332,980 B2 | 5/2016 | George et al. |
| 9,492,162 B2 | 11/2016 | Murillo et al. |
| 9,700,299 B2 | 7/2017 | Saliman et al. |
| 9,848,868 B2 | 12/2017 | Saliman |
| 9,861,354 B2 | 1/2018 | Saliman et al. |
| 9,913,638 B2 | 3/2018 | Saliman et al. |
| 10,004,492 B2 | 6/2018 | Hendricksen et al. |
| 2001/0041938 A1 | 11/2001 | Hein |
| 2002/0019649 A1* | 2/2002 | Sikora ............... A61B 17/0401 606/232 |
| 2002/0103493 A1* | 8/2002 | Thal ................ A61B 17/0469 606/144 |
| 2002/0147456 A1* | 10/2002 | Diduch ............. A61B 17/0469 606/144 |
| 2002/0169477 A1 | 11/2002 | Demopulos et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0078617 A1 | 4/2003 | Schwartz et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0059416 A1* | 3/2004 | Murray ............... A61L 27/52 623/13.15 |
| 2004/0117014 A1 | 6/2004 | Bryant |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0043746 A1 | 2/2005 | Pollak et al. |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0178680 A1 | 8/2006 | Beverly et al. |
| 2006/0282098 A1 | 12/2006 | Shelton et al. |
| 2007/0032799 A1 | 2/2007 | Pantages et al. |
| 2007/0038230 A1 | 2/2007 | Stone et al. |
| 2007/0156174 A1 | 7/2007 | Kaiser et al. |
| 2007/0185532 A1 | 8/2007 | Stone et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0027468 A1 | 1/2008 | Fenton et al. |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0140094 A1 | 6/2008 | Schwartz et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0275553 A1 | 11/2008 | Wolf et al. |
| 2008/0294256 A1 | 11/2008 | Hagan et al. |
| 2009/0012520 A1 | 1/2009 | Hixson et al. |
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0112232 A1 | 4/2009 | Crainich et al. |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249806 A1 | 9/2010 | Oren et al. |
| 2010/0249809 A1 | 9/2010 | Singhatat et al. |
| 2010/0256656 A1 | 10/2010 | Park |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0071563 A1 | 3/2011 | Magliani |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1 | 11/2011 | Denham et al. |
| 2012/0101524 A1 | 4/2012 | Bennett |
| 2012/0303046 A1 | 11/2012 | Stone et al. |
| 2013/0072948 A1 | 3/2013 | States, III et al. |
| 2013/0085512 A1 | 4/2013 | Wyman et al. |
| 2013/0253536 A1 | 9/2013 | Harris et al. |
| 2014/0188136 A1 | 7/2014 | Cournoyer et al. |
| 2014/0222034 A1 | 8/2014 | Saliman |
| 2015/0034694 A1 | 2/2015 | Cappola |
| 2015/0073442 A1 | 3/2015 | Saliman et al. |
| 2015/0157317 A1 | 6/2015 | Bagaoisan et al. |
| 2015/0173742 A1 | 6/2015 | Palese et al. |
| 2015/0173743 A1 | 6/2015 | Palese et al. |
| 2015/0209029 A1 | 7/2015 | Hendricken et al. |
| 2015/0257756 A1 | 9/2015 | Sauer |
| 2015/0297215 A1 | 10/2015 | Hendricksen et al. |
| 2015/0313589 A1 | 11/2015 | Hendricksen et al. |
| 2016/0220244 A1 | 8/2016 | Murillo et al. |

(56) References Cited

U.S. PATENT DOCUMENTS

| | | |
|---|---|---|
| 2016/0242765 A1 | 8/2016 | George et al. |
| 2016/0302789 A1 | 10/2016 | Hiratsuka et al. |
| 2017/0020512 A1 | 1/2017 | Murillo et al. |
| 2017/0027558 A1 | 2/2017 | Murillo et al. |
| 2017/0119372 A1 | 5/2017 | Peter et al. |
| 2018/0116651 A1 | 5/2018 | Saliman |
| 2018/0125479 A1 | 5/2018 | Saliman et al. |
| 2018/0199931 A1 | 7/2018 | Saliman et al. |

FOREIGN PATENT DOCUMENTS

| | | |
|---|---|---|
| CN | 103298503 A | 9/2013 |
| CN | 103717149 A | 4/2014 |
| EP | 0647431 A2 | 4/1995 |
| EP | 2030575 A1 | 3/2009 |
| EP | 2184015 A2 | 5/2010 |
| EP | 2081481 B1 | 11/2015 |
| JP | 3032847 U | 3/1991 |
| JP | 2009138029 A | 6/2009 |
| JP | 2009538190 | 11/2009 |
| SU | 376089 A | 4/1973 |
| SU | 728848 A1 | 4/1980 |
| SU | 1725847 A1 | 4/1992 |
| WO | WO 92/05828 A1 | 4/1992 |
| WO | WO 95/13021 A1 | 5/1995 |
| WO | WO98/11825 A1 | 3/1998 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO01/56478 A1 | 8/2001 |
| WO | WO 02/07607 A1 | 1/2002 |
| WO | WO 02/096296 A1 | 12/2002 |
| WO | WO 03/028532 A2 | 4/2003 |
| WO | WO 03/077771 A1 | 9/2003 |
| WO | WO 2006/001040 A1 | 1/2006 |
| WO | WO 2006/007399 A1 | 1/2006 |
| WO | WO 2006/040562 A1 | 4/2006 |
| WO | WO 2010/036227 A1 | 4/2010 |
| WO | WO 2010/050910 A1 | 5/2010 |
| WO | WO 2010/141695 A1 | 12/2010 |
| WO | WO 2011/057245 A2 | 5/2011 |

OTHER PUBLICATIONS

Brazilian Informal Translation The Preliminary of the Office Action Application No. BR112013028339-4.

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filing date and any foreign priority date) 2006, 4 pages.

Baena et al.; Inside-out medial meniscus suture: an analysis of the risk of injury to the popliteal neurovascular bundle; Arthroscopy; 27(4):516-21; Apr. 2011.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Ceterix; Novocut suture manager; retrieved from the internet (https://web.archive.org/web/20150314071511/http://www.ceterix.com:80/im-a-physician/products/) on Oct. 11, 2017; 1 page; Mar. 12, 2015.

Ceterix; Novocut suture manager; retrieved from the internet (https://www.youtube.com/watch?v=6txqBJxvnuA) on Oct. 11, 2017; 1 page; Mar. 5, 2015.

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2 pgs.

Depuy Mitek, Inc; Raynham, MA, "Versalok Surgical Technique for Rotator Cuff Repair: The next generation in rotator cuff repair," Product brochure, (year of pub. sufficiently earlier than effective US filing date and any foreign priority date) 2007, 18 pages.

dictionary.com; Adjacent (definition); 5 pgs.; retrieved from the internet (http://www.dictionary.com/browse/adjacent) on Apr. 5, 2016.

Duerig, T. et al., "An overview of nitinol medical applications" Materials Science and Engineering A273-275, pp. 149-160; May 1999.

Eggli et al.; Long-term results of arthroscopic meniscal repair. An analysis of isolated tears; Am J Sports Med; 23(6):715-20; Nov.-Dec. 1995.

Grant et al.; Comparison of inside-out and all-inside techniques for the repair of isolated meniscal tears: a systematic review; Am J Sports Med preview; Jul. 7, 2011; pp. 1-10.

Klecker et al.; The aberrant anterior tibial artery: magnetic resonance appearance, prevalence, and surgical implications; Am J Sports Med; 36(4):720-7; Apr. 2008.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Lozano et al.; All-inside meniscus repair: a systematic review; Clin Orthop Relat Res; 455:134-41; Feb. 2007.

Ma et al; "Biomechanical Evaluation of Arthroscopic Rotator Cuff Stitches," J Bone Joint Surg Am, Jun. 2004; vol. 86(6):1211-1216.

Medsfera; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No.1, Jan. 2007: pp. 94-102.

Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).

Paxton et al.; Meniscal repair versus partial meniscectomy: a systematic review comparing reoperation rates and clinical outcomes; Arthroscopy; 27(9):1275-88; Sep. 2011.

Pujol et al.; Meniscal healing after meniscal repair: a CT arthrography assessment; Am J Sports Med; 36(8):1489-95; Aug. 2008.

Rimmer et al.; Failure Strength of Different Meniscal Suturing Techniques; The Journal of Arthroscopic and Related Surgery; vol. 11; No. 2; pp. 146-150; Apr. 1995.

Rockborn et al.; Results of open meniscus repair. Long-term follow-up study with a matched uninjured control group; J Bone Joint Surg Br; 82(4):494-8; May 2000.

Schneeberger, et al.; "Mechanical Strength of Arthroscopic Rotator Cuff Repair Techniques: An in Vitro Study," J Bone Joint Surg Am., Dec. 2002; 84:2152-2160.

Small et al.; Avoiding Complications in Meniscal Repair; Techniques in Orthopaedics; 8(2):70-75; Summer Jun.-Aug. 1993.

Smith&Nephew; Fast-Fix Meniscal Repair System (product webpage); 4 pgs.; downloaded Nov. 21, 2011 (http://endo.smith-nephew.com/fr/node.asp?NodeId=3562).

Stärke et al.; Current Concepts: Meniscal Repair; Arthroscopy: The Journal of Arthroscopic and Related Surgery; vol. 25; Issue 9; pp. 1033-1044; Sep. 2009.

(56) References Cited

OTHER PUBLICATIONS

Strobel; Manual of Arthroscopic Surgery (1st Edition); Springer Verlag, Hiedelberg © 2002; pp. 127-129; Dec. 15, 2001.
USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.
USS SportsMedicine ArthroSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.

* cited by examiner

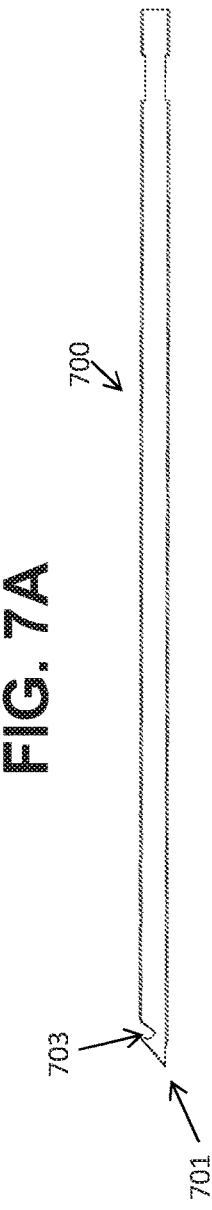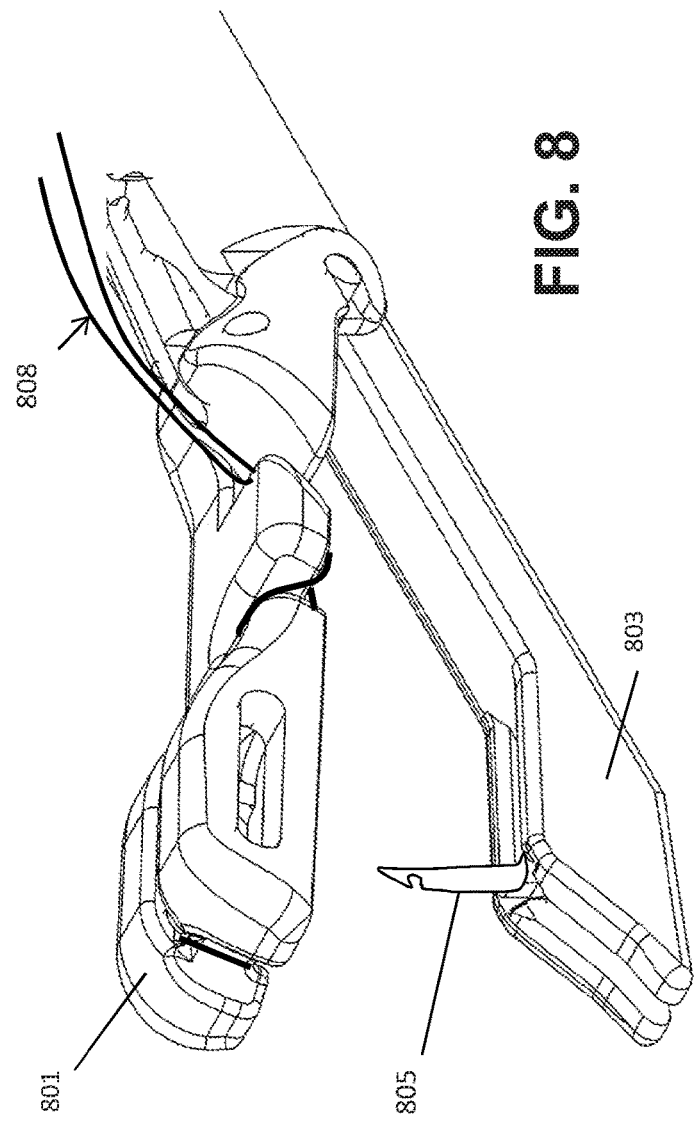

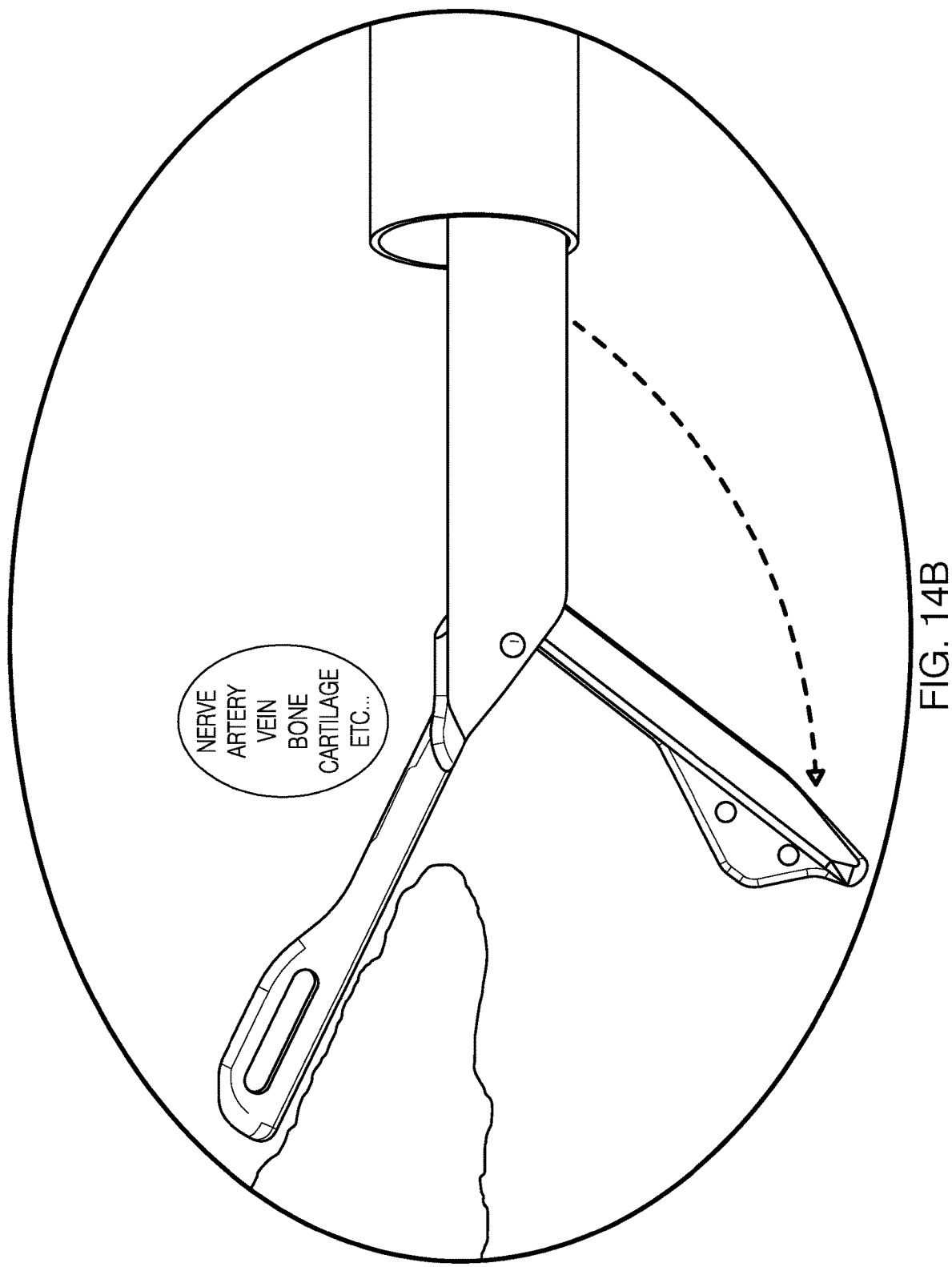

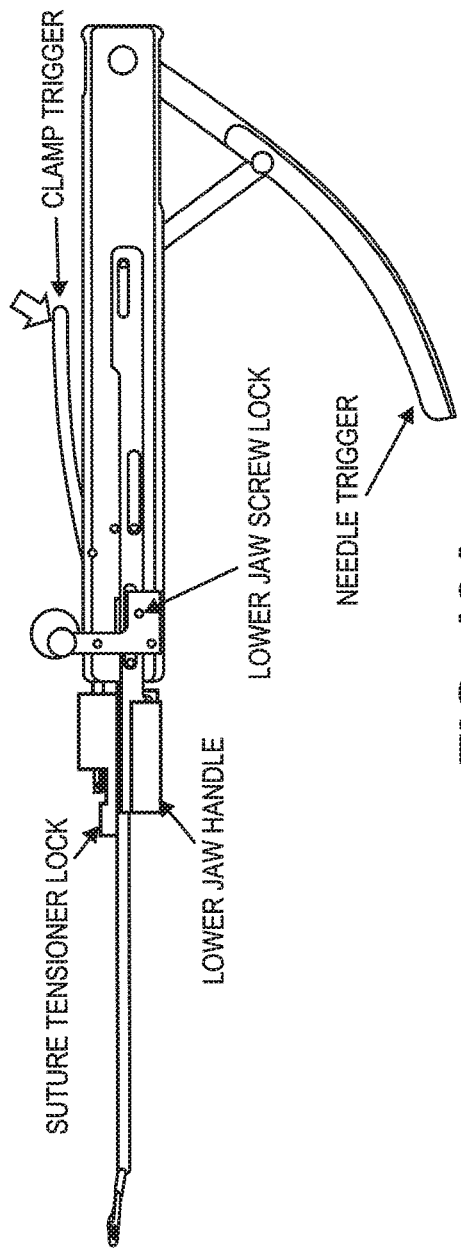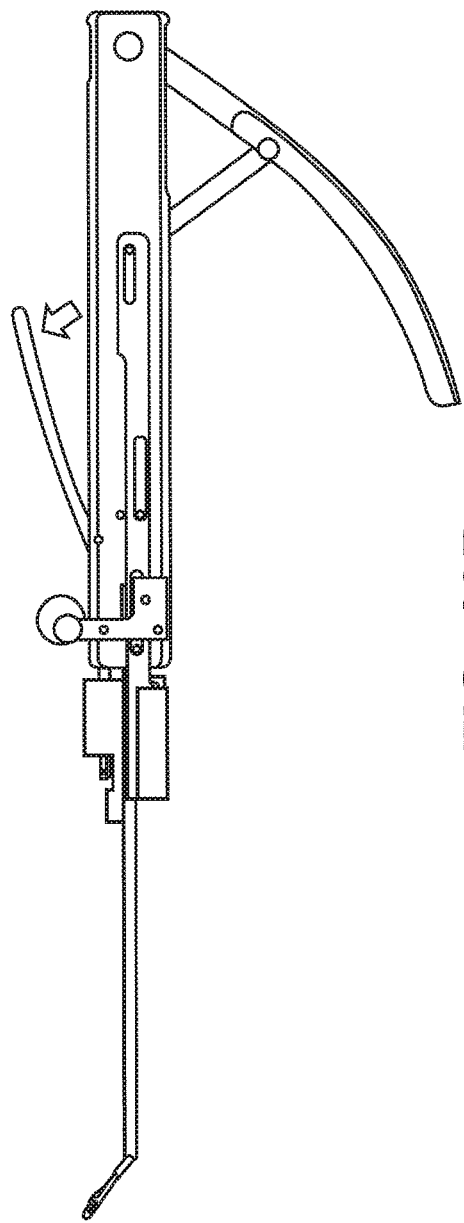
FIG. 19A
FIG. 19B

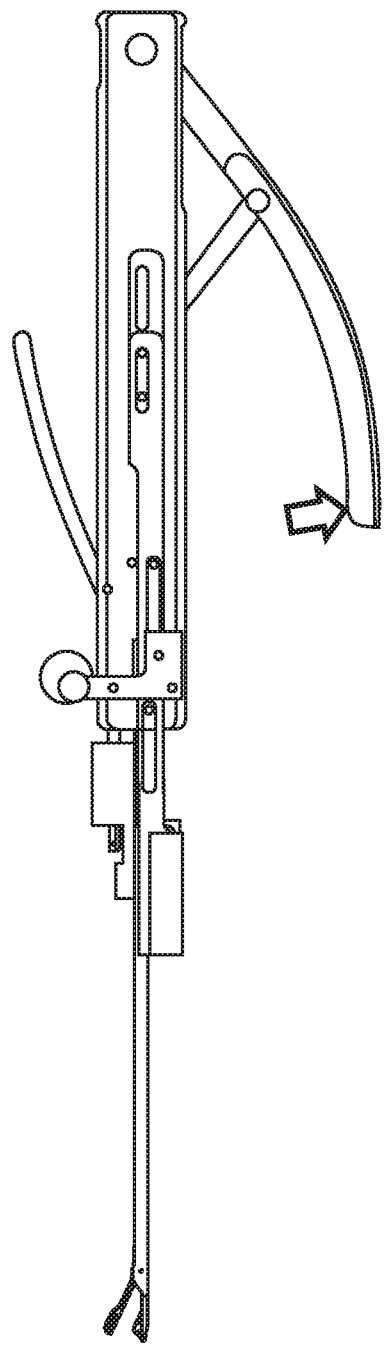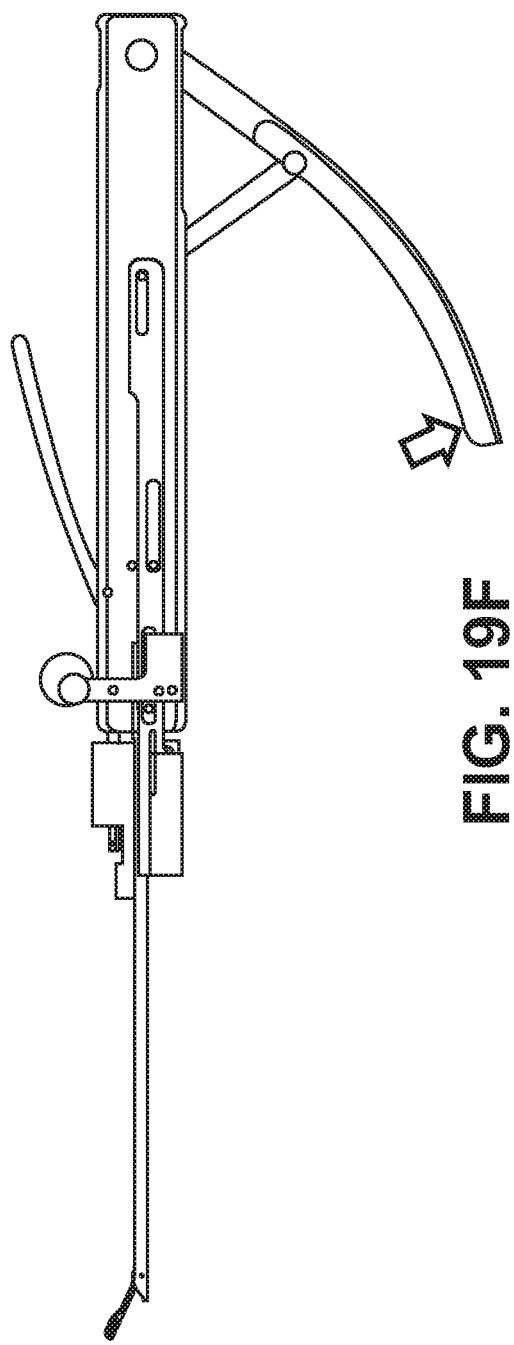

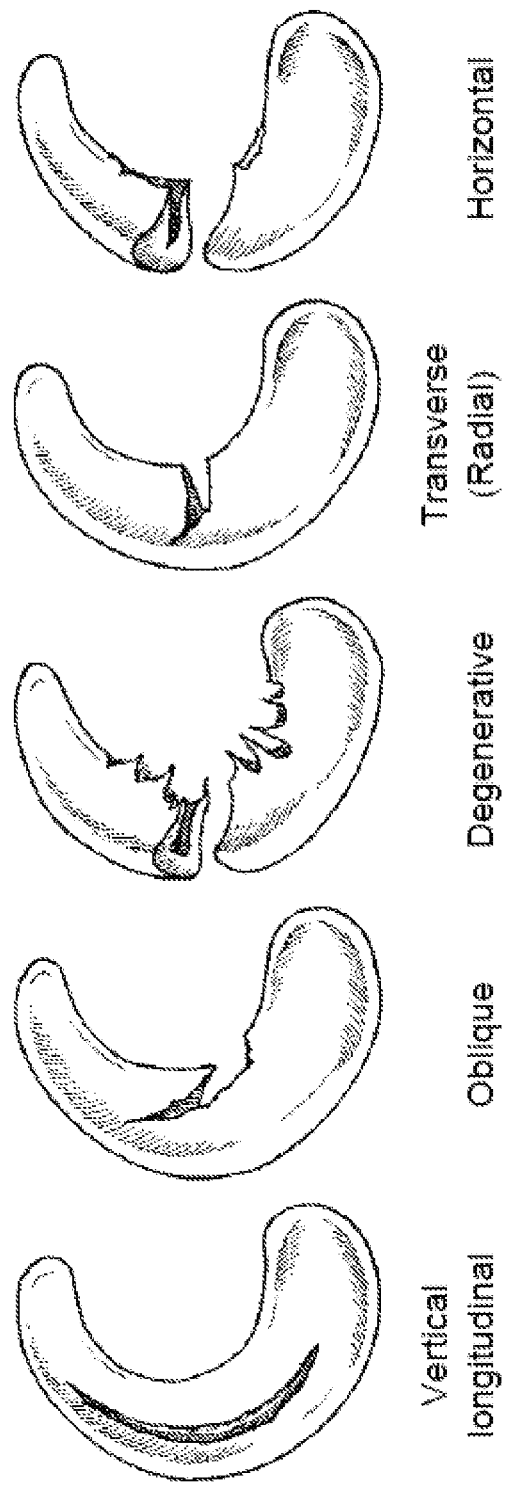

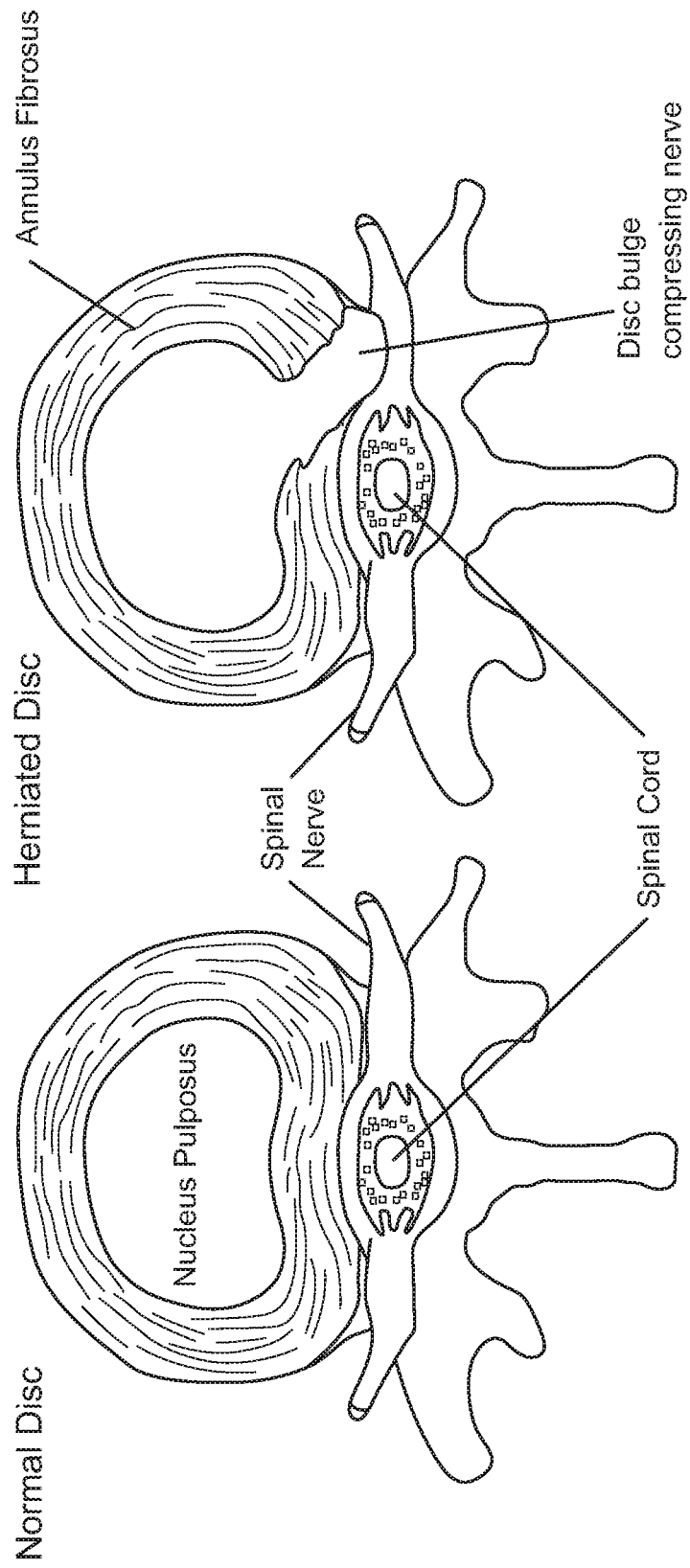

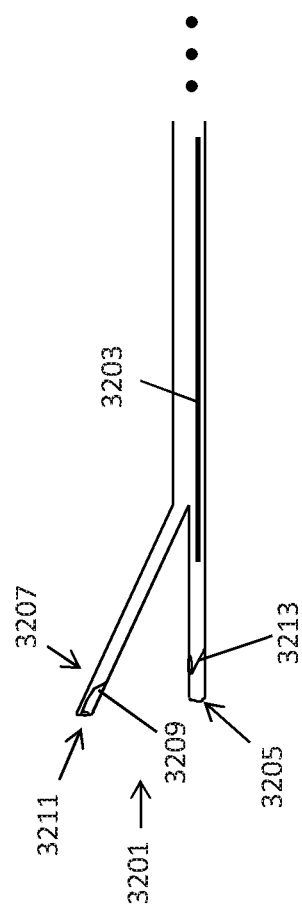
FIG. 32A
FIG. 32B
FIG. 32C

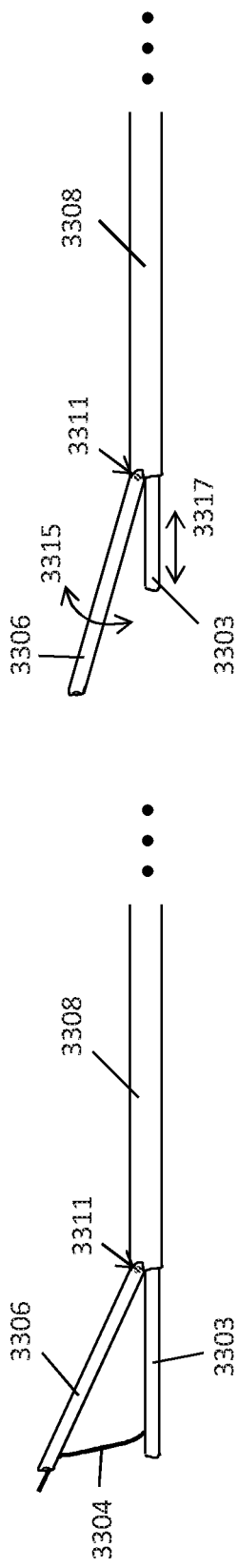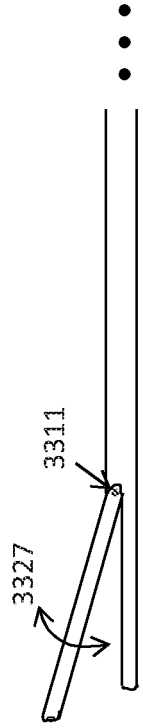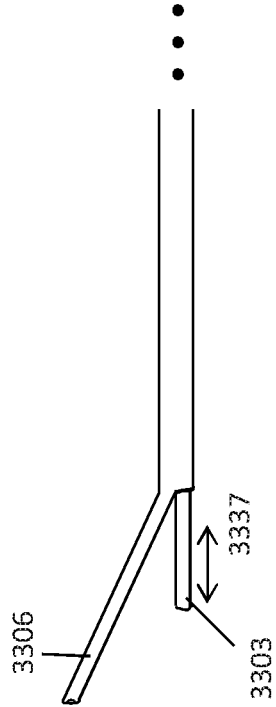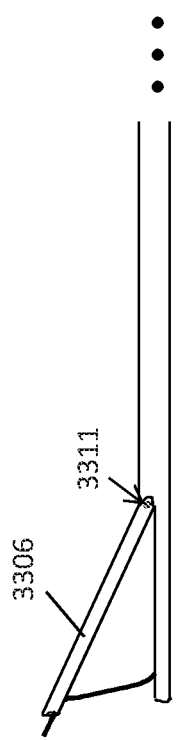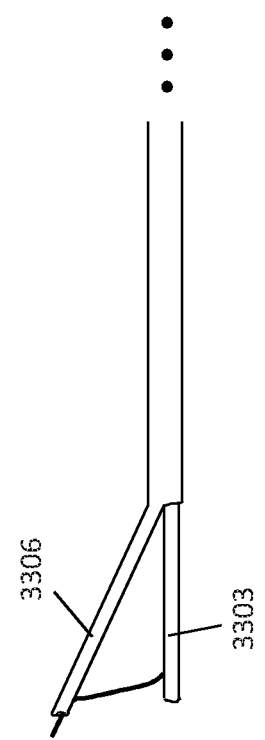
FIG. 33A FIG. 33B FIG. 33C FIG. 33D FIG. 33E FIG. 33F

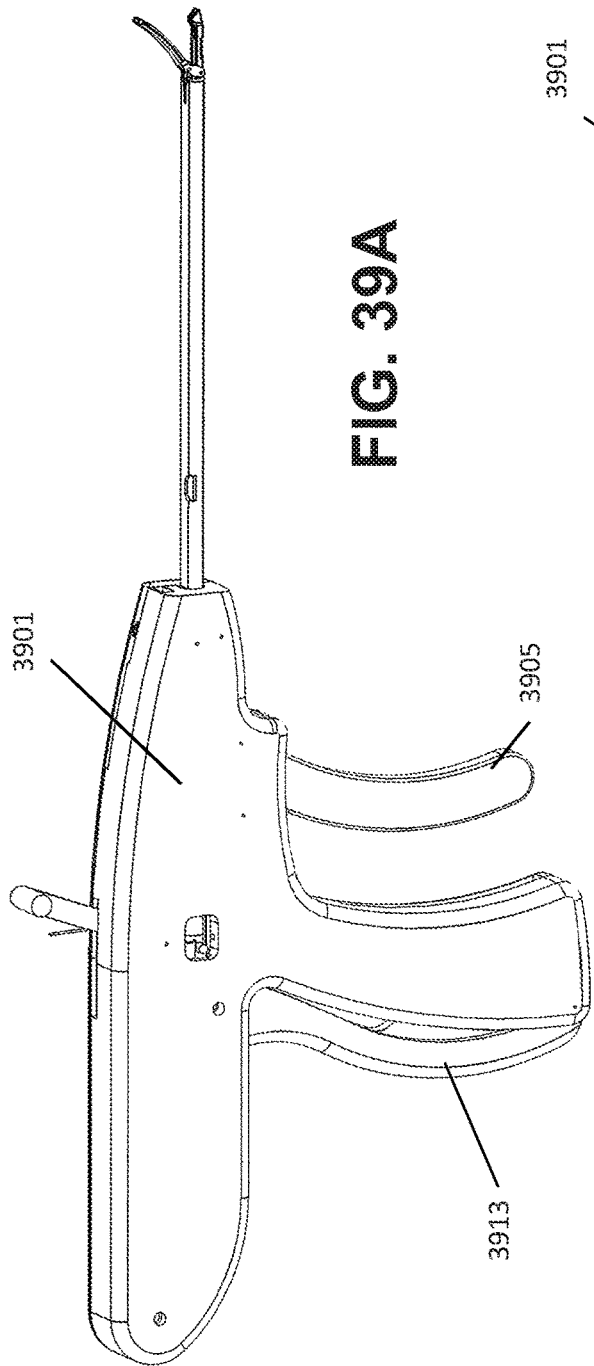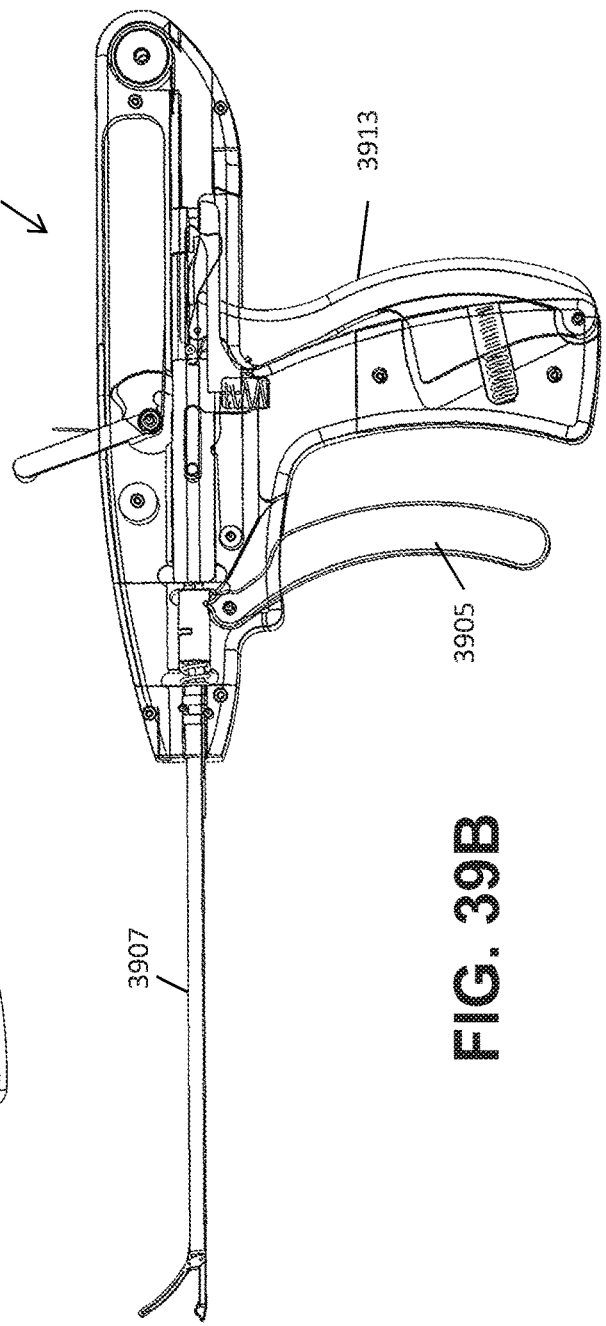

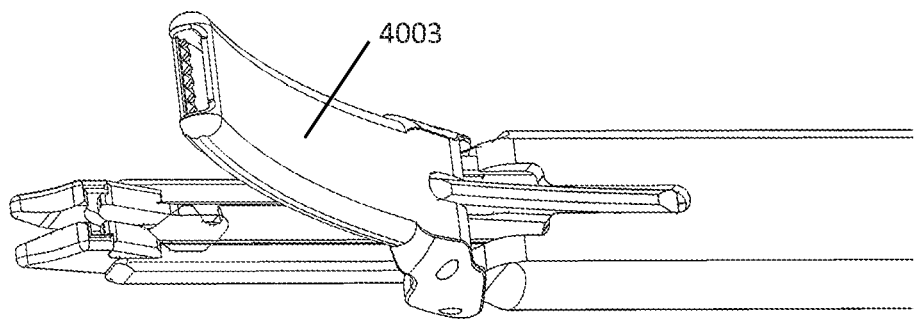
FIG. 40A
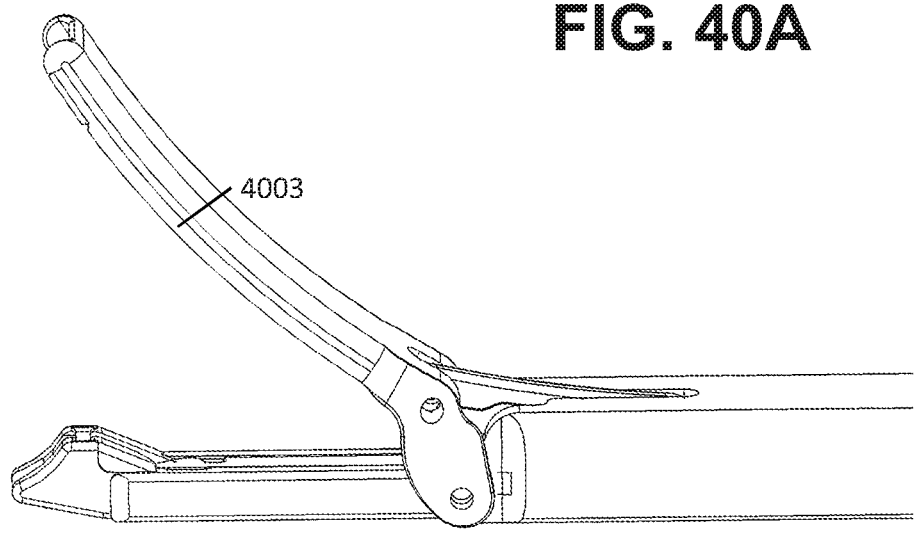
FIG. 40B
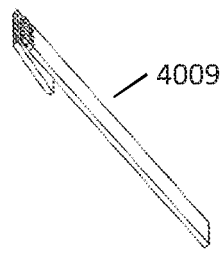
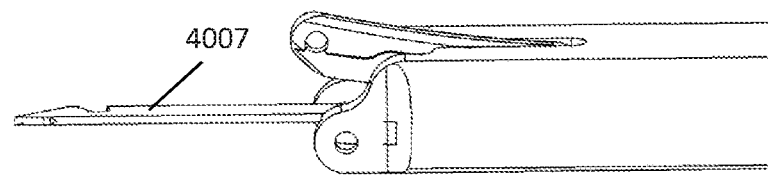
FIG. 40C

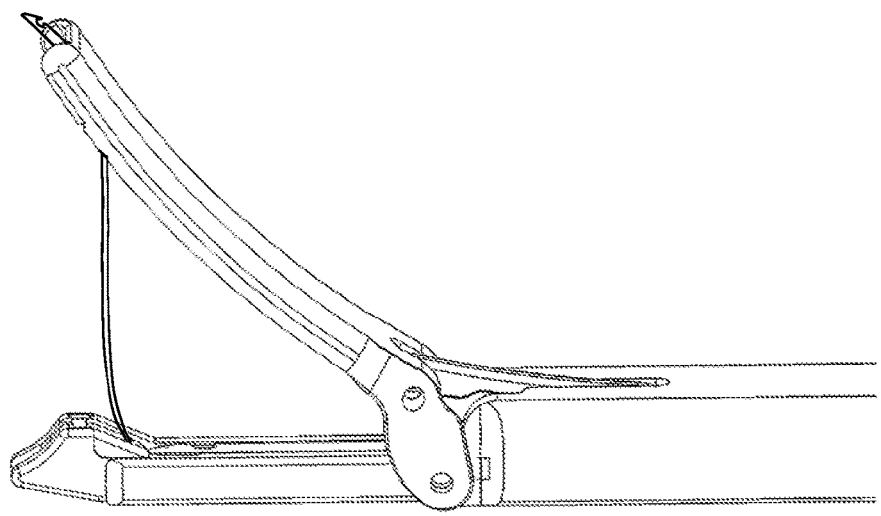
FIG. 40D
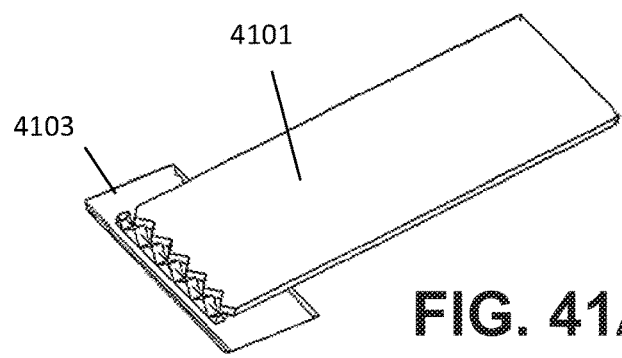
FIG. 41A
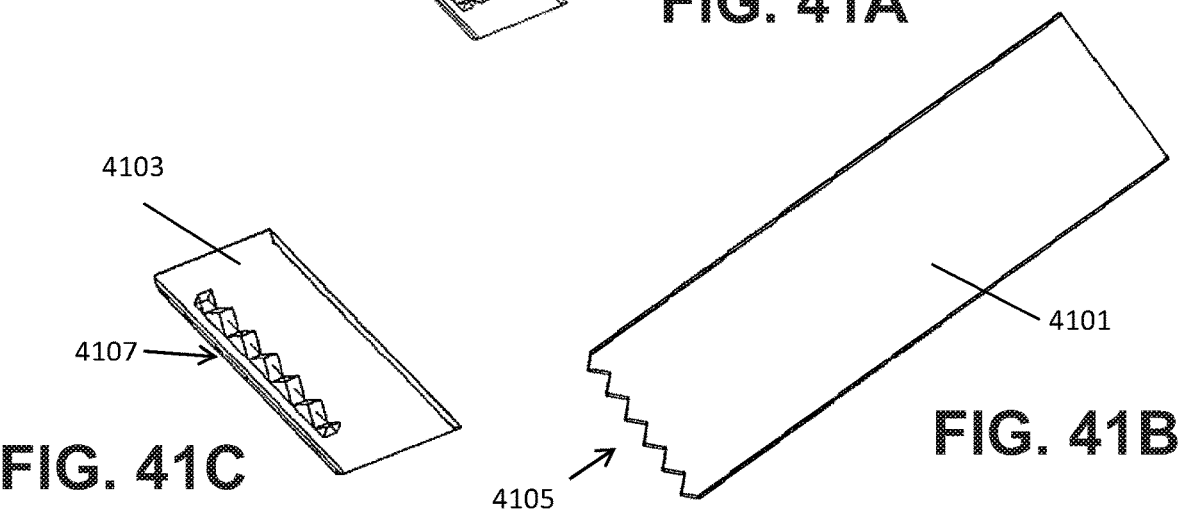
FIG. 41C
FIG. 41B

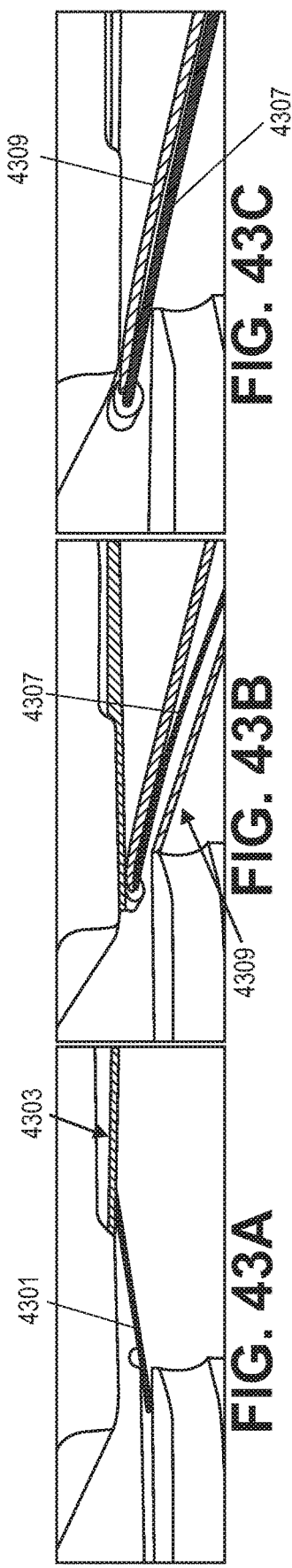

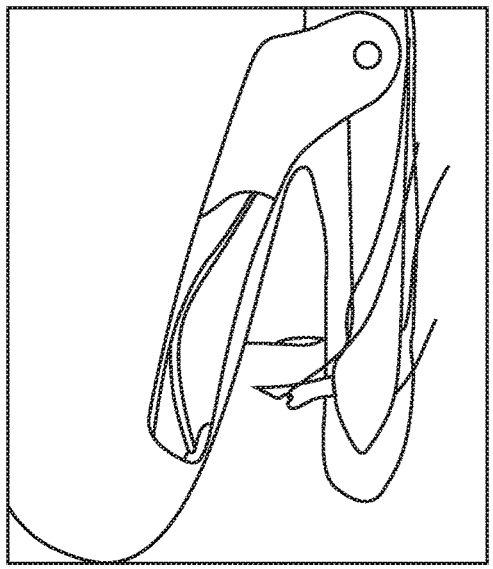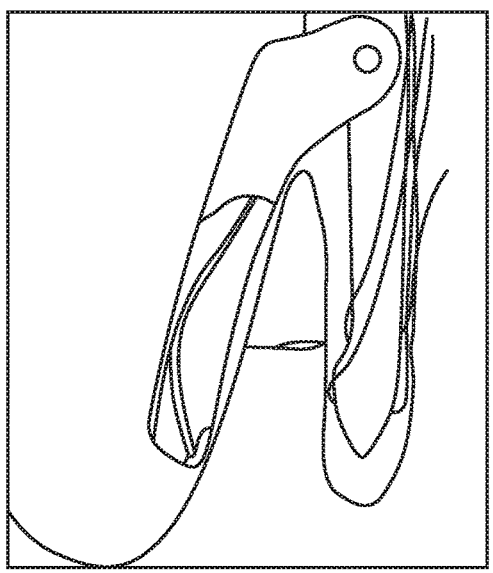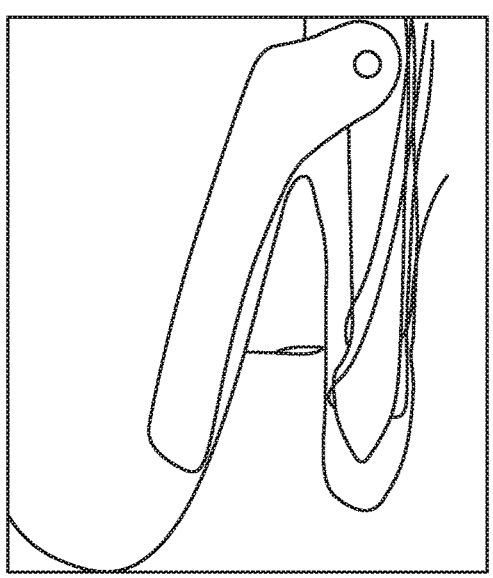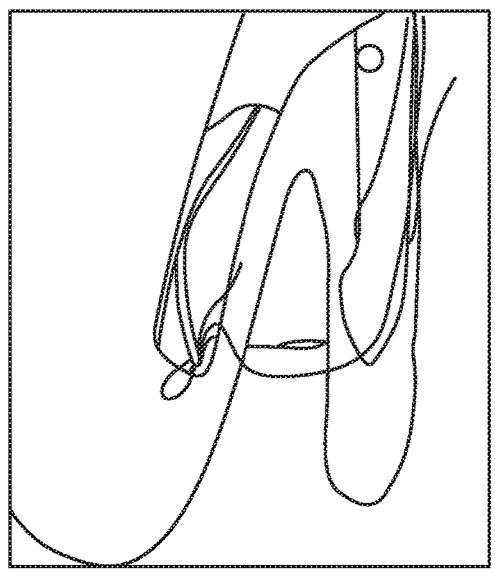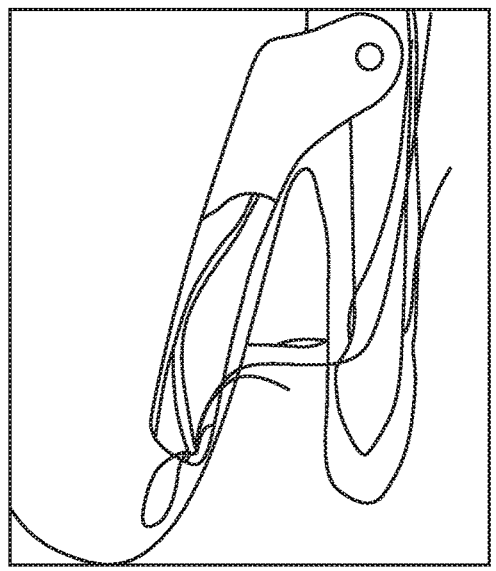

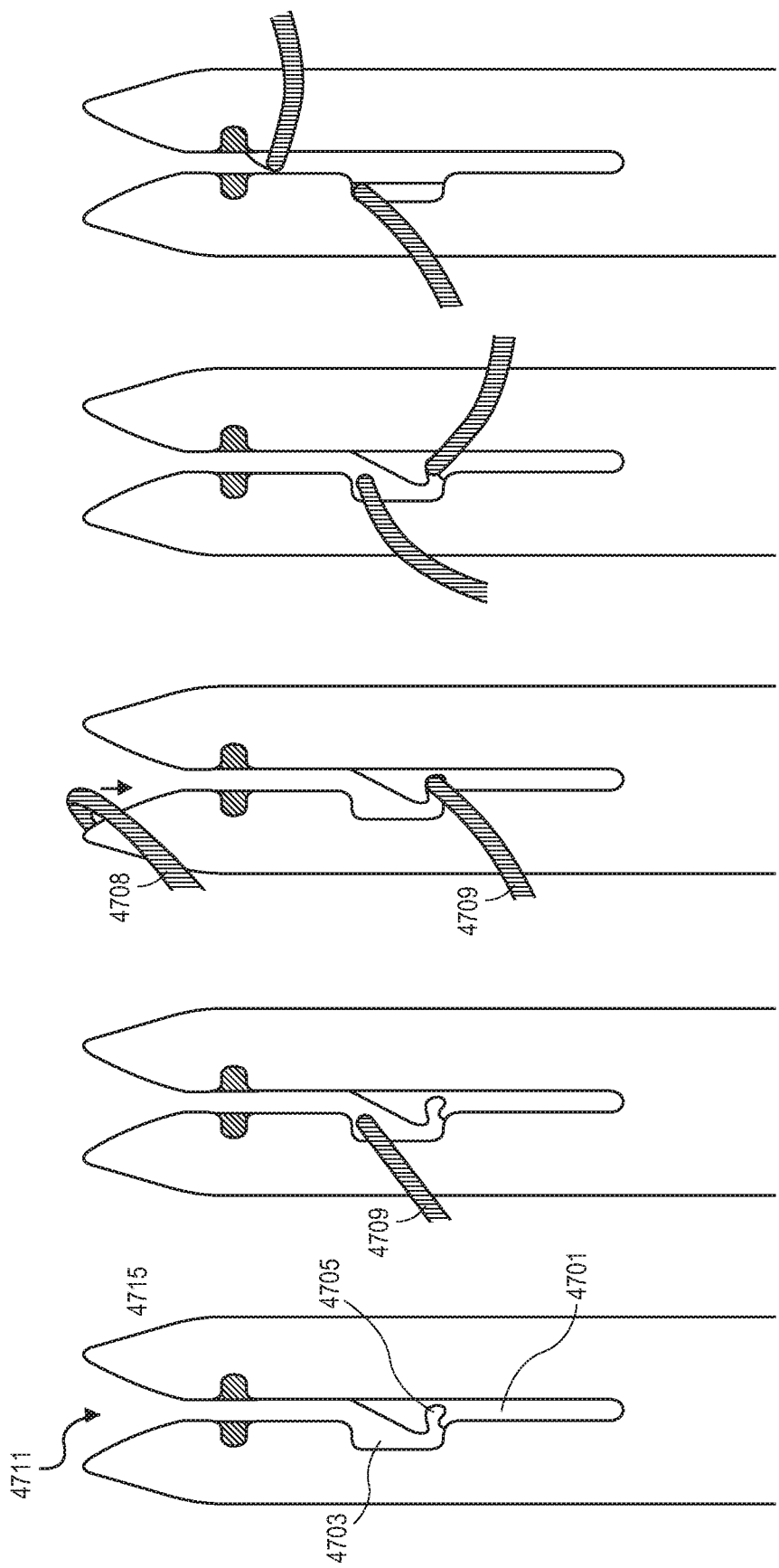

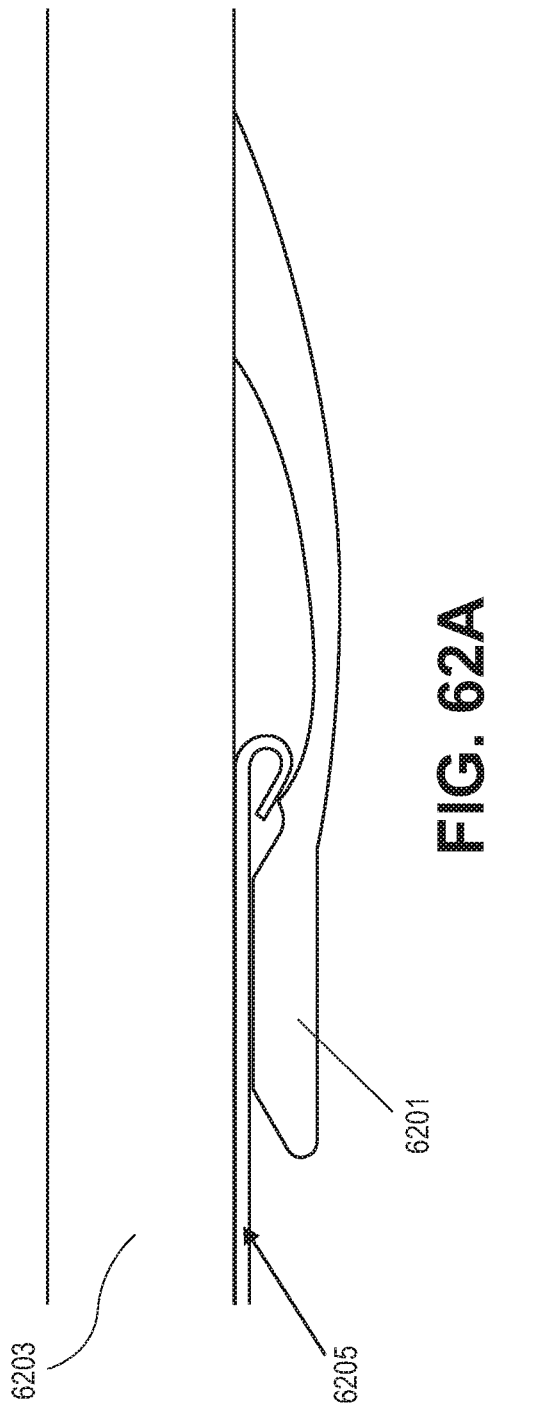
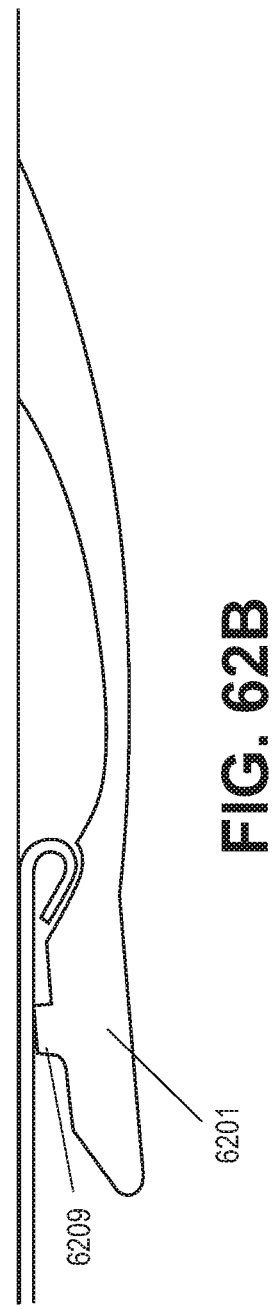

SUTURE PASSER DEVICES AND METHODS

CROSS REFERENCE TO RELATED APPLICATIONS

This patent application is a continuation-in-part of U.S. patent application Ser. No. 15/012,790, titled "SUTURE PASSER DEVICES AND METHODS," filed Feb. 1, 2016, which is a continuation of U.S. patent application Ser. No. 13/893,154, titled "SUTURE PASSER DEVICES AND METHODS," filed May 13, 2013, now U.S. Pat. No. 9,247,934, which is a continuation of U.S. patent application Ser. No. 13/462,773, titled "SUTURE PASSER DEVICES AND METHODS," filed May 2, 2012, now U.S. Pat. No. 8,465,505, which is a continuation-in-part of U.S. patent application Ser. No. 13/323,391, titled "SUTURE PASSER DEVICES AND METHODS," filed Dec. 12, 2011, now U.S. Pat. No. 9,700,299. U.S. patent application Ser. No. 13/462,773 also claims priority to the following provisional patent applications: U.S. Provisional Patent Application No. 61/483,200, titled "MENISCUS REPAIR," filed May 6, 2011, and U.S. Provisional Patent Application No. 61/511,922, titled "MENISCUS REPAIR," filed Jul. 26, 2011.

This patent application is also a continuation-in-part of U.S. patent application Ser. No. 15/853,531, titled "SUTURE METHODS FOR FORMING LOCKING LOOPS STITCHES," filed Dec. 22, 2017, now U.S. Patent Application Publication No. 2018-0116651, which is a continuation of U.S. patent application Ser. No. 14/292,695, filed May 30, 2014, titled "SUTURE METHODS FOR FORMING LOCKING LOOPS STITCHES," now U.S. Pat. No. 9,848,868, which claims priority as a continuation-in-part of U.S. patent application Ser. No. 13/893,209, filed May 13, 2013, titled "IMPLANT AND METHOD FOR REPAIR OF THE ANTERIOR CRUCIATE LIGAMENT," now U.S. Pat. No. 8,888,848, which is a continuation of U.S. patent application Ser. No. 13/347,184, filed Jan. 10, 2012, titled "IMPLANT AND METHOD FOR REPAIR OF THE ANTERIOR CRUCIATE LIGAMENT," now U.S. Pat. No. 8,500,809, which claims priority to U.S. Provisional Patent Application No. 61/431,293, filed Jan. 10, 2011, titled "IMPLANT AND METHOD FOR REPAIR OF THE ANTERIOR CRUCIATE LIGAMENT." U.S. patent application Ser. No. 14/292,695 also claims the benefit of U.S. Provisional Patent Application No. 61/829,169, filed May 30, 2013, titled "SUTURE PASSER DEVICES AND METHODS."

This patent application is also a continuation-in-part of U.S. patent application Ser. No. 15/054,072, filed Feb. 25, 2016, titled "SUTURE PASSER WITH RADIUSED UPPER JAW," now U.S. Patent Application Publication No. 2016-0192926, which is a continuation of U.S. patent application Ser. No. 14/659,471 filed Mar. 16, 2015, titled "SUTURE PASSER WITH RADISED UPPER JAW," now U.S. Patent Application Publication No. 2015-0209029, which is a continuation of U.S. patent application Ser. No. 14/265,848 filed Apr. 30, 2014, titled "SUTURE PASSER WITH RADIUSED JAW," now U.S. Pat. No. 9,011,454; which is a continuation-in-part of U.S. patent application Ser. No. 13/873,841 filed Apr. 30, 2013, titled "DEVICES, SYSTEMS AND METHODS FOR MENISCUS REPAIR," now U.S. Pat. No. 8,808,299; which is a continuation of U.S. patent application Ser. No. 13/462,728 filed May 2, 2012, titled "DEVICES, SYSTEMS AND METHODS FOR MENISCUS REPAIR," now U.S. Pat. No. 8,449,533; which is a continuation of U.S. patent application Ser. No. 12/942,803 filed on Nov. 9, 2010 now U.S. Pat. No. 8,562,631, which claims priority to U.S. Provisional Patent Application No. 61/259,572 filed Nov. 9, 2009; U.S. Provisional Patent Application No. 61/295,354 filed on Jan. 15, 2010, titled "DEVICES, SYSTEMS AND METHODSFOR MENISCUS REPAIR," and U.S. Provisional Patent Application No. 61/318,215 filed Mar. 26, 2010 and titled "CONTINUOUS SUTURE PASSERS HAVING TISSUE PENETRATING SUTURE SHUTTLES." U.S. patent application Ser. No. 14/265,848 also claims priority as a continuation-in-part of Ser. No. 13/893,154 filed May 13, 2013, titled "SUTUR PASSER DEVICES AND METHODS," now U.S. Pat. No. 9,247,934, which is a continuation of U.S. patent application Ser. No. 13/462,773 filed May 2, 2012, titled "SUTURE PASSER DEVICES AND METHODS," now U.S. Pat. No. 8,465,505, which is a continuation-in-part of U.S. patent application Ser. No. 13/323,391, filed Dec. 12, 2011, titled "SUTURE PASSER DEVICES AND METHODS, now U.S. Pat. No. 9,700,299, which claims priority to U.S. Provisional Patent Application No. 61/483,200 filed May 6, 2011 titled "MENISCUS REPAIR," and U.S. Provisional Patent Application No. 61/511,922 filed Jul. 26, 2011 and titled "MENISCUS REPAIR." U.S. patent application Ser. No. 14/265,848 also claims priority as a continuation-in-part of PCT/US2014/030137 filed on Mar. 17, 2014.

All of these applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods, devices and systems described herein may be used to suture tissue, particularly in difficult to access regions. In particular, described herein are highly maneuverable suture passers configured to be deployed around a target tissue to be sutured.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, as well as problems with the reliable functioning of the suture passer.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

For example, some variations of suture passers, such as those described in U.S. Pat. No. 7,377,926 to Taylor, have opposing jaws that open and close over tissue. One, or in some variations, both, jaws open, scissor-like, so that tissue may be inserted between the open jaws. Unfortunately, such devices cannot be adequately positioned for use in hard to navigate body regions such as the joints of the body, including the knee (e.g., meniscus) and the shoulder.

The meniscus is a C-shaped piece of fibrocartilage which is located at the peripheral aspect of the joint (e.g., the knee) between the condyles of the femur and the tibia on the lateral and medial sides of the knee. The central two-thirds of the meniscus has a limited blood supply while the peripheral one third typically has an excellent blood supply. Acute traumatic events commonly cause meniscus tears in younger patients while degenerative tears are more common in older patients as the menisci become increasingly brittle with age. Typically, when the meniscus is damaged, a torn piece of meniscus may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult to perform because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for visualization of the structures within that joint. Then, using miniature instruments which may be as small as 1/10 of an inch, the structures are examined and the surgery is performed.

FIGS. 21A, 21B and 22 illustrate the anatomy of the meniscus in the context of a knee joint. As shown in FIG. 22 the capsule region 202 (the outer edge region of the meniscus) is vascularized. Blood enters the meniscus from the menisculocapsular region 212 lateral to the meniscus. A typical meniscus has a flattened bottom (inferior surface or side) and a concave top (superior surface or side), and the outer cross-sectional shape is somewhat triangular. The outer edge of the meniscus transitions into the capsule. FIG. 23 illustrates the various fibers forming a meniscus. As illustrated in FIG. 23, there are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed.

For example, FIGS. 24A-24E illustrate various tear patterns or injuries to a meniscus. Tears may be vertical/longitudinal (FIG. 24A), oblique (FIG. 24B), degenerative (FIG. 24C), including radially degenerative, transverse or radial (FIG. 24D) and horizontal (FIG. 24E). Most prior art devices for suturing or repairing the meniscus are only capable of reliably repairing vertical/longitudinal tears. Such devices are not typically useful for repairing radial or horizontal tears. Furthermore, prior art device mechanisms have a high inherent risk for iatrogenic injury to surrounding neurovascular structures and chondral surfaces.

Thus, there is a need for methods, devices and systems for suturing tissue, particularly tissue in difficult to access regions of the body including the joints (shoulder, knee, etc.). In particularly, it has proven useful to provide a device that may simply and reliably reach and pass sutures within otherwise inaccessible tissue regions. Finally, it is useful to provide a suturing device that allows the tissue to be sutured to be held within an adjustable jaw so that it can be predictably sutured, and done so in a manner that protects fragile surrounding tissues from iatrogenic injury. The methods, devices and systems described herein may address this need.

SUMMARY OF THE DISCLOSURE

The present invention relates to devices, systems and methods for suturing tissue, including a torn meniscus. In general, described herein are suturing devices, such as suture passers, as well as methods of accessing and repairing tissue using these suture passers, including methods of suturing tissue. The device and methods described herein allow methods of suturing and repairing tissue that were previously impossible or impractical to perform during a surgical procedure.

In particular, the suture passers described herein may be configured so that a tissue penetrating element (tissue penetrator, needle, etc.) is configured to travel in an approximately sigmoidal pathway when passing a suture. For example, the suture passer may be configured so that the tissue penetrator extends first distally within a first jaw member of the suture passer, then deflects from this distal direction to travel nearly perpendicular to the distal direction and across the mouth of the suture passer (and through a tissue held in the mouth of the suture passer); the tissue penetrator is then deflected to continue to extend distally within a second jaw member and eventually extend out of a distal opening in the second jaw member.

In some variations, the suture passers described herein may also be configured as dual deployment suture passers, because the tissue engaging region of the suture passer comprises a distal-facing opening formed between two jaws (a first jaw member and a second jaw member), and each jaw member moves (is deployed) independently with a different type (e.g., axis, plane, range, etc.) of motion. Many of the devices described herein may also be referred to as clamping/sliding suture passers, because the first jaw member acts to clamp onto the tissue, by changing the angle of the first jaw member relative to the more proximal elongate body region of the device, and the second jaw member slides, moving axially relative to the more proximal elongate body region of the device.

Thus, in many of the dual deployment suture passers described herein, the first jaw member generally extends distally from a proximal elongate body region; the angle of the first jaw member relative to the proximal elongate body region is adjustable. These dual deployment suture passers also have a second jaw member that may be moved from a position proximal to the first jaw member and/or proximal to the distal end of the elongate body region to a distal position to form a distal-facing jaw opening with the first jaw member.

Because of this novel jaw movement, a dual deployment suture passer may readily access and be positioned around tissue to be sutured in ways not possible with more traditional suture passers. Generally a dual deployment suture passer may be positioned within the tissue by adjusting the angle of the first jaw member to help avoid non-target tissue as the device is advanced so that the first jaw member is adjacent to the target tissue. The second jaw member may then be extended distally from the proximal position (e.g., by sliding axially, by swinging distally, etc.) so that the tissue is held between the first and second jaw members in a distal-facing jaw opening. The tissue to be sutured may then be clamped securely between the first and second jaw members (e.g., by adjusting the angle of the first jaw member), and a suture may be passed between the two by extending a tissue penetrator from within one of the first or second jaw members, across the opening and through the tissue, to either drop off or pick up a suture at the opposite jaw member. The tissue penetrator can then be retracted back into the jaw member that houses it.

For example, described herein are methods of arthroscopically placing a suture. The suture may be placed entirely arthroscopically. For example, two or fewer incisions may be made into the body (e.g., knee, shoulder, etc.), and a camera and suture passer may be placed within the knee. In any of these methods, the suture may be placed by independently or sequentially moving a first distal jaw member through a first range of motion before, during or after placing the distal end of the suture passer into the tissue region. A second jaw member is typically held proximally to the first jaw member either within or aligned with the more proximal elongate body region of the suture passer. After positioning the distal end of the suturing device, including the distally-extending first jaw member against the target tissue to be sutured, the second jaw member may be advanced distally until it is positioned opposite from the first jaw member. The tissue may be secured between the first and second jaw members. In general the second jaw member may be moved into position by moving the second jaw member in a path of motion that is different from that of the first jaw member. For example, the first jaw member may be hinged to move at an angle relative to the elongate body of the device, while the second jaw member extends distally (and retracts proximally) by sliding axially relative to the elongate body of the device.

For example, described herein are dual deployment suture passer devices. In some variations these devices include: an elongate body having a proximal end region and a distal end region; a first jaw member extending from the distal end region of the elongate body and configured for angular movement relative to the elongate body; a second jaw member configured to extend axially relative to the elongate body, the second jaw configured to form an opening with the first jaw member when the second jaw member is axially extended; and a tissue penetrator deployably held within either the first or second jaw member and configured to pass a suture between the first and second jaw members by extending and retracting between the first and second jaw members when the first and second jaw members form the opening.

In some variations, the second jaw member may be contained within the elongate body; in other variations, it is held outside of the elongate body (e.g., secured adjacent to the outside of the elongate body). The elongate body may be straight, curved, or bendable; in some configurations the elongate body is tubular and extends as an elongate tube. In general, the elongate body may have any appropriate cross-section, including round, oval, square, triangular, or the like. The cross-section of the elongate body may be uniform, or it may vary along its length. In some variations, the elongate body may be narrower towards the distal end, which may allow the device to be inserted into various regions of the body.

In general, the device may be configured so that the tissue penetrator extends between the first and second jaw members when they are fully deployed distally. In this configuration, they may be referred to as distal opening or having a distal-facing opening. In some variations the first jaw member and the second jaw member are deployed or deployable to form a distal facing opening into which the target tissue can be positioned or held. In some variations the distal opening formed between the jaws is formed around the target tissue by placing the first or the second jaw members adjacent the target tissue and moving the other jaw member (e.g., second or first jaw members) on the opposite side of the target tissue.

The tissue penetrator may be any appropriate tissue penetrating member. For example, the tissue penetrator may be a needle or tissue penetrating probe. The tissue penetrator may include a suture engagement region for releaseably engaging a suture. In some variations the suture engagement region is a hook, notch, clamp, grasper, eyelet, slot, or the like. The suture engagement region may be positioned at or near the distal end, or just proximal to the distal end of the tissue penetrator. The distal end of the tissue penetrator may be sharp (e.g., pointed, beveled, etc.) or it may be substantially dull. The tissue penetrator may be a metal, polymeric, alloy, ceramic, composite, or other material. Shape memory or superelastic materials, including superelastic alloys (such as Nitinol) may be used. Thus, as mentioned, the device may include a suture engagement region at or near a distal tip of the tissue penetrator configured to couple with a suture.

In general, the tissue penetrator may extend between the first and second jaw members only when the first and second jaw members are positioned to form an opening between which tissue may be held. In some variations the suture passer includes a lock or other element preventing or limiting (e.g., a limiter) the tissue penetrator motion from extending between or beyond the first and second jaw members.

During operation, the tissue penetrator generally extends from either the first or second jaw members, and across the opening between the first and second jaw members (including through any tissue between the jaw members), to engage with a suture retainer on the opposite jaw. The suture retainer may hold a suture so that it can be engaged (grabbed) by the tissue penetrator. For example, in some variations the tissue penetrator extends across the opening between the first and second jaw members until it engages with a suture held by the opposite jaw member (e.g., in a suture retainer); thereafter the tissue penetrator can be retracted back across the opening and pull the suture with it. In some variations the suture is preloaded onto the tissue penetrator and the suture retainer grabs the suture from the tissue penetrator (or the tissue penetrator deposits the suture in the suture retainer) and holds the suture in/on the opposite jaw as the tissue penetrator is retracted back across the opening and through any tissue there between.

The motion of the tissue penetrator may be regulated to prevent the tissue penetrator from extending beyond the opening formed between the first and second jaw members as it extends across this opening. In particular, a dual deployment suture passer may be configured to prevent the tip of the tissue penetrator from extending beyond the outside of a jaw member. Extending beyond the jaw member may result in damage to surrounding (non-target) tissues. For example, the suture passer may be configured so that the extent of travel of the tissue penetrator is limited based on how "open" the jaw members are; in variations in which the size of the opening can be modified by adjusting the angle of the first jaw member relative to the elongate body of the device, a limiter may prevent the tissue penetrator from extending further beyond the side of a jaw member opposite from the jaw member housing the tissue penetrator. For example, the tissue penetrator may be configured to extend and retract between the first and second jaw members without extending substantially beyond a lateral side of the first or second jaw members opposite the opening. Thus, the devices described herein may also include a movement limiter configured to limit the movement of the tissue penetrator based on a position of the first jaw member, the second jaw member or both the first and second jaw members, relative to the elongate body.

In some variations the limiter (e.g., a travel limiter) may be employed to keep the tissue penetrator from extending beyond the opening and opposite jaw member. For example, a limiter may include a barrier, block, cage, or the like on the opposite jaw member preventing the tip of the tissue penetrator from extending beyond the jaw member when the tissue penetrator is extended across the opening.

Thus, the suturing device may also include a travel limiter configured to prevent the tissue penetrator from extending substantially beyond a lateral side of the first or second jaw members opposite the opening.

One of the jaw members (e.g., the second jaw member) may be configured to move axially by extending distally or retracting proximally from the distal end region of the elongate body. Thus, the second jaw member may extend parallel to the long axis of the elongate body; in curved variations of the elongate body, the second jaw member extends distally in the direction continuing the distally moving trajectory of the elongate body. The second jaw member may extend axially from within the elongate body, or from adjacent to the elongate body. In some variations the entire second jaw member may retract within the elongate body.

In some variations, the opening formed between the first and second jaw members by extending the second jaw member distally is a distal-facing opening, as described above. In some variations the device includes a holdfast to hold one or both jaw element(s) in a fixed position; the holdfast may be released or engaged by user control. For example, the suturing device may include a first and/or second jaw holdfast configured to hold the first and/or second jaw members in a fixed position relative to the elongate body. In one variation, the device includes a first jaw holdfast configured to hold the first jaw member in an angular position relative to the elongate body and/or a second jaw holdfast to hold the second jaw element in a fixed axial position relative to the elongate body.

Any of the device variations described herein may include a handle at the proximal end of the device. The handle may be controlled by a user (e.g., surgeon) to actuate the various elements of the device, including the first jaw member, the second jaw member, and the tissue penetrator. The handle may therefore include one or more controls. For example, the device may include a first control for controlling the angular position of the first jaw member relative to the elongate body and a second control for controlling the axial position of the second jaw member relative to the elongate body. These controls may be on the proximal handle.

The device may also include an indicator for indicating when the second jaw is in a predetermined axially extended position relative to the elongate body. The indictor may be visual, tactile, aural, or the like, including some combination of these. In some variations a separate indicator is not necessary; the full extension of the second (or first) jaw member may be the fully engaged position. Thus, when further actuation of the control (e.g., squeezing a trigger, moving a level, dial, or the like) does not result in any further actuation. In some variations the control may "stop" when the jaw member is fully extended.

Thus, in some variations, the device includes a proximal handle having controls for controlling at least one of the angular movement of the first jaw member, the axial movement of the second jaw member or the extension and retraction of the tissue penetrator.

Also described herein are suture passer devices (e.g., a dual deployment suture passers) comprising: an elongate body having a proximal end region and a distal end region; a first jaw member extending from the distal end region of the elongate body and configured for angular movement relative to the elongate body; a second jaw member configured to extend distally or retract proximally from the distal end region of the elongate body; and a tissue penetrator configured to pass a suture between the first and second jaws and further configured to extend and retract between the first and second jaw members when the second jaw member is extended distally to form a distal-facing opening with the first jaw member.

Any of the features described above may be included in these variations as well. For example, the device may also include a suture engagement region near a distal tip of the tissue penetrator, the suture engagement region configured to couple with a suture. In some variations the device also includes a movement limiter configured to limit the movement of the tissue penetrator based on a position of the first jaw member, the second jaw member or both the first and second jaw members.

Also described herein are suture passer devices including: a hinged first jaw member extending from a distal end of an elongate body and configured to controllably bend relative to a longitudinal axis of the elongate body; an axially sliding second jaw member configured to extend distally and retract proximally relative to the distal end of the elongate body to form a distal-facing opening with the first jaw member when the second jaw member is extended distally; a tissue penetrator housed within the second jaw member and configured to extend across the distal-facing opening to the first jaw member; a suture engagement region disposed near a distal end of the tissue penetrator and configured to engage a suture; and a travel limiter configured to engage the tissue penetrator and prevent the tissue penetrator from extending beyond a lateral side of the first or second jaw members opposite the distal-facing opening.

Although many of the device variations just described include a second jaw member that is axial movable, in some variations the second jaw member is movable in other dimensions in addition to, or alternatively to, the axial direction. Generally the second jaw member is movable in a direction that is different from the manner of movement of the first jaw member, and extends the second jaw member from a position in which the distal end (e.g., tip) region of the second jaw member is proximal to the distal end of the elongate body. Movement of the second jaw member may be independent of the movement of the first jaw member.

Also described herein are methods of suturing a tissue, the method comprising: moving a first jaw member of a dual deployment suture passer so that the first jaw member extends distally from a proximal elongate body region of the suture passer at an angle with respect to a longitudinal axis of the proximal elongate body region; positioning the first jaw member adjacent to a tissue to be sutured; extending a second jaw member of the suture passer distally relative to the elongate body region to form a distal-facing opening between the first and second jaw members, so that the tissue to be sutured is within the distal-facing opening; and passing a suture through the tissue within the distal-facing opening by moving a tissue penetrator coupled to a suture between the first and second jaw members.

The method may also include the step of preventing the tissue penetrator from extending beyond a lateral side of the first or second jaw members opposite the distal-facing opening when passing the suture. In some variations, the method also includes the step of retracting the second jaw member proximally relative to the elongate body and withdrawing the suture passer from the tissue.

This method may be used to treat (e.g., suture) as part of a variety of treatments, including, but not limited to, repair of a torn meniscus, repair of a torn ACL, labral tear repair, hip labrum repair, spinal disc repair, etc. In any of these variations, the method of treatment (method of suturing tissue) may include the step of positioning the first jaw adjacent to the tissue to be sutured, such as the meniscus, labrium, ACL, spinal disc/annulus, etc. For example, the step of positioning the first jaw member may comprise positioning the first jaw member adjacent to meniscus tissue.

These devices and methods may be used as part of a minimally invasive (e.g., percutaneous) or open procedure. For example, the method of suturing may also include the step of percutaneously inserting the suture passer near the tissue to be sutured.

The step of passing the suture through the tissue may comprise extending the tissue penetrator from the second jaw member through the tissue to the first jaw member, engaging the suture held in the first jaw member and retracting the tissue penetrator back to the second jaw member while holding the suture with the tissue penetrator. In some variations, the step of passing the suture through the tissue comprises extending the tissue penetrator coupled to a suture from the second jaw member through the tissue to the first jaw member, engaging the suture with a suture retainer in the first jaw member and retracting the tissue penetrator back to the second jaw member.

Any of the suture passer devices described herein may be configured to include a tissue penetrator that travels in an approximately sigmoidal pathway. Further, any of these devices may be configured so that the tissue penetrator extends distally from one of the jaw members. For example, in some variations the suture passer is configured so that the tissue penetrator extends distally through a distal opening in one jaw member of the suture passer after extending across a distal-facing mouth formed by a pair of jaw members.

For example, described herein are suture passer devices having a suture-passing tissue penetrator that travels in a sigmoidal pathway. The suture passer device may include: a first jaw member extending distally from an elongate body, wherein the first jaw member includes a deflection surface and a distal opening; a second jaw member extending distally from the elongate body, wherein the first jaw member and the second jaw member form a distal-facing mouth; and a tissue penetrator configured to extend from the second jaw member, across the distal-facing mouth, into the first jaw member, deflect against the deflection surface and extend distally from the distal opening of the first jaw member.

In general, the suture passer may push (or in some variations pull or push and pull) a suture with the tissue penetrator through the tissue from one jaw member to the other. For example, in some variations the device includes a suture stripper in the first jaw member configured to strip a suture from the tissue penetrator and retain the suture in the first jaw member. A suture stripper may be configured as a leaf spring element that strips a suture from the tissue penetrator and retains the suture in the first jaw member; the tissue penetrator may push against and pass the stripper, displacing it, but causing the suture to be held or caught by the stripper and secured within the jaw member, even when the tissue penetrator is retracted back across the mouth formed by the jaws of the device.

As mentioned, in some variations the device is configured so that the first jaw and the second jaw are separately movable and therefore independently adjustable. For example, the first jaw member may be configured to pivot relative to the distal end region of the elongate body, and the second jaw member may be configured to slide distally and proximally relative to the elongate body. In any of these variations, the device may include a proximal handle comprising a first control for controlling the angle of the first jaw member relative to the elongate body and a second control for controlling distal and proximal extension of the second jaw member.

Any of the devices described herein may include a suture retainer region on the tissue penetrator that is configured to hold a length of suture as the tissue penetrator extends between the first and second jaw members. The suture retainer region may comprise a lateral cut-out region of the tissue penetrator (e.g., configured as a hook, catch, or the like).

As mentioned, the tissue penetrator may typically extend from the distal end of the jaw member after crossing the mouth formed by the pair of jaws. Extending distally may allow the tissue penetrator to extend more fully from a first jaw member, across the distal facing mouth and may facilitate transferring the suture into a suture receiving region (suture dock or receiver) on the opposite jaw. By extending the distal tip of the tissue penetrator distally, the tissue penetrator may prevent the tip from damaging adjacent (lateral) tissue, and fit into protected or low-risk anatomical regions. This is particularly true when the device is used in regions such as the joints. The device may be particularly well suited to repair a meniscus, as discussed herein. The tissue penetrator may extend any appropriate distance distally from the opening at the distal end of the jaw member. For example, in some variations, the tissue penetrator may be configured to extend distally from the distal opening of the tissue penetrator by more than about 1 mm (or more than about 2 mm; more than about 3 mm, between about 0.5 mm and about 5 mm, etc.).

Any of the devices described herein may be configured so that they can pass more than one length of suture though the tissue sequentially. For example, in some variations, it is beneficial to form a loop of suture around a tissue or tear in a tissue. Thus, the device may be configured to pass a first end of the suture and then (without removing the suture from the tissue) pass the second (opposite) end of the suture at a different location on the tissue, thereby forming a loop of suture which can be tied off by tying the ends of the suture (suture bights) to each other or to a device after they've been passed.

In some variations, the second jaw member comprises a suture loading region configured to hold a second length of suture while a first length of suture is held within a suture retainer region of the tissue penetrator. Thus, the device may be adapted so that more than one length of suture (e.g., the opposite end regions of a suture) can be loaded (including pre-loaded) into the device for passing. In some variations the device is configured so that after passing the first length of suture, the second length of suture is automatically pushed and loaded into the suture retainer of the tissue penetrator. Although two or more separate sutures may be passed, in some variations the device is adapted to pass two regions (e.g., the end regions) of the same suture.

For example, in some variations, the suture passer is configured to include: a first jaw member extending distally from an elongate body; a second jaw member extending distally from the elongate body, wherein the first jaw member and the second jaw member form a distal-facing mouth; a tissue penetrator configured to extend from the second jaw member, across the distal-facing mouth, into the first jaw member, deflect against the deflection surface and extend distally from the distal opening of the first jaw member; a first suture retainer region in the tissue penetrator configured to hold a suture in the tissue penetrator as it extends from the second jaw member; a suture loading region in the second jaw configured to hold a second suture so that it can be loaded into the first suture retainer region when the first suture holder region is empty; and a suture stripper in the first jaw member configured to strip the suture from the tissue penetrator and to retain the suture within the first jaw member.

In some variations, the suture passer has a suture-passing tissue penetrator that travels in a sigmoidal pathway and the device includes: a first jaw pivotally coupled to the distally end region of an elongate body, wherein the first jaw is configured to pivot relative to the elongate member; a deflection surface within the first jaw; a second jaw configured to slideably extend distally from the elongate body, wherein the first jaw and the second jaw are configured to form a distal-facing mouth; a tissue penetrator housed within the second jaw and configured to extend from the second jaw across the distal-facing mouth and into the first jaw, deflect against the deflection surface, and extend distally from a distal opening in the first jaw; and a suture retainer region on the tissue penetrator configured to retain a suture as the tissue penetrator is extended across the distal-facing mouth. As mentioned above, in some variations, the device is configured so that the pivoting motion of the first jaw is independent of sliding motion of the second jaw.

As mentioned, any of these suture passers may include a suture stripper (e.g., in the first jaw) that is configured to strip a suture from the tissue penetrator and retain the suture in the first jaw. For example, the suture stripper may be a leaf spring element configured to strip a suture from the tissue penetrator and retain the suture in the first jaw.

Any of the devices described herein may include a proximal handle. The proximal handle may include one or more controls for controlling extension/retraction of the tissue penetrator, and/or controls from controlling the motion(s) of the jaws. For example, described herein are proximal handles comprising a first control for controlling pivoting and angle of the first jaw member relative to the elongate body and a second control for controlling distal and proximal extension of the second jaw.

In general, the suture retainer region may be configured to hold the suture (or an element coupled to the suture) as it is pulled or pushed through the tissue following the path of the tissue penetrator. For example, the tissue penetrator may include a suture retainer region that is a lateral cut-out region of the tissue penetrator. In some variations, the suture retainer is a hook region for holding a length of suture.

Also described herein are methods of using the suture passers described herein to pass a suture and/or form a loop of suture around a tissue, and particularly a tissue tear. Although a variety of tissues (and/or explants, implants, graphs, and the like) may be sutured using these devices and methods, methods for repairing the meniscus of the knee are illustrated herein. Thus, any of the methods described herein may be used to repair or treat (and generally, suture) a meniscus. The methods and devices described herein may be performed in an open, semi-open, and/or minimally invasive (e.g., percutaneous) procedure.

For example, described herein are methods of passing a suture through tissue using a suture passer having a first jaw member and a second jaw member that are configured to form a distal-facing mouth and a suture passer device having a suture-passing tissue penetrator that travels in a sigmoidal pathway. In some variations, the method may include all or some of the steps including: extending the tissue penetrator from within the second jaw member, across the distal-facing mouth and though the tissue, and into the first jaw member; deflecting the tissue penetrator within the first jaw member and extending the tissue penetrator distally out of a distal opening in the first jaw member; and retracting the tissue penetrator back into the first jaw member, across the distal-facing mouth and into the second jaw member; wherein the tissue penetrator carries a suture through the tissue when extending from the second jaw member or retracting into the first jaw member.

In some variations, the method includes positioning the tissue within the distal facing mouth, for example, by placing the first jaw member adjacent to one side of the tissue and thereafter extending the second jaw member distally so that it is adjacent to a second side of the tissue. In some variations, placing the first jaw member adjacent to one side of the tissue comprises adjusting the angle of the first jaw member relative to a proximal shaft region of the suture passer.

Any of these methods may include stripping a suture from the tissue penetrator while the tissue penetrator is within the first jaw member and retaining the suture within the first jaw. For example, stripping the suture may include displacing a suture stripper when extending the tissue penetrator distally within the first jaw member.

Also described herein are methods of passing a suture through tissue using a suture passer having a first jaw member and a second jaw member that are configured to form a distal-facing mouth and a suture passer device having a suture-passing tissue penetrator that travels in a sigmoidal pathway, the method comprising: positioning the suture passer with the tissue within the distal facing mouth; extending the tissue penetrator holding a length of suture from the second jaw member, across the distal-facing mouth, though the tissue, and into the first jaw member; deflecting the tissue penetrator within the first jaw member and extending the tissue penetrator distally out of a distal opening in the first jaw member; stripping the length of suture from the tissue penetrator and retaining the length of suture within the first jaw member; and retracting the tissue penetrator back into the first jaw member, across the distal-facing mouth and into the second jaw member. The method may also include positioning the first jaw member over the tissue to be sutured and then sliding the second jaw member distally to form the distal-facing mouth with the tissue between the first and second jaw members of the distal facing mouth.

Also described herein are methods of suturing a tissue using a suture passer having a first jaw member and a second jaw member that are configured to form a distal-facing mouth. For example, the method may include the steps of: positioning the suture passer with a first region of the tissue between the first and second jaw members of the distal facing mouth; extending a tissue penetrator containing a first region of a suture from the second jaw member, across the distal-facing mouth, though the tissue, and into the first jaw member; holding the first end of the suture within the first jaw member and withdrawing the tissue penetrator back into the second jaw member; repositioning the suture passer with a second region of the tissue between the first and second jaw members of the distal facing mouth; extending the tissue penetrator containing a second region of the suture from second jaw member, across the distal facing mouth, through the tissue, and into the first jaw member; holding the second region of the suture within the first jaw member and withdrawing the tissue penetrator back into the second jaw member; and withdrawing the suture passer from the tissue and pulling the first and second regions of the suture.

The minimally invasive methods of repairing a meniscus within a patient's knee described herein may include: inserting a suture passer into the patient's knee to minimally invasively approach the meniscus from an apex of the meniscus; passing a suture between an inferior side and a superior side of the meniscus to form the suture into a loop around the apex, the inferior and the superior sides of the meniscus (e.g., without removing the suture passer from the knee); and knotting the suture to close the loop. Approaching the meniscus from the apex region of the meniscus, and securing a loop of suture over the apex as well as from the superior to inferior surfaces, as described herein, may be referred to as a hay bale stitch that may be particularly and unexpectedly advantageous in securing the meniscus, and has not previously been possible.

BRIEF DESCRIPTION OF THE DRAWINGS

FIG. 7A shows a side view of one variation of a tissue penetrator.

FIG. 7B shows a side perspective view of the tissue penetrator of FIG. 7A.

FIG. 8 shows the perspective view of FIG. 4 with a tissue penetrator partially extended between the first and second jaw members, and with a suture loaded in the first jaw member.

FIGS. 14A-14C illustrate operation of one variation of a dual deployment suture passer configured as a clamping/down-swinging suture passer.

FIGS. 19A-19F illustrate operation of one variation of dual deployment suture passer.

FIGS. 24A-24E illustrate various tear patterns that may be repaired using the invention described herein.

FIG. 28 shows an exemplary section through a spine showing a normal disc.

FIG. 29 shows a similar section through a spine having a herniated disc.

FIGS. 32A-32C illustrate a generic variation of a suture passer including a tissue penetrator traveling in a sigmoidal path in which the distal end of the tissue penetrator extends distally from the upper jaw.

FIG. 33A is another variation of a suture passer having a tissue penetrator that extends distally from the upper jaw; FIG. 33B illustrates the motion of the upper and lower jaw of the suture passer of FIG. 33A.

FIG. 33C is another variation of a suture passer having a tissue penetrator that extends distally from the upper jaw; FIG. 33D illustrates the motion of the upper jaw of the suture passer of FIG. 33C.

FIG. 33E is another variation of a suture passer having a tissue penetrator that extends distally from the upper jaw; FIG. 33F illustrates the motion of the lower jaw of the suture passer of FIG. 33A.

FIGS. 39A, 39B and 39C show another variation of a suture passer.

FIGS. 40A, 40B, and 40D show top and two side perspective views, respectively of the distal end of the suture passer shown in FIG. 39A.

FIG. 40C illustrates the arrangement of the tissue penetrator and suture stripper in the distal end region of the suture passer of FIG. 39A.

FIGS. 41A-41C show a suture stripper including a stripper plate (FIG. 41B) and base (FIG. 41C).

FIGS. 43A-43E illustrate operation of a suture stripper.

FIGS. 46A-46L show another illustrate of a method for suturing meniscal tissue similar to that shown in FIGS. 44A-44G.

FIGS. 47A-47E illustrate one method of loading a suture passer with two loops of suture that may be sequentially passed by the suture passer.

FIGS. 62A and 62B illustrate another variation of a suture cleat.

FIG. 63A shows a side sectional view and FIG. 63B shows a top perspective view.

DETAILED DESCRIPTION

Described herein are suture passers. In general, these devices may be referred to as suture passers and/or suturing devices. Different variations of the devices described herein may also be referred to as snake-tongue, sigmoidal, dual deployment suture passers, and/or clamping/sliding suture passers.

Figure 1:
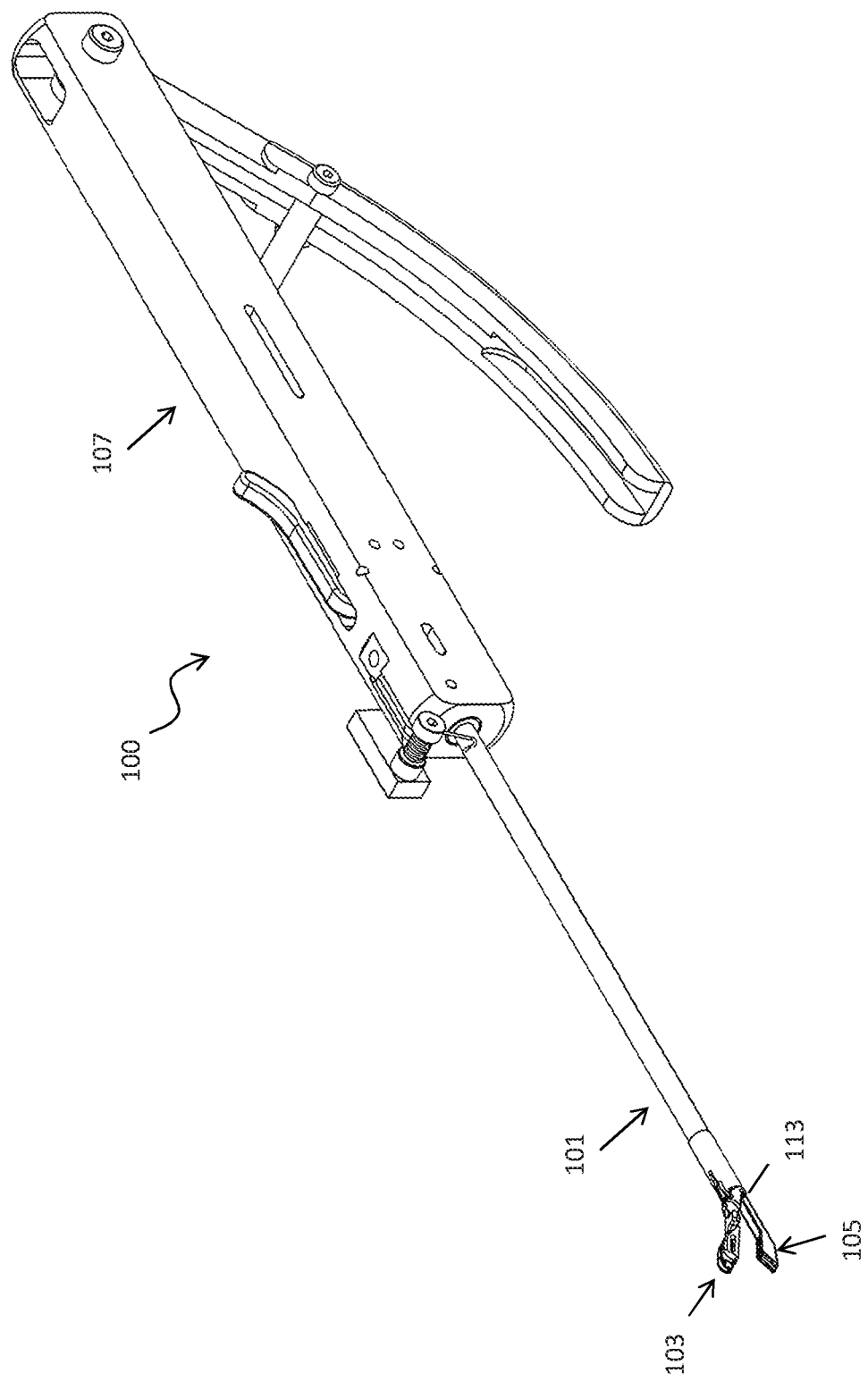
FIG. 1 shows one variation of a dual deployment suture passer as described herein.

In general, the suture passers described herein include a first jaw member and second jaw member that extend from the end of an elongate body region to form a distal-facing mouth into which tissue to be sutured fits. In some variations one or both jaws forming the mouth may be independently moved. FIG. 1 illustrates one variation of a dual deployment suture passer 100. In this example, the device has a first (upper) jaw member 103 extending distally from the distal end of a more proximal elongate member 101. A second jaw member 105 is shown extended distally beneath the first jaw member 103. A handle 107 is located at the proximal end of the device and includes multiple controls for independently controlling the movements of the first jaw member, second jaw member, and tissue penetrator. The handle in this example also includes a second jaw member lock for locking/unlocking the movement of the second jaw member.

The suture passer shown in FIG. 1 is positioned with the first jaw member held at an angle relative to the long axis of the proximal elongate member. The first jaw member in this example is shown having a hinge region 113 about which the first jaw member may be angled relative to the elongate member. In some variations this hinge region is a pinned hinge; non-pinned (e.g., living hinges) regions may be used. Any appropriate articulating region that allows the first jaw member to move at an angle relative to the proximal portion of the device (e.g., the elongate member) may be used. In some variations this first jaw member is referred to as an upper jaw member, but alternative variations (in which the first jaw member is a lower jaw member) are also possible.

The first jaw member may be actuated by any appropriate mechanism, including a tendon member (e.g., push rod, pull rod, or the like), and may be held (locked) at any angle (e.g., between 0° and 180° relative to a line extending from the distal end of the elongate body, between about 0° and 90°, between about 0° and 60°, etc.). In some variations the device has a neutral position during which no force is applied to the controller to move the first jaw member, so that the first jaw member is angled "open" (e.g., at 30°, 45°, 50°, 90° or at any angle between about 15° and about 90°) relative to the elongate body; actuating the control on the handle results in the first jaw member moving towards the "closed" position (e.g., reducing the angle with respect to a line extending from the distal end of the elongate body). In some variations the jaw member is in the neutral position when angled with 0°/180° relative to the elongate body.

The first jaw member shown in FIG. 1 also includes a suture retainer region near the distal end (described in greater detail below). This suture retainer region may hold the suture or be configured to hold a suture. In some variations the suture retainer includes a channel or guide for holding the suture in a preferred position. In some variations the suture retainer includes a pair of graspers, or deflectable members into which the suture may be pushed and held (e.g., handed off from the tissue penetrator). A suture retainer generally holds the suture so that it can be either removed by the tissue penetrator, or so that a suture can be passed into the suture retainer from the tissue penetrator. In FIG. 1, the suture retainer is a channel across which the suture extends so that it can be reliably engaged and pulled down by the tissue penetrator as described in more detail below. In some variations the second jaw member includes a suture retainer, rather than the first jaw member.

The second jaw member is shown in FIG. 1 as a lower jaw member. In this variation, the lower jaw member is configured to slide proximally towards and into the proximal elongate body of the device. The second jaw member typically moves axially, in the direction of the proximal-distal axis of the suture passer. In some variations the second jaw member moves axially completely past the distal end of the elongate body; alternatively, the second jaw member slides axially in the proximal direction only partially (e.g. to align with the hinge region of the first jaw member). The second jaw member shown in FIG. 1 retracts completely into, and extends out of, the lower portion of the elongate body. In some variations the second jaw member moves axially in parallel with the lower jaw member, or only a portion of the lower jaw member extends into the elongate body.

A tissue penetrator (not shown in FIG. 1) may be housed within either the first or second jaw member. As described in more detail below, the tissue penetrator may be configured as a needle, wire, knife, blade, or other element that is configured to extend from within either the first or second jaw members and across the opening between the jaw members to engage a suture retainer and either drop off or pick up a suture therefrom. In general, the tissue penetrator may be configured to completely retract into the jaw member housing. It may be extended across the opening between the jaws by actuating a member in the handle to push or otherwise drive it across the opening, and though any tissue held between the jaws.

The second jaw member 105 shown in FIG. 1 completely houses the tissue penetrator and includes a deflection region that drives the tissue penetrator up and out of the second jaw member by deflecting it across the opening between the two.

The elongate body 101 shown in FIG. 1 is illustrated as a relatively straight cylindrical body, though other shapes may be used. For example, the elongate body may be curved, bent, or angled. In some variations the elongate body is configured to be bent, curved or angled dynamically (e.g. by changing the bend or curve).

The elongate body may be any appropriate length. For example, the elongate body may be between about 6 and about 24 inches long, e.g., 6 inches long, 8 inches long, 10 inches long, 12 inches long, etc. The suture passers described herein may be used for arthroscopic surgeries and therefore may be dimensioned for use as such. Thus the diameter of the device may be configured to be small enough for insertion into a cannula, tube or the like for insertion into the body.

FIGS. 2A-2D illustrate one variation of the distal end region of a dual deployment suture passer forming a distal-facing opening and extending a tissue penetrator across the distal opening. For example, in FIG. 2A the distal end of the device is shown with the first jaw member 201 (shown here as an upper jaw member) extended distally at 0° relative to a line extending from the distal end of the elongate body 203. This "straight" configuration may be helpful for inserting and/or removing the distal end of the device into the tissue (e.g., through a cannula). The first jaw member can then be bent, or allowed to bend in some variations, at an angle relative to a line extending from the distal end of the elongate body.

In this example, the first jaw member pivots around a hinge point 205, and is controlled by a pulling member 208 that pushes and/or pulls proximally and/or distally to control the bend of the first jaw member. The pulling member may include a shaft, wire, tendon, tube, cannula, or the like, and may extend to the proximal end of the device where it can be controlled. The arrow 211 in FIG., 2A illustrates the plane and direction of motion of the first jaw member.

Figure 2A:
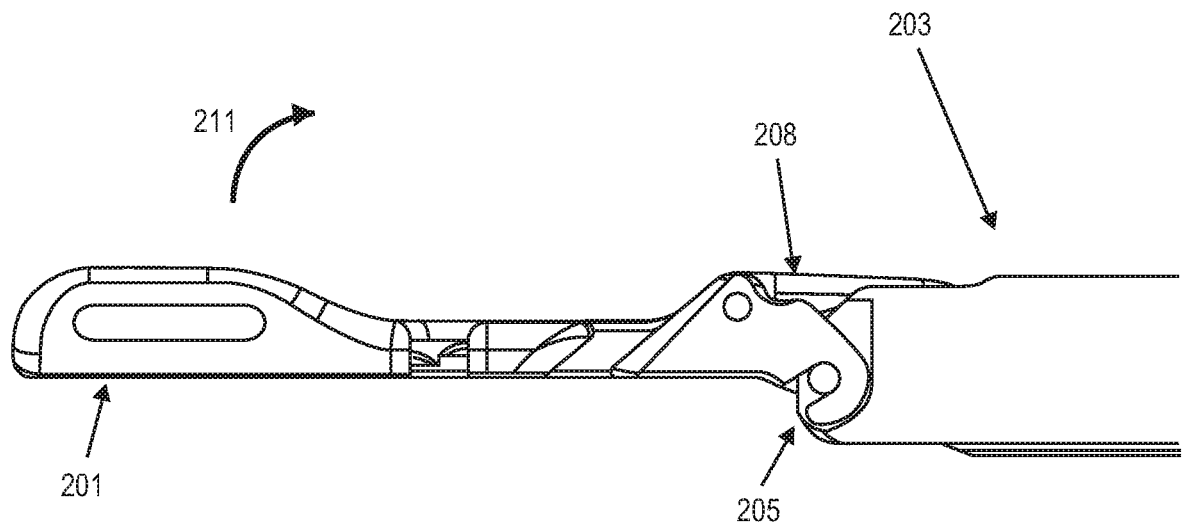
FIGS. 2A through 2D illustrate actuation of the first jaw member, second jaw member and tissue penetrator for one variation of a suture passer.
Figure 2B:
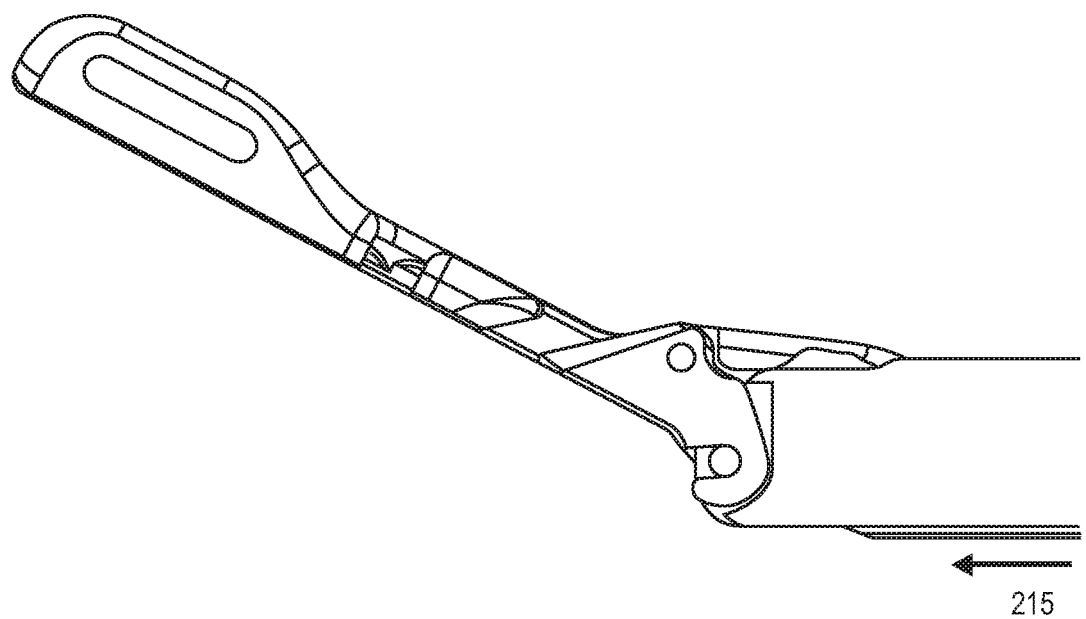
Figure 2C:
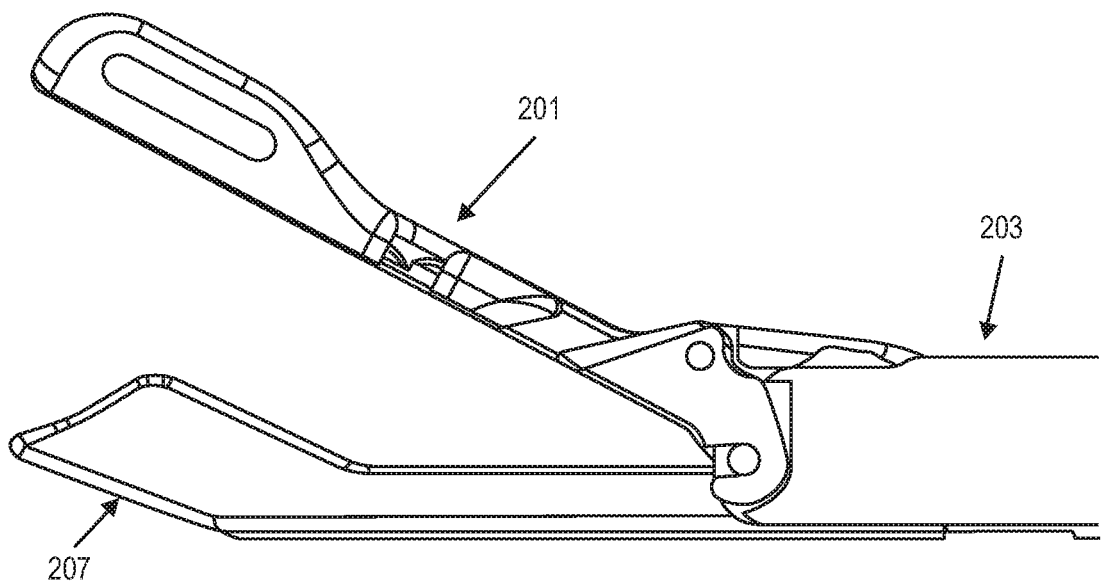

In FIG. 2B the first jaw member has been moved (or allowed to move) so that it forms an angle of approximately 30° with a line extending from the distal end of the elongate body. The arrow 215 in FIG. 2B illustrates the direction of axial motion that the lower jaw (not yet visible in FIG. 2B) will be moved. This is illustrated in FIG. 2C, in which the lower jaw member 207 has been extended distally from the proximal region of the device. In this example the second jaw member 207 is shown fully extended distally relative to the elongate body region 203. Although this example shows the second jaw member extending from completely within the elongate body region (as in FIG. 2B), in some variations the lower jaw member is held outside of the elongate body region, or only partially within the elongate body region. In some variations the second jaw member is completely retracted proximally so that much (or all) of the second jaw member is held proximal to the distal end of the elongate body region 203.

Figure 2D:
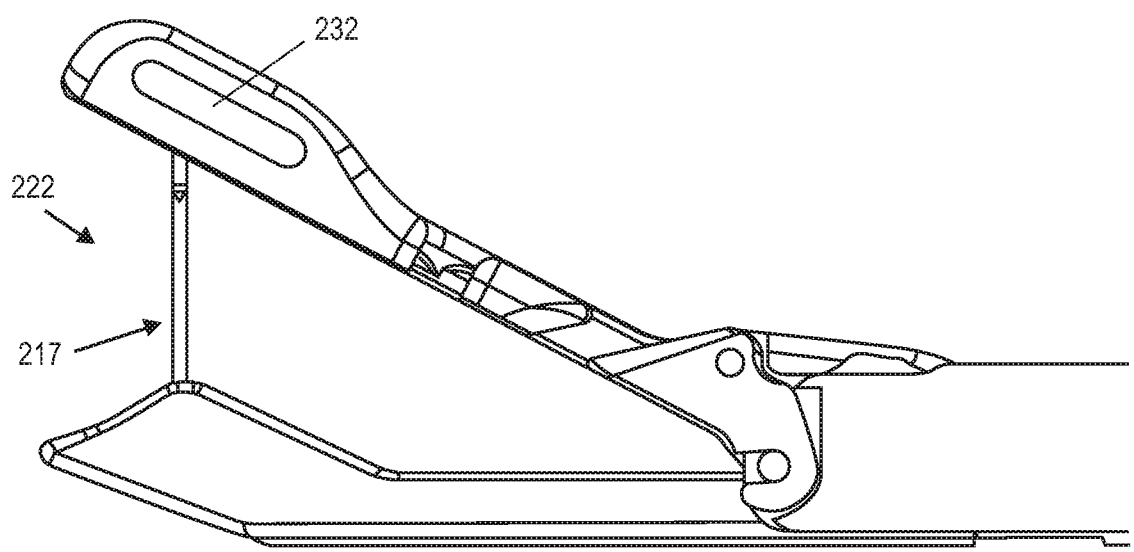

Once the first and second jaw members are completely extended distally (as shown in FIGS. 2C and 2D, the tissue penetrator may be sent across the distal-facing opening 222 as shown in FIG. 2D. Although (as described in greater detail below) in some variations the distal end of the tissue penetrator may be configured to extend distally from an opening in a jaw member, in other variations, the tissue penetrator may be prevented from exiting the opposite side of the jaw member. For example, the tissue penetrator may be prevented from extending distally beyond the jaw member by a limiter (e.g., a travel limiter and/or a movement limiter). In FIG. 2A-2D the first jaw member includes a cage or shield region 232 that prevents the tip of the tissue penetrator from extending out of the first jaw member where it may cut or damage the non-target tissue. In some variations the device may also include a movement limiter, which limits the movement of the tissue penetrator so that it can only extend to just couple with the opposite jaw member (and pass or grab a suture held therein). Since the jaws may be open to varying positions, a movement limiter may help prevent the tissue penetrator from overextending even when the first jaw member is only slightly angled with respect to a line extending from the distal end of the elongate body.

In some variations the tissue penetrator may be prevented from extending across the opening between the first and second jaw members unless the second (axial moving) jaw member is extended distally relative to the elongate body. This may allow the tissue penetrator to mate properly with the suture engagement region on the first jaw member. For example, a lock or other mechanism may be used to prevent the tissue penetrator from engaging with a control at the proximal end of the device until the second jaw member is fully extended.

Figure 3:
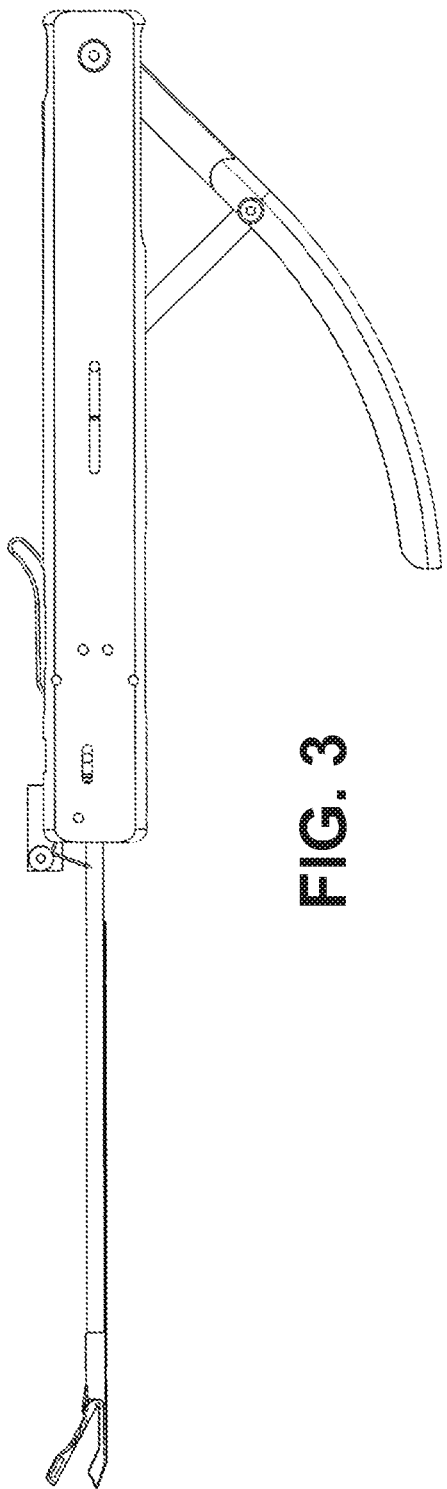
FIG. 3 is a side view of the suture passer shown in FIG. 1.

A side view of the device shown in FIGS. 1-2D is provided in FIG. 3.

Figure 4:
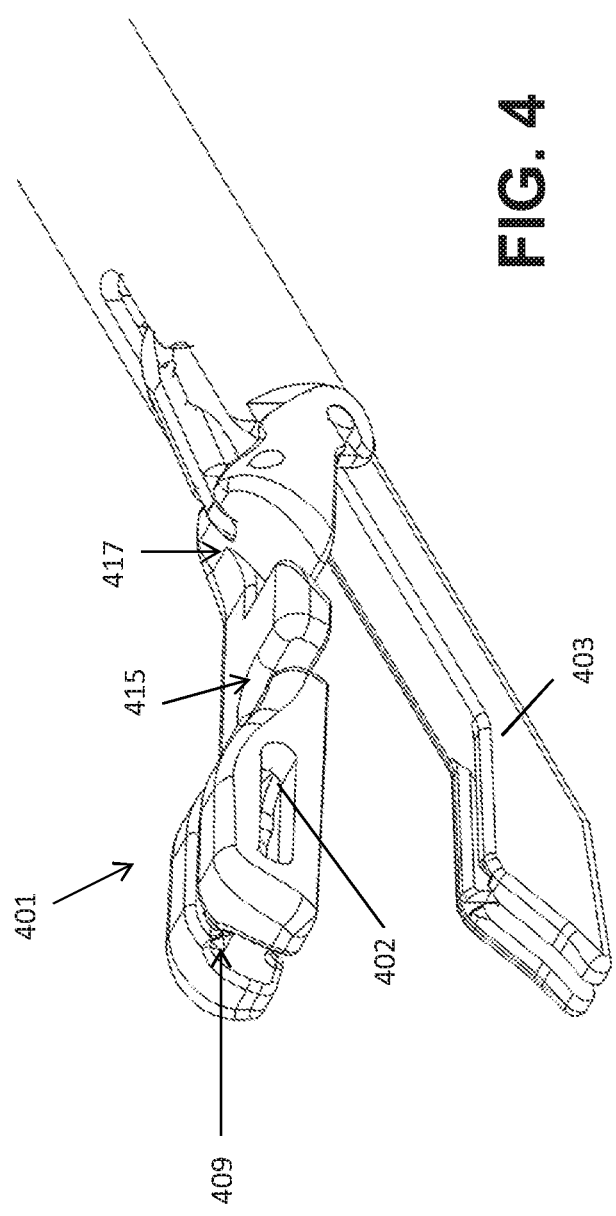
FIG. 4 is a front perspective view of the suture passer shown in FIG. 3 in which the first jaw member is positioned at an angle relative to the longitudinal axis of the elongate body of the device, and the second jaw member is extended fully distally relative to the elongate body to form a distal-facing jaw opening.

FIG. 4 shows a front perspective view of the distal end region of the device of FIGS. 1-3 with the second jaw member extended fully distally and the first jaw member angled slightly (e.g., approximately 30° relative to a line extending distally from the longitudinal axis of the elongate body). In this variation the lower jaw member 403 may be configured to fit within the upper jaw member 401 when the two jaw members are closed down on one another (not shown). Thus the upper (first) jaw member 401 is wider than the lower (second) jaw member 403. The first jaw member in this example also includes optional side windows 402. The first jaw member may also include a suture engagement region; in FIG. 4, this suture engagement region includes a channel 409 through the midline (extending proximally to distally) and a first 415 and second 417 notch or protrusion cut into the first jaw member. A suture may be wrapped around the first jaw member by passing from the proximal end of the device, under the proximal notch 417 and along the bottom (e.g., the side of the first jaw facing the extended second jaw) around the distal end of the first jaw member and along the top (e.g., the side of the first jaw facing away from the second jaw) and, under the distal notch 415 and back up out of the proximal notch 417 so that the suture may extend distally. This loop of suture held by the suture engagement region of the jaw member may be held under sufficient tension so that the suture may be engaged by the suture engagement region of the tissue penetrator (e.g., hook, grasper, etc.). In some variations a tensioning member may be included in the suture engagement region.

In some variations (not shown here) the suture may be contained within the elongate body of the device. Alternatively, the suture may be kept outside of the device. In some variations the suture may be loaded by the user. For example, a user may load a suture on the device by placing a loop of suture over the first jaw member. In some variations the suture holder may be placed along the length of the device to hold or manage the suture so that it doesn't interfere with the operation of the device or get tangled.

Figure 5A:
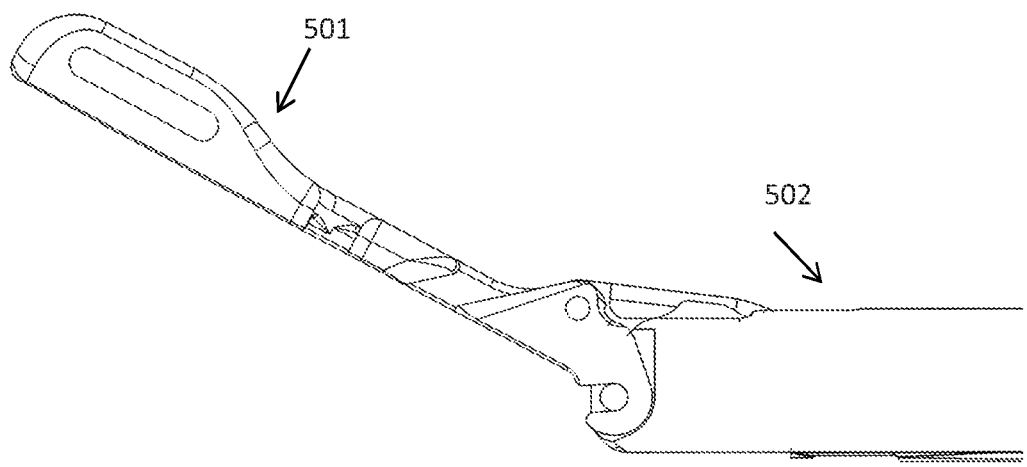
FIG. 5A is a side perspective view of the suture passer variation shown in FIG. 4 with the second jaw member retracted proximally.
Figure 5B:
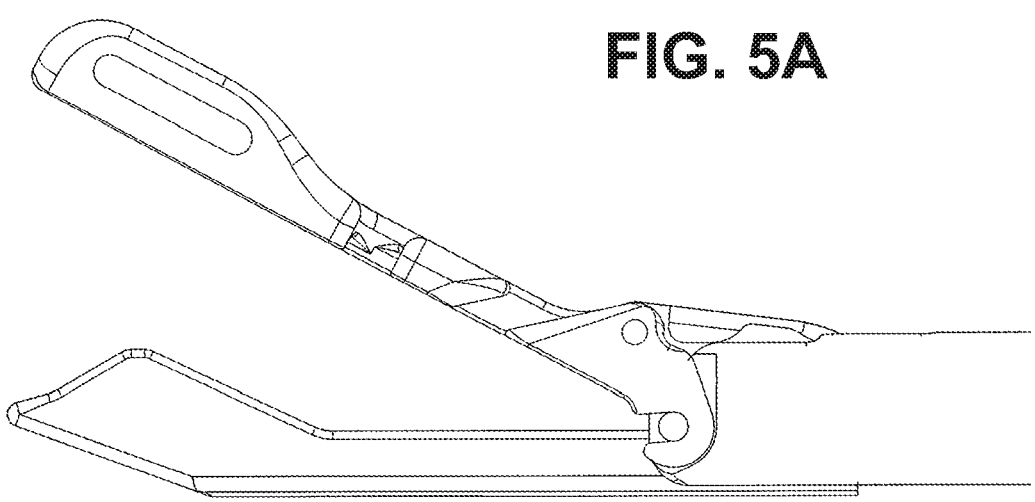
FIG. 5B shows the suture passer of FIG. 5A with the second jaw extended distally.
Figure 5C:
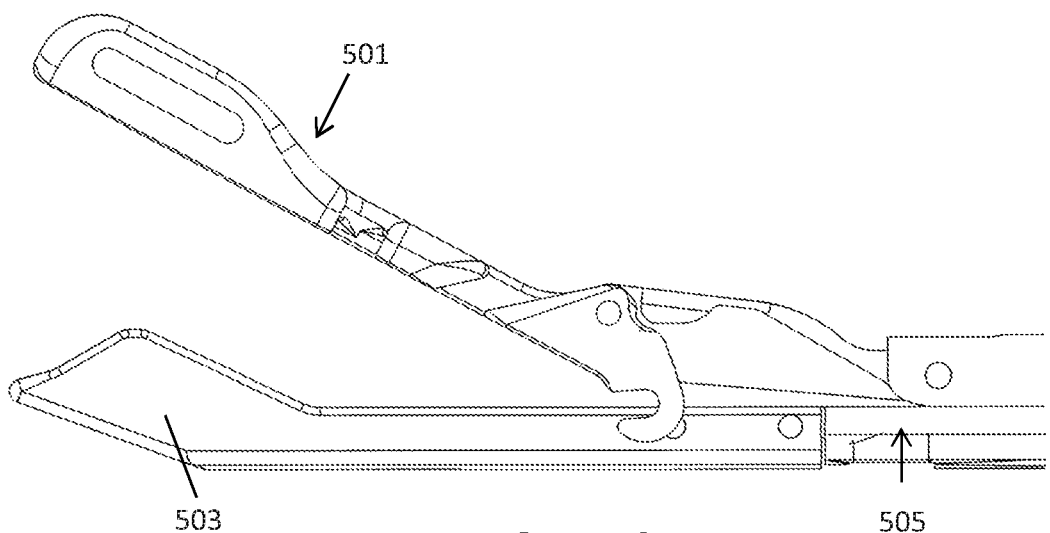
FIG. 5C shows FIG. 5B with the outer region of the elongate body removed.
Figure 6A:
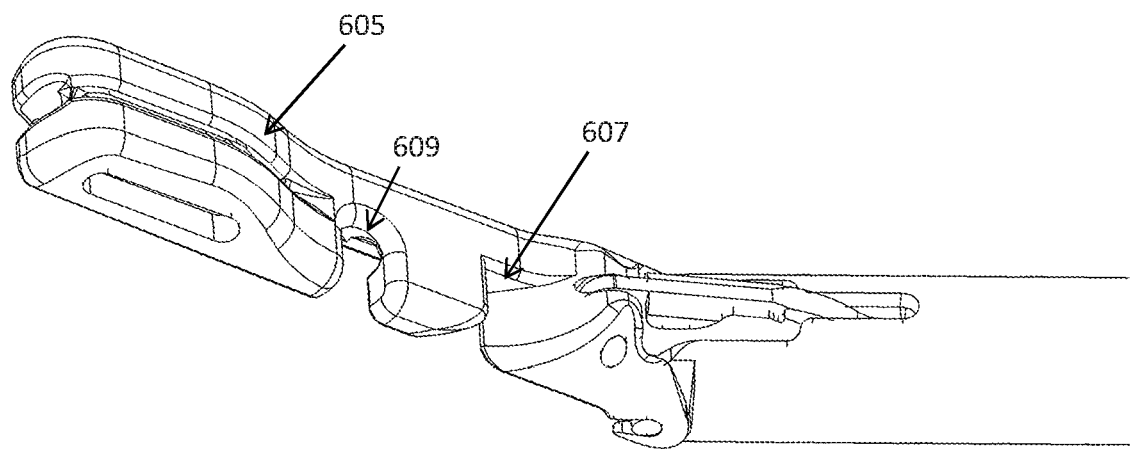
FIG. 6A shows a top perspective view of the suture passer shown in FIG. 5A.

FIGS. 5A-5C and 6A-6C illustrate different views of the first and second jaw members in one variation. For example, in FIG. 5A the first jaw member is shown with the second jaw member retracted proximally. FIG. 6A shows a top perspective view of the same first jaw member shown in FIG. 5A. In FIG. 6A, the first jaw member includes a channel 605 extending along the longitudinal length of the first jaw member; this channel may form part of the suture engagement region. The channel may hold the suture so that it extends along the midline of the first jaw member on the underside of the first jaw member. The notches 607, 609 in the first jaw member near the proximal end extend toward the midline of the first jaw member and allow the suture to pass from the top of the first jaw member to the bottom and back out, as discussed above. Thus, the suture may be held close to the elongate body of the device even when the first jaw is open to various angles.

Figure 6B:
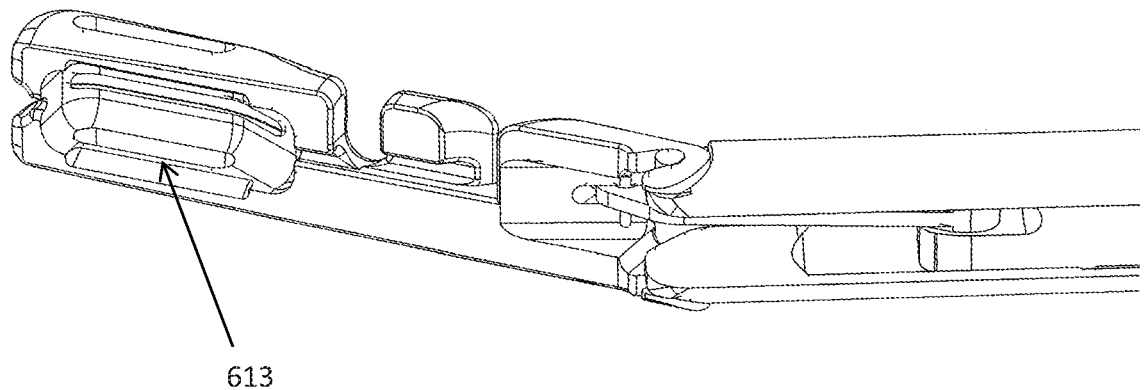
FIG. 6B shows a bottom perspective view of the suture passer of FIG. 5B.
Figure 6C:
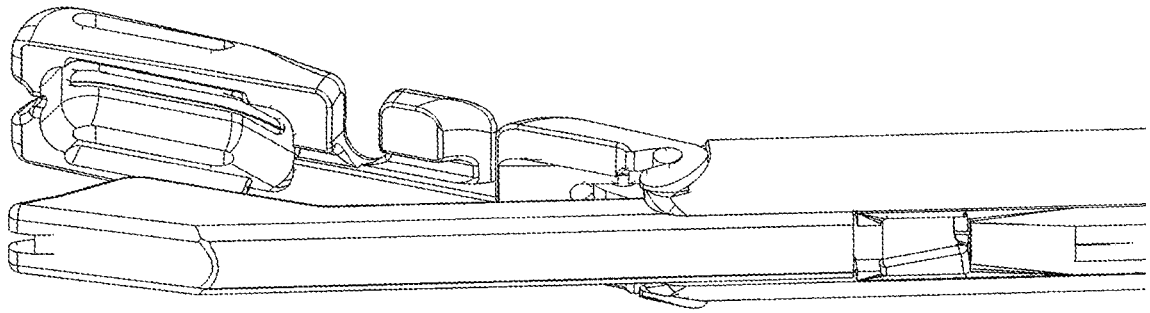
FIG. 6C shows a bottom perspective view of the suture passer of FIG. 5C.

FIG. 6B illustrates the underside or bottom of the first jaw member shown in FIG. 6A. The suture management region is the entire opening formed at the distal end. This cavity 613 is surrounded by the inside of the first jaw member, and (as mentioned above) may act as a limiter to limit the tip of the tissue penetrator from extending outside of the first jaw member. FIG. 6C shows the same view as in FIG. 6B, but with the second jaw member axially extended distally.

Returning now to FIG. 5B, a side view of the distal end of one variation of a suture passer is shown with the second jaw member extended distally. FIG. 5C shows the same view as in FIG. 5B but with the outer cannula covering for the elongate member removed, showing the connection between the second jaw member and the pushing/pulling element (rod 505). The pushing/pulling element may be a wire, shaft, tendon, or the like, allowing the second jaw member 503 to be controllably slid distally and proximally. Not visible in FIGS. 5A-6C is the tissue penetrator, which is fully retracted into the second jaw member in this exemplary embodiment.

FIG. 7A shows one variation of a tissue penetrator 700 as described herein. In this example, the tissue penetrator includes a sharp, pointed distal tip 701 and just proximal to the distal tip is a suture engagement region configured as a hooked cut-out region 703. The proximal end of the tissue penetrator includes a coupling region for coupling the tissue penetrator with a pusher/puller mechanism, such as a shaft, rod, wire, tendon, or the like.

FIG. 8 shows the same perspective view of FIG. 4, but with the tissue penetrator 805 partially extended across the distal-facing opening formed between the first jaw member 801 and the second jaw member 803. A suture 808 is looped around the first jaw member 801. Both ends of the suture pass into the notched region and are held close to the elongate body, allowing the loop of suture to be held in tension within the suture engagement region.

Figure 9A:
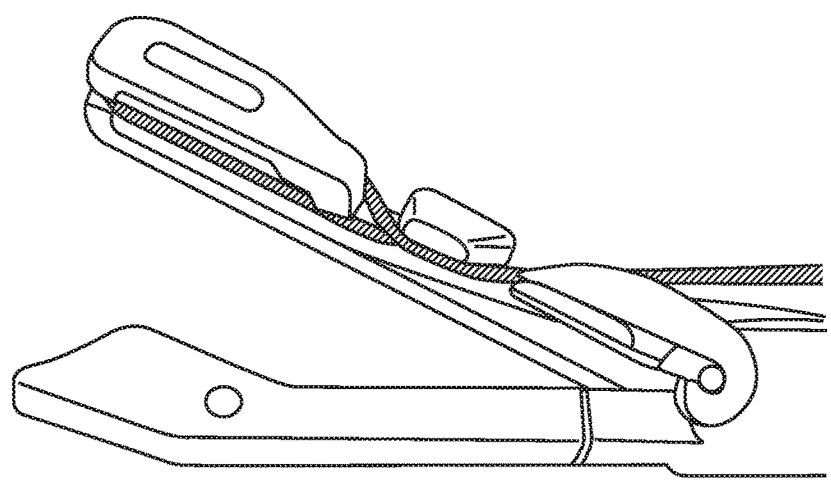
FIGS. 9A-9C illustrate actuation of a suture passer such as the one shown in FIG. 8 to pass a suture from the upper jaw to the lower jaw.
Figure 9B:
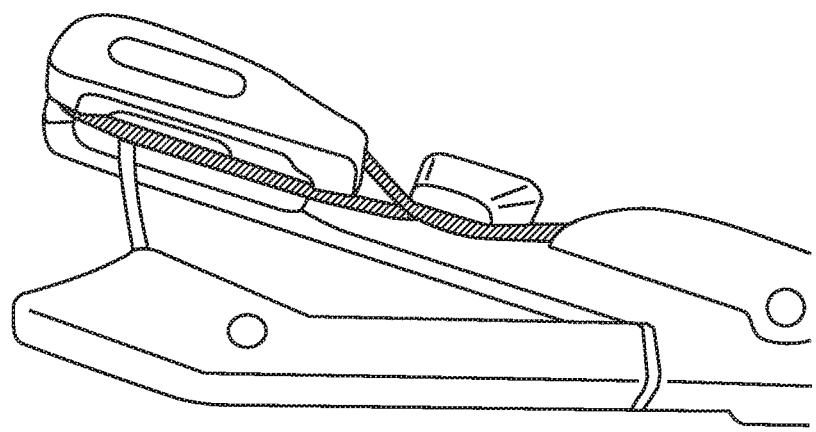
Figure 9C:
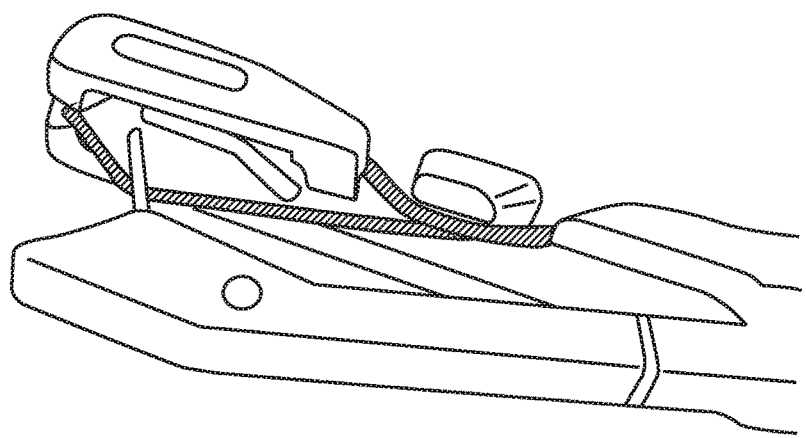

FIGS. 9A-9C illustrate the variation of the device described above passing a suture from the first jaw member to the second jaw member. In FIG. 9A, the distal end of the second jaw member for the dual deployment suture passer has been extended fully. The upper jaw is held at an angle relative to the elongate body region of the device proximal to the joint (e.g., hinge, bend region, etc.) of the first jaw member. A suture has been loaded into the suture engagement region, and extends along the length of the midline of the first jaw member. In FIG. 9B, the first jaw member has been moved slightly (decreasing the angle between the first jaw and the fully extended lower jaw member). This may be typical of situations in which tissue is held between the first and second jaw members. Clamping the tissue to be sutured in this manner allows the tissue to be secured within the jaws, preventing it from moving undesirably, and helping the tissue penetrator to penetrate through the tissue. Further, in FIG. 9B the tissue penetrator has been extended from the lower second jaw member across the distal-facing opening, towards the first jaw member and the suture retained therein. Once the tissue penetrator contacts the suture, it may be grabbed or otherwise engaged by the suture engagement member of the tissue penetrator. Thereafter, the suture can be pulled back down with the tissue penetrator as it retracts back into the second jaw member. In this variation, the loop of suture is pulled back through the tissue.

Figure 10A:
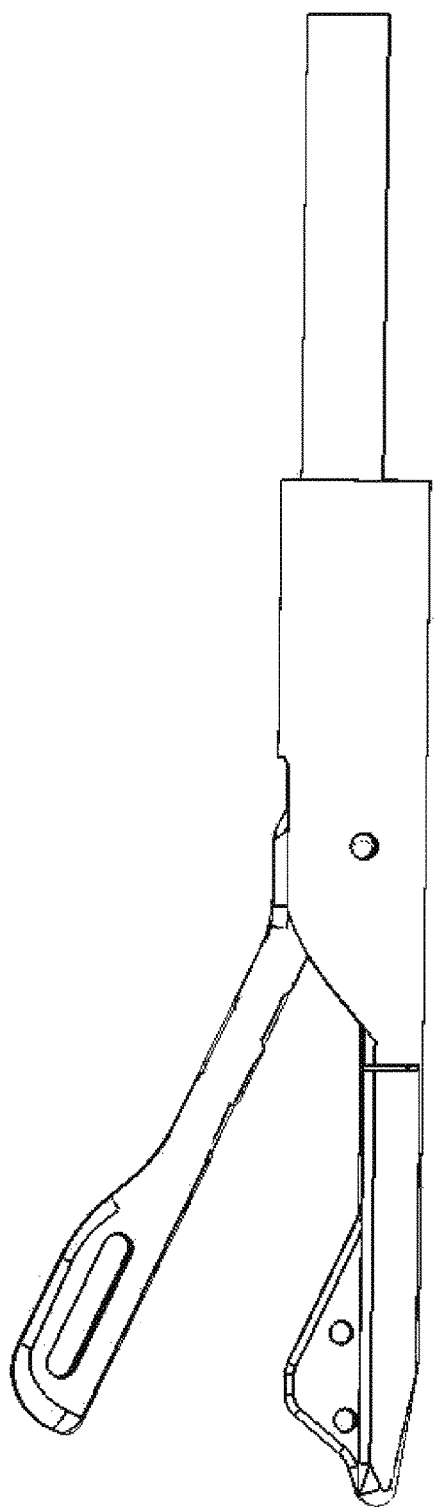
FIG. 10A shows a side view of one variation of the distal end region of a suture passer, showing a first and second jaw member extended in to form a distal facing opening.
Figure 10B:
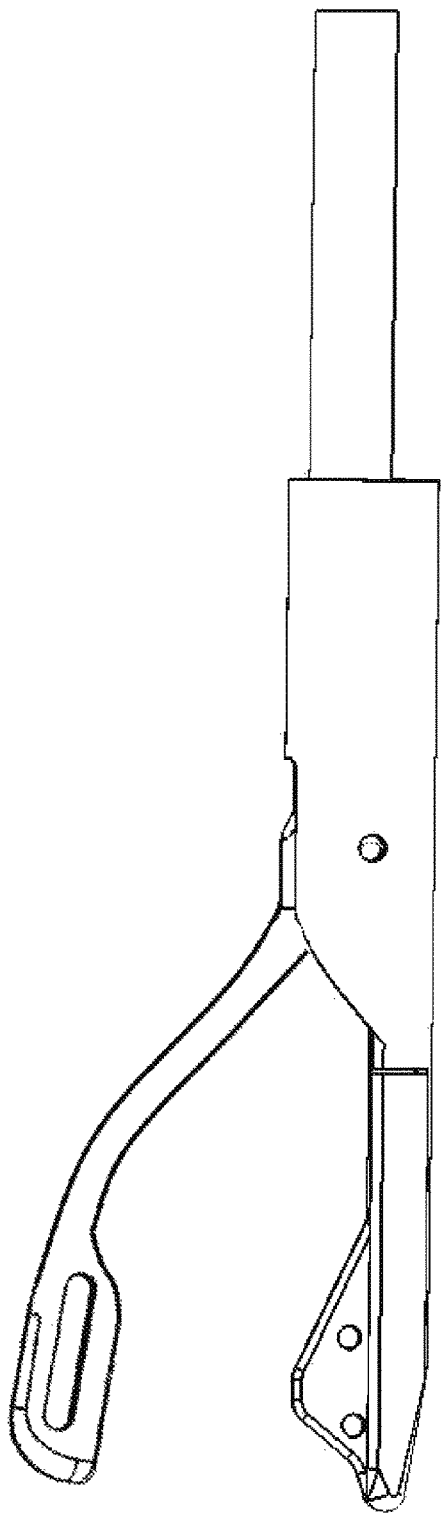
FIG. 10B shows another variation of the distal end region of a suture passer with the first and second jaw member extended in to form a distal facing opening.

Although the variation of the suture passer shown and discussed above includes relatively straight first and second jaw members, other configurations of jaw members are possible. For example, FIGS. 10A and 10B illustrate two variations of the upper jaw member. In particular, FIG. 10B shows a variation in which the straight jaw member of the first jaw member is instead a curved jaw member; the curve may allow a greater thickness of tissue to be placed between the jaws and may also be useful for navigating certain tissue regions, such as the labrum and ACL.

Figure 11:
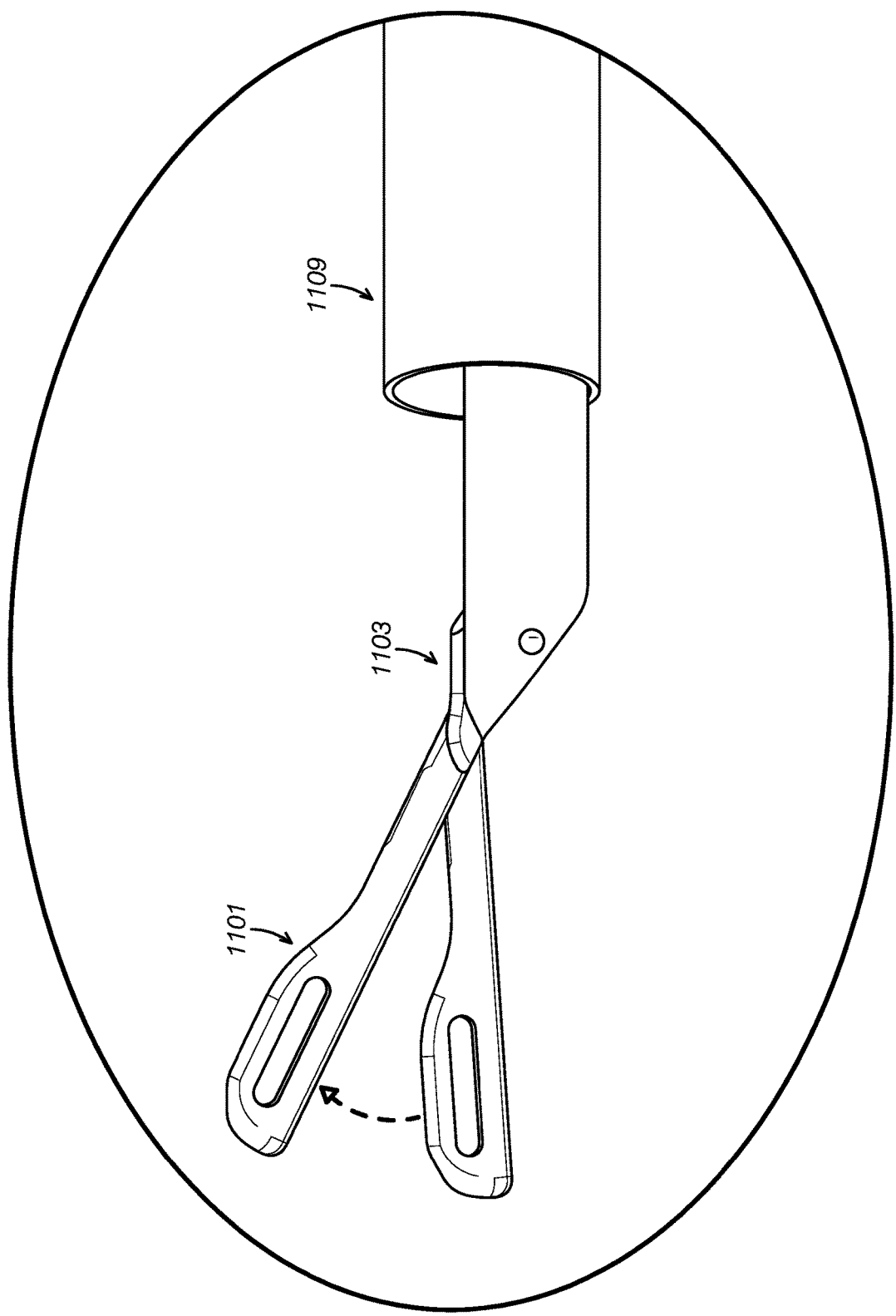
FIG. 11 illustrates one variation of a first jaw member having a hinge allowing angular motion relative to the long axis of the elongate member region of the suture passer.

In general, the first jaw member in many of the variations described herein may be dynamically angled with respect to the elongate body of the device. The first jaw member may be connected to and extend from the distal end of the elongate body, or may be connected to an intermediate region between the elongate body and the first jaw member. For example, in FIG. 11, a first jaw member is hinged to the elongate body, so that it can be controllably moved to change the angle between with the elongate body long axis. The first jaw member hinge 1103 thus allows the position of the first jaw member 1101 to be adjusted (e.g., more opened or closed) as the device is positioned within the body towards a desired tissue to be sutured. This adjustability may allow the suturing device to be inserted further into the space, hence farther from any insertion cannula 1109. This scissoring jaw mechanism, in combination with the absence of a second (lower) jaw member, which may be retracted proximally, enables the device to surround a target tissue without being trapped within the cannula 1109 opening (the jaws don't have to be opened as traditional jaws would be) as it is being positioned.

Figure 12A:
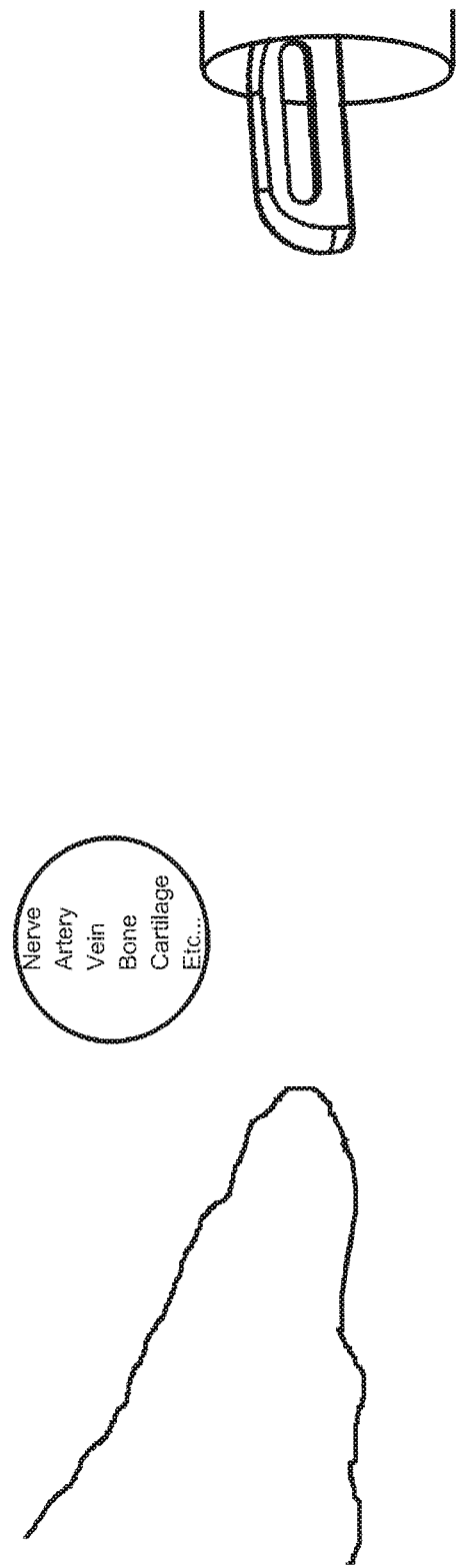
FIGS. 12A-12E illustrate operation of one variation of a dual deployment suture passer configured as a clamping/sliding suture passer.
Figure 12B:
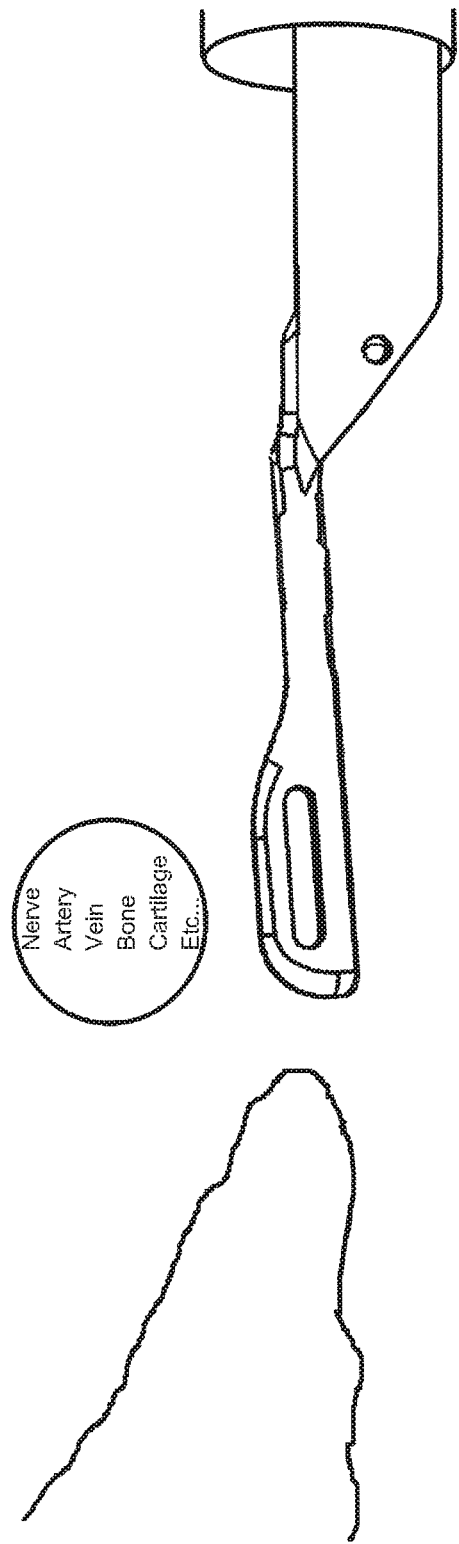
Figure 12C:
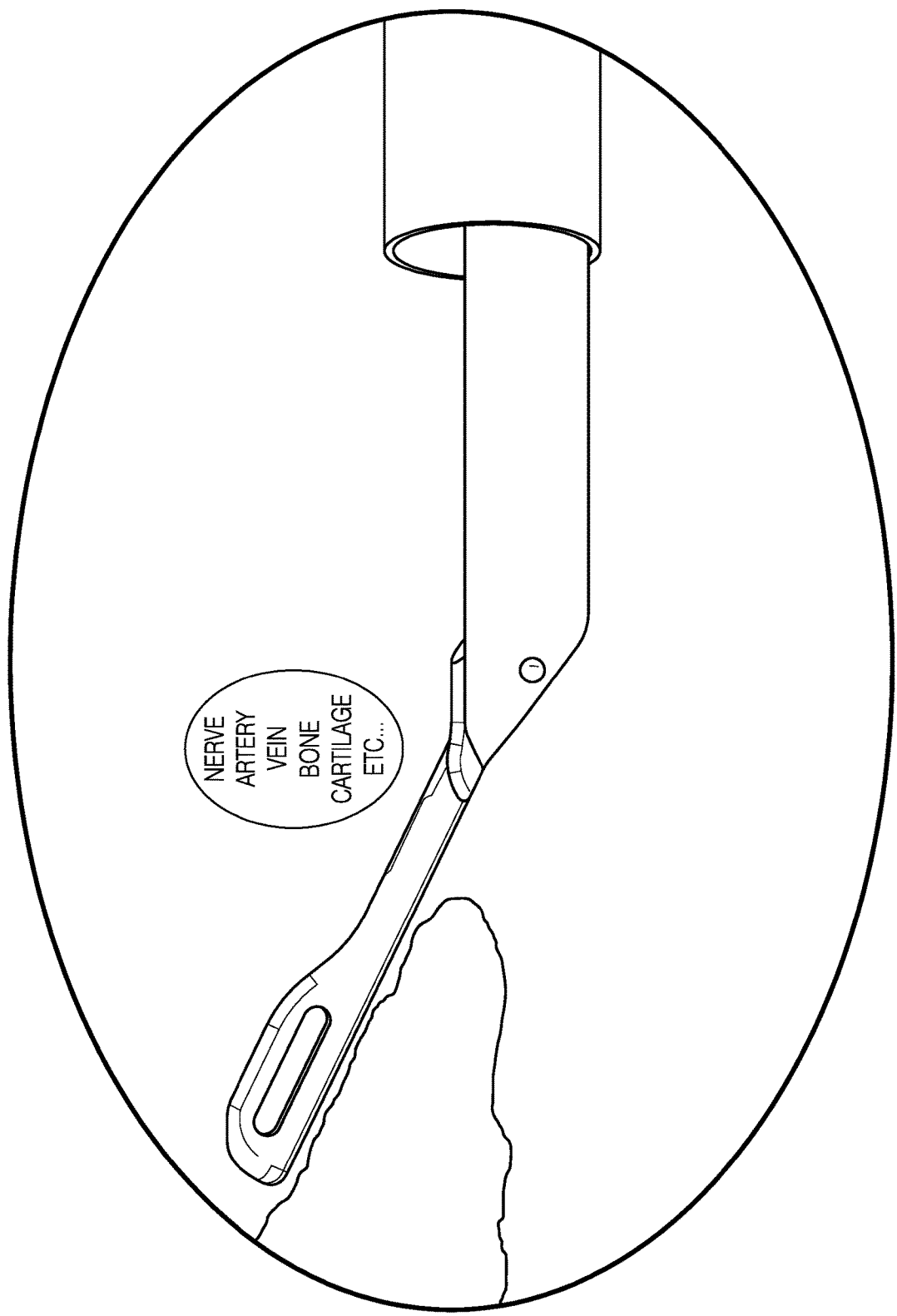
Figure 12D:
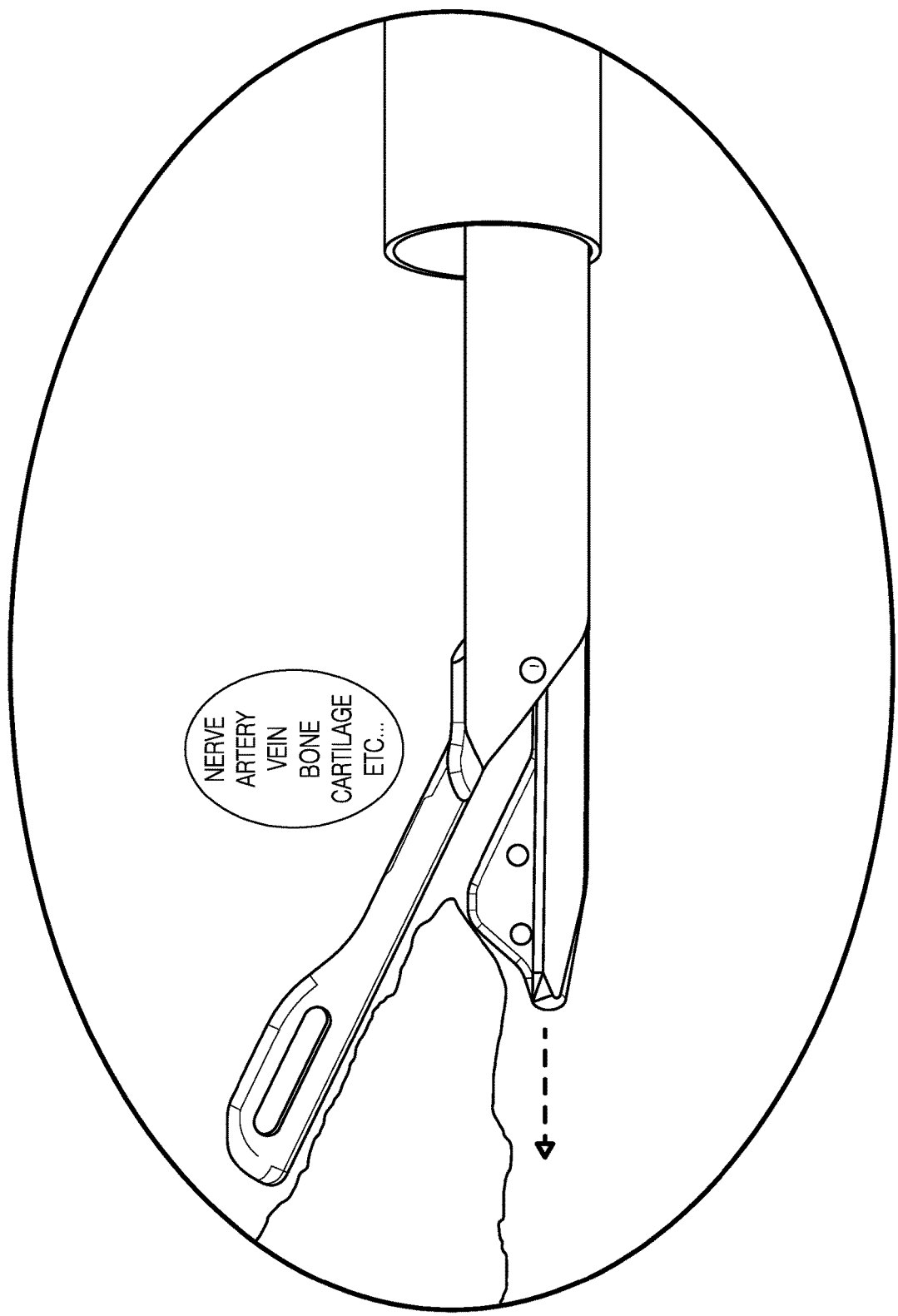
Figure 12E:
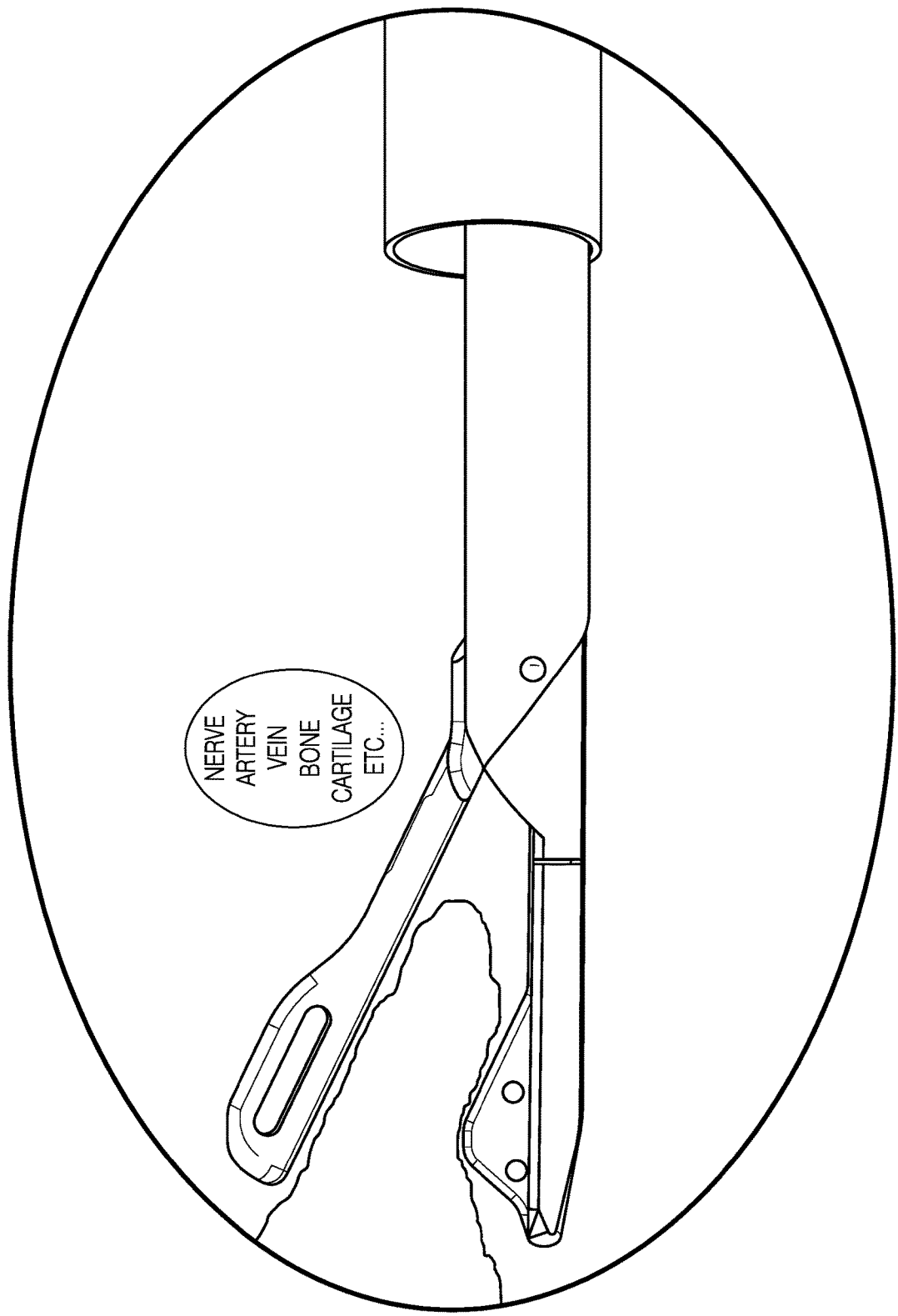

For example, FIGS. 12A-12E illustrate one variation of the operation of a dual deployment suturing device in which the first (upper) jaw member is hinged and the second (lower) jaw member slides axially relative to the elongate body region proximal to the first jaw member. This design allows the device to surround tissue in difficult to reach areas, while at the same time protecting nearby tissue from iatrogenic damage. In FIG. 12A a cannula has been placed within the body near the target tissue. Non-target tissue to be avoided is also nearby. For example the non-target tissue region may be a nerve, an artery, a vein, bone, cartilage, etc. In FIG. 12B, the suturing device is extended from the cannula with the distal end of the first jaw member leading. The first jaw member may be held in a horizontal position (at an angle of 0° relative to the long axis of the elongate body). In this example, the second jaw member is retracted proximally and is therefore kept out of the way of the distal end region of the device as it is positioned near the target tissue. In FIG. 12C the first jaw member is angled "up" (at an angle of about 30° with respect to the long axis of the elongate body) allowing the device to maneuver around the potentially sensitive non-target tissue so that it can be positioned adjacent to the target tissue. All of these maneuvers may be performed with the help of visualization, such as arthroscopic visualization. In FIG. 12D, once the first jaw member is adjacent to the tissue, the second jaw member may be distally extended by moving axially from the distal end of the elongate body, as shown. This motion of the second jaw member may also be referred to as a telescoping motion, as it is extending out of the proximal region toward the distal end by axially sliding. As the second jaw member extends distally it surrounds the tissue between the first and second jaw members, forming a distal-facing opening in which the target tissue resides, as shown in FIG. 12E. Thereafter, the tissue penetrator may be extended between the first and second jaw members, allowing the tissue penetrator to pass the suture from the first to the second jaw member. When the suture has been passed and the tissue penetrator retracted back into the second jaw member, the second jaw member may be retracted back towards the elongate member, proximally, and the entire device withdrawn from the tissue or away from the target tissue. The suture passing through the tissue may then be knotted or otherwise anchored.

Figure 13A:
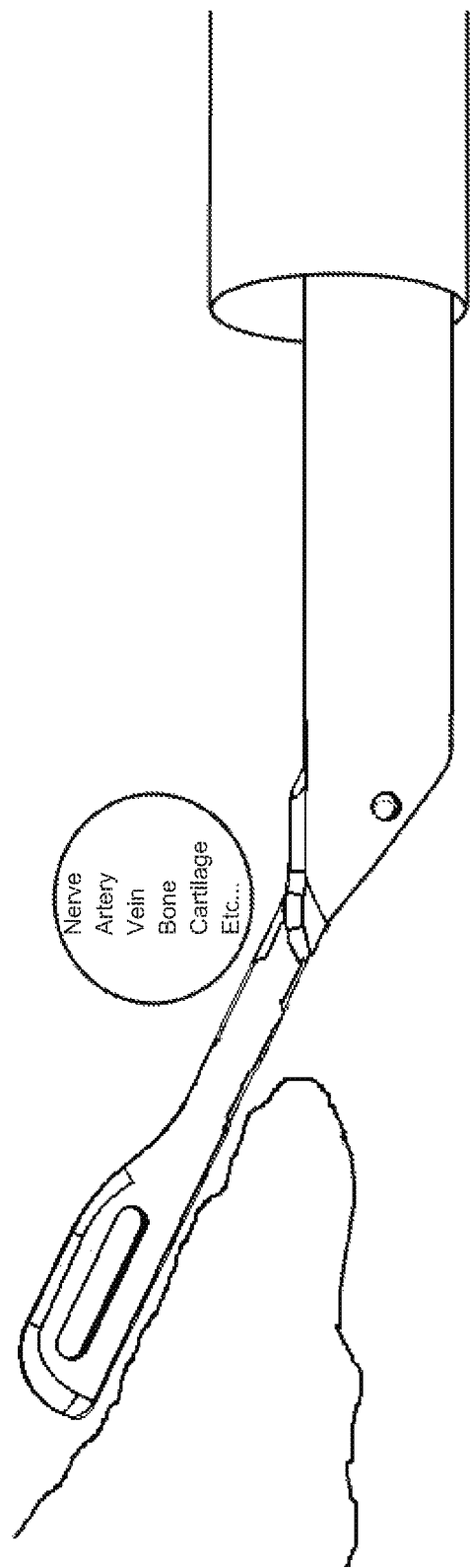
FIGS. 13A-13C illustrate operation of one variation of a dual deployment suture passer configured as a clamping/side-swinging suture passer.
Figure 13B:
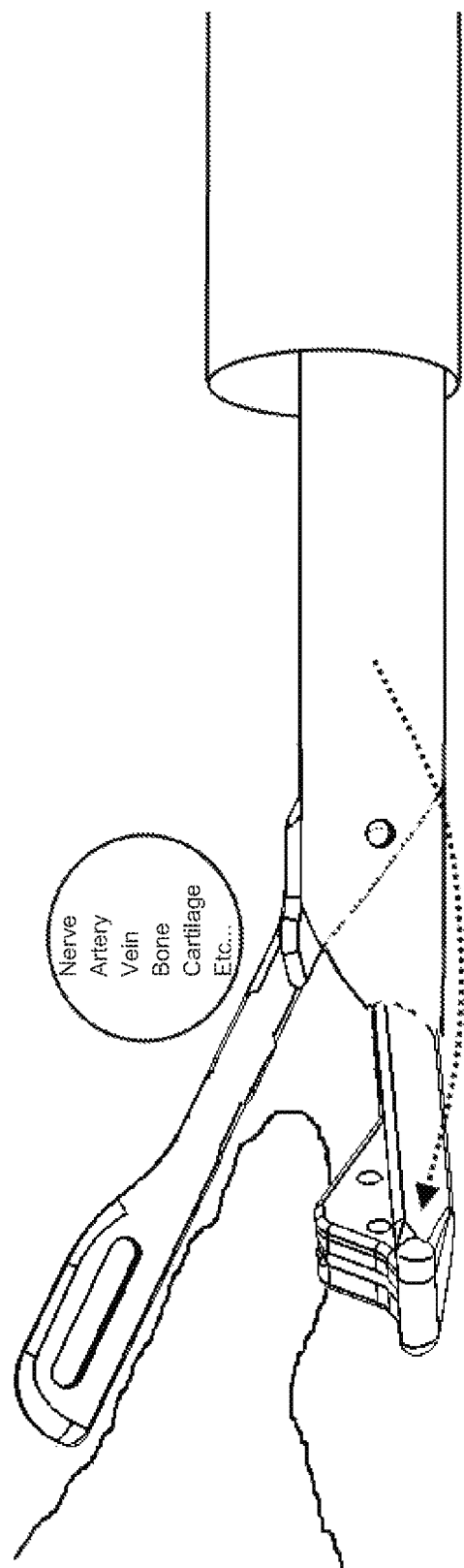
Figure 13C:
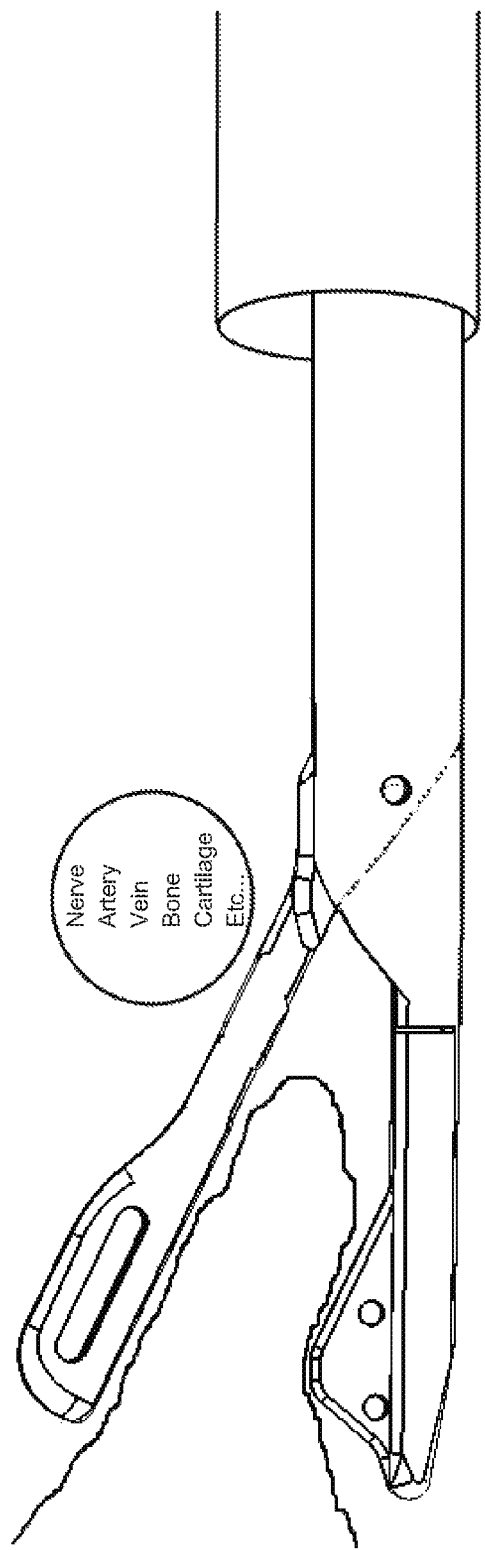

FIGS. 13A to 13C illustrate operation of another variation of a suture passer in which the second jaw member is a side swinging member. In this variation the second jaw member extends from the proximal portion (e.g., behind the first jaw member or the hinge of the first jaw member) to a distal position by a side swinging motion. Although this motion would not be permitted everywhere in the body, there may be some variations in which this side swinging motion may be desired.

Figure 14A:
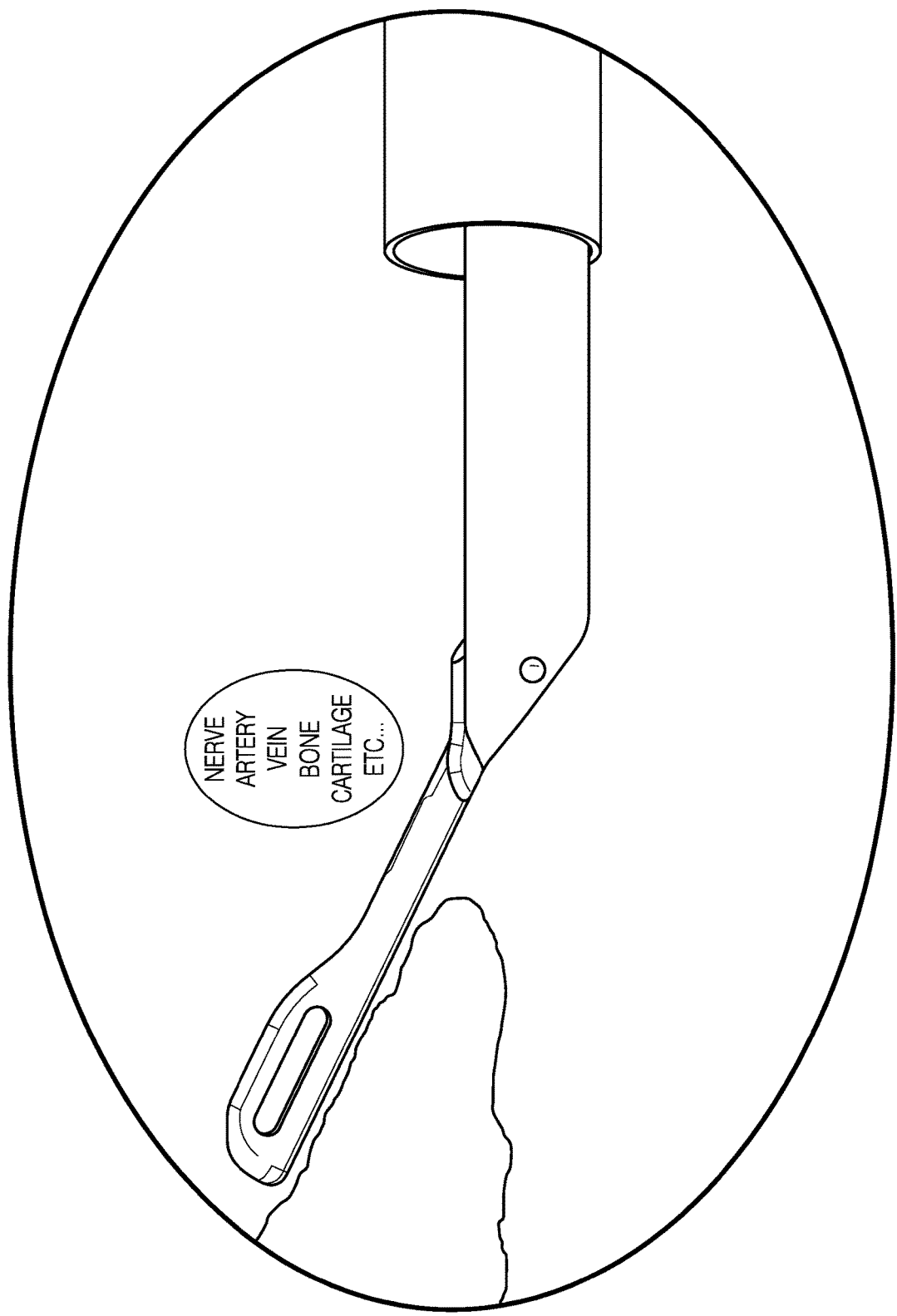
Figure 14C:
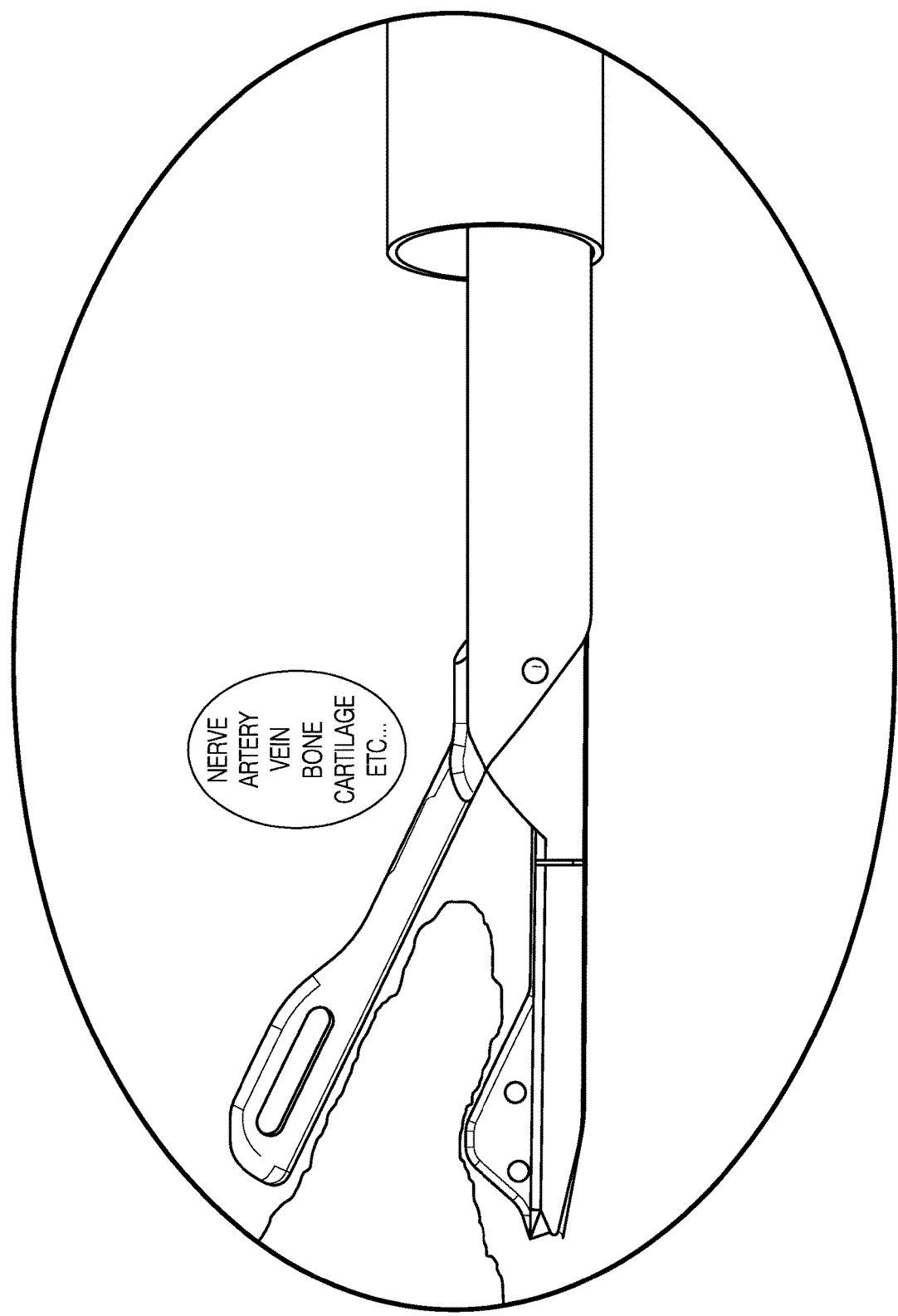

FIGS. 14A-14C illustrate operation of another variation of a suture passer having a first jaw member that swings from a proximally located position (e.g., proximal to the upper jaw) to a distal position able to form a distal-facing jaw opening with the second jaw member. In this variation the second jaw member swings down (away from the long axis of the device) and back up to be positioned distally and opposite the first jaw member as shown in FIG. 14B and 14C.

Figure 15A:
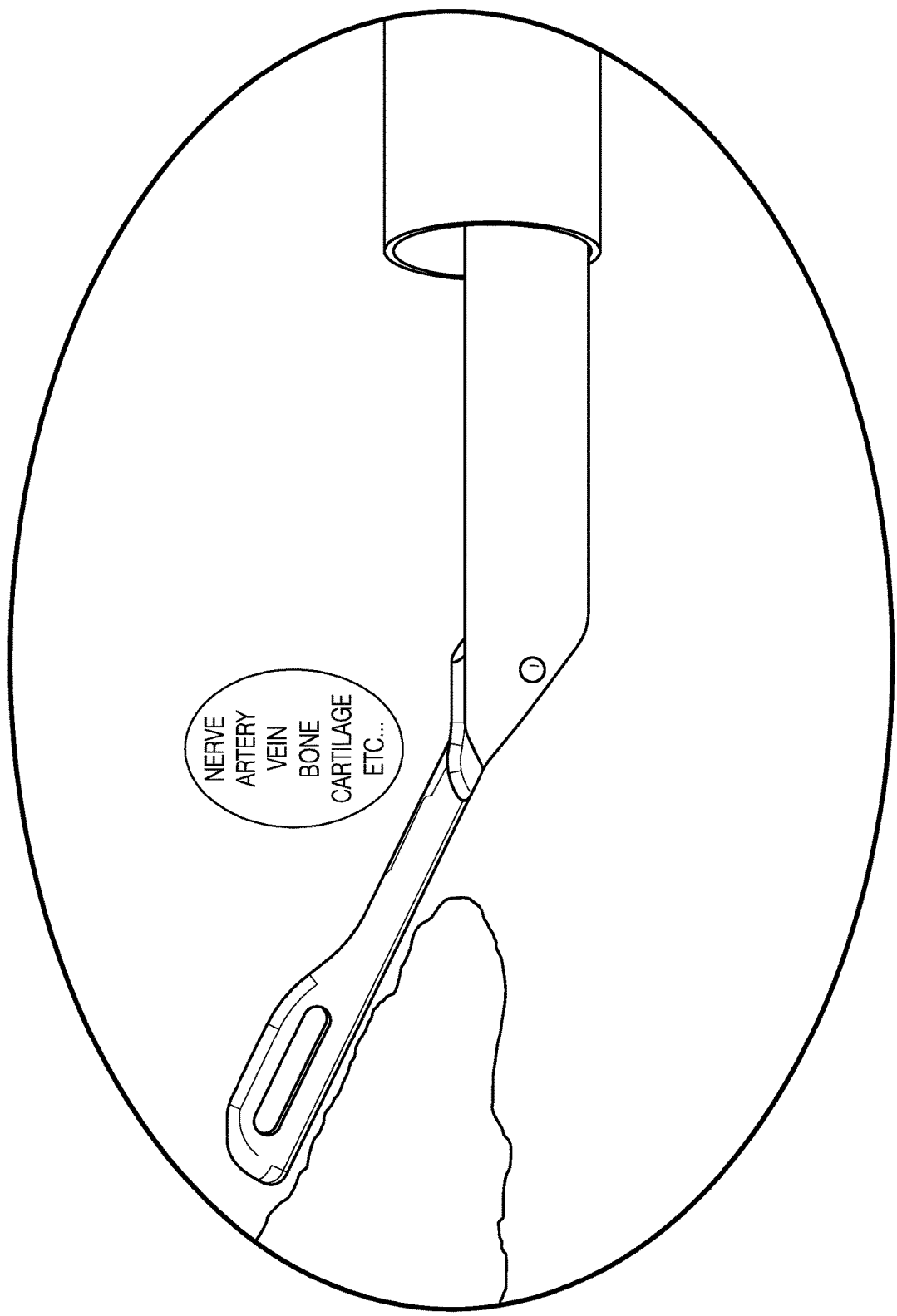
FIGS. 15A-15C illustrate operation of one variation of a dual deployment suture passer configured as a clamping/complex motion suture passer.
Figure 15B:
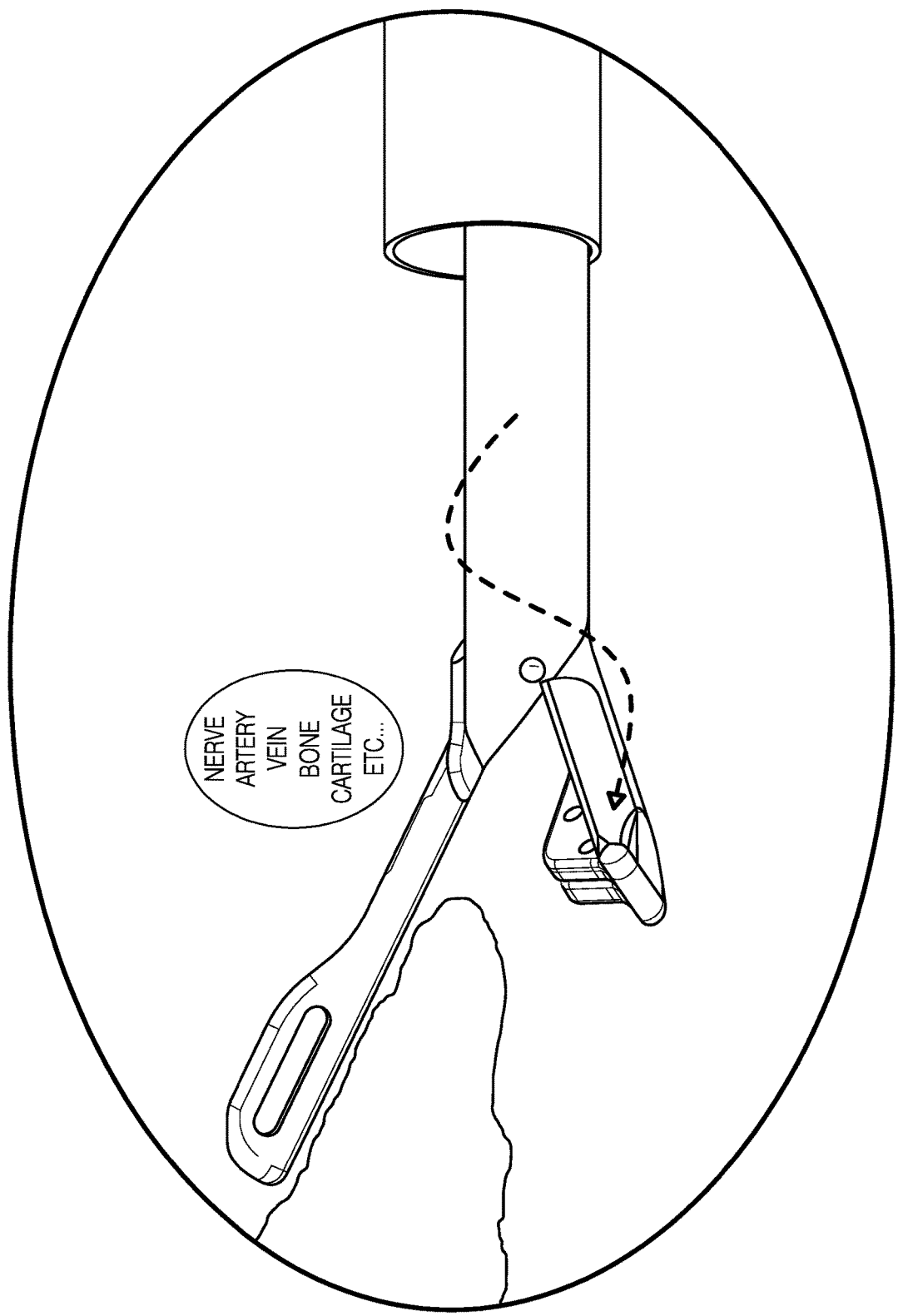
Figure 15C:
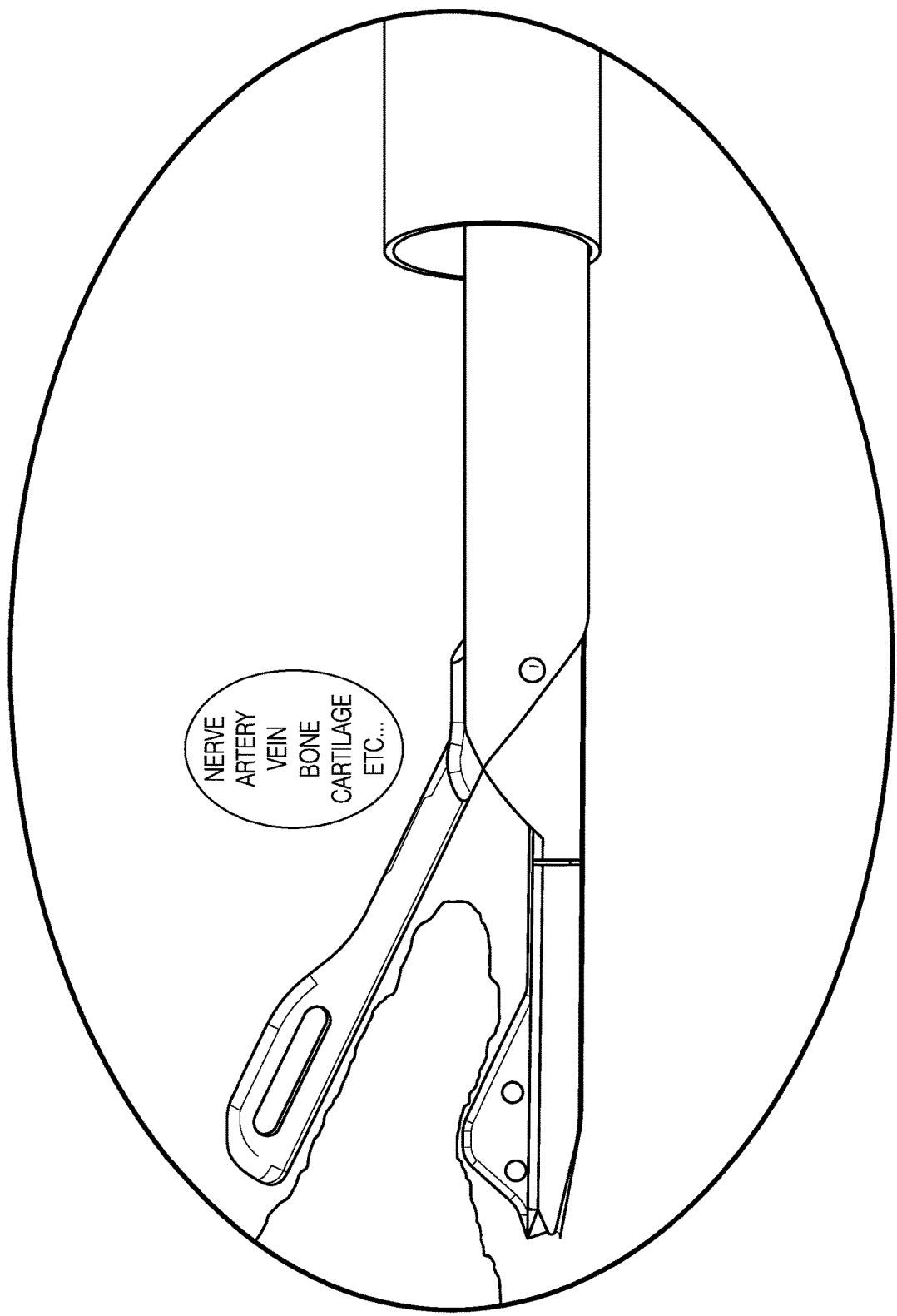

Other variations of motion of the second jaw member are possible, including compound motions that combine more than one of the axial motion, side-swinging motion and down-swinging motion. For example, FIGS. 15A-15C illustrate a second jaw member having a compound or composite motion. In any of these variations, the second jaw member typically goes from a retracted position in which it is held proximal to first jaw member and/or proximal to the distal end of the elongate body, to an extended distal direction.

Figure 17A:
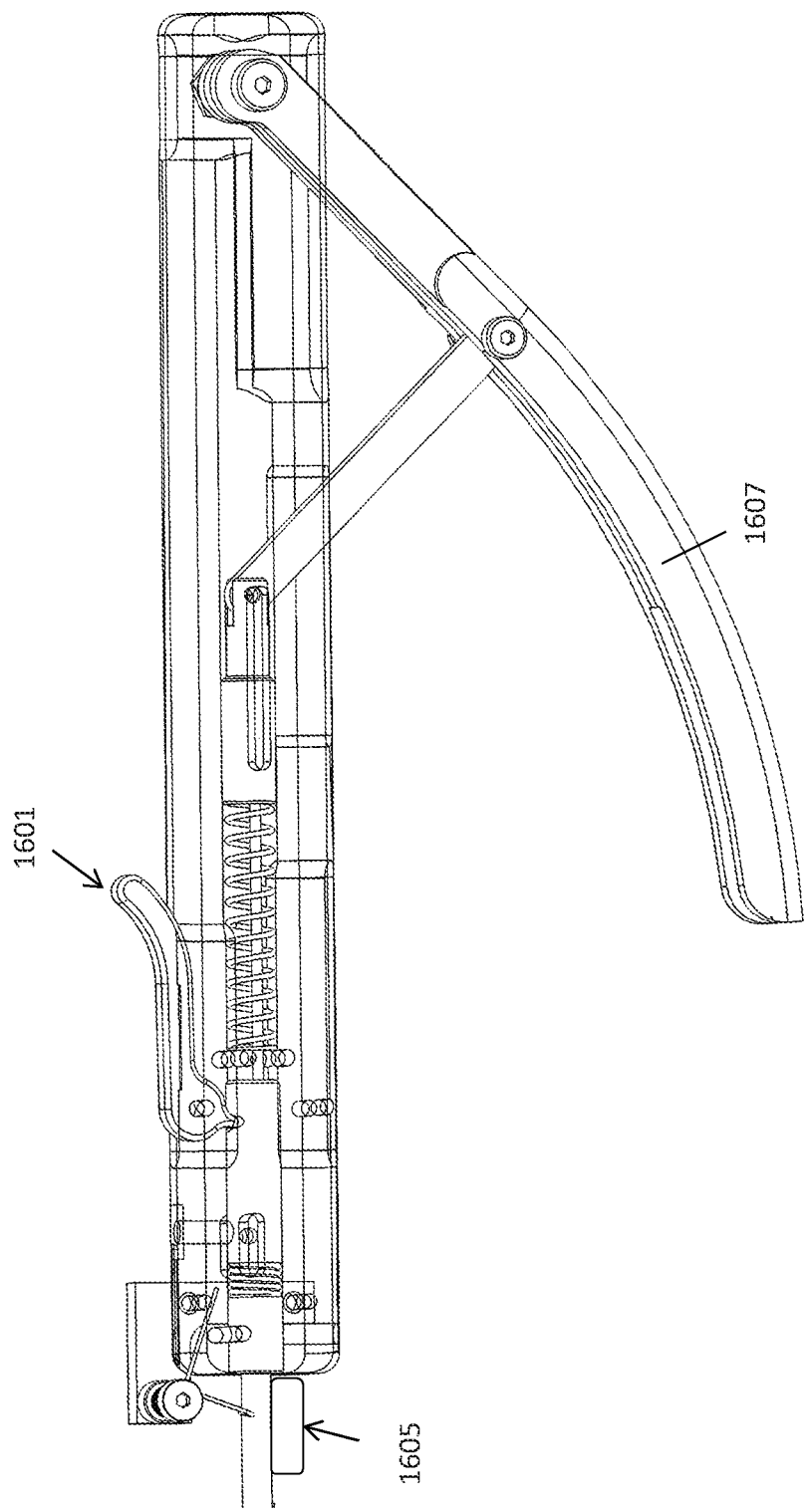
FIG. 17A shows one variation of a proximal handle with controls for controlling action of a dual deployment suture passer.

The position of the first jaw member and the second jaw member may be separately and/or independently controlled. For example, any of the variations described herein may include a proximal handle having controls for controlling the activation of the first jaw member, the second jaw member, and the tissue penetrator. For example, FIG. 17A is an enlarged view of the handle region of the suture device discussed above in FIGS. 1-3. In this example, the handle includes a control to control the motion of the first jaw member (which may also be referred to herein as a clamp trigger), a second jaw member control 1605 (or lower jaw handle), and a tissue penetrator control 1607 (or needle trigger). Additional controls may include a lower jaw screw lock to lock the position of the lower jaw member. The operation of this handle variation in controlling a dual deployment suture passer is described below with respect to FIGS. 19A-19F.

Figure 17B:
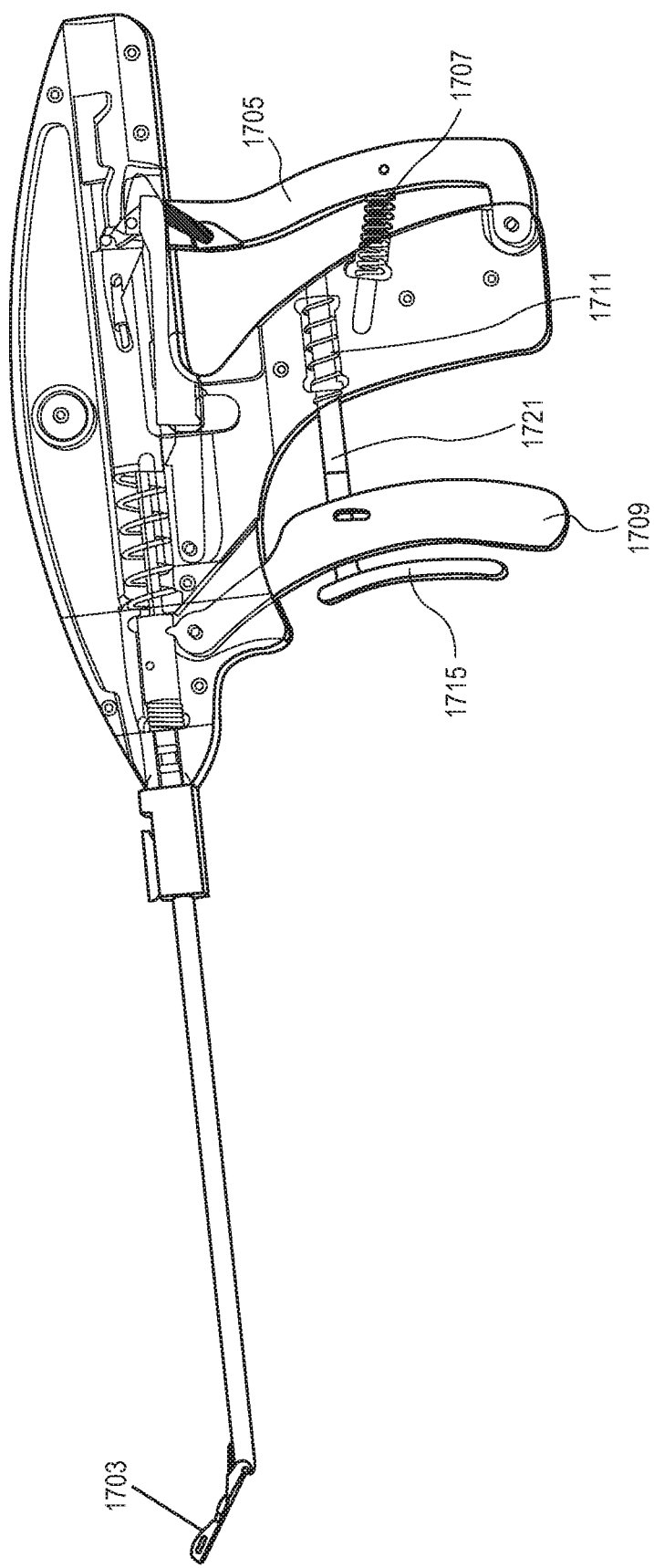
FIG. 17B shows another variation of a proximal handle with controls for controlling action of a dual deployment suture passer.

FIG. 17B illustrates another variation of a handle for a dual deployment suture passer. In this variation the handle controls are triggers/handles. The proximal trigger 1705 is a squeeze handle that controls the angle of the first jaw member relative to the elongate body. The control and handle are configured with a bias element (spring 1707) that tends to keep the first jaw member at an angle with respect to the elongate member; in this example, the angle is about 30° relative to a line extending distally from the long axis of the elongate body region of the device. A second grip control 1709 controls the extension of the second (lower) jaw member (not visible in FIG. 17B). In this variation a second biasing element (spring) 1711 tends to hold the control so that the second jaw element is retracted proximally and, in this example, into the elongate member. A third trigger control 1715 controls the extension of the tissue penetrator. This control is arranged to include a lock that prevents the control from engaging with the tissue penetrator until the second jaw member is completely extended. Further, the control also includes a travel limiter 1721 that limits how far the tissue penetrator may be extended from within the second jaw element based on how angled the first jaw member is, preventing the tissue penetrator from trying to extend beyond the first jaw element.

In any of the devices described herein, the controls may be handles or triggers (as illustrated in FIGS. 17A and 17B) or other controls, such as dials, buttons, sliders, switches, or the like.

Figure 16A:
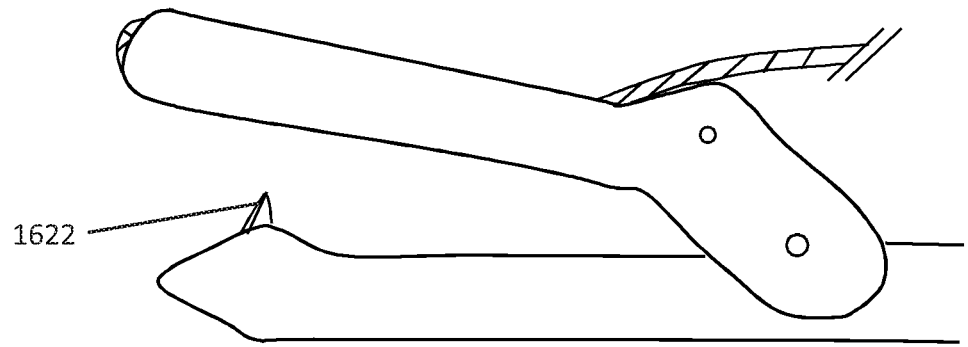
FIGS. 16A-16C illustrate another variation of a dual deployment suture passer configured so that the distal end of the tissue penetrator extends distally from the first jaw.
Figure 16B:
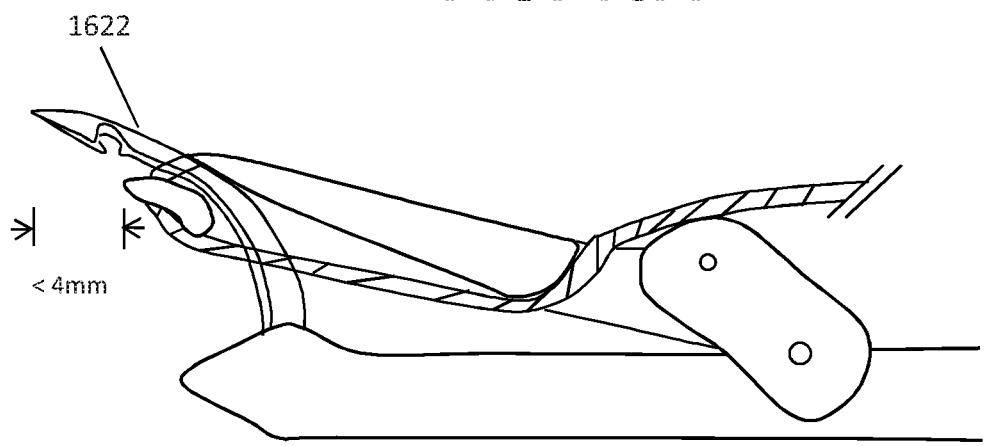
Figure 16C:
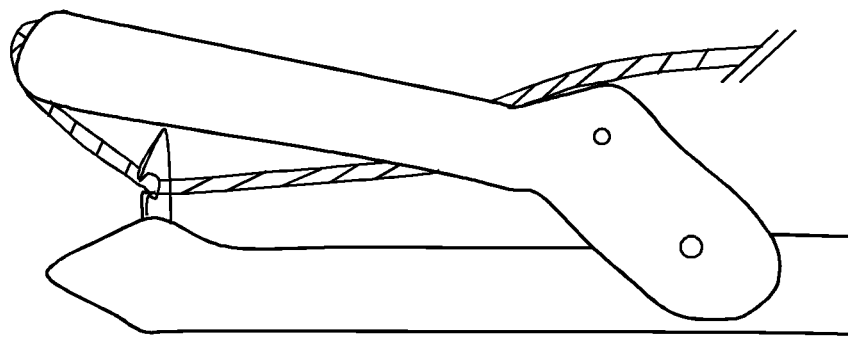

As mentioned above, although many of the suture passer devices (including the dual deployment suture passers described above) limit the travel of the tissue penetrator to prevent it from extending beyond the opposite jaw member from where it is housed when not extended, in some variations it may be beneficial to allow the tissue penetrator to extend distally out of the opposite jaw member, as illustrated in FIGS. 16A-16C. In this example the tissue penetrator is deflected within the opposite jaw member and allowed to extend distally out of the opposite jaw member some amount (e.g., less than 5 mm, about 5 mm, less than 4 mm, about 4 mm as shown in FIG. 16B, less than 3 mm, about 3 mm, etc.). For example, as shown in FIG. 16A, the tissue penetrator may be housed in the second jaw member and may be deployed across the distal-facing opening formed when the first and second jaw members are extended fully distally. The tissue penetrator is shown partially extended from the second jaw member in FIG. 16A, however it should be understood that the tissue penetrator (including the tip of the tissue penetrator) may be fully retraced or retractable into the second jaw member. Also, for convenience in FIGS. 16A-16C, the jaw members are shown close together, e.g., with only a little space between the first and second jaw members; the jaws may be more opened, for example, by moving the first (upper) jaw member at an angle with respect to the more proximal region of the device.

In FIG. 16B the tissue penetrator 1622 extends from within the second jaw and across the distal-facing opening to pass into an opening on the opposite (first or upper) jaw member. The tip of the needle is pointed in this example, and a side region of the needle proximal to the pointed distal tip is recessed to form a suture engagement region that is hook-shaped. Extending the needle into and partially out of the first jaw member as shown in FIG. 16B allows the suture engagement region on the tissue penetrator to engage the suture held by the first jaw member, as shown. The tissue penetrator in this example extends out of the distal end of the first jaw member distally (not laterally) and is limited to extending just a finite amount (e.g., less than 4 mm) from the distal tip of the first jaw member. In FIG. 16C, the tissue penetrator is retracted back to the second jaw member, pulling the suture with it in the suture engagement region.

The variation of the suture passer illustrated in FIGS. 16A-16C in which the tip of the tissue penetrator extends distally, has various features or advantages including simplifying the coordination between the various parts. For example, less coordination is required to limit the needle motion (e.g., stopping it before it crashes into the first or upper jaw). This may allow greater tolerances, and the parts may require less precision. Also, extending the tissue penetrator distally may allow for "over travel" of the tissue penetrator and provide for more reliable engagement (hooking) of the suture by the suture engagement region. The distal end of the first jaw member may include sufficient space for the tissue penetrator to over-travel the suture so that the hook (suture engagement feature) on the tissue penetrator can grab the suture on its way back to the lower (second) jaw member. With this variation, the height of the first jaw member can be compressed sizably, and the over-travel necessary to pick up the suture is directed in a manner that doesn't require additional height. Further, the additional over-travel opportunity offered by this configuration may allow use of a symmetric distal tip region for the suture penetrator, e.g., having a point in the middle of the tissue penetrator distal tip region. Asymmetric tissue penetrators may also be used (e.g., having a point on one side of the tissue penetrator). Other examples of suture passers (including dual deployment suture passers) having tissue penetrators configured to extend beyond the distal end of a jaw member are described and illustrated below, including in FIGS. 32A to 55DD.

Figure 18A:
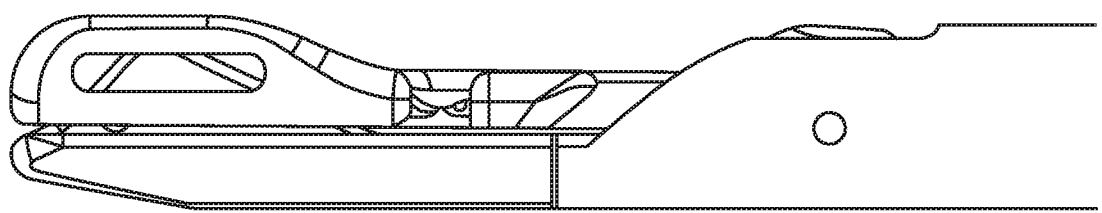
FIGS. 18A-18C show another variation of a suture passer as described.
Figure 18B:
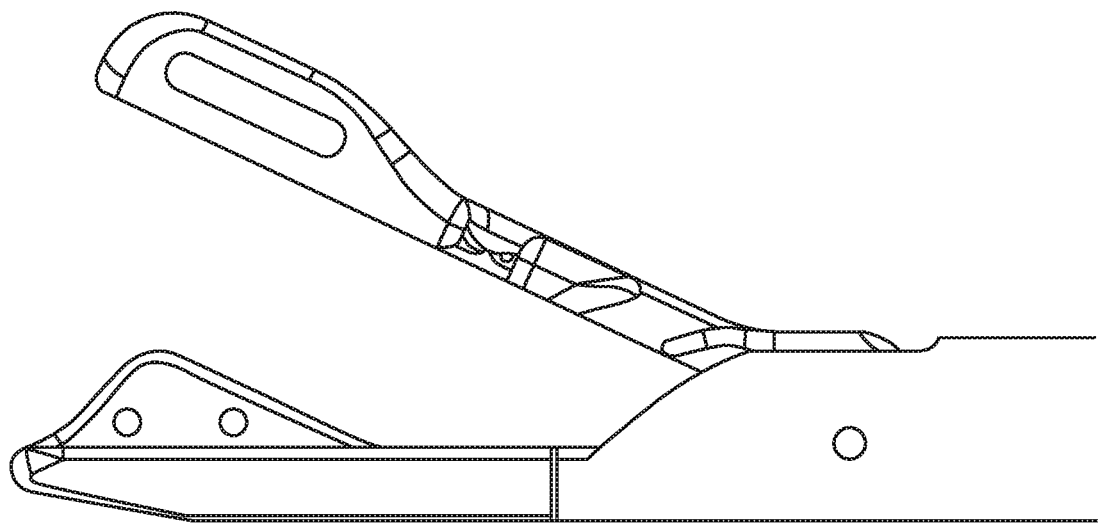
Figure 18C:
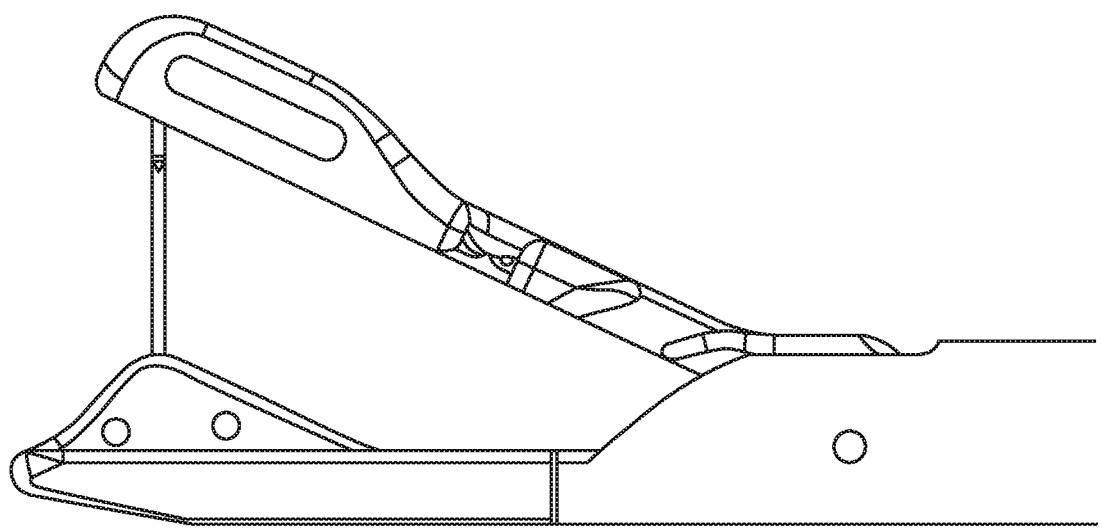

FIGS. 18A-18C illustrate another variation of a suture passer. In FIG. 18A, the second jaw member is not retracted proximally, and the first and second jaw members are clamped together. The first jaw member may be opened as shown in FIG. 18B, and the tissue penetrator may be extended across the distal-facing opening, as shown in FIG. 18C.

Methods of Use

In general, the devices described herein may be used to suture any appropriate tissue. These devices are particularly well suited for passing a suture in a minimally invasive procedure to reach difficult to access regions. Examples of the use of these devices are provided below, and illustrated in FIGS. 19A to 31F.

Figure 19C:
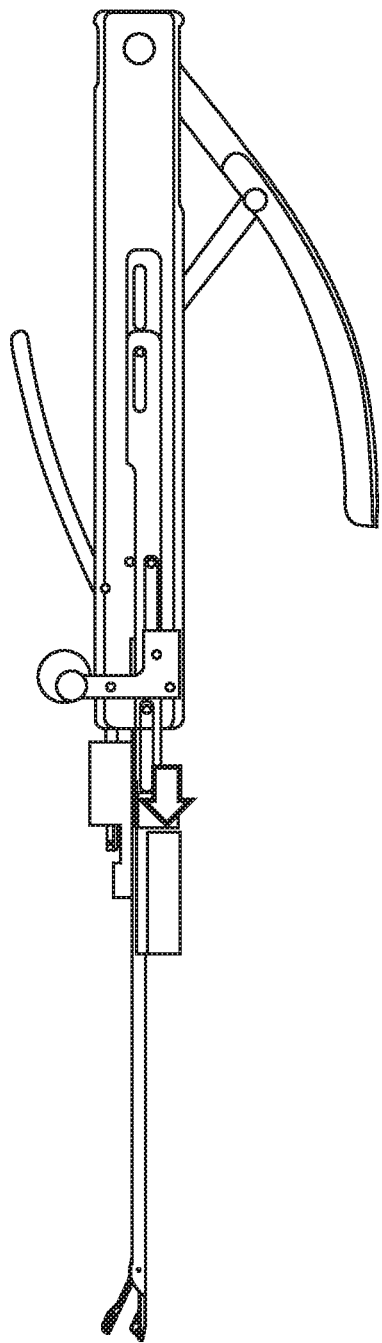

The general operation of one variation of a dual deployment suture passer is illustrated in FIGS. 19A-19F. The clamping/sliding suture passer illustrated in FIG. 19A includes a handle such as the one shown in FIG. 17A, above. Before use, a suture may be loaded on the first jaw member of the device. For example, a loop of suture may be loaded onto the first jaw member. The free ends of the suture may be coupled to a suture control element such as a tensioning screw, as shown in FIG. 19A. For example, the two free ends may be cinched onto a tensioner screw. The suture passer may be loaded outside of the body by the user, or it may be pre-loaded. Once loaded, the suture passer may be inserted into the body near the target tissue. For example, the device may be inserted into the body through a cannula. As shown in FIG. 19A, the second (lower) jaw member may be fully retracted proximally, and the upper jaw may be clamped down fully so that it is in-line with (straight) relative to the elongate member; the first jaw member may be locked in this position for insertion, or it may be moved or dynamically adjusted as it is inserted.

Thereafter, the device may be positioned relative to the target tissue. For example, the first jaw member may be positioned adjacent to the target tissue. As shown in FIG. 19B, the device may then be positioned and the clamp trigger adjusted or released.

Once the tissue is adjacent to the first jaw member, the second jaw member may be extended to surround a target tissue, as shown in FIG. 19C. In this example, the control for the second jaw member (the lower jaw lock) may be actuated to slide the lower jaw member distally, forming the distal-facing opening, and surrounding (at least partially) the target tissue to be sutured. As shown in FIG. 19C, this may be achieved by sliding in and locking the lower jaw with the lower jaw handle by releasing the lower jaw screw lock and sliding the lower jaw into position. The lower (second) jaw may then be locked in a fully extended position.

Figure 19D:
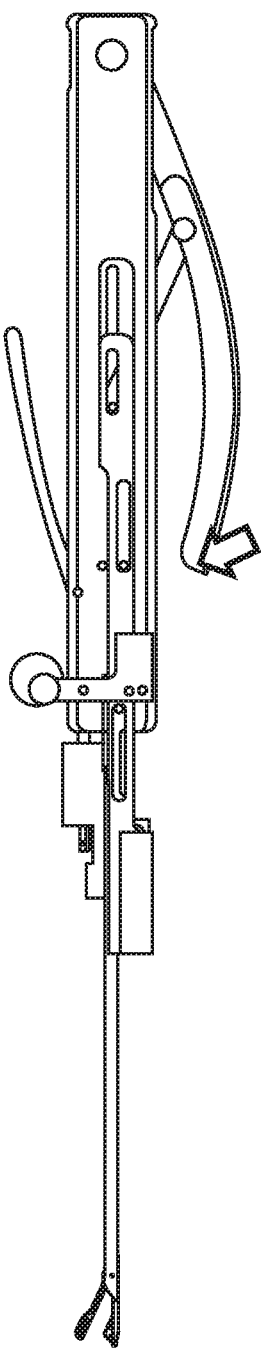

The upper (first) jaw member may be adjusted to clamp or hold the target tissue securely between the upper and lower (first and second) jaw members, as illustrated in FIG. 19D. Thereafter, the tissue penetrator may be actuated (e.g., by squeezing the needle trigger) to extend from within the lower jaw member, through the tissue between the first and second lower jaw members, and across to the upper jaw. To engage a suture held within the suture engagement region in the upper jaw. The tissue penetrator may then pick up the suture from the upper jaw and pull it back down through the tissue, as shown in FIGS. 19D and 19E.

Once the suture has been hooked, the tissue penetrator may be retraced back into the second jaw member (in this example), as shown in FIG. 19F, and the lower jaw member may be retraced proximally, in the reverse to the process described above, so that the suture passer, which having passed the suture successfully, may be withdrawn from the patient.

Figures 20A, 20B:
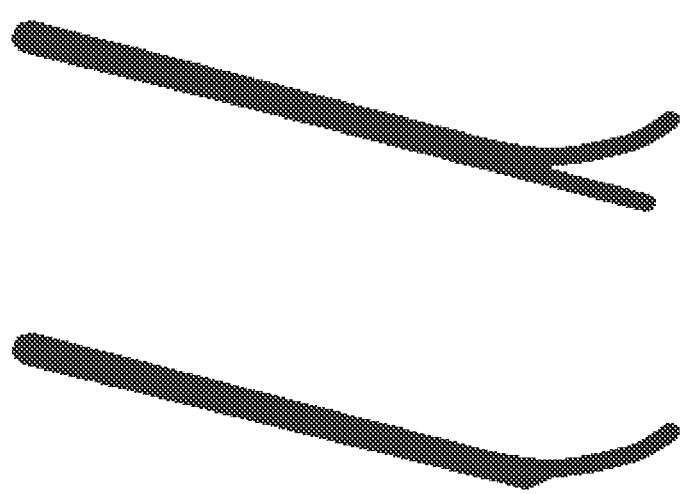
FIGS. 20A and 20B show a generic form of a dual deployment suture passer.
Figure 21B:
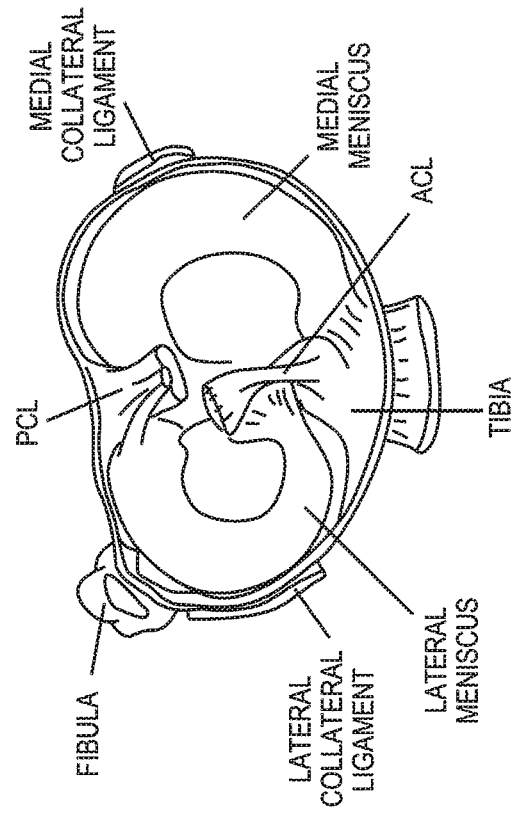
FIGS. 21A and 21B illustrate the anatomy of the meniscus.
Figure 21A:
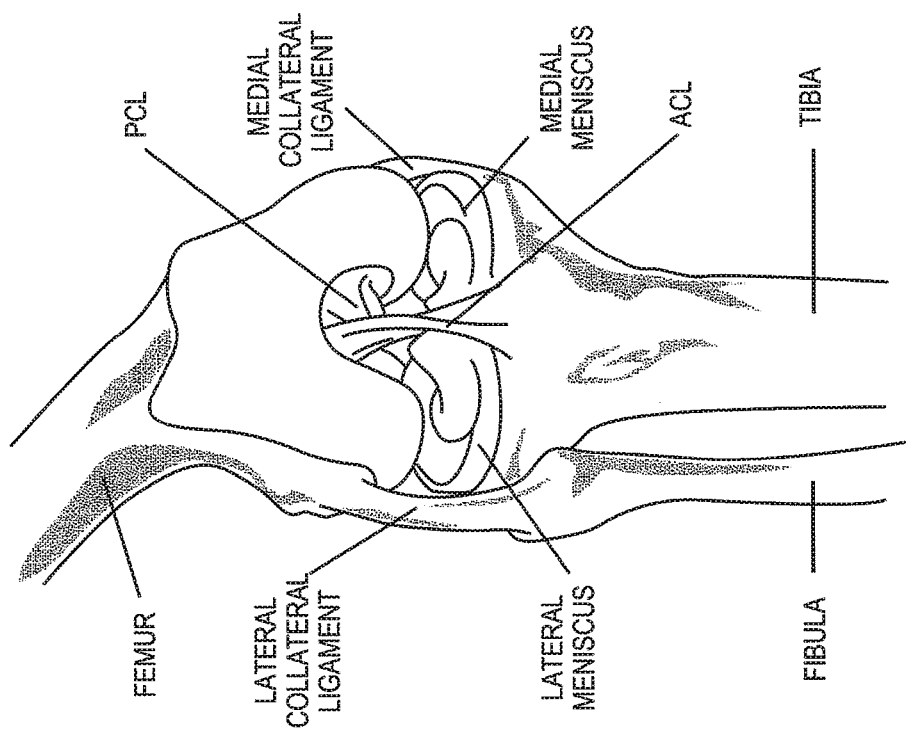
Figure 22:
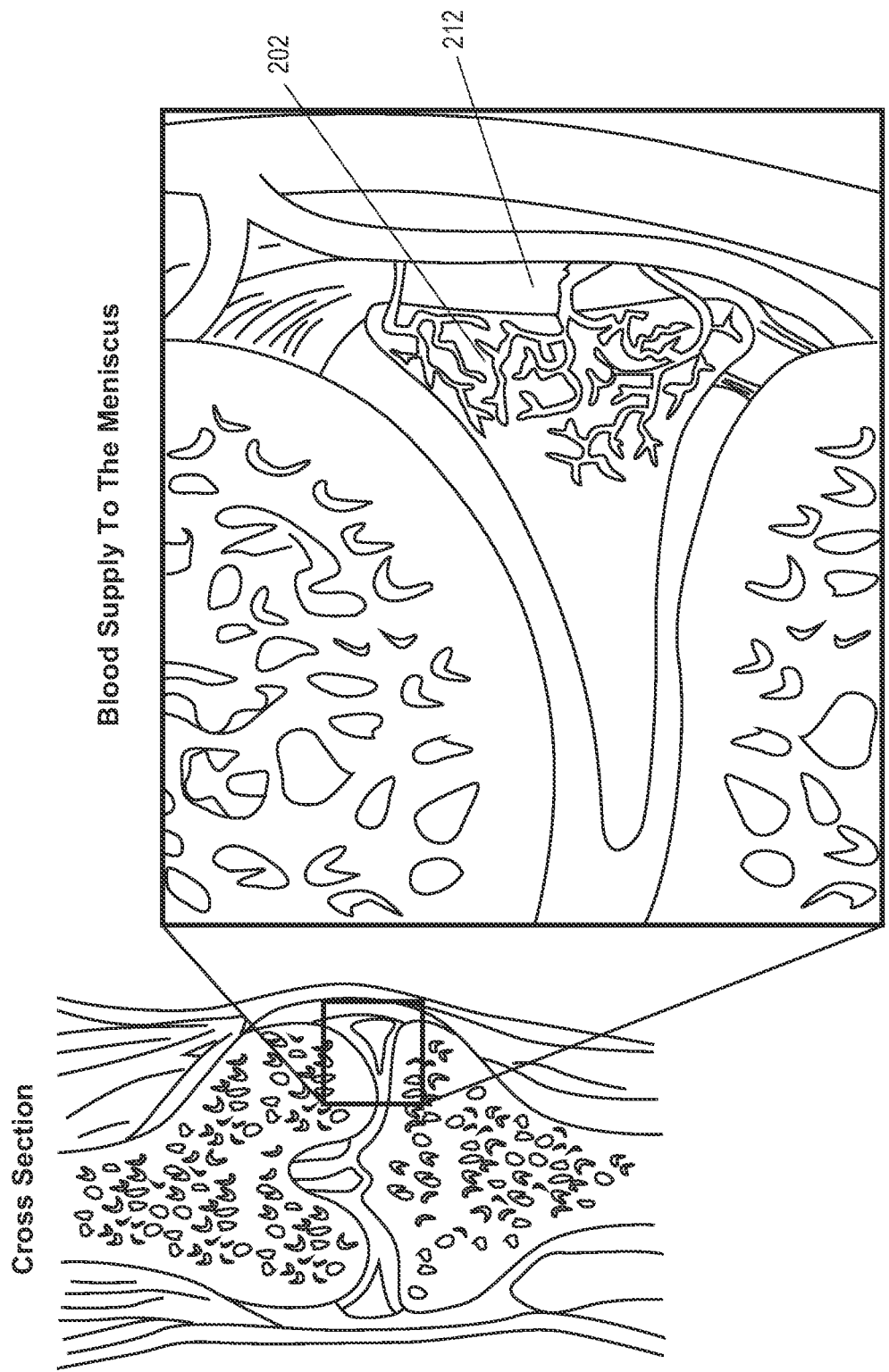
FIG. 22 illustrates the anatomy of the meniscus, including the capsule and associated vascular tissue.
Figure 23:
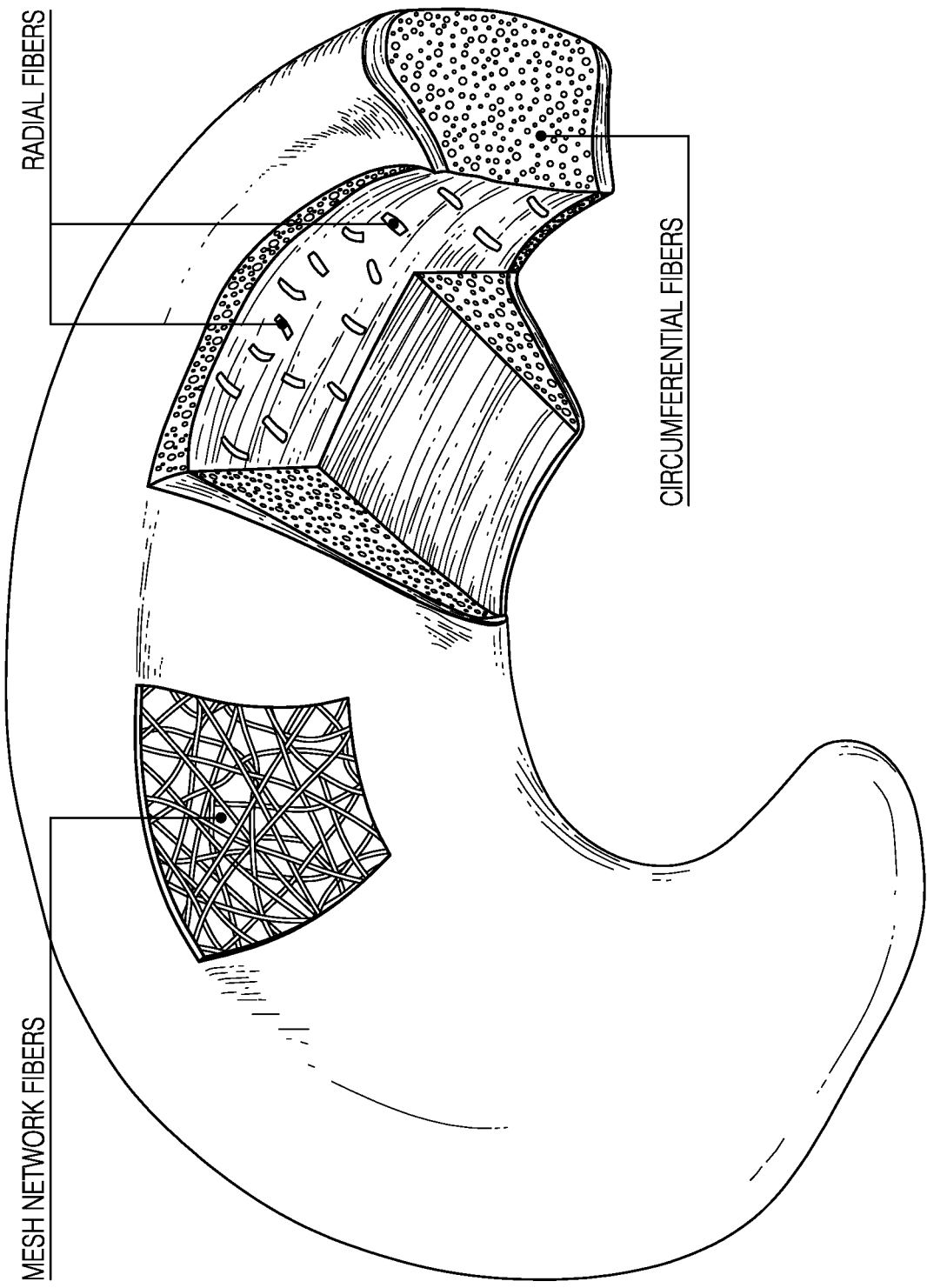
FIG. 23 illustrates the structure of a meniscus.

FIGS. 20A-20B show a generic version of a dual deployment suture passer. FIG. 20A shows a suture passer having a second jaw member in a retracted state; FIG. 20B shows the same suture passer with the lower jaw in an extended state. This generic schematic of a dual deployment (e.g., clamping/sliding) suture passer may be used to illustrate operation of the device in different tissues.

Figure 25A:
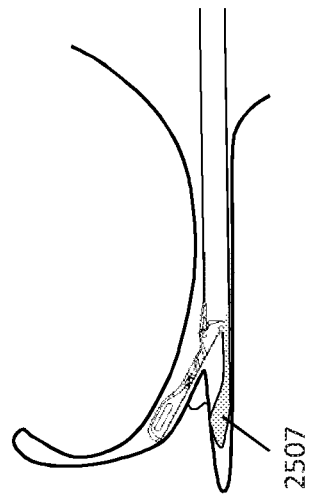
FIGS. 25A-25H illustrate the use of a dual deployment suture passer to suture a torn meniscus.
Figure 25B:
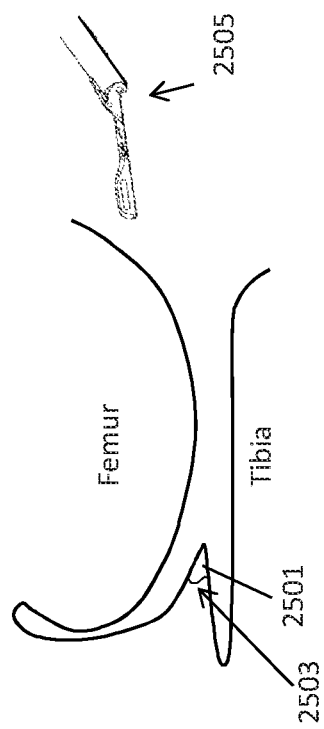

Any of the devices described herein may be used to suture and treat a torn meniscus of the knee. For example, in FIGS. 25A-25H a torn meniscus 2503 is repaired using the device as discussed above. In FIG. 25A the suture passer 2505 is inserted into the knee with just the first jaw member extended. The jaw member can easily fit between the femur and tibia of the knee to approach the meniscus 2501. The first jaw member can then be slid between the superior surface of the meniscus and the femur (as shown in FIG. 25B). The angle of the first jaw member may be dynamically adjusted as the suture passer is inserted to best match the tissue. This procedure may be observed arthroscopically.

Figure 25C:
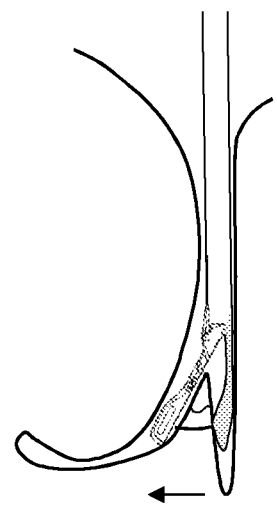

Thereafter, the second jaw member 2507 may be advanced under the meniscus between the inferior surface of the meniscus and the tibia, until the second jaw member is fully extend and the target tissue, including the meniscal tear 2503 is surrounded within the jaws of the device as shown in FIG. 25C.

Figure 25D:
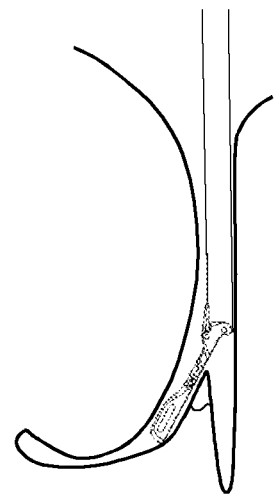
Figure 25E:
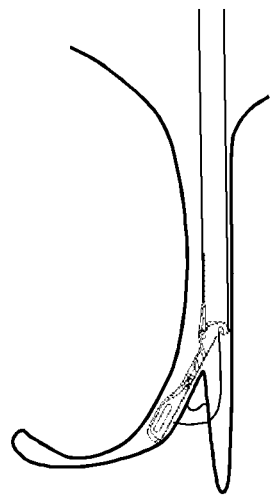
Figure 25F:
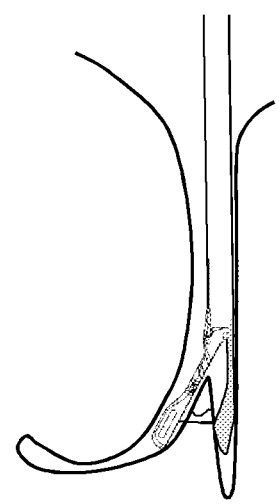
Figure 25G:
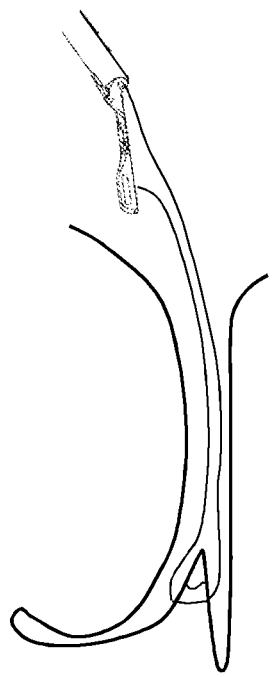
Figure 25H:
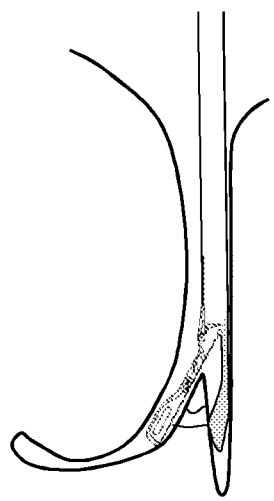

The meniscus tissue may then be clamped between the first and second jaw members, and the tissue penetrator may be extended across the tissue, as shown in FIG. 25D. The arrow indicates the direction of the tissue penetrator from the lower (second) jaw member, through the meniscus and into the upper (first) jaw member. The tissue penetrator may then engage the suture held in the first jaw member. The tissue penetrator is prevented (e.g., by a limiter) from extending beyond the upper jaw member, and may then be retracted, as shown in FIG. 25E, by withdrawing the tissue penetrator back down through the meniscus and into the lower (second) jaw member, pulling the suture loop with it. In FIG. 25F, the suture has been completely drawn through the meniscus and the tissue penetrator completely retracted. Thereafter the lower jaw member may also be withdrawn by axially retracting it proximally, as shown in FIG. 25G. The suture passer may then be withdrawn from the meniscus, as shown in FIG. 25H. The looped suture may be pulled so that one free end of the suture is pulled through the meniscus (leaving a single suture length, rather than a loop of suture passing though the meniscus). The suture may then be knotted.

Figures 26A, 26B:
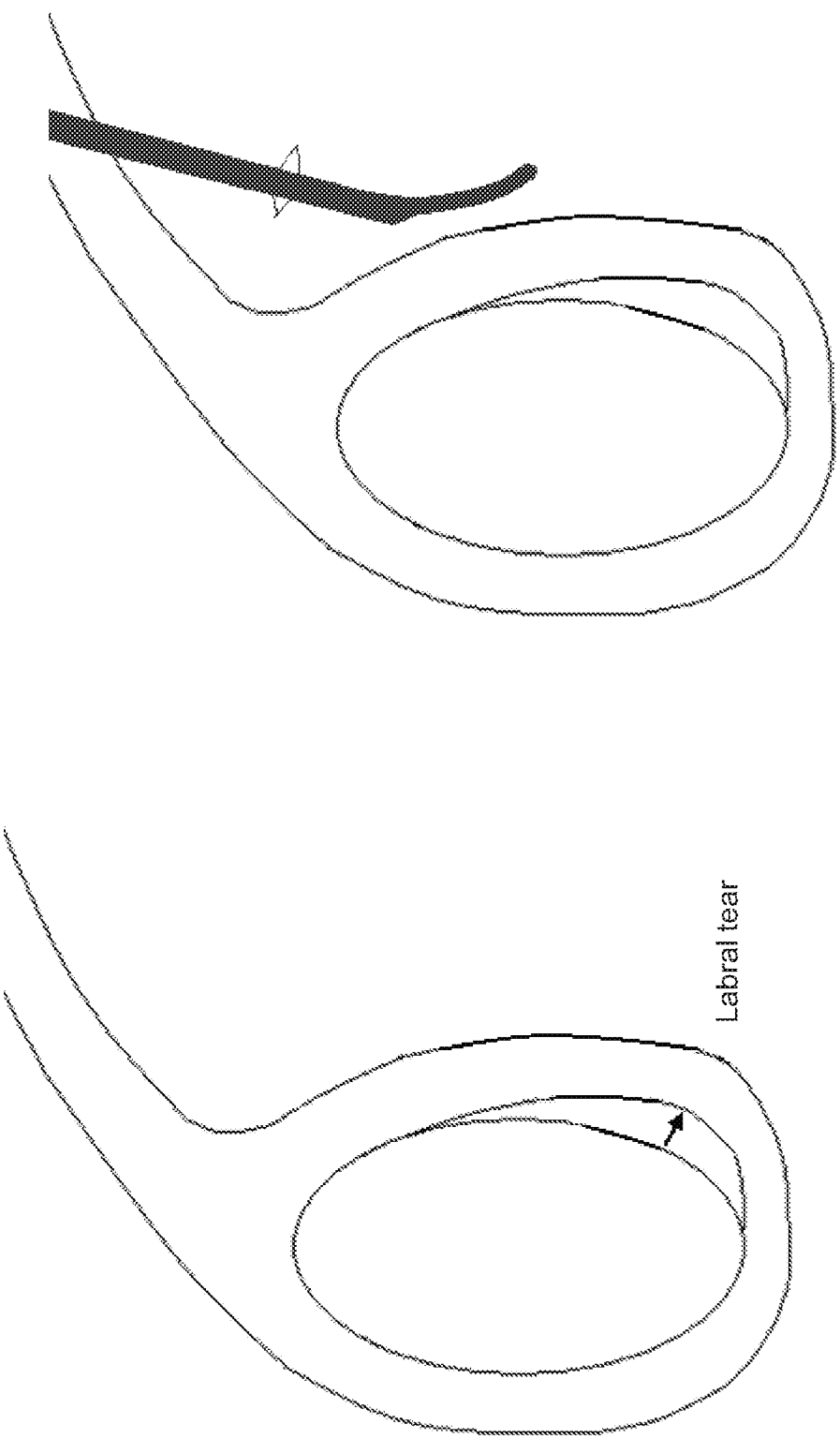
FIGS. 26A-26H illustrate the use of a dual deployment suture passer to suture a labral tear.
Figure 26D:
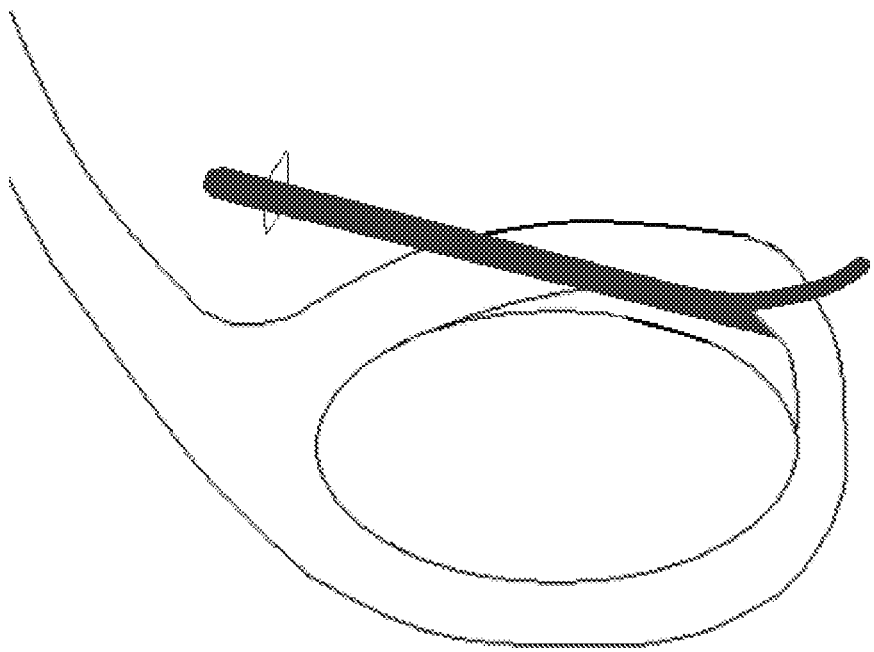
Figure 26C:
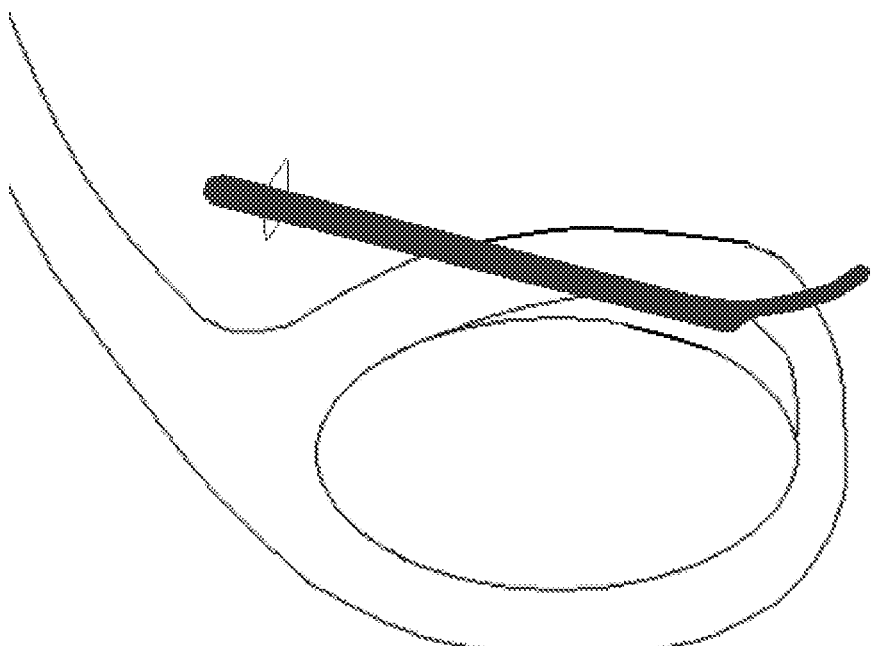
Figure 26F:
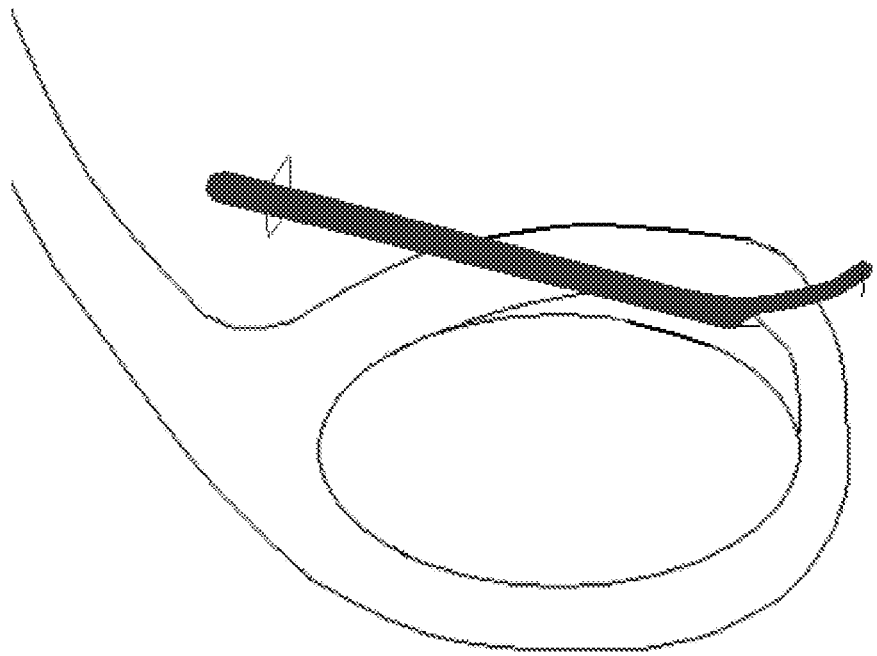
Figure 26E:
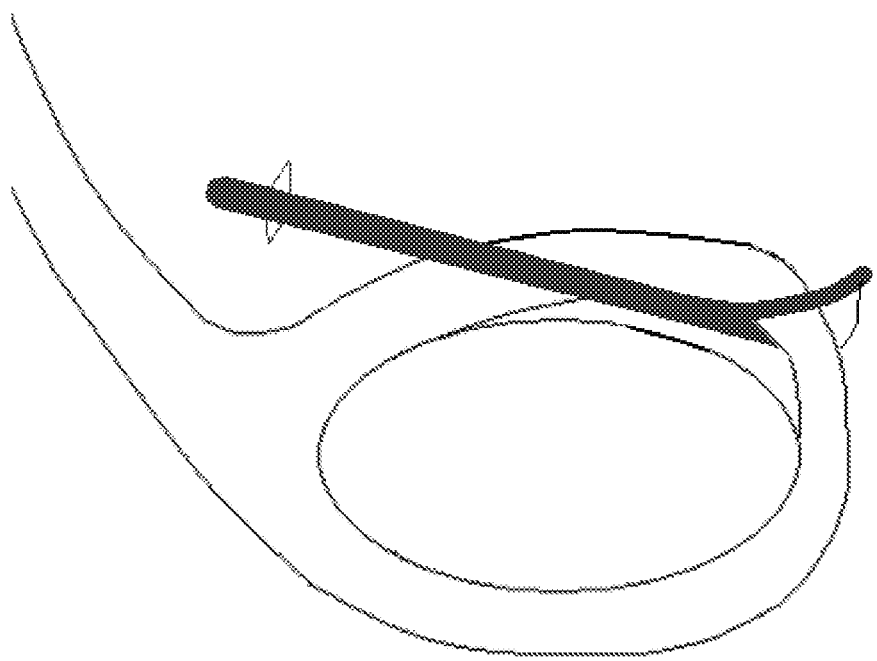
Figure 26H:
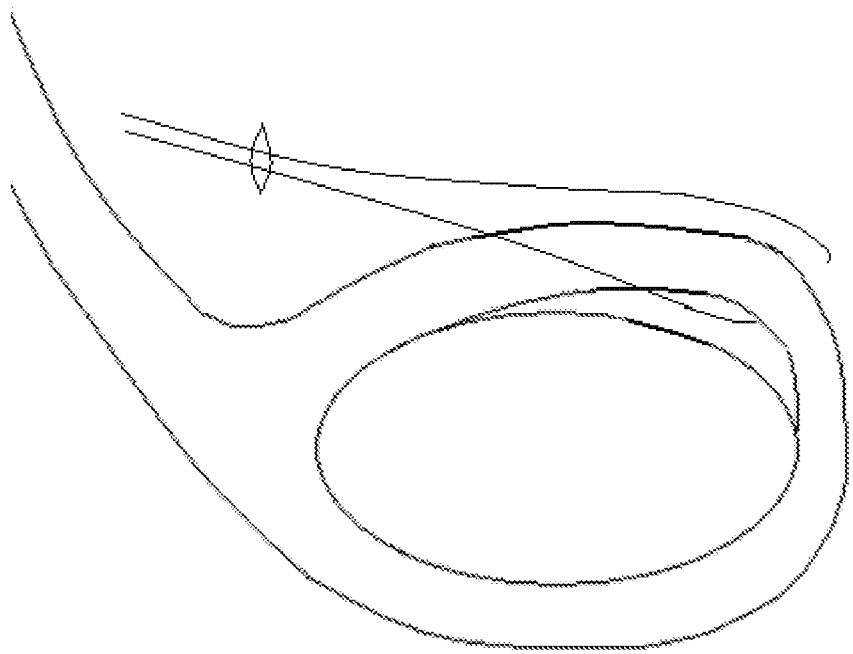
Figure 26G:
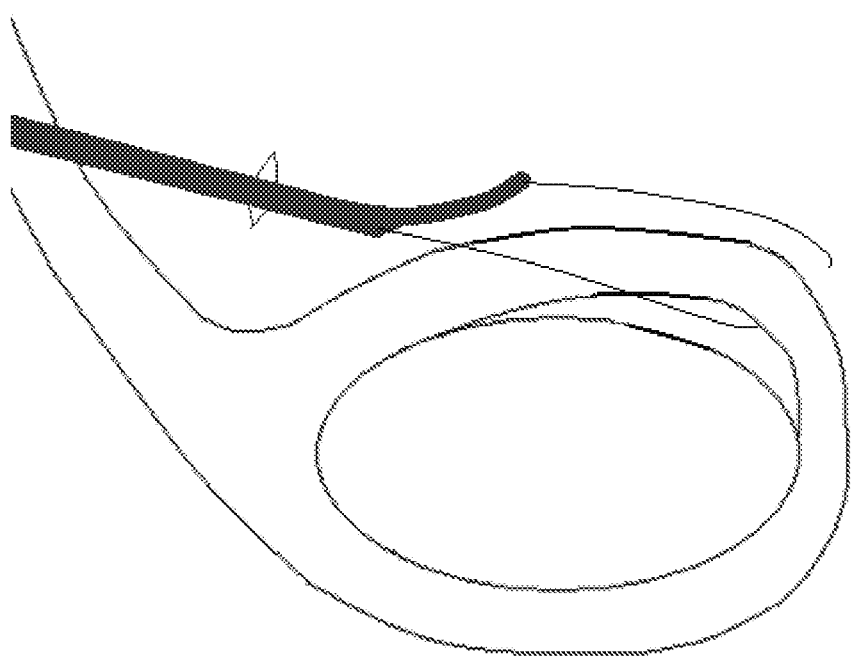

FIGS. 26A-26H illustrate another variation of a method of using the suture passer devices described herein to treat a patient. In this example, the method is used to treat a Bankart tear, an anterior inferior (or posterior inferior) labral tear. FIG. 26A illustrates the labral tear. In FIG. 26B the suture passer is inserted into the shoulder and the first jaw member is positioned (by dynamically adjusting the angle of the first jaw member) adjacent to the torn tissue, as shown in FIG. 26C. In FIG. 26C, the first jaw member is placed over the labrum and the anterior-inferior capsule. The lower (second) jaw member may then be axially extended so that the jaws now encompass the labro-capsular region, as shown in FIG. 26D. The first jaw may be adjusted to clamp the target tissue securely between the jaws and the tissue penetrator may be extended to pass a suture between the jaws, as shown in FIG. 26E. The lower (second) jaw member may then be retracted (FIG. 26F), and the device may be removed, as shown in FIG. 26G. A knot or tie may then be slid over the suture ends to tie off the suture as shown in FIG. 26H.

Figure 27A:
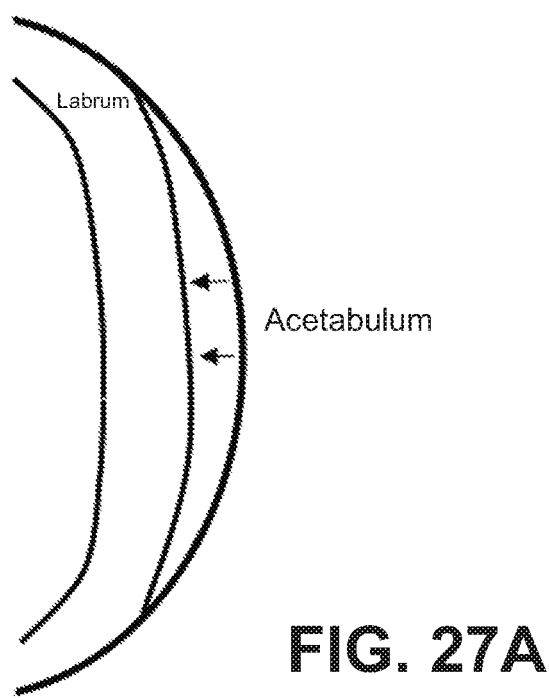
FIGS. 27A-27G illustrate the use of a dual deployment suture passer to repair a hip labrum.
Figure 27B:
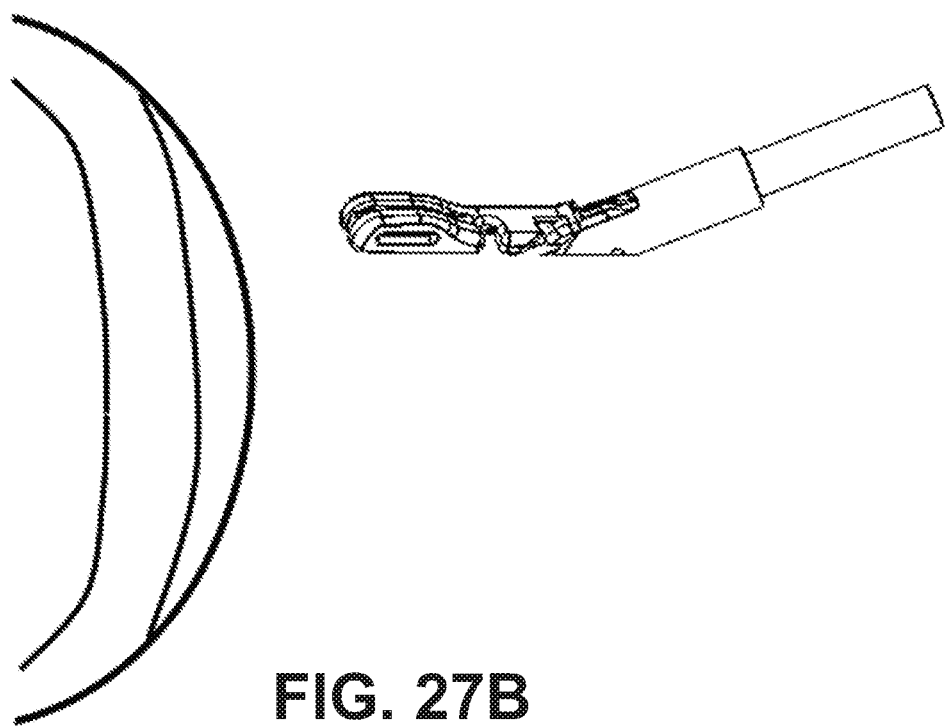
Figure 27C:
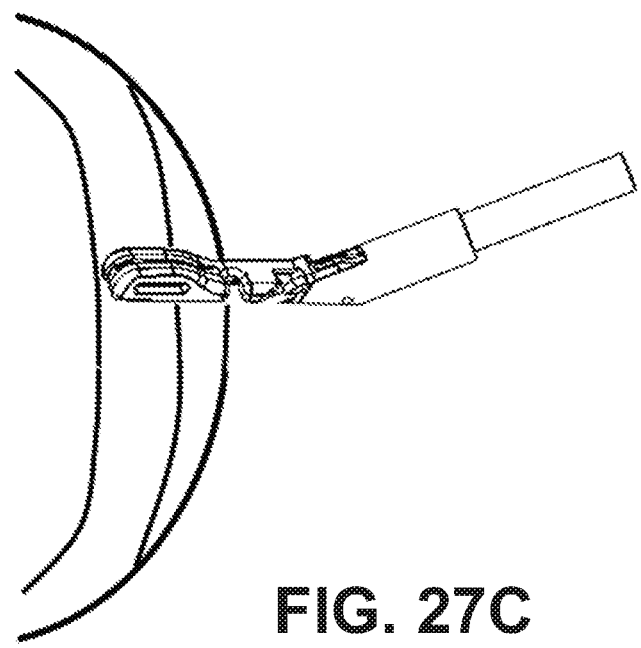
Figure 27D:
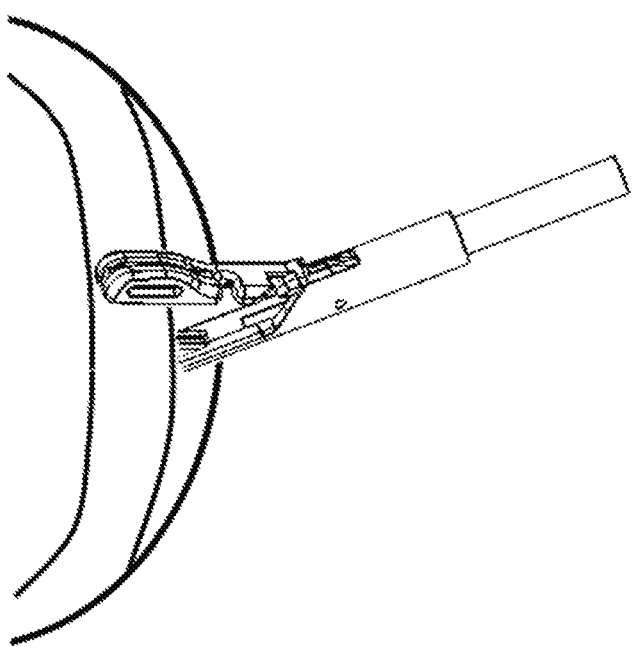
Figure 27E:
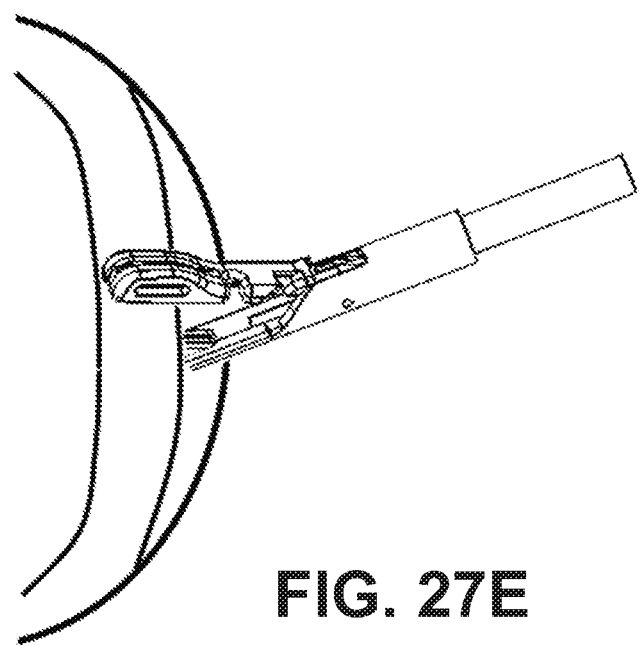
Figure 27F:
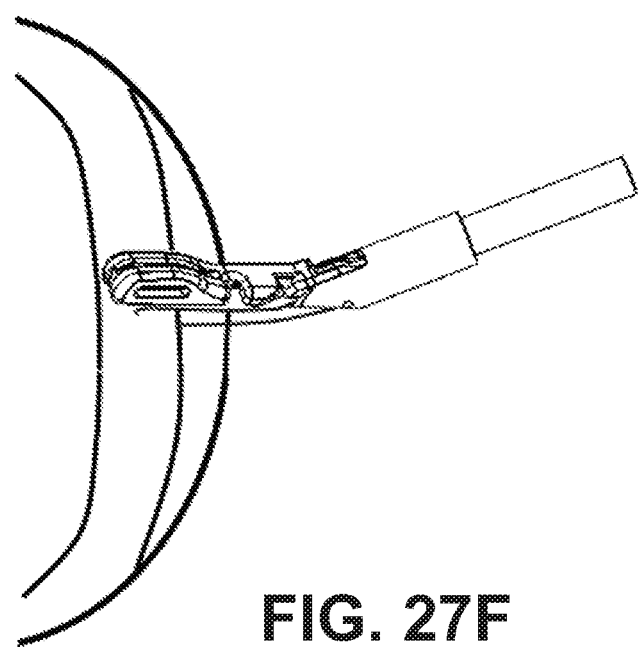
Figure 27G:
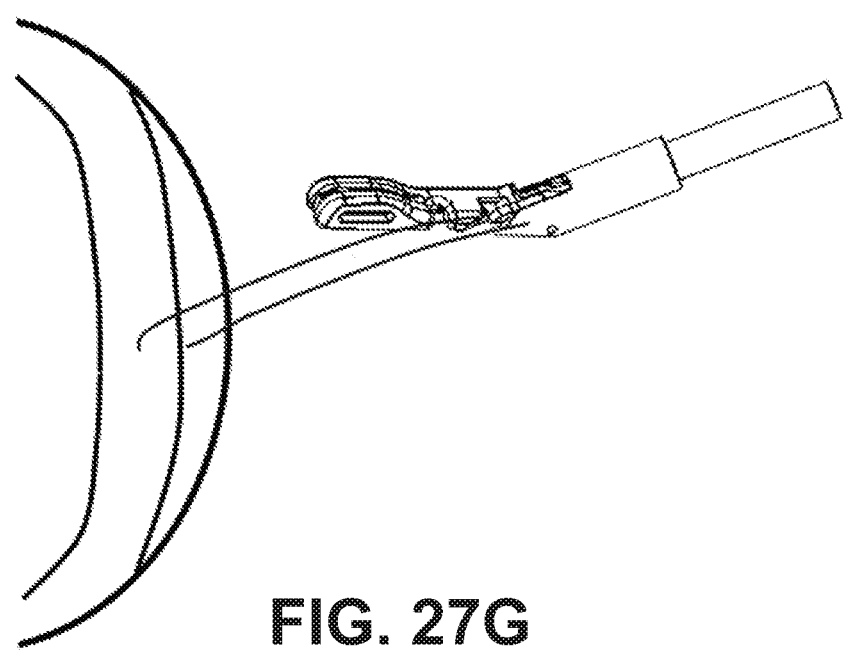

The suture passer devices and methods describe herein may also be used to repair a hip labrum, as illustrated in FIGS. 27A-27G. In FIG. 27A-27B, the hip labrum may be approached by the suture passer having the second jaw member retracted and the first jaw member extended distally. The angle of the first jaw member may be dynamically adjusted to help pass the suture passer near the labrum to be sutured, as shown in FIG. 27C. In FIG. 27D, the second jaw member may be axially extended from a proximal position to slide beneath the labrum and form a distal-facing opening so that the first and second jaw members surround the labrum tissue as shown in FIG. 27D. In FIG. 27E the tissue penetrator may then be extended across the distal-facing opening and through the tissue to grab (or in some variations drop off) a suture in the suture engagement region of the opposite jaw member. The tissue penetrator can then be retracted, and the second jaw member can also be retracted proximally, as shown in FIG. 27F. Finally, the device can be withdrawn from the tissue, as shown in FIG. 27G.

In any of the methods described herein the device may be controlled from the proximal end by a handle such as those illustrated above (e.g., FIGS. 17A and 17B). The device may be controlled using a single hand.

Figure 30A:
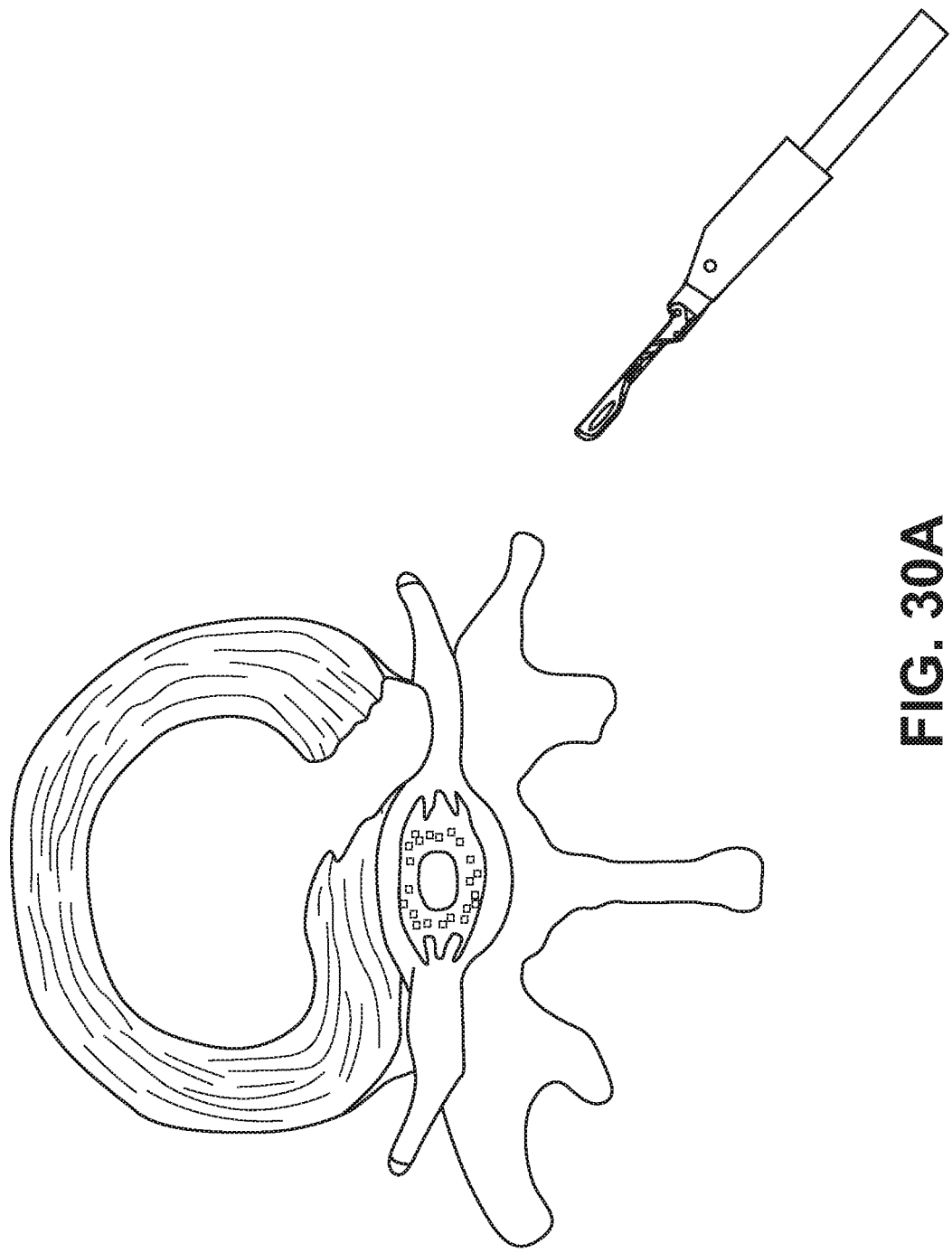
FIGS. 30A-30F illustrate the use of a dual deployment suture passer to repair a herniated disc.
Figure 30C:
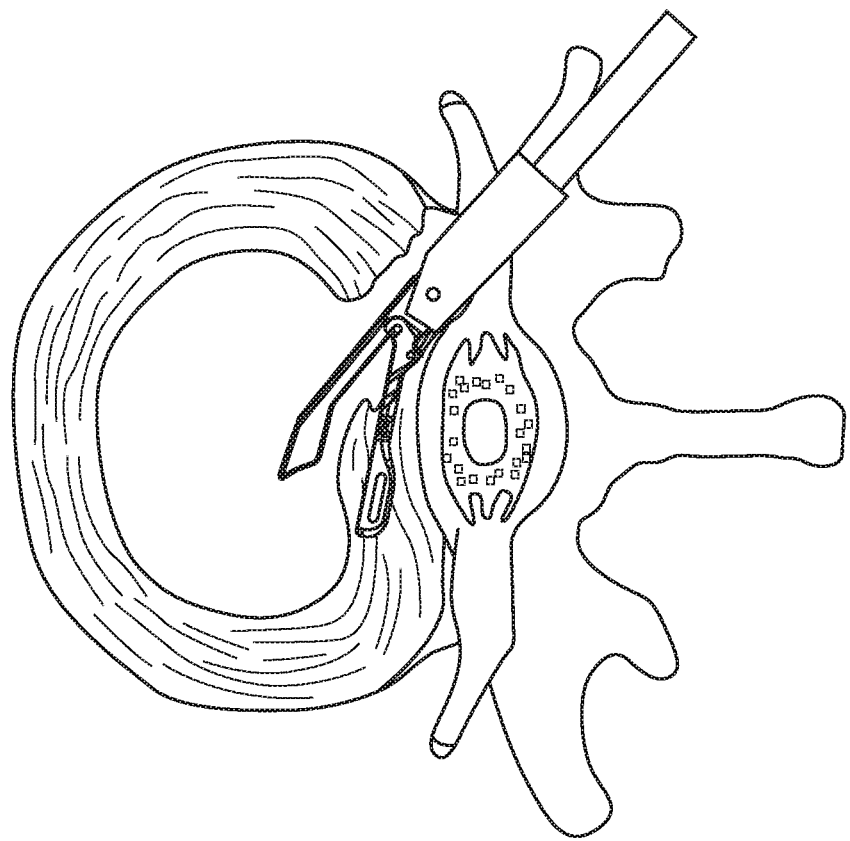
Figure 30B:
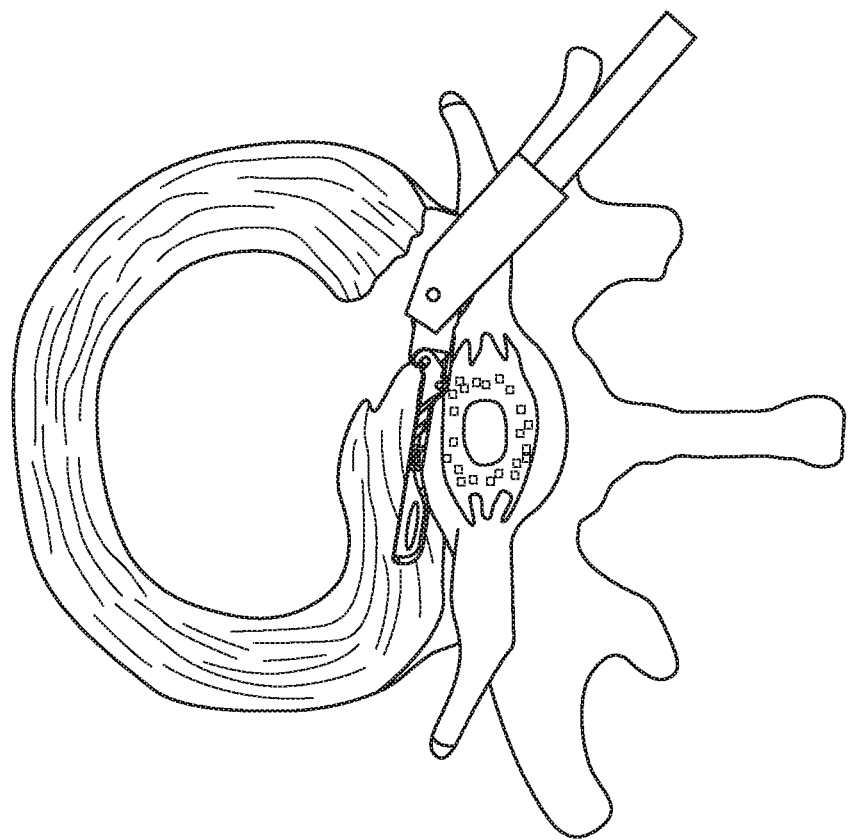
Figure 30E:
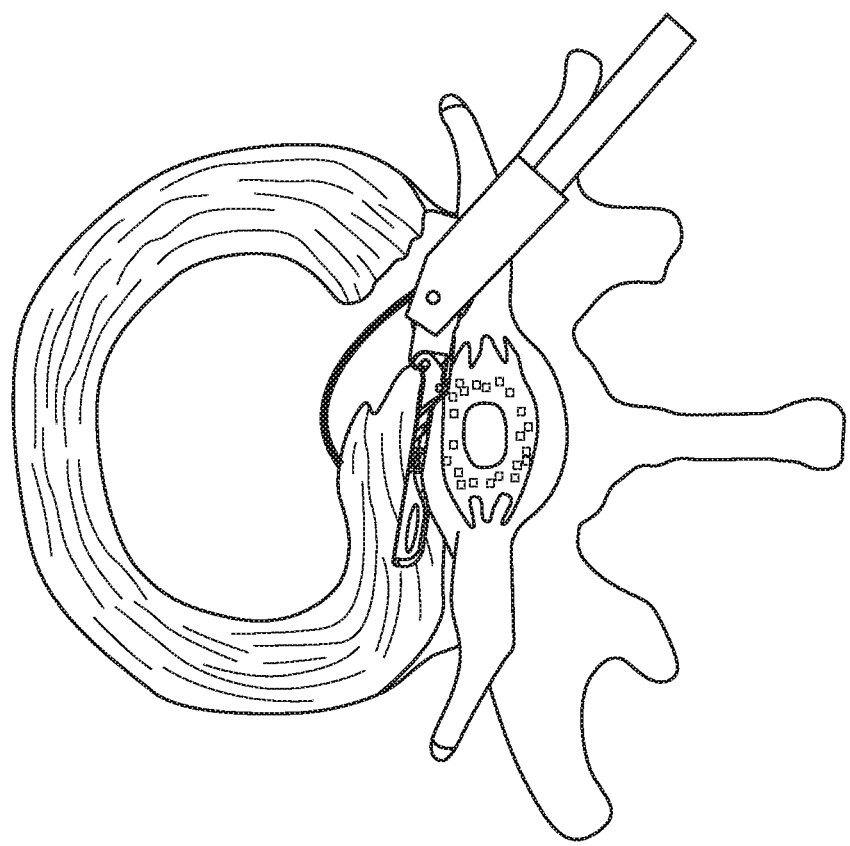
Figure 30D:
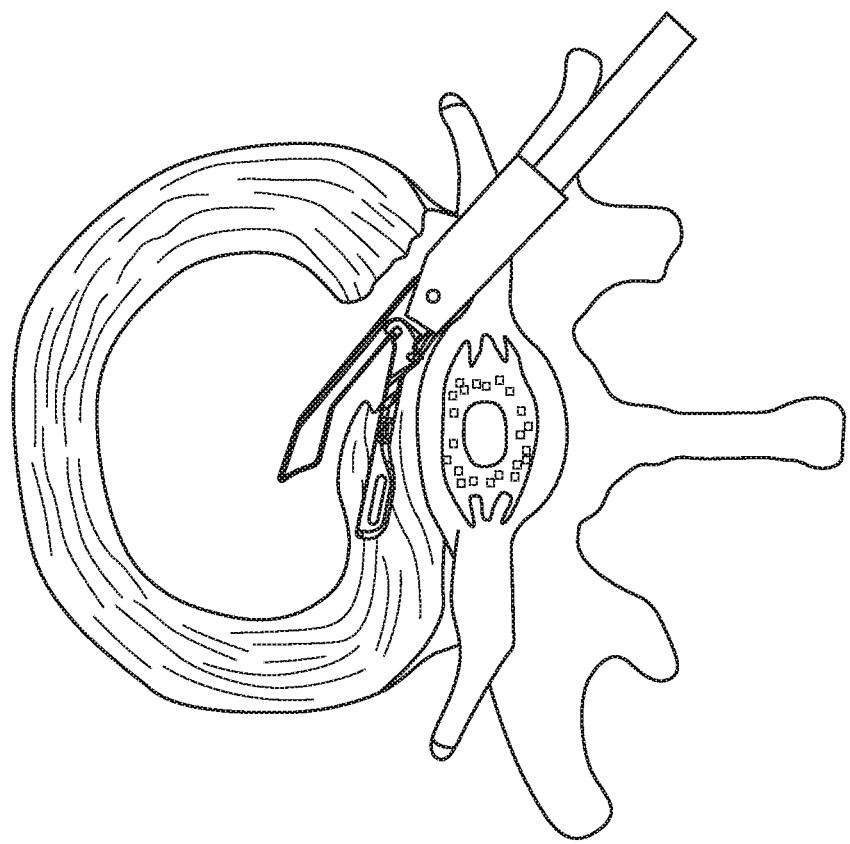
Figure 30F:
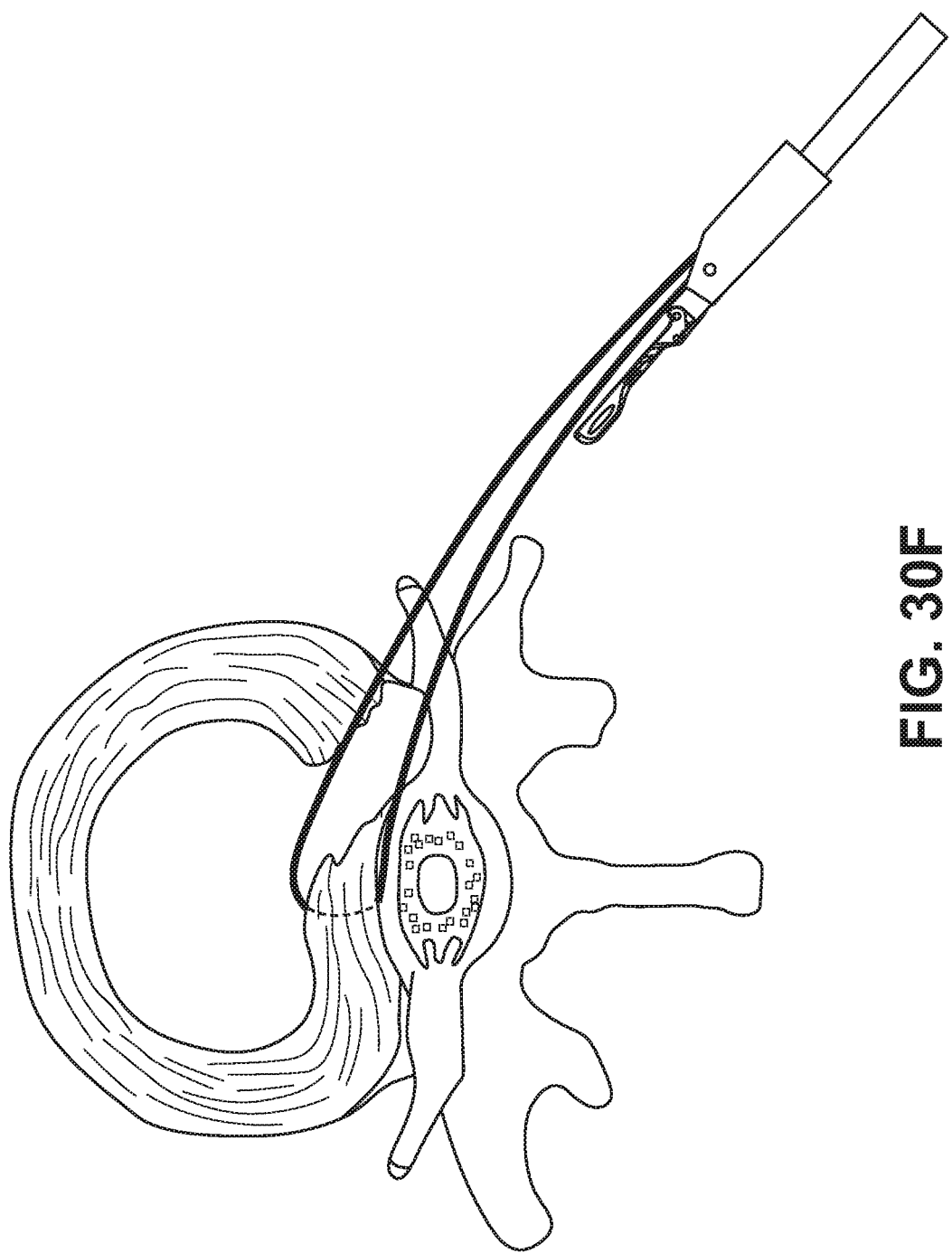

FIGS. 28, 29, 30A-30F and 31A-31F illustrate the use of a suture passer device such as the one illustrate herein to repair spinal tissue. For example, FIG. 28 shows a normal disc of a spine (a schematic illustration of a section through the spine is shown). In contrast, FIG. 29 shows a herniated disc. Traditionally this region has been difficult to access and thus difficult to suture. One variation of a device as described herein may be used to suture the disk annulus. For example, FIG. 30A shows a suture passer as described herein approaching the herniated disc. The angle of the first jaw member may be dynamically adjusted to help position the first jaw member adjacent to the tissue (e.g., the annulus) to be sutured. Once in position, as shown in FIG. 30B, the second jaw member may be extended so that the tissue to be treated is between the jaws, as shown in FIG. 30C. Thereafter the tissue penetrator may be extended across the jaws and through the tissue either to push a suture to the opposite side (FIG. 30D), or in some variations, to pull the suture from the opposite side back through the tissue. The second jaw member may then be retracted (FIG. 30E) and the entire device withdrawn from the disc region, as shown in FIG. 30F, leaving the suture behind.

In general, a suture may be passed from the first jaw member to the second jaw member or vice versa. Further, the tissue penetrator may be configured to push the suture through the tissue or it may be configured to pull the suture through the tissue; the suture engagement region on the opposite side of the jaw from that housing the tissue penetrator may be adapted for either receiving a suture (e.g., having a clamping region or gripping region, a hook, or the like) or for passing on a suture (e.g., holding the suture in position where it may be grabbed by the tissue penetrator). In addition, the tissue penetrator may be in either the second jaw member (as primarily illustrated above) or it may be in the first jaw member; the appropriate engagement region may be present on the opposite jaw as well.

Figure 31A:
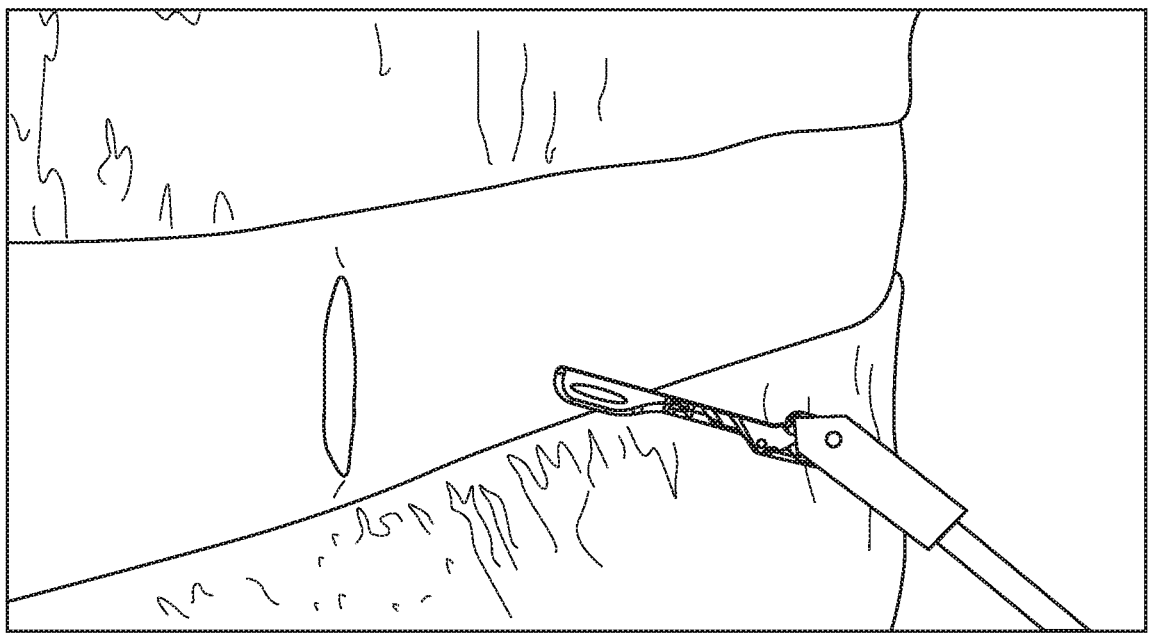
FIGS. 31A-31F illustrate another example of using a dual deployment suture passer to repair a spinal region.
Figure 31B:
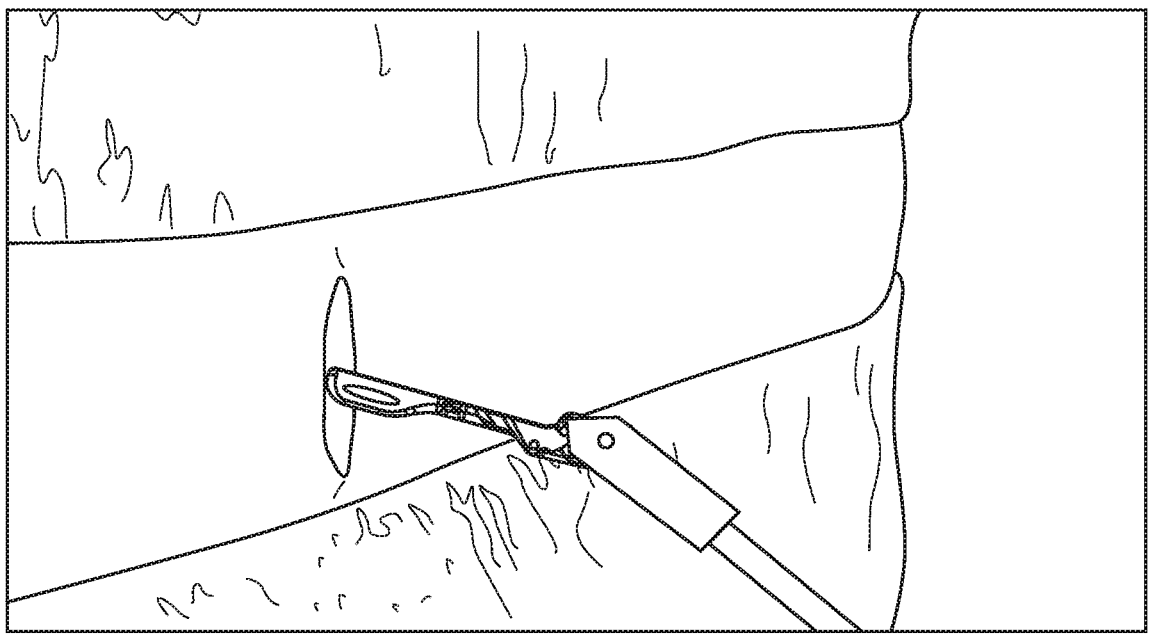
Figure 31C:
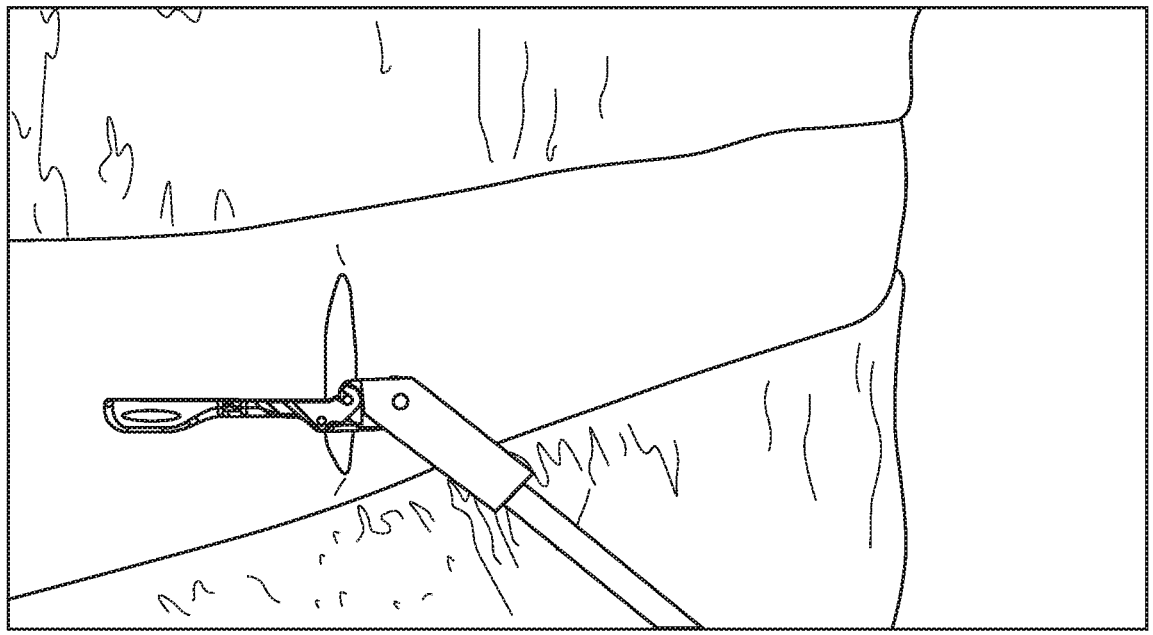
Figure 31D:
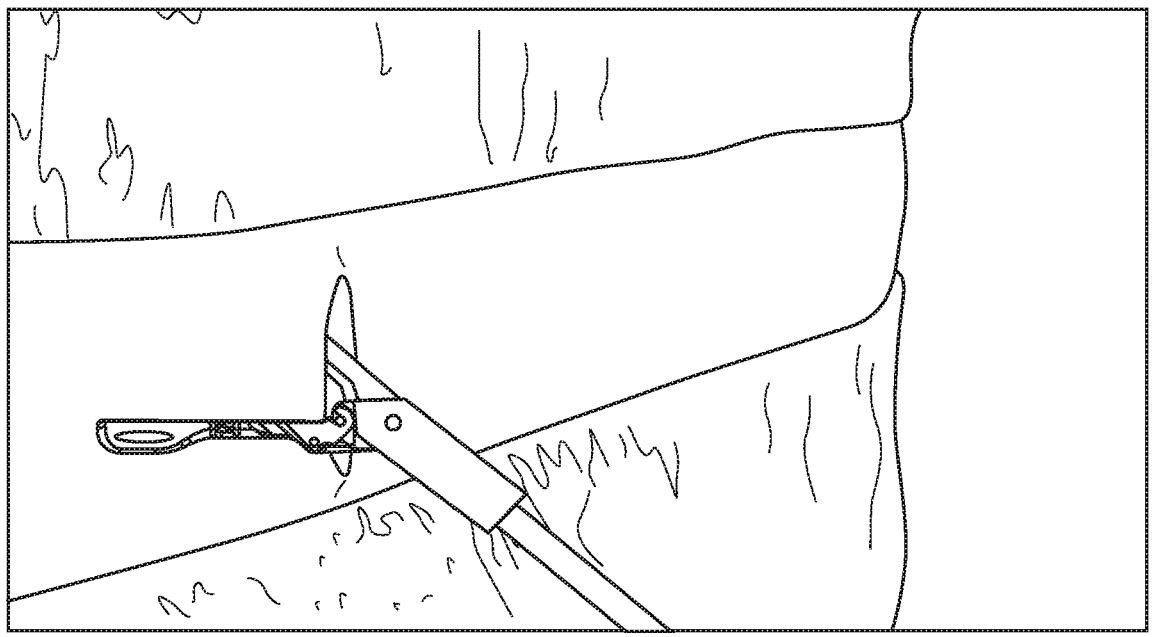
Figure 31E:
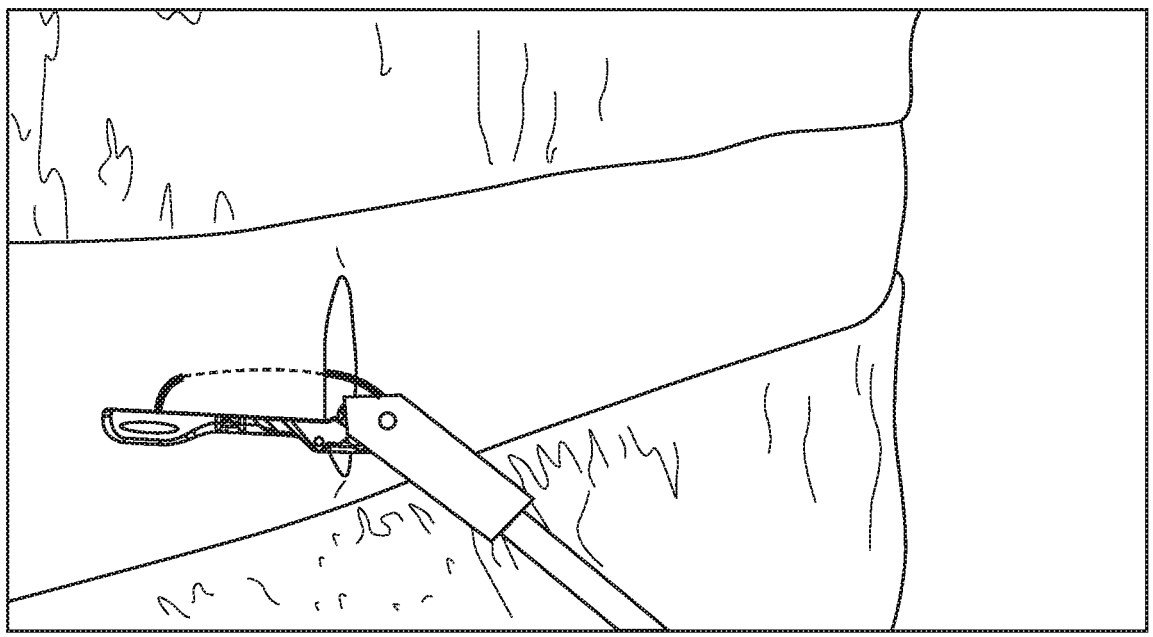
Figure 31F:
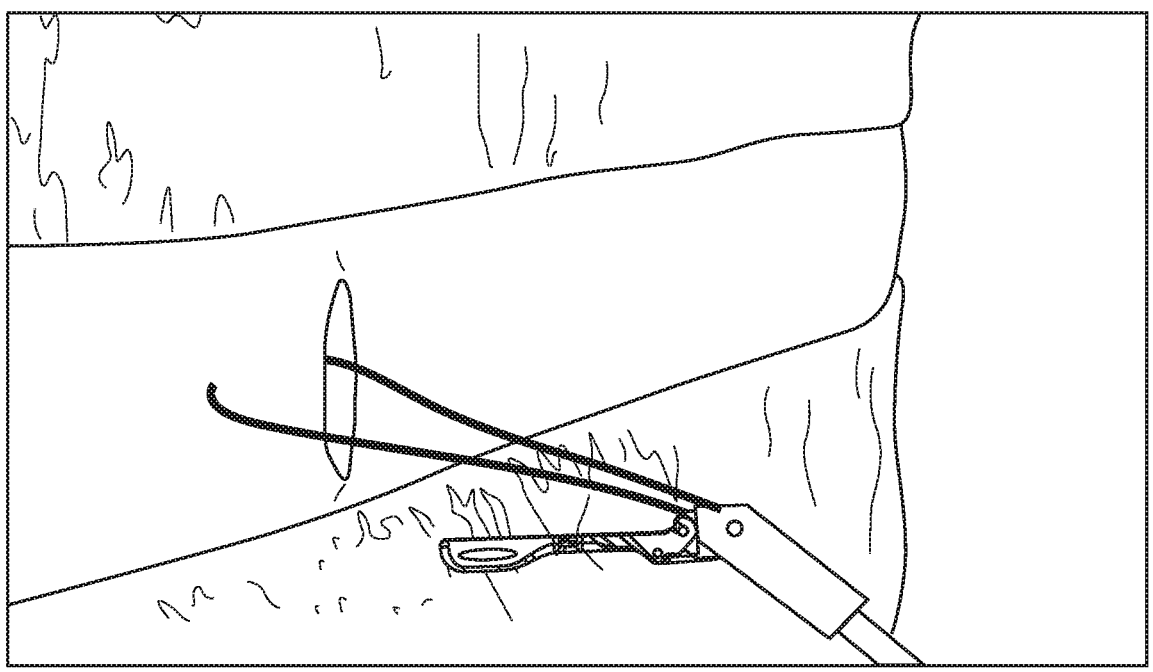

FIGS. 31A-31F show another view of the method for suturing an annulus of a disc of a spine. For example, in FIGS. 31A to 31C, the suture passer including an extended first jaw member approaches the torn tissue to be sutured. In FIG. 31D the second jaw member is axially extended on the opposite side of the tissue to be sutured, and the tissue penetrator is extended to pass the suture through the tissue. In FIG. 31 the tissue penetrator has been retracted and the second jaw member has also been retracted, so that the suturing device may be withdrawn while pulling the suture through the tissue, as shown in FIG. 31F.

Sigmoidal Tissue Penetrators

As discussed above, in reference to FIGS. 16A-16C, any of the devices described herein may be configured so that the tissue penetrator may extend distally from the distal end of one of the jaw members. Thus, in some variations, a tissue penetrator includes a mouth that opens in a distal-facing direction. The mouth is formed from a first jaw (e.g., upper jaw) and a second jaw (e.g., lower jaw); the tissue penetrator may extend between the first and second jaw in an approximately sigmoidal pathway. This is illustrated in FIGS. 32A-32C.

FIGS. 32A-32C show a schematic of one variation of a tissue penetrator having a distal-facing mouth 3201. The tissue suture passer has been made semi-transparent to show the tissue penetrator 3203 within the lower jaw member in FIG. 32A. In this example, the suture passer is configured so that the tissue penetrator may be extended distally first (in FIG. 32A) through the lower jaw member 3205 until it is deflected out of the lower jaw and across the distal facing mouth 3201. In this example, the lower jaw includes a deflector 3213 that redirects the tissue penetrator out of the lower jaw and towards the upper jaw, as shown in FIG. 32B. The tissue penetrator may pass through any tissue held within the open mouth 3201, and eventually meet the upper jaw member 3207. Once within the upper jaw member 3207, the tissue penetrator may then be deflected so that it extends distally within the upper jaw member. As shown in FIG. 32C, the tissue penetrator 3203 may be deflected distally by an internal deflector 3209 within the upper jaw member 3207. The tissue penetrator 3203 may extend distally out of a distal opening 3211 at the distal end of the upper jaw member 3207.

Although many of the suture passer variations configured for sigmoidal movement of the tissue penetrator, in which the tissue penetrator extends distally from a jaw member, may be configured as dual deployment suture passers (e.g., in which the two jaw members move independently with different types of motion), suture passers with fixed jaws or suture passers in which only one jaw moves relative to the suture passer may be used. For example, FIGS. 33A-33F show three different variations of suture passers having a distally extending tissue penetrator that travels in an approximately sigmoidal path.

For example, in FIG. 33A the upper and lower (first and second) jaws forming the distal-facing mouth of the suture passer are both movable, as described above for the dual deployment configuration. The tissue penetrator 3304 is shown extending from the lower jaw member 3303, across the distal-facing opening, and into the upper jaw member 3306, where it then extends distally slightly beyond the distal end of the upper jaw 3306. The suture passer of FIG. 33A is also shown in FIG. 33B, illustrating the movement of the upper and lower jaw members. As indicated in FIG. 33B, the upper jaw 3306 can pivot 3315 around a hinge point 3311 at the distal end region of the elongate member 3308. The lower jaw member 3303 can move axially (proximally and distally) 3317 relative to the elongate member 3308.

In FIGS. 33C and 33D, only one of the jaw members (the upper jaw member) may move; the opposite jaw member is fixed. In FIG. 33C, similar to FIG. 33A, the tissue penetrator extends distally from the upper jaw member 3306 out of a distal opening (not shown), along a sigmoidal path. As shown in FIG. 33D, the upper jaw includes a hinge point 3311 so that it can be controllable pivoted 3327 (using a proximal control) to form an angle with respect to the distal end region of the elongate shaft.

In FIGS. 33E and 33F, the upper jaw is shown as fixed (e.g., in a pre-formed bend or angle relative to the distal end of the elongate member) and the lower jaw may be moved axially distally/proximally 3337.

Figure 34A:
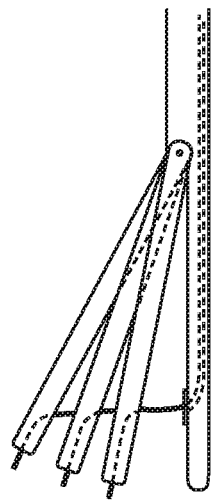
FIG. 34A illustrates different paths for a tissue penetrator in a suture passer having an upper jaw member that pivots.
Figure 35A:
FIGS. 35A and 35B show top and side views, respectively of one variation of a tissue penetrator.
Figure 35B:
Figure 34B:
FIGS. 34B-34E illustrate sigmoidal paths that may be taken by a tissue penetrator as described herein.
Figure 34C:
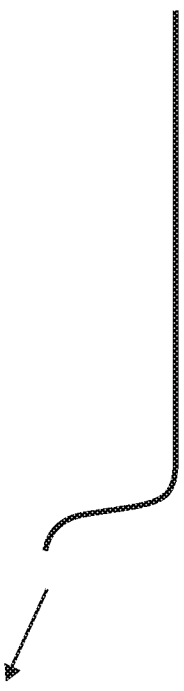
Figure 34D:
Figure 34E:

The path taken by the tissue penetrator may be approximately sigmoidal, as illustrated in FIGS. 34A-34E. FIG. 34A illustrates the different paths for a tissue penetrator in a suture passer having an upper jaw member that pivots. In any of the angled positions shown the suture passer may take an approximately sigmoidal path. FIGS. 34B-34E illustrate different sigmoidal paths for the tissue penetrator. In general the term sigmoidal path should be understood to be approximately sigmoidal when viewed in profile, as shown in FIGS. 34B-34E. In these examples the distal end of the tissue penetrator may extend distally at approximately the same angle as the upper jaw member (as indicated by the arrows to the left of each of FIGS. 34B-34E), rather than horizontally and parallel to the lower jaw member, as in a completely sigmoidal path. FIGS. 35A and 35B show one variation of a tissue penetrator from a top (FIG. 35A) and side (FIG. 35B) view. The distal end region of the tissue penetrator includes a suture retainer region 3505 configured as a hook.

In general, the needle width may be between 0.1" and 0.02". For example, in some variations the needle is approximately 0.058" in width. The needle may be relatively thin, e.g., having a thickness between about 0.02" and about 0.005". For example, in some variations the needle is approximately 0.0115" thick. In some variations the needle has a thickness of about 0.008". In general, the needles described herein have sufficient column strength to push through the tissue, and can be bent or deflected with sufficiently low force to accomplish the sigmoidal bend described herein; these needles may also have sufficient fatigue life to withstand multiple (e.g., 5×, 10×, 20×) extensions and withdrawals between the upper and lower jaw members and out of the distal opening in the upper jaw member.

Figure 36A:
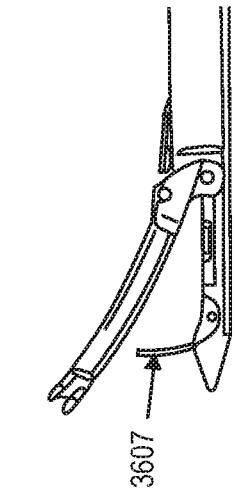
FIGS. 36A-36E illustrate operation of one variation of a suture passer having a tissue penetrator that extends distally from the upper jaw and travels in a sigmoidal path.

FIGS. 36A-36E illustrate another variation of a dual deployment suture passer having a tissue penetrator that is configured to travel in a sigmoidal path and extend distally from a distal opening in the distal end of the device. In this variation, the upper jaw may pivot and the lower jaw extends distally/proximally in the axial direction. A suture (not shown) may be loaded in the upper jaw so that it may be captured by the suture passer and pulled back through the tissue down to the second (lower) jaw member, as described in FIGS. 16A-16C, above. In FIG. 36A, the suture passer is shown in an undeployed state, with the pivoting upper jaw member 3601 at a 45° angle relative to the long axis of the elongate body 3603. As discussed above, in practice the device may be easily inserted into the tissue and adjacent to the target tissue, and the angle of the upper jaw member may be adjusted to help position the device. In this variation the upper jaw is relatively flat (e.g., has a narrow profile).

Figure 36B:
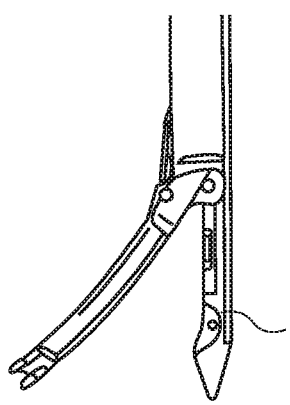
Figure 36C:
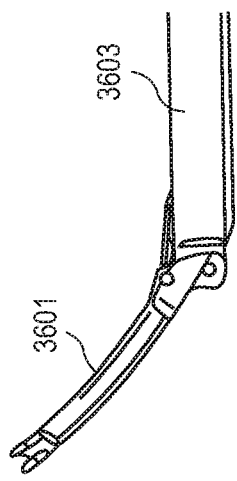
Figure 36E:
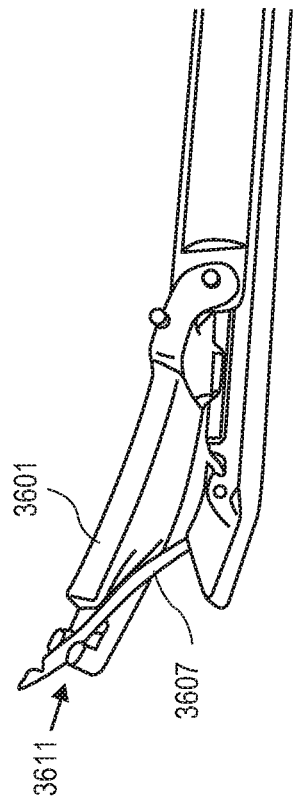
Figure 36D:
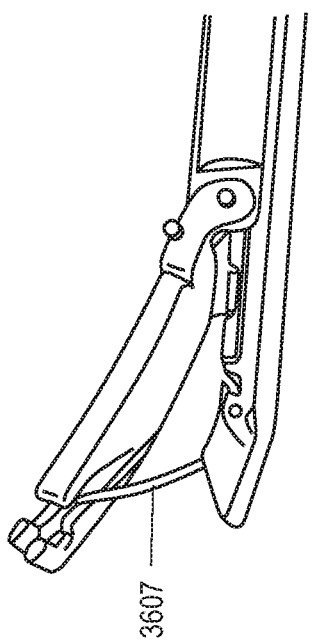

In FIG. 36B, the lower jaw 3605 has been extended distally from the distal end of the elongate body. In FIG. 36C, the upper jaw member has been pivoted downward ("clamping" down) so that the angle relative to the long axis of the elongate body is approximately 30°, and the tissue penetrator 3607 is being extended from the lower jaw 3605 and across the distal-facing mouth to the upper jaw, as also shown in FIG. 36D. The tissue penetrator finally extends distally from the opening 3611 at the distal end of the upper jaw 3601 as shown in FIG. 36E.

Figure 37A:
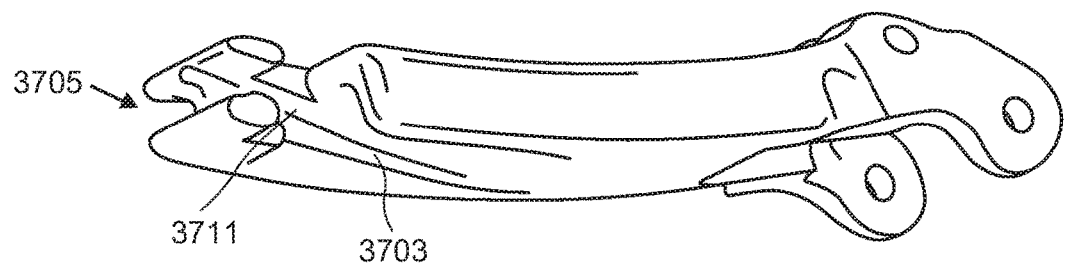
FIGS. 37A and 37B show side perspective views of one variation of an upper jaw member for a suture passer such as the suture passer shown in FIG. 36A.
Figure 37B:
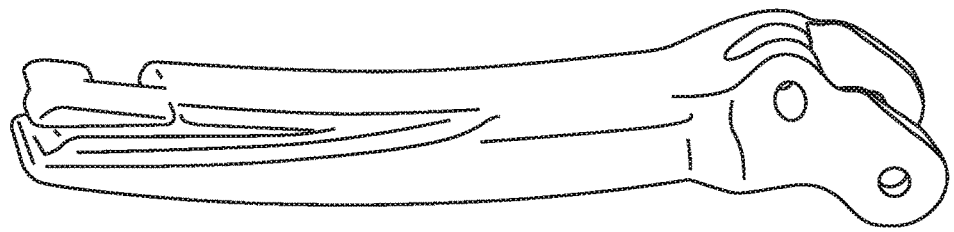

FIGS. 37A and 37B show side and top perspective views, respectively, of one variation of such an upper jaw member. This variation is similar to that shown in FIGS. 36A-36E, and allows loading of a suture on the upper jaw member as previously shown in FIG. 16A-16C. In FIGS. 37A and 37B, the upper jaw member includes a deflection surface 3703 and a distal opening 3705 out of which the tissue penetrator (not shown) may exit distally. The upper jaw shown in FIGS. 37A to 37B also includes a suture loading region 3711 into which one or more sutures may be threaded and/or pre-loaded so that they may be engaged by the tissue penetrator and pulled from the upper jaw to the lower jaw. In this variation the suture loading region is a channel that is adjacent to the deflection surface 3703. A tensioning element (not shown) may be used to hold the suture in the loading region. The tensioning element may be on the upper jaw member, or it may be located more proximally, including on the proximal handle. The tensioning element may be configured to pinch or bind the suture to hold it in position (and in tension) so that it can be engaged by the suture retainer region on the tissue penetrator.

Figure 38A:
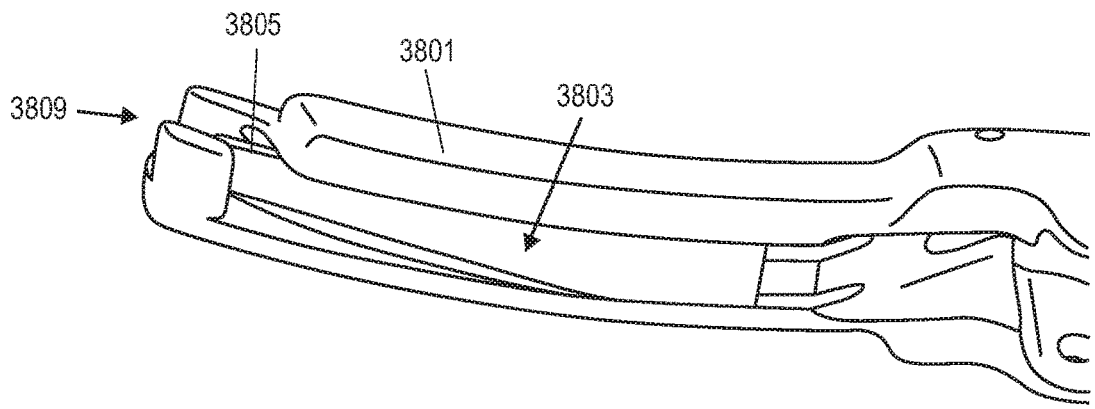
FIGS. 38A and 38B show side perspective views of another variation of an upper jaw member for a suture passer including a suture stripper.
Figure 38B:
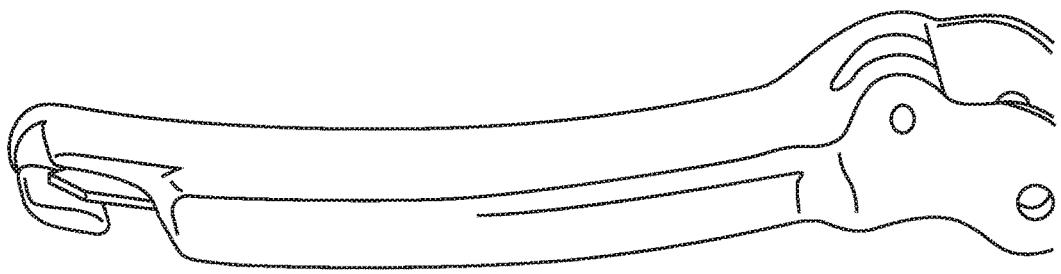

FIGS. 38A and 38B illustrate another variation of the upper jaw member of a suture passer, in which the upper jaw member includes a suture stripper for removing (stripping) the suture off of the suture retainer region of the tissue penetrator and holding the suture (or a loop or bight of suture) in the upper jaw. In FIG. 38A, the upper jaw member 3801 includes a deflector region 3803 that is formed, in part, from the suture stripper 3805. The stripper is formed of a flexible material (e.g., a metal, polymer, or other material, including shape memory alloys) that can be resiliently deflected to allow the tissue penetrator to pass and extend distally from the distal opening 3809, while stripping the suture off of the tissue penetrator and holding the suture in the upper jaw. This is described in more detail below. In FIG. 38A, the suture stripper is configured as a leaf-spring structure that is secured to the upper jaw member at the proximal end and the opposite end is free and held in tension against a distal surface of distal opening at the distal end of the device; the tissue penetrator may push against the stripper and past it, forcing a suture held in the tissue penetrator's retainer region against the stripper. As the tissue penetrator is withdrawn, the suture may be pinched against the stripper and the upper jaw, holding it in place while allowing the tissue penetrator to be withdrawn. In some variations the end of the stripper and/or the distal opening includes an edge (e.g., having serrations, teeth, etc.) to hold the suture as the tissue penetrator is withdrawn.

Figure 39C:
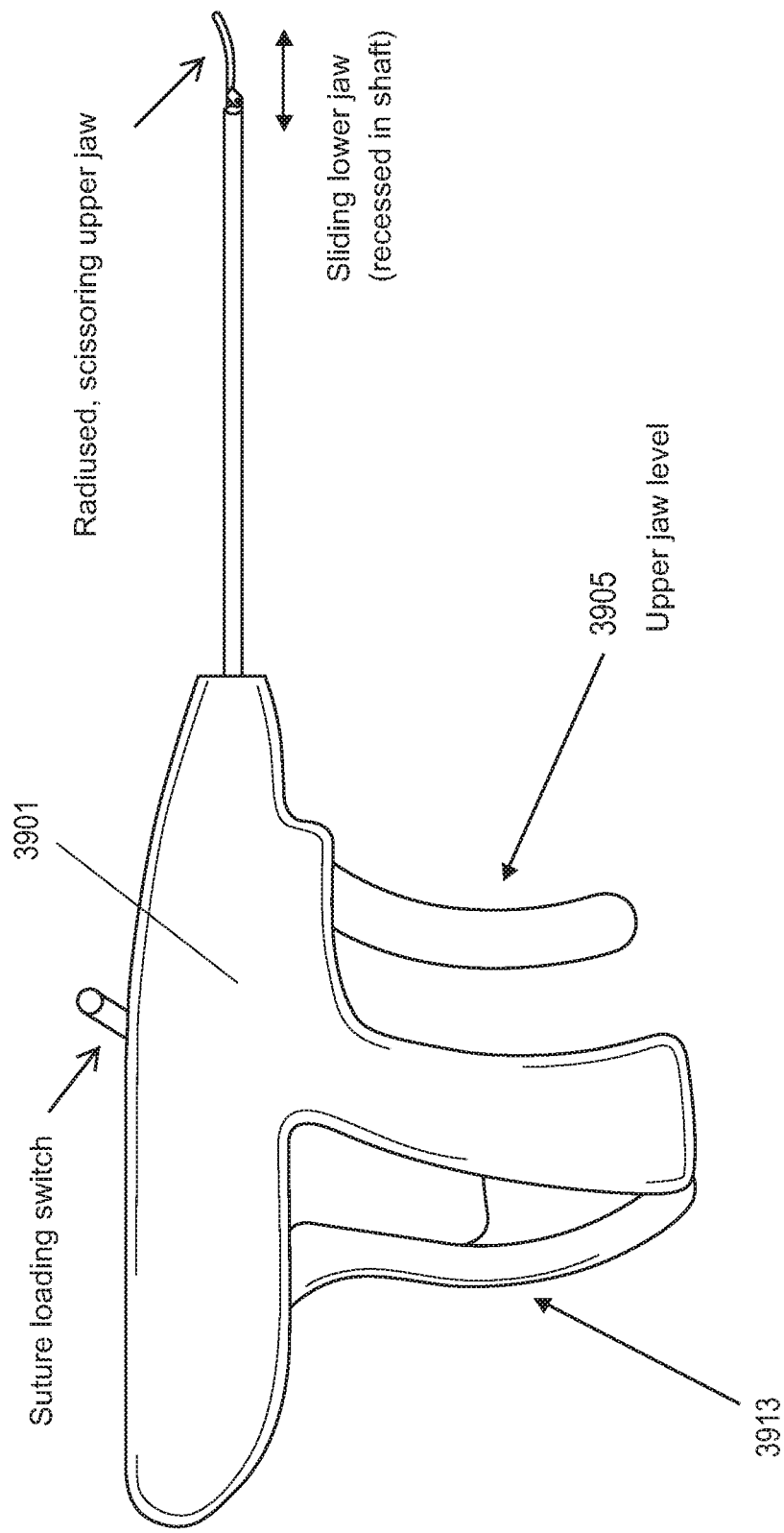

FIGS. 39A-39C illustrate one variation of a suture passer having a tissue penetrator that extends distally from a distal opening in the upper jaw. The tissue penetrator travels in a sigmoidal path from the lower to upper jaw. In this variation, two lengths of a suture (including two lengths of the same suture, e.g., two ends of the same suture) can be loaded into the lower jaw and sequentially passed from the lower jaw, through different regions of the tissue and retained in the upper jaw, to pass a loop of suture through the tissue. The suture passer show in FIGS. 39A-39C is also configured so that the upper jaw member can pivot to assume a different angle relative to the elongate body of the device, and the lower jaw member is axially extendable distally from the distal end of the elongate member to form a distal-facing mouth with the upper jaw member. The proximal handle includes a plurality of controls for controlling the pivoting of the upper jaw member, the axial sliding of the lower jaw member, and the extension/retraction of the tissue penetrator from the lower jaw member.

FIG. 39B shows the device of FIG. 39A with the outer housing of the proximal handle 3901 removed, revealing some of the connections between the controls and the device. In FIG. 39B, the distal most control 3905, the proximal handle is configured as a trigger or lever that controls the motion of the upper jaw member ("upper jaw control"). The upper jaw control may be pulled to reduce the angle of the upper jaw relative to the long axis of the elongate member 3907. In this variation the upper jaw control is pinned and allowed to drive a tendon in the elongate member distally when compressed to drive the upper jaw down (reducing the angle between the upper jaw and the long axis of the elongate member). This pivoting motion may also be referred to as scissoring (scissoring motion).

A distal control 3913 is also configured as a lever or trigger, and may be squeezed or otherwise actuated to extend and/or retract the lower jaw to form a distal-facing mouth with the upper jaw, as shown in FIGS. 39A-39B. In some variations the control is further configured to control deployment of the tissue penetrator in the sigmoidal path. For example, in some variations squeezing the distal control after completely extending the lower jaw may deploy the tissue penetrator from the lower to the upper jaw so that the distal end of the tissue penetrator extends out of the upper jaw. As it extends between the upper and lower jaw, the tissue penetrator may carry a first length (bight) of suture through the tissue. Upon reaching the opposite jaw member, the suture may be removed from the tissue penetrator and held (e.g., by a stripper) in the upper jaw. Upon release of the distal control, the tissue penetrator may withdraw back into the lower jaw. Actuating (e.g., squeezing) the distal control 3913 again may result in the extending the tissue penetrator (along with any second length of suture) back through the tissue from the lower jaw to the upper jaw, where the second length of suture can be retained. Alternately, in some variations, the controls (e.g., to control motion of the upper and/or lower jaw) may be separate from each other, and/or from extending/withdrawing the tissue penetrator. Additional controls may also be included in the proximal handle, include a suture loading control (e.g., switch, toggle, etc.) for loading and/or tensioning the suture within the lower jaw member.

FIGS. 40A-40D show an enlarged view of the distal end of the device of FIGS. 39A-39C. For example, in FIGS. 40A and 40B the upper jaw 4003 is thin and slightly radiused (e.g., curved), and is hinged to the elongate shaft region of the device. The upper jaw is also connected to a control (handle, etc.) on the proximal handle by a push/pull member (tendon, wire, rod, etc.), allowing adjustment of the angle of the upper jaw member relative to the elongate member.

Figure 42B:
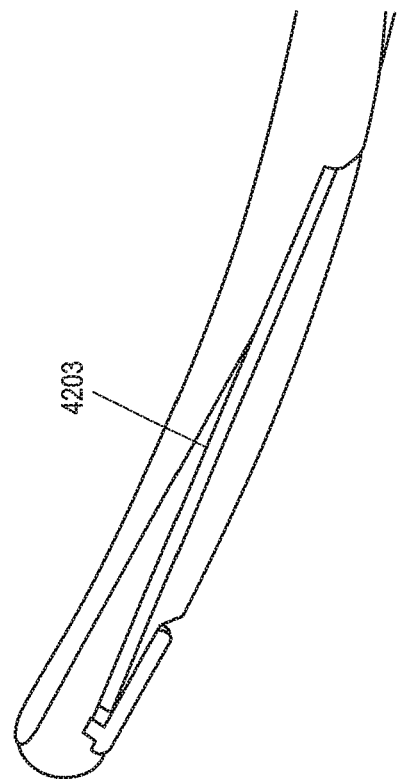
FIGS. 42A and 42B show side perspective views of the distal end region of a jaw member including a suture stripper.
Figure 42A:
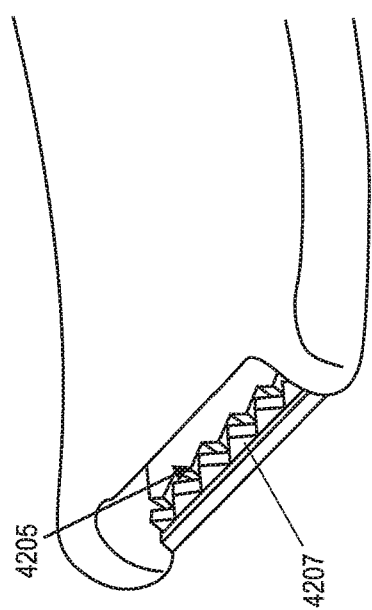

In FIG. 40C, the upper and lower jaw members have been removed from the distal end of the device shown in FIG. 40B, revealing the tissue penetrator 4007 within the lower jaw and the stripper 4009 in the upper jaw. FIG. 40D shows the distal end of the device of FIG. 40B after the tissue penetrator has been extended across the distal-facing mouth. FIGS. 42A and 42B illustrate one variation of an upper jaw region having a suture stripper. In FIG. 42A, the suture stripper is visible from the distal opening at the distal end of the jaw member. In this example, the stripper includes a stripper plate 4203 with a sawtootth edge 4205. The jaw member also includes a receiver region for the stripper plate having a sawtooth edge 4207.

FIGS. 41A-41C show greater detail on one variation of a suture stripper that may be used. This variation is the same as the variation shown in FIGS. 42A and 42B. Although the examples provided herein show the suture stripper in the upper jaw member, in some variations a suture stripper may be present on the lower jaw member (e.g., where the tissue penetrator is configured to pass a length of suture from the upper jaw to the lower jaw). In FIG. 41A, the stripper includes a flexible plate 4101 that is fixed at the proximal end (e.g. to the upper jaw member), and pressed against a receiving plate 4103 at the distal end 4105. In some variations the receiver is not a separate receiving plate, but merely a region of the jaw member. Either or both the suture stripper plate 4101 and the receiver 4103 may include an edge that is adapted to catch the suture. In FIGS. 41A-41C, both the plate 4101 and receiver 4103 include edges having teeth 4105 and 4107. In this example the teeth are saw-tooth structures that are adjacent (or abutting) in the upper jaw member. The tissue penetrator may pass between the plate 4101 and the receiver 4103 by deflecting the plate 4101; as the end of the tissue penetrator passes the edges 4105 and 4107, a length of suture held by the tissue penetrator may be caught by the stripper and held between the plate and receiver as the tissue penetrator is withdrawn. This is illustrated in FIGS. 43A-43E.

For example, FIG. 43A shows a cross-section through a mount that mimics the stripper device and upper jaw member shown in FIGS. 42A and 42B. In FIG. 43A, the stripper 4301 is configured as a leaf-spring structure that is fixed at the proximal end 4303 and can be displaced by the tissue penetrator at the distal end. In FIG. 43B a tissue penetrator 4307 holding a length (loop or bight) of suture 4309 is advanced distally, deflecting off of the bottom surface of the stripper 4301; the tissue penetrator 4307 causes the stripper to deflect upwards as the tissue penetrator 4307 is passed out of the distal end of the jaw member, as shown in FIG. 43C. As the tissue penetrator 4307 is withdrawn, as shown in FIG. 43D, the length of suture 4309 (which has passed beyond the distal end/edge of the stripper) is pinched between the stripper and the receiver (e.g., the lower surface of the jaw member). Once the tissue penetrator 4307 has been completely withdrawn, the suture 4309 remains held by the stripper in the jaw member.

In practice, a suture passer having a distally-extending tissue penetrator may be used to repair a tissue such as the meniscus of the knee. FIGS. 44A-44F illustrate one method of repairing a torn meniscus using a suture passer such as the one shown above in FIGS. 39A-39C.

The devices described herein may be used to pass a loop of suture and specifically, may be used to form a vertical or horizontal stitch to repair tissue. When repairing the meniscus, a vertical stitch typically provides the strongest repair with the least amount of displacement relative to horizontal stitches or other "all-inside" approaches. The devices and methods described herein may also be referred to as "all-inside" devices and meniscal repair techniques allow the meniscus to be sutured directly. The suture passers described herein may place a fully-circumferential, vertical stitch around meniscal tears. This stitch may provide uniform compression along the entire height of the meniscus and maintain coaptation of the tear at both the inferior and superior meniscal surfaces. Further, because of the jaw and needle configuration, the distal extending tissue penetrator does not penetrate the capsule wall, reducing or eliminating risk to posterior neurovascular structures. These features may allow a greater healing response due to complete tissue coaptation along the entire substance of the tear, improved clinical outcomes due to the greater healing response and to the anatomic reduction and fixation of the meniscus tear, may avoid scalloping or puckering of the meniscus, and may result in less extrusion or peripheralization of the meniscus caused by over-tensioning of suture or hybrid tensioners to the capsule. These devices can also be used to treat radial, horizontal, flap, and other complex tears in addition to longitudinal tears.

In some variations, the suture passer devices described herein can be fired blindly where arthroscopy camera access is poor, as knee structures are protected from the needle path.

Returning now to FIGS. 39A-39C, as mentioned above, the device (e.g., in FIG. 39C) has a scissoring upper jaw that is curved (radiused). This curve may be configured to follow the radius of the femoral condyle. The lower jaw in this example is straight. The lower jaw may be recessed into the shaft, and may slide proximal-to-distal in order to slide under the meniscus along the tibial plateau after the upper jaw is in place along the superior surface of the meniscus. The lower jaw contains a flexible needle, which moves vertically from the lower to upper jaw.

Figure 44C:
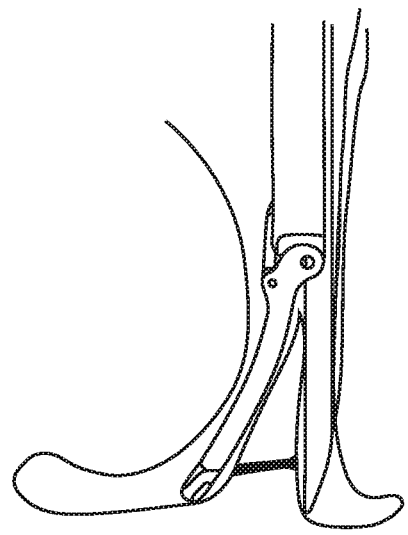
FIGS. 44A-44G and 45A illustrate one method of suturing a tissue in a loop using a suture passer such as the suture passer shown in FIG. 39A.
Figure 44F:
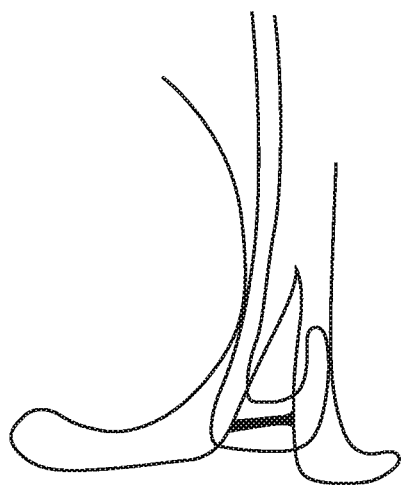
Figure 44B:
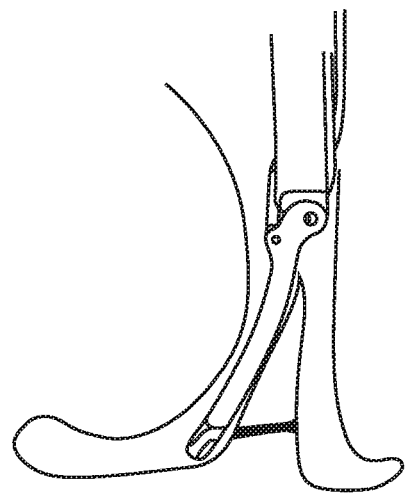
Figure 44E:
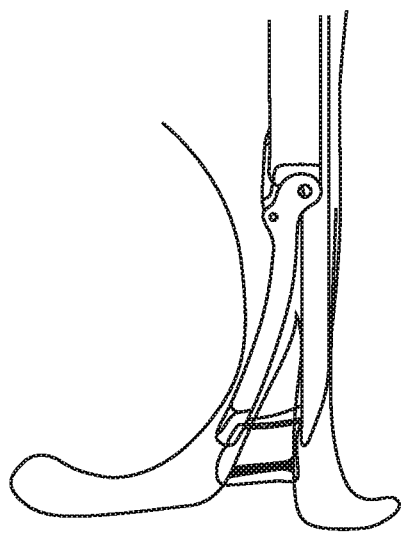
Figure 44A:
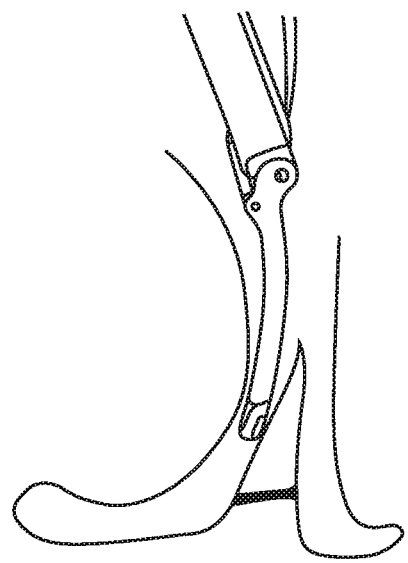

FIGS. 44A-44F illustrate one method of using a suture passer as illustrated in FIGS. 39A-39C to repair a torn meniscus. As mentioned, the upper jaw of the suture passer may be positioned between the superior surface of the meniscus and the femoral condyle, as shown in FIG. 44A. The thin and slightly curved upper jaw follows the curve of the femoral condyle. The lower jaw is retracted within the elongate body, and has been loaded with two lengths of suture (from end regions of the same suture).

Figure 44D:
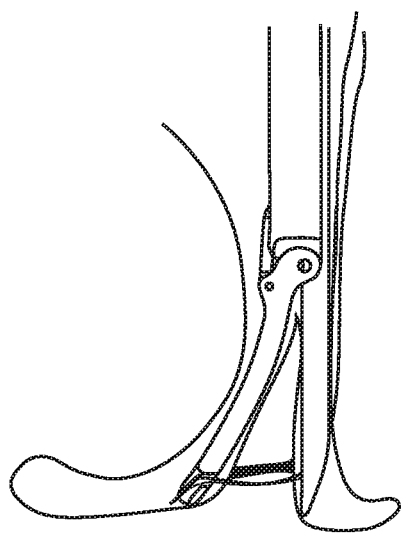

In FIG. 44B, the lower arm is initially retracted; after the upper arm is positioned adjacent to the torn region to be sutured, the lower jaw is extended underneath the meniscus, as shown in FIG. 44C. The sliding lower jaw may more easily accommodate the spatial constraints of the knee than a fixed or scissoring lower jaw. As described above, the lower jaw member in this exemplary device houses a flexible tissue penetrator (e.g., needle) that can be advanced through the meniscus to deliver suture bights from the lower jaw to the upper jaw. Once the device is in position distal to a longitudinal tear or adjacent to a radial tear, the tissue penetrator is advanced from the lower arm to the upper arm. The tissue penetrator pulls one end of the suture strand from the lower jaw to the upper jaw, where it is retained. The tissue penetrator does not pass through the upper jaw, so the femoral condyle remains protected; instead the tissue penetrator extends from a distal opening in the upper jaw, as shown in FIG. 44D. The tissue penetrator is withdrawn into the lower jaw where it engages the opposite end of the suture strand. The device is then repositioned for the second bight, either proximal of a longitudinal tear (see FIG. 44E) or to the other side of a radial tear (not shown in the example). Once in position, the tissue penetrator is advanced to deposit the remaining suture bight in the upper jaw, as shown in FIG. 44E.

Figure 45C:
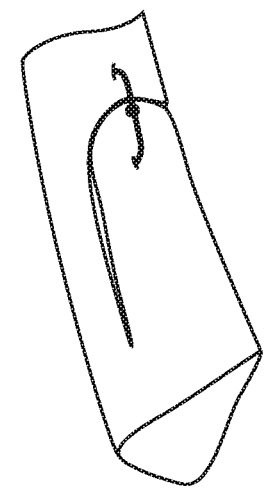
FIGS. 45B and 45C illustrate suturing complex meniscal tears, including those having a radial tear, using a suture passer such as the one shown in FIG. 39A.
Figure 44G:
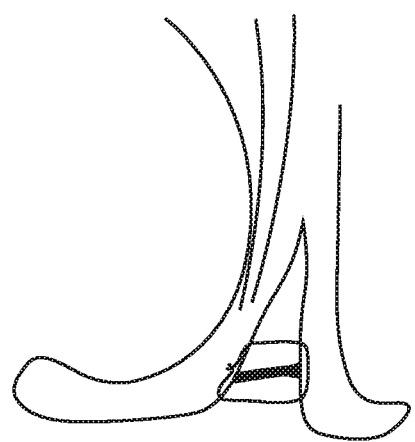
Figure 45B:
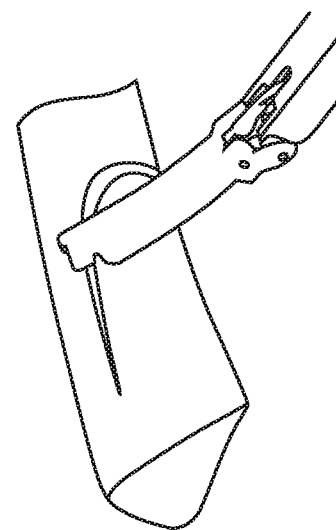
Figure 45A:
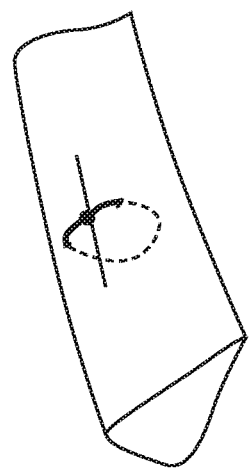

The tissue penetrator can then be brought back into the lower jaw, the lower jaw retracted, and the device may be withdrawn from the knee, leaving a suture loop surrounding the tear, as shown in FIG. 44F, with both ends exiting on the femoral side. A surgeon may then tie and advance a sliding knot (or individual throws) percutaneously, and the loose ends cut, as shown in FIG. 44G. Since both suture-ends may be retrieved through the same track, a cannula is not required to prevent tissue bridging. This may result in a fully-circumferential, vertical stitch around the tear, as shown in FIG. 44G. This vertical stitch completely surrounds the meniscal tear, bringing the superior and inferior margins of the tear in apposition along with the meniscal area in between. FIG. 45A shows a perspective view of a portion of a meniscus repaired in this manner. FIGS. 45B and 45C illustrate how the device and methods described above may also be used to suture more complex meniscal tears, including those having a radial tear.

Figure 46I:
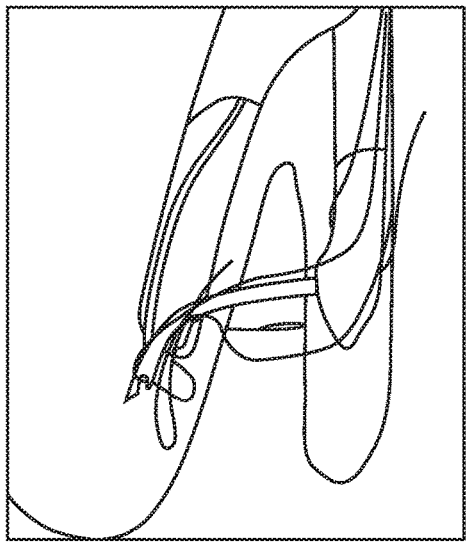

FIGS. 46A-46L illustrate another example of a method for suturing a torn meniscus by passing a loop of meniscus. As just described, the exemplary device shown in FIGS. 39A-39C may be used or other variations of the suture passer devices described herein may be used to suture a torn meniscus. In this example, two regions of a suture are initially loaded into the suture passer in the lower jaw. For example, the first length of suture may be loaded into the tissue penetrator and a second length of suture may be held in a holding region of the lower jaw; the lower jaw may be configured so that once the first length of suture has been passed into the upper jaw member and the tissue penetrator has been retracted, the second length of suture may be loaded into the tissue penetrator for passing through the tissue. In FIG. 46A, the ends of the suture are shown loaded into the lower jaw. In FIG. 46B and subsequent FIGS. 46C-46K, the upper jaw has been removed from the device shown in FIG. 46A to show the deflecting surface and suture stripper (a sheet of metal) in the upper jaw. In FIG. 46C, the tissue penetrator may then be extended from the lower jaw, carrying a length of suture, and pushed through the meniscus towards the upper jaw. The suture passer may then enter into the upper jaw and be deflected by the deflector region within the upper jaw so that it extends distally out of the upper jaw member, as shown in FIG. 46D. In this example, as the tissue penetrator pushes up into the upper jaw it pushes the stripper out of the way, allowing the suture to advance beyond the end of the stripper. In FIG. 46E, retracting the tissue penetrator leaves the suture held by the stripper in the upper jaw. The stripper places a downward force on the tissue penetrator as it retracts, this force strips the suture off of the tissue penetrator and then pins the suture length in the upper jaw.

As shown in FIG. 46F, the device may then be repositioned to fire a second time. The device is moved to the second location. Moving the device does not dislodge the suture from the upper jaw, as it is secured by the stripper. Retracting the tissue penetrator into the lower jaw may cause the second end of the suture to be loaded into the tissue penetrator, as shown in FIG. 46G.

Figure 46H:
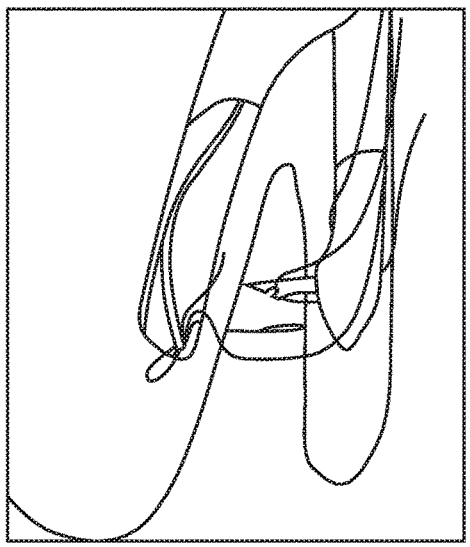
Figure 46G:
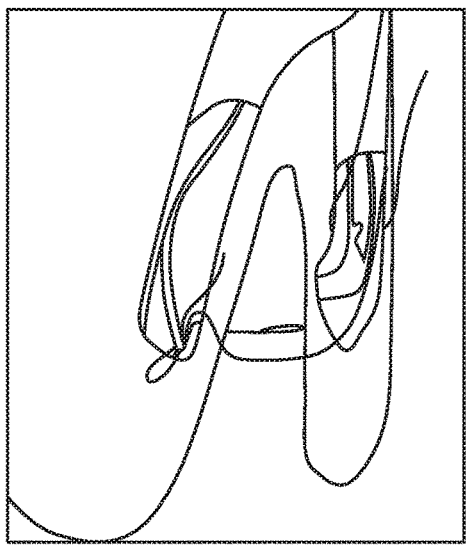
Figure 46L:
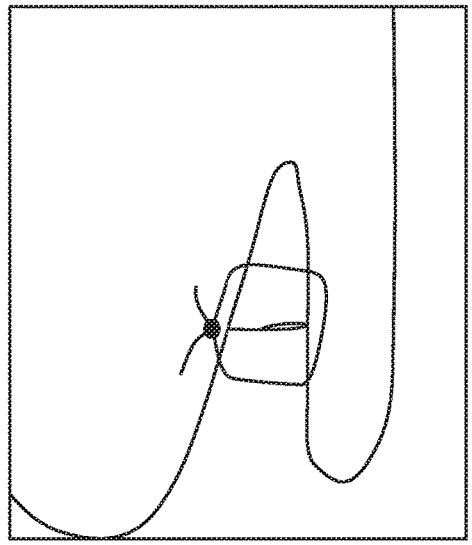
Figure 46K:
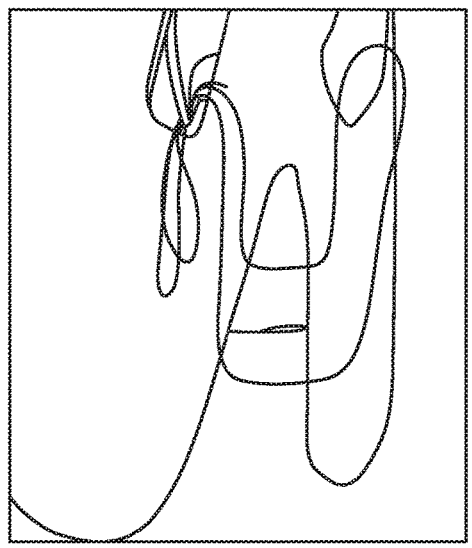
Figure 46J:
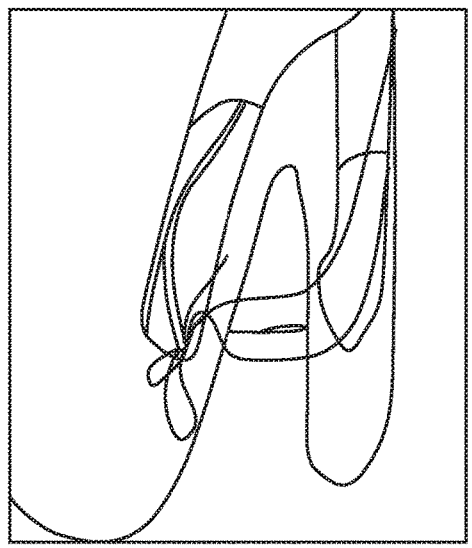

The tissue penetrator can then be extended back across the tissue from the second position on the opposite side of the meniscal tear, as shown in FIG. 46H. The tissue penetrator carries the second length of suture with it to the upper jaw, and past the stripper again, as shown in FIG. 46I. As before, withdrawing the tissue penetrator after extending it out of the distal end of the upper jaw so that the second length of suture extends beyond the stripper results in the stripper retaining the second length of suture along with the first length of suture, as shown in FIG. 46J. The device may then be retracted with both sutures pinned in the upper jaw, as shown in FIG. 46K. The device may be fully retraced, and the ends of the suture tied, as shown in FIG. 46L.

As mentioned above, in some variations the suture passer may be loaded (including preloading or manually loaded) with two or more lengths of suture (e.g., two loops or bights of suture) than may be passed sequentially. FIGS. 47A-47E illustrate one variation of a lower jaw and tissue penetrator that are configured to be used as part of a suture passer that can hold and pass two lengths of suture. In FIG. 47A, a jaw member (e.g., lower jaw member) that has a suture loading region 4703 adapted to hold a second length of suture while the first length of suture is held in a suture retainer region 4705 in the tissue penetrator 4701. The jaw member shown in FIG. 47A is not yet loaded with a suture, and includes a central channel 4711 into which the suture may be fed to load the device. The tissue penetrator 4701 is held within the jaw, and is configured to slide axially distally/proximally and can exit the jaw member though a deflecting exit 4715 that directs the tissue penetrator across an opening formed between the jaw members. FIGS. 47B-47E illustrate loading of a pair of suture loops into the tissue penetrator and suture loading region 4703. For example, in FIG. 47B, the first suture loop 4709 has been passed into the central channel 4711 of the jaw member. This first loop of suture 4709 passes though the suture loading region 4703 of the jaw member and into the suture retainer or holder region 4705 in the tissue penetrator, as shown in FIG. 47C. This may be achieved by positioning the tissue penetrator at a particular region within the jaw member so that the suture retainer region 4705 is continuous with the edge (which may be curved) of the suture loading region 4703 so that the suture passes into the suture retainer region of the tissue penetrator. A second loop of suture 4708 may then be loaded by again passing the loop over a portion of the jaw member and into the central channel 4711. The tissue penetrator may be moved distally or proximally to make room for the second suture loop within the suture loading region 4703 without interfering with the suture already in the tissue penetrator, as shown in FIG. 47D. Once loaded, the tissue penetrator may be advanced slightly distally to secure the two suture loops within the lower jaw, as shown in FIG. 47E. After the first length of suture has been passed to the opposite jaw and held there, the tissue penetrator may then be extended back into jaw member and loaded with the second loop of suture, similar to FIG. 47C.

In some variations, the devices described herein may include one or more suture management features such as suture tensioners, suture cleats, suture clamps, suture channels, and/or other structures that guide, hold, apply tension, and release the suture. These suture management features may be generically referred to herein as suture cleats.

A suture management feature such as a cleat and/or tensioner may be used to hold one or more lengths of suture, and may generally aid in preventing the suture from dropping off of the device and/or becoming tangled. A suture management feature may also help in automatically loading a length of suture in a tissue penetrator, as described above in reference to FIGS. 47A-47E. A suture management feature may maintain and/or control the tension on the suture as the device is operated. For example, a suture cleat may be biased (e.g., spring loaded) to maintain a relatively constant tension on the suture during operation, or may be used with a tensioning member (such as a tension arm or pin). As mentioned, a suture management feature such as a cleat may include a projection, pin, clamp, tensioner or other structure that holds the suture (or multiple lengths of suture). Further, in some variations a suture management feature such as a cleat may be releasable, either manually or automatically, so that when a suture or multiple lengths of suture are secured by the cleat the suture(s) may be released from the cleat by triggering a cleat release.

As used herein, a suture cleat may include an opening into which the suture may be held. For example, a suture cleat may include a projection to which a length of suture may be secured. The cleat may hold the length of suture by clamping the suture or by providing a typically wedge-shaped opening into which the length of suture may be captured. In some, but not all, variations the suture may be wrapped around the cleat. In some variation, the cleat may actively, e.g., by spring or biasing member, pinch the suture(s) between one or more surfaces to secure the suture(s). A suture may be removed from the cleat manually (e.g., by manually pulling the suture out of the cleat) or automatically. For example, a cleat may include a pushing member that pushes the suture out of the cleat. In some variations a projecting portion of the cleat may be configured to retract, e.g., into the jaw member, releasing any suture held therein. In some variations, a clamping portion of the cleat may be configured to release or relax any clamping force holding the cleat. Release of a length of suture from the cleat may be triggered by an actuation mechanism including a mechanical mechanism (e.g., lever, toggle, cam, etc.) or electrical/magnetic mechanism (e.g., solenoid, motor, magnetic catch, etc.). In some variations the cleat may be triggered to release a length of suture during a particular step in the operation of the suture passer. For example, the suture may be released from the cleat when the tissue penetrator is retracted for reloading with a second bight of suture; the suture cleat may release the suture so that a bight of suture can be transferred from a suture loading region in a jaw into a tissue penetrator.

Thus, in variations in which multiple bights of suture are loaded in to the device, a suture management feature may be used to hold and/or tension a second length of suture within the lower jaw member so that it may engage with the tissue penetrator after the first loop of suture has been passed. For example, FIG. 59A shows a distal portion of a lower jaw member 5901 and tissue penetrator 5903 into which two loops of a suture have been loaded. A first loop 5905 has been loaded into the tissue penetrator, and a second loop 5909 has been loaded into a suture loading region of the jaw, as described in FIGS. 47A-47E. The ends 5915, 5917 are loose, as is the length of suture between the two bights 5913. In some instances it may be beneficial to secure the free ends of the bight 5909 that is loaded in the suture loading region 5917, 5913. It may also be advantageous to hold the second bight under tension. By securing the ends 5917, 5916 of this second loop/bight 5909, and by holding it in tension, it may be primed for automatically loading into the needle after the needle has passed the first bight to the opposite jaw, as described above. This is illustrated in FIG. 59B, showing the second bight 5916 held taught with the ends of the bight 5916, 5917 (not visible in FIG. 59B) secured to a suture cleat.

Figure 59B:
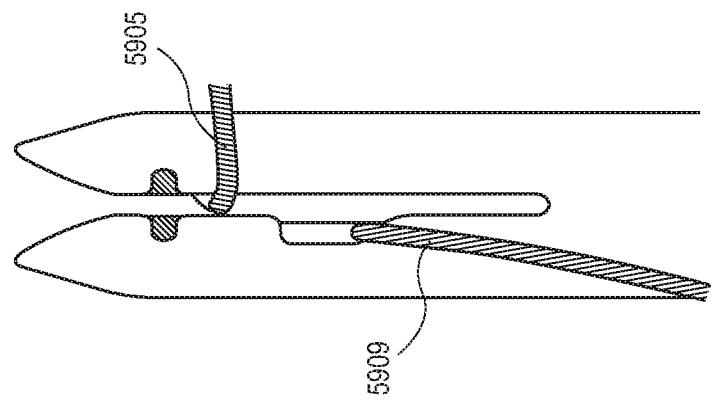
FIG. 59B shows a top views of the jaw member of FIG. 59A in which the second suture bight is held taught by a suture management element.
Figure 59A:
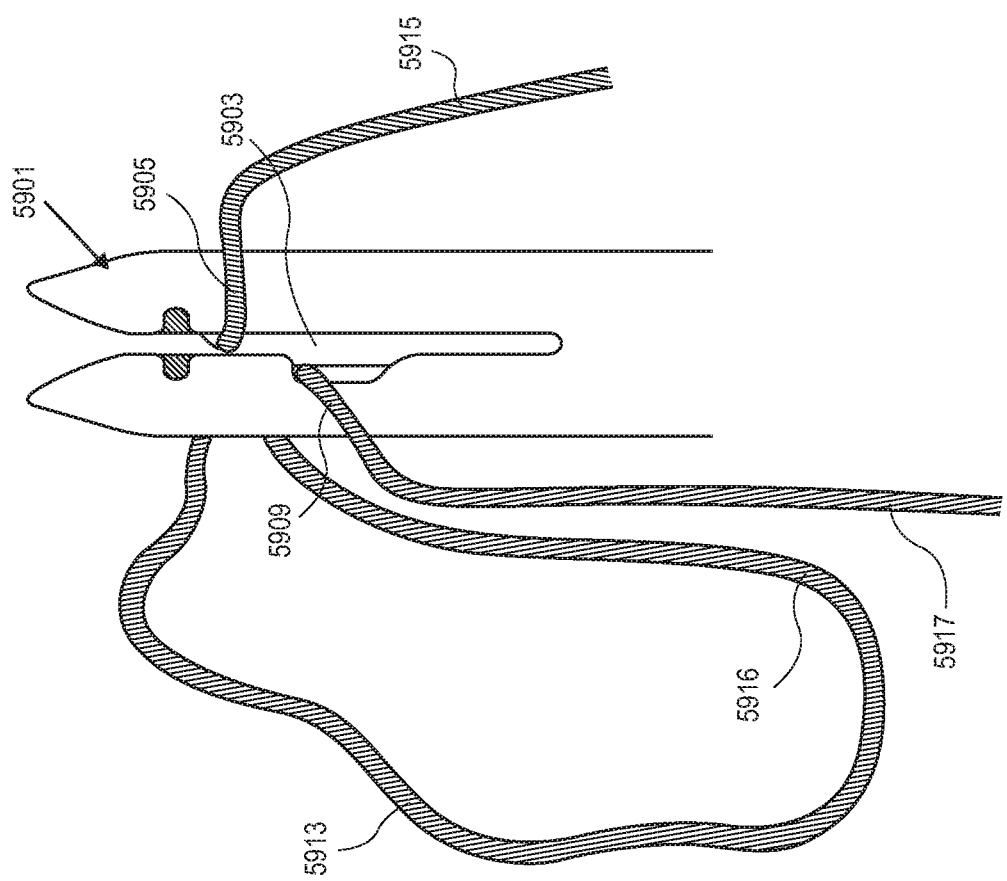
FIG. 59A shows a top view of one variation of a jaw member in which to loops (bights) of suture have been loaded.
Figure 59C:
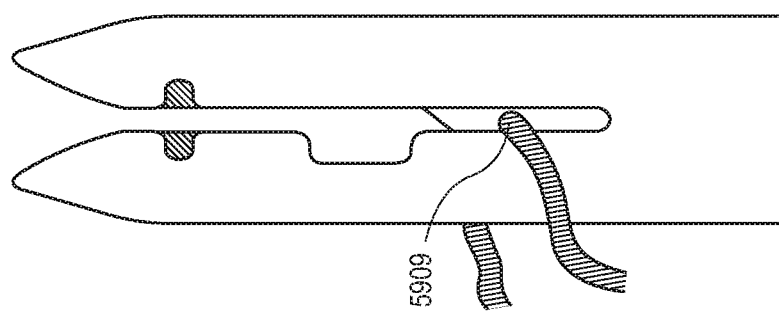
In FIG. 59C the suture bight has been automatically loaded into the suture retainer region of a tissue penetrator.
Figure 59D:
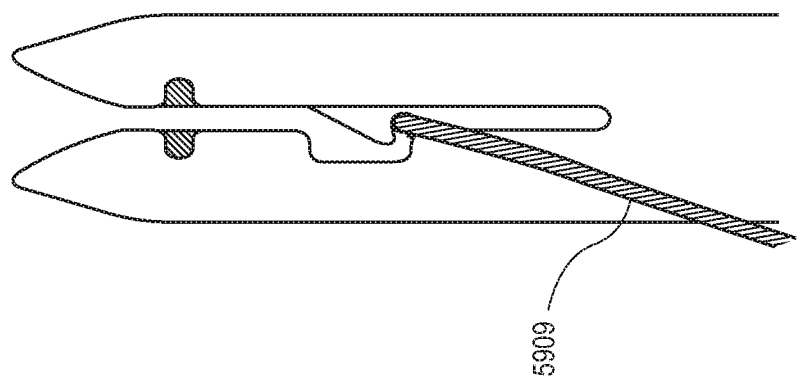
FIG. 59D shows the same view of the jaw member after the suture management element has released the suture bight.

Pulling this second suture bight taught as shown in FIG. 59B by holding the ends of the suture bight in the cleat may help with automatically loading the second bight into the tissue penetrator, as illustrated in FIG. 59C. In this example, the tissue penetrator has been retracted proximally, exposing the opening of the suture retainer region. Tension on the suture loop, as well as the shape of the suture holder region on the jaw has driven the suture loop 5909 into the suture retainer region. Thereafter, the tissue penetrator may be withdrawn further proximally, and the suture cleat automatically (or manually) disengaged, releasing the ends of the second bight so that the second loop is loose, though held in the suture retainer region of the tissue penetrator, as shown in FIG. 59D.

Figure 59E:
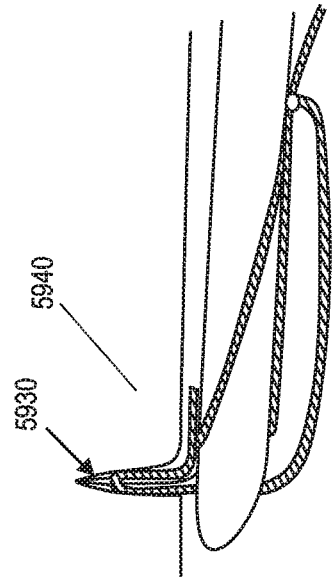
FIGS. 59E-59H illustrate the use of a suture management feature to secure and apply tension to one of the loops of suture loaded into the jaw member of FIG. 59A during loading and operation of a suture passer.
Figure 59F:
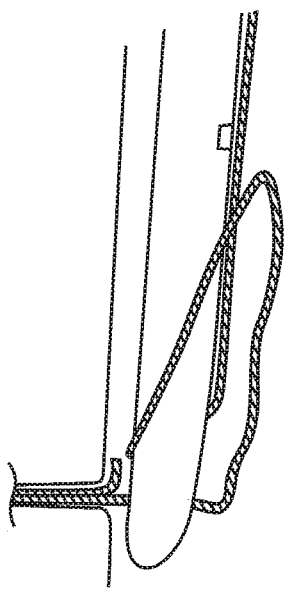
Figure 59G:
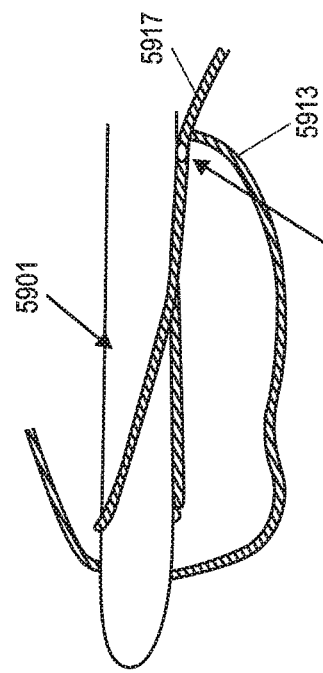
Figure 59H:
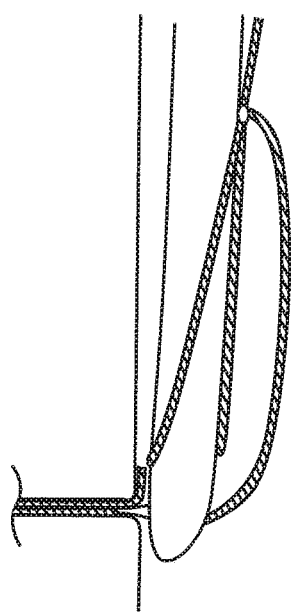

FIGS. 59E-59H show a side view of the distal end of the lower jaw region shown in FIGS. 59A-59D, in which the loose ends of the second bight are secured (with slight tension) using a cleat. In FIG. 59E, which is a side view of a jaw member corresponding to the top view shown in FIG. 59B, the free ends of the second suture bight are held in tension against the lower jaw 5901 by a cleat 5920. The loop of suture is held in slight tension, pulling the suture bight proximally within the suture holding region and preventing it from falling out of the suture loading region which may also help pull it into the suture holding region of the tissue penetrator after passing the first bight. For example, in FIG. 59F the lower jaw is shown adjacent to a region of tissue 5940; the upper jaw is presumed to be positioned on the opposite side of this portion of tissue (not shown). The tissue penetrator 5930 is shown extending though the tissue, pushing the first bight through the tissue, while the second bight is held securely in the lower jaw by the cleat. FIG. 59G shows the device and tissue after withdrawing the tissue penetrator, leaving the first bight in the tissue. The side view of FIG. 39G corresponds to FIG. 59C. Thereafter, the tissue penetrator may be retracted proximally to engage the second bight so that it may be passed through a different region of the tissue. After retracting the tissue penetrator and re-loading it with the second bight, one or both ends of the second bight may be released from the cleat. In some variations the cleat holding the second bight may be configured to automatically release one or both ends of the suture, as illustrated in FIG. 59H. FIG. 59H is a side view corresponding to the top view of FIG. 59C. In this example, retraction of the tissue penetrator (not visible) proximally may trigger release of the suture from the cleat; in FIG. 59H the cleat has been retracted into the lower jaw, dropping the lengths of suture. In some variations the cleat may pinch or engage the length(s) of suture by a friction or grasping mechanism, and retraction of the tissue penetrator and/or loading of the second bight onto the suture passer may cause the release of the lengths of suture from the cleat.

The lengths of suture shown in FIGS. 59A-59H may not be to scale, and may not be as loose within the body as they are shown. For example, when using the device in the region of the meniscus, the suture may be held between the lower jaw member and the tibia/meniscus. For simplicity, the lengths of suture are shown relatively free; in operation within the (more crowded) tissue spaces, the principles described herein apply.

Figure 60:
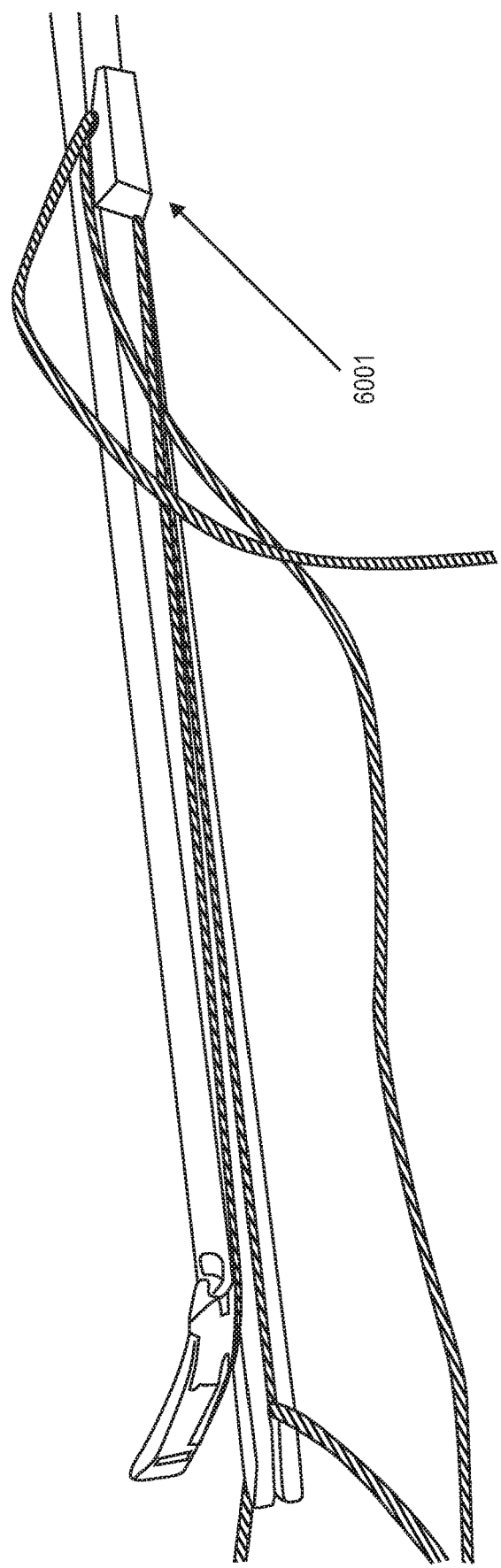
FIG. 60 shows a bottom perspective view of one variation of a suture passer device similar to the device shown in FIGS. 39A-40D, including a suture cleat holding a suture.

FIG. 60 shows a bottom view of one variation of a suture passer device similar to the variation shown in FIGS. 39A-39D, including a suture management feature (a suture cleat in this example) securing the end of a bight of suture that has been loaded into the suture passer. In this example, a suture cleat 6001 is located on the lower or second jaw member that is axially movable in the long axis of the device. Thus, as the lower jaw is extended or retracted, the cleat moves with the lower jaw. In some variations the cleat is a tensioning member that may adjust the tension on the suture and/or suture loop. One or more suture management features may be included on any appropriate region of the suture passer, including the first jaw member, second jaw member, tissue penetrator, elongate member, handle, etc.

Figure 61A:
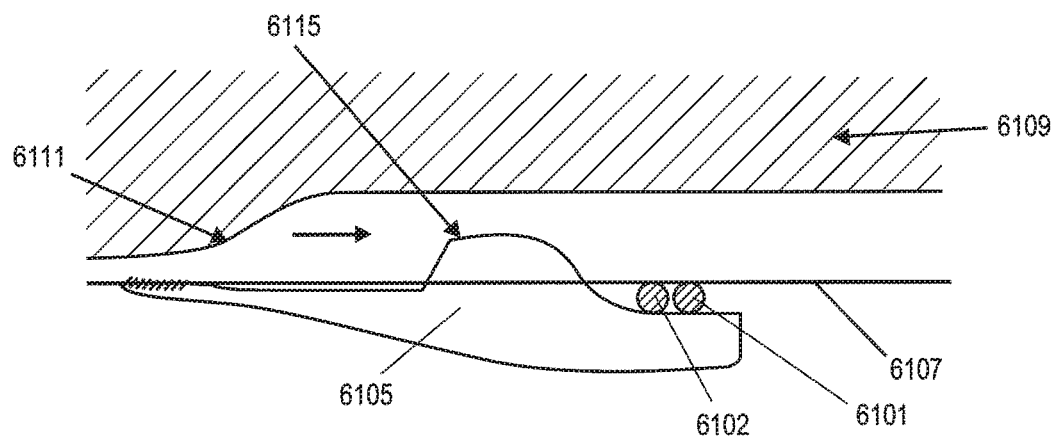
FIGS. 61A and 61B illustrate one variation of a suture management feature (e.g., cleat) configured to automatically release one or more lengths of suture during operation of a suture passer.
Figure 61B:
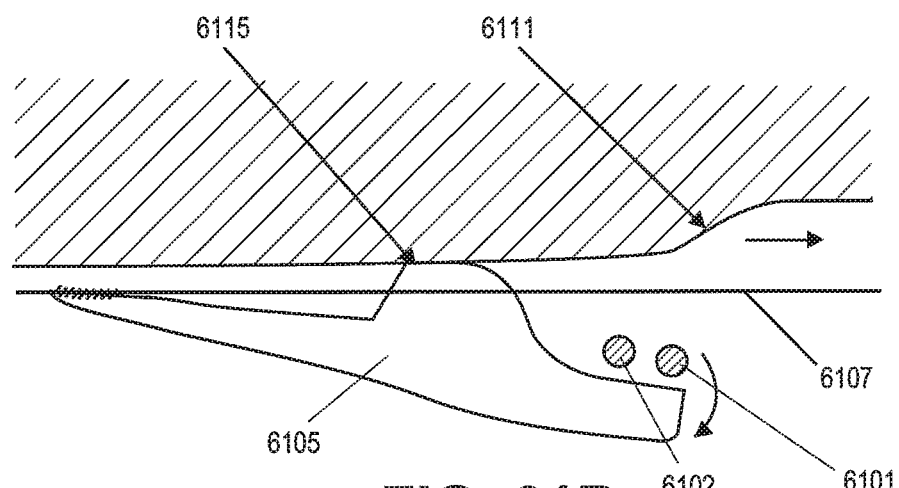

As mentioned, a suture cleat may be configured to automatically release a length(s) of suture, or reduce or release tension on the suture, when the second length of suture is ready to be loaded onto the tissue penetrator. One example of an automatic release cleat is illustrated in FIG. 61A. In this example, the cleat holds two lengths of suture 6101, 6102 securely against the outer surface of the lower jaw. In FIGS. 61A and 61B the suture is shown only in cross-section, where they are held and released by the cleat. For example, in FIG. 61A, the cleat 6105 pinches the lengths of suture 6101, 6102 against the wall 6107 of the lower jaw member. In this example, the cleat is configured as a leaf spring that is pre-biased against the lower jaw member; the distal end of the cleat is secured to the lower jaw. The cleat includes an internal cam surface 6115. Pushing against this cam surface may drive the cleat away from the wall of the lower jaw member, allowing the lengths of suture to be released, as shown in FIG. 61B. In this example, the cleat is automatically released when the cam surface 6115 is driven against a complimentary release cam surface 6111 within the lower jaw. In some variations this release cam surface is part of the tissue penetrator. Thus, as the tissue penetrator is drawn proximally to load the second bight, this release cam surface (formed as a region of the tissue penetrator) drives release of the lengths of suture from the cleat. In some variations a separate lever or other mechanism may be used. The cleat may also include a more active release mechanism, in which the lengths of suture are driven out of the cleat. For example, a release cam surface may be driven into the cleat proximally as the tissue penetrator is withdrawn proximally to load the second bight onto the tissue penetrator, and this release cam surface may drive the sutures out of the cleat.

FIGS. 62A and 62B illustrate another variation of a suture cleat, similar to the variation shown in FIG. 61A. In this example, the suture cleat 6201 is also attached at one side to the lower jaw of the suture passer 6203, and a suture 6205 is held (clamped) in the jaws at the opposite end of the suture cleat 6201. The clamping region of the cleat may be deflected away from the lower jaw, as shown in FIG. 62B. In this example, the suture (or multiple lengths of suture) can be clamped or held in the long axis of the clamping region of the cleat. Opening the clamp region allows the suture to be released, as shown in FIG. 62B. The clamp region of the cleat may be deflected by pushing against a cam surface that is connected to the clamping region. In FIG. 62B the cleat includes a region 6209 that can be used to deflect the clamping region. Thus, as just described, a suture passer for repairing meniscal tears may place two legs of a circumferential stitch with only a single insertion of the instrument into the knee. In some variations the suture passer device may be loaded with two ends of a length of suture into one jaw (i.e. the lower jaw), inserting the suture passer into the knee, having a tissue penetrator pass one suture end up to the other jaw (i.e. the upper jaw) where it is removed off of the tissue penetrator. The tissue penetrator may then return to the lower jaw and pick up the second end of the length of suture. The instrument is placed in another location, and the tissue penetrator is again advanced, passing the suture off onto the upper jaw. With both ends of the suture having traveled from the lower jaw to the upper jaw, removing the suture passer will result in a circumferential stitch around the meniscus.

In the above embodiment, one configuration for loading two ends of a single suture into the suture passer so that a single tissue penetrator can pass them with sequential advances of the tissue penetrator involves specific jaw features. For example, the lower jaw may contain a track for guiding the tissue penetrator. One section of the track is cut out leaving a space for a second suture to reside beyond the width of the needle. The space (suture holding region 4703) is identified in FIG. 47A.

Figure 48:
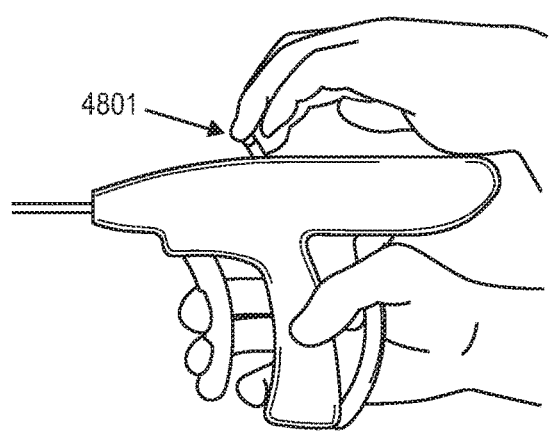
FIG. 48 shows one variation of a suture handle having a control to aid in loading the suture by adjusting the position of the tissue penetrator.

In some variations the device includes a control (e.g., switch, lever, button, etc.) that moves the tissue penetrator to assist in loading. For example, a suture passer including a proximal handle is shown in FIGS. 39C and 48. In the embodiment shown, a suture loading control 4801, to move the tissue penetrator distally or proximally within the jaw to assist in loading of the pair so suture, is indicated.

The procedure for loading a suture passer may include first loading one end of the suture into a notch contained on the tissue penetrator (e.g., FIG. 47A-47C). A suture can be pinched in place by pulling the tissue penetrator back. Next the other end of the suture may be loaded into the space that is cut out of the tissue penetrator guiding track. This second end of the suture is pulled taught away from the tissue penetrator as shown in FIG. 47D. While the second end is pulled taught into this space away from the tissue penetrator, the user flips a switch on the handle causing the needle to move distally a small amount.

Figure 49:
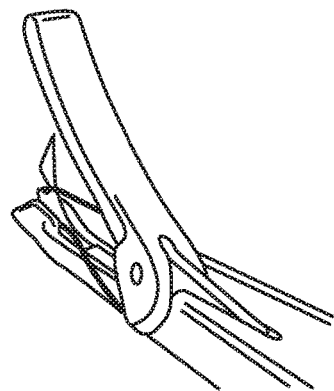
FIG. 49 shows one variation of a suture passer and tissue penetrator configured to sequentially pass two lengths of suture.

Once the suture passer has been loaded in the manner as described above, the lower jaw can be retracted. The suture passer can then be inserted into the joint with the upper jaw placed above the superior surface of the meniscus. The lower jaw is then advanced such that the meniscus is surrounded by the lower jaw and upper jaws. The tissue penetrator can then be advanced out of the lower jaw to pass the first suture leg through the meniscus. The needle may be advancing with the first suture leg without the meniscus present, as shown in FIG. 49. In this figure, the second end can be shown waiting to the side of the tissue penetrator in its space at the distal end of the lower jaw Once the tissue penetrator has passed through the meniscus, it interacts with the inferior surface of the upper jaw which causes the tissue penetrator to redirect itself tangent to the undersurface of the upper jaw. The tissue penetrator, with the first end of the suture in tow, progresses toward a suture trap which comprises a leaf spring with teeth formed at the distal end and another feature of the upper jaw also containing teeth. A cross section of an upper jaw trap is shown in FIG. 42B.

In the exemplary jaw member and method of loading and/or using the device, the two ends of the suture are loaded into the distal end with two bights: one bight for each end. One leg of the bight resides on the inferior surface of the lower jaw, and the other leg resides on the superior surface of the lower jaw. Because of the tight space in the knee joint, these legs underneath the inferior surface of the lower jaw may get pinched between the tibia and the lower jaw, restricting movement of the sutures during operation.

Figures 50A, 50B:
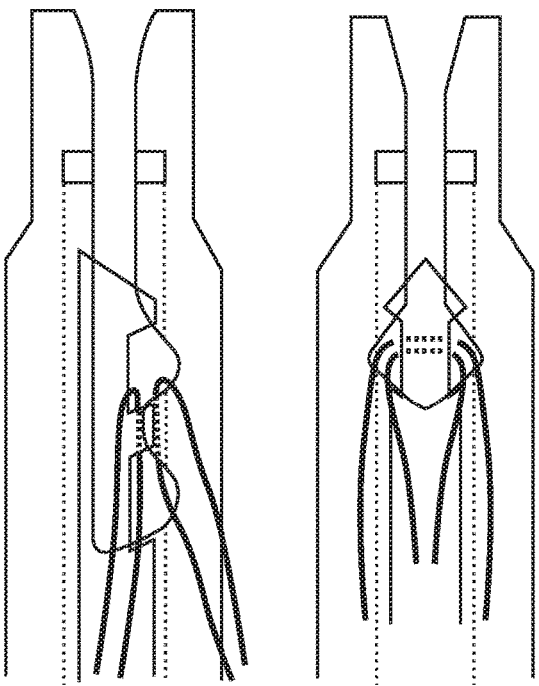
FIGS. 50A and 50B schematically illustrate two variations of suture passers in which both legs of a loop of suture are held on the same side of the jaw of the suture passer.

In some variations, the suture passer is configured to be loaded with one or more sutures so that the bights of the two ends of the suture both reside on the superior surface of the lower jaw. FIGS. 50A-50B illustrate schematically two variations in which both legs of a loop of suture are held on the same side of the device (e.g., the superior surface of the lower jaw) when loaded. These embodiments may include tissue penetrators that have two notches, allowing a suture to wrap around the tissue penetrator so that the suture can originate on the superior surface of the lower jaw, wrap around the tissue penetrator, and return on the superior surface of the lower jaw. FIG. 50A shows a tissue penetrator having two notches (adjacent to each other) on one side of the tissue penetrator, and FIG. 50B shows a tissue penetrator having two notches on opposite sides of the tissue penetrator. In both cases the suture loop may wrap around the tissue penetrator so that the length of suture before and after the loop region extends on the same side or surface of the suture passer. In both examples, the jaw in which the tissue penetrator resides is also adapted for loading the two or more sutures, and may include a suture loading region (or regions) to hold a suture loop until the suture holder in the tissue penetrator is empty of another suture.

Figure 52:
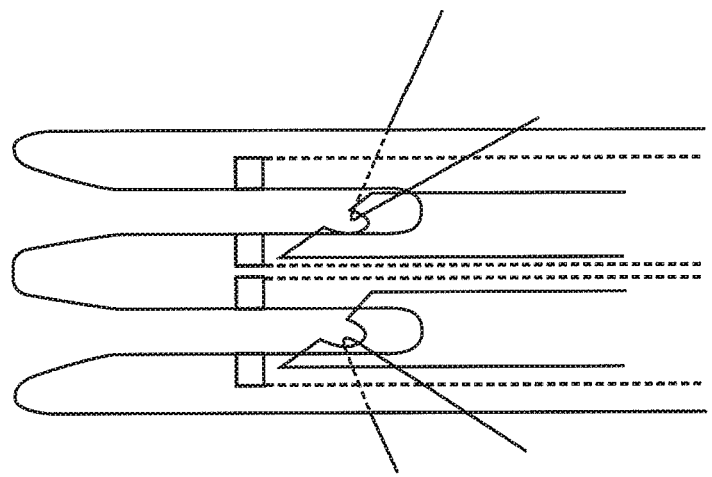
FIG. 52 shows another variation of a suture passer configured to pass two lengths of suture.
Figure 51:
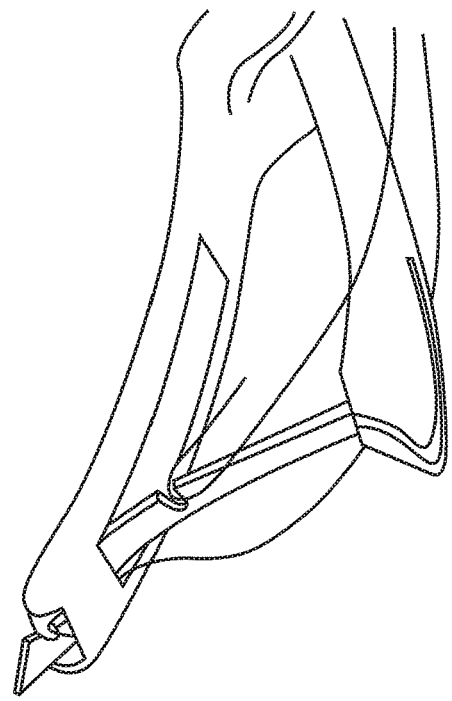
FIG. 51 shows another variation of a suture passer configured to sequentially pass two lengths of suture.

In some variations multiple loops of suture may be sequentially delivered with a tissue penetrator in which the tissue penetrator has multiple suture retainer regions. In some variations the suture retainer regions are configured as one or more notches. The suture retainer regions may be positioned along the proximal to distal length of the tissue penetrator. For example, in some variations, a second suture retainer region is positioned proximal to a first suture retainer region along the length of the tissue penetrator. In this variation, an example of which is shown in FIG. 51, the proximal handle of the suture passer may coordinate travel of the tissue penetrator so that to pass the first loop of suture in the distal most suture retainer region of the tissue penetrator, the distal suture retainer (e.g., notch) passes the suture stripper in the upper jaw while the second suture does not (by limiting the distal extension of the tissue penetrator). This is shown in FIG. 51. The second loop of suture is passed by (e.g., via a control on the handle or automatically) advancing the tissue penetrator more distally so that the more proximal suture retainer region on the tissue penetrator extends past the suture stripper in the upper jaw, trapping both the first and second loops of suture. Another variation of a suture passer adapted for passing at least two loops of suture (either sequentially or simultaneously) is shown in FIG. 52. In this example, two tissue penetrators are included in parallel, each one loaded with a suture. In some variations the tissue penetrators are side-by-side as shown in FIG. 52; alternatively, the tissue penetrators may be atop each other. The sutures may be delivered by extending each (or both) of the tissue penetrators across the tissue and into the second jaw member where a suture stripper can retain the suture(s).

As mentioned above, any of the suture passers described herein could be used for repair of soft tissue in joints, and/or to sew in allografts or artificial soft tissue constructs such as an artificial meniscal scaffold or graft. Although well adapted for meniscus repair, these devices and the underlying features of the devices are not limited to meniscus repair, and may be used and/or adapted for use in other body regions, including other joints. For example, the shape and/or dimensions of the jaw members may be adapted for use with other body regions, such as the radiusing (curve) of the upper jaw member, the thickness of the upper jaw member, and the like.

Figure 53A:
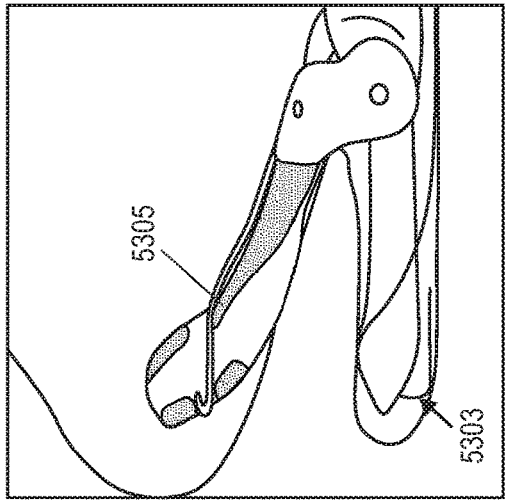
FIGS. 53A-53L illustrate another variation of a method of suturing meniscal tissue with a suture passer having a suture snare.
Figure 53B:
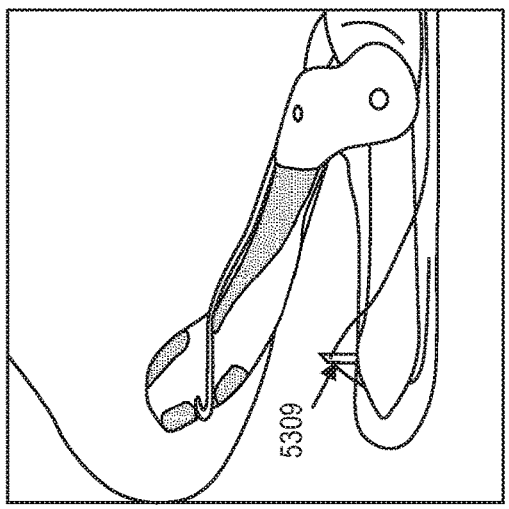
Figure 53C:
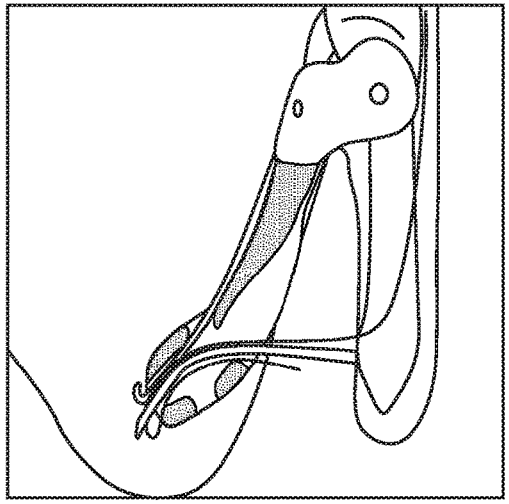
Figure 53D:
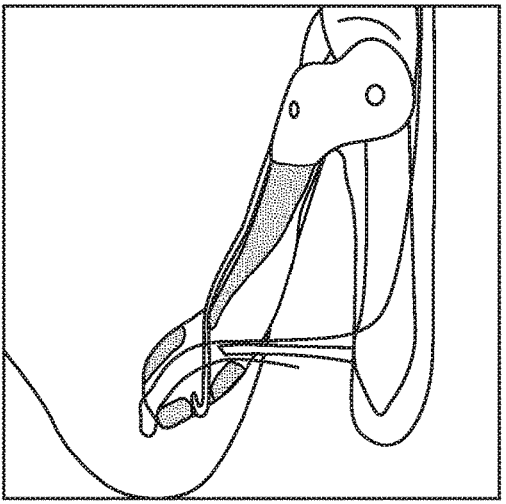
Figure 53E:
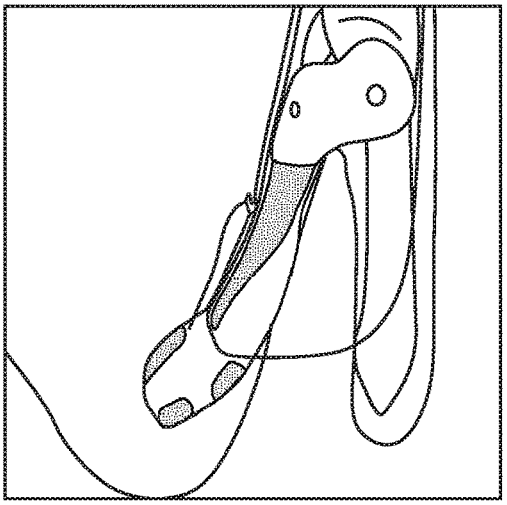
Figure 53F:
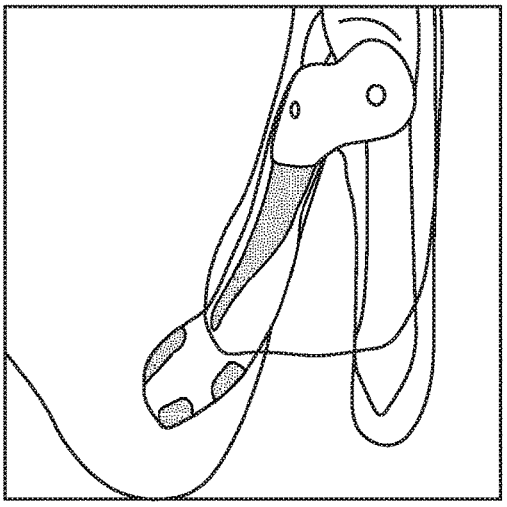

In some variations the suture passer devices include a suture puller or suture capture element for capturing and/or pulling a portion of a suture from the distal end of the suture passer toward the proximal end after it has been passed between the distal-facing jaws. FIGS. 53A-53L illustrate one variation of a suture passer and method of using the suture passer to form a loop of suture through a tissue that uses a suture puller/suture capture element (which may be referred to as a suture capture and pull element or suture snare). In this example, the suture passer may be similar to the suture passers described above, with the addition of a suture snare on the upper jaw member configured to capture and pull the suture proximally after it has been passed from the lower to the upper jaw. In FIG. 53A, the suture snare 5305 is positioned where the previously described suture stripper is located, and may function like a suture stripper. The lower jaw is loaded with a length of suture 5303 having a long end and a short end. The tissue penetrator in the lower jaw initially extends from the lower jaw carrying the loop of suture, as shown in FIG. 53B (the jaws of the suture passer may be positioned around the tissue in any appropriate manner, including those described above using pivoting upper jaw and axially extending lower jaw members). The tissue penetrator extends with the suture into the upper jaw and the distal end of the tissue penetrator extends distally from an opening in the upper jaw member, which allows the region of the tissue penetrator including the suture (the suture retainer region) to extend past the suture snare, as shown in FIG. 53C. Withdrawal of the tissue penetrator from the upper jaw and back into the lower jaw (along the sigmoidal path shown) results in the loop of suture being captured in the upper jaw by the suture snare, as shown in FIG. 53D. In this example, the suture snare is configured as a sheet of metal (configured to have a finger or teeth to help retain the suture) that detains the suture in the upper jaw. The suture snare may then be used to draw the end of the suture proximally, as shown in FIG. 53E. In some variations one end of the suture is pulled proximally out of the patient; in other variations the end of the suture is pulled only partially along the upper jaw. The suture may then be tensioned in the upper jaw. In some variations the suture snare may apply tension, in other variations the suture may be manually tensioned. As shown in FIG. 53G, the suture passer may then be repositioned on the tissue so that the rest of the loop of suture may be formed (e.g., around a tear in the tissue). As is apparent from the figures, the tissue shown in the example of FIGS. 53A-L is meniscal tissue; however any appropriate tissue may be sutured using the device and method.

Figure 53I:
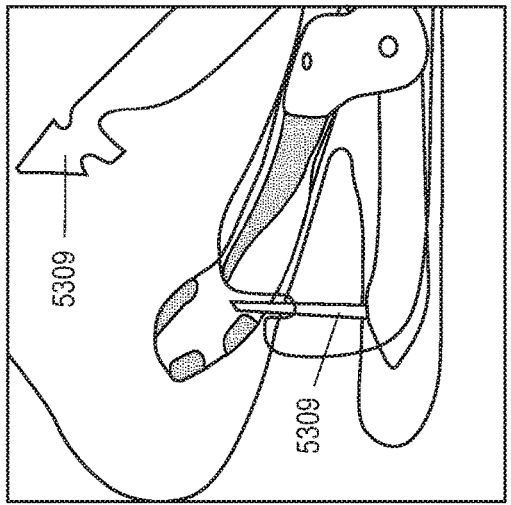
Figure 53L:
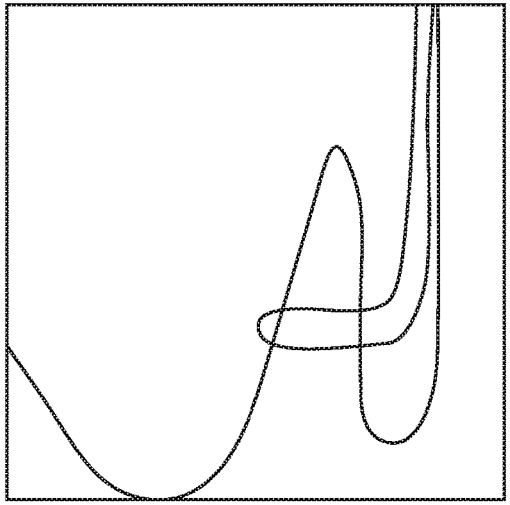
Figure 53H:
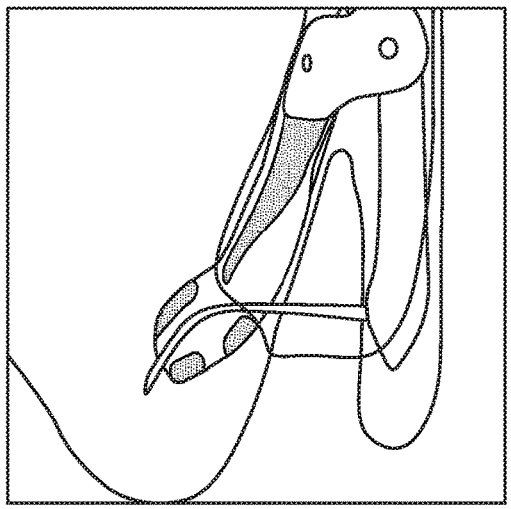

Once the suture passer is repositioned, the tissue penetrator may then be extended through the tissue to engage the end of the suture held in the upper jaw, as shown in FIGS. 53H and 53I. The tissue penetrator may be configured as a push/pull tissue penetrator. FIG. 53I illustrates one variation of a push/pull tissue penetrator 5309 that may be used. In this example, the tissue penetrator includes dual suture retainer regions: one for retaining the suture as it is driven from the lower to the upper jaw, and one for retaining the suture as it is withdrawn from the upper to the lower jaw. In some variations the tissue penetrator is configured so that a single suture retainer region can hold the suture in both directions. For example, a hook region may be configured to hold the suture in both directions.

Figure 53K:
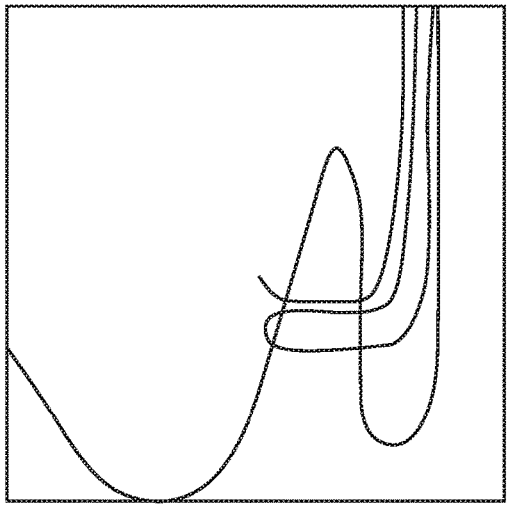
Figure 53G:
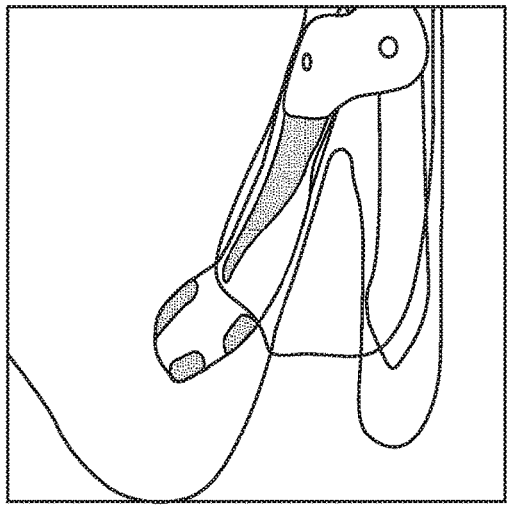
Figure 53J:
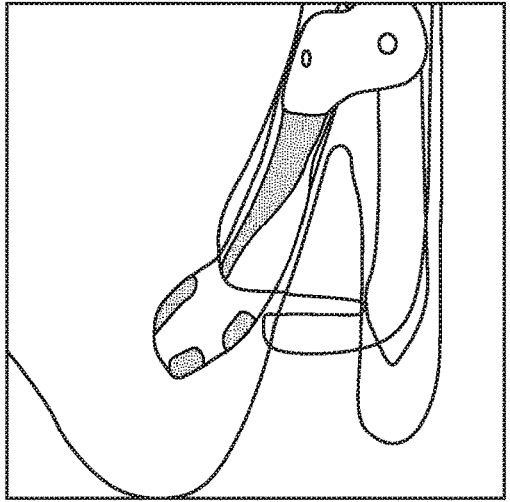

In FIG. 53J the suture has been pulled back to the lower jaw and captured by the lower jaw (e.g., within the tissue penetrator and/or a suture capture region and/or suture stripper in the lower jaw). The device may then be removed from the tissue, as shown in FIG. 53K, pulling the loose end of the suture through the tissue and creating a loop passing through the tissue, as shown in FIG. 53L. The ends of the suture may then be knotted (e.g., to each other), completing the loop.

Figures 54A, 54B:
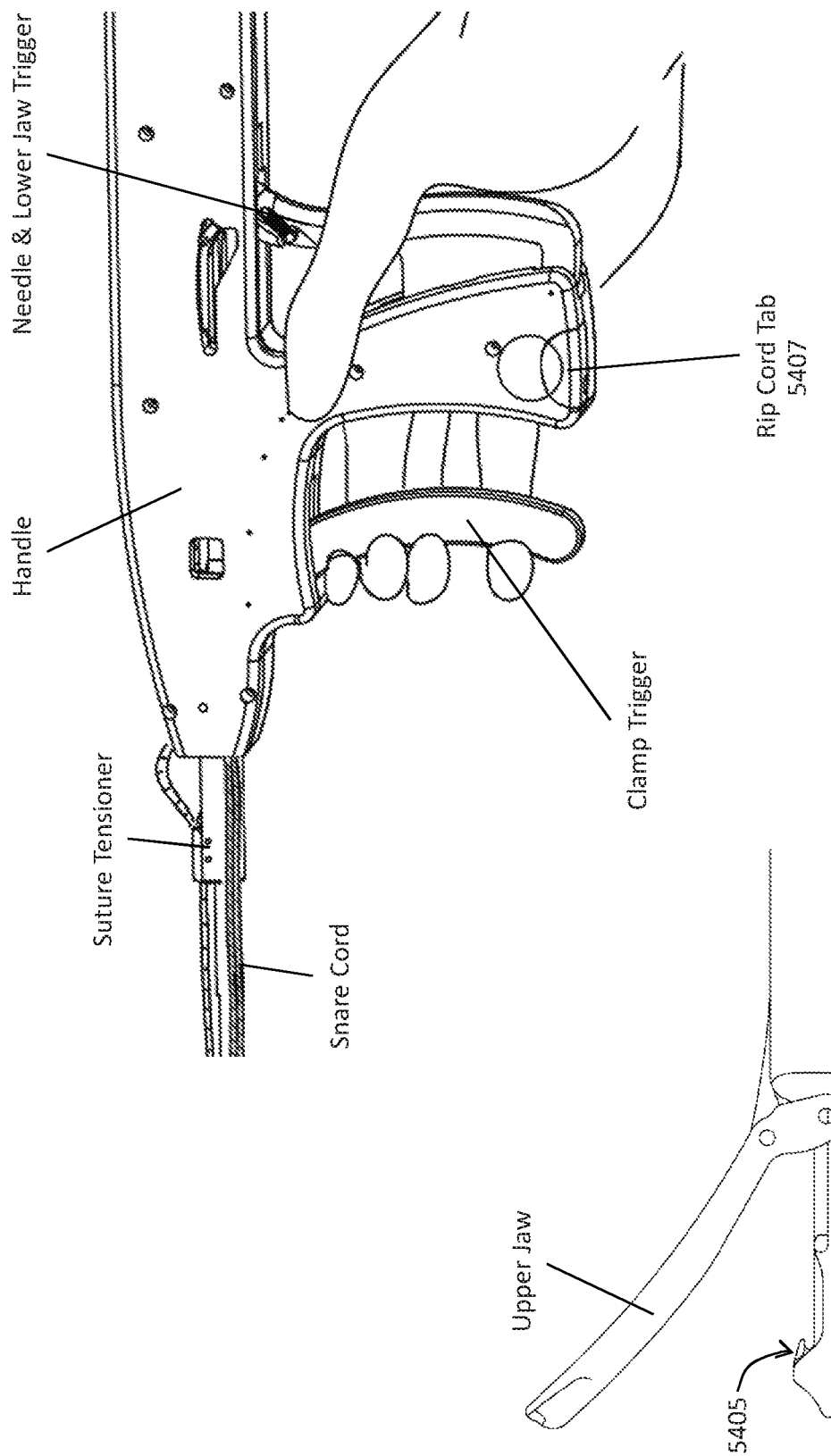
FIG. 54A illustrates another variation of a suture passer and FIG. 54B shows greater detail on the distal end of the suture passer.

Another variation of a suture passer including a suture snare is shown in FIG. 54A. In this example, the suture passer include a distal facing opening formed from a pivoting upper jaw and an axially sliding lower jaw, and a suture snare 5405 on the lower jaw configured as a loop that may be withdrawn (via a snare cord) proximally after passing the first suture bight. In this example the suture snare is connected at the proximal handle to a rip cord and rip cord tag 5407. This variation of the device may be loaded (e.g., preloaded) with a suture in the upper jaw member. FIG. 54B shows an enlarged view of the distal end of the device, The upper jaw is configured to be pre-loaded with a suture that can be held in tension in the upper jaw. The lower jaw houses the tissue penetrator that is configured to move in a sigmoidal path as well as the suture snare described above. The end of the tissue penetrator may pass through the snare as it extends and retracts, allowing it to choke onto the suture after it has been passed, as illustrated in FIGS. 55A-55DD.

In operation, the suture passer device of FIG. 54A may be used pass a suture in a loop around a target tissue (e.g., meniscus). For example, in FIG. 55A, the distal end of the device is first inserted into the knee. The suture is preloaded (or has already been loaded) on the upper jaw and tensioned (e.g., cleated) so that the suture has sufficient tension to allow it to be engaged by the tissue penetrator and drawn down through the tissue.

Figure 55C:
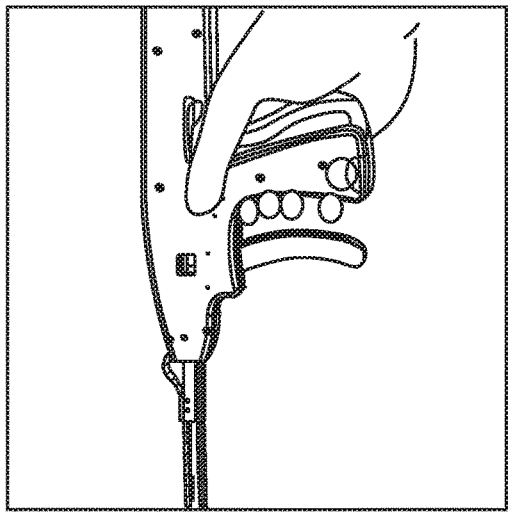
FIGS. 55A-55DD illustrate a method of suturing meniscal tissue using the suture device of FIG. 54A.
Figure 55F:
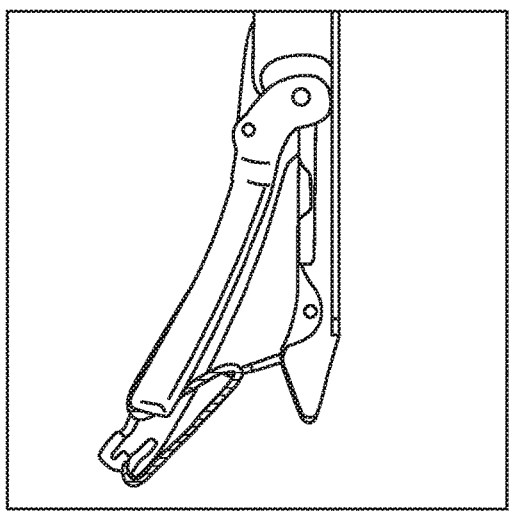
Figure 55B:
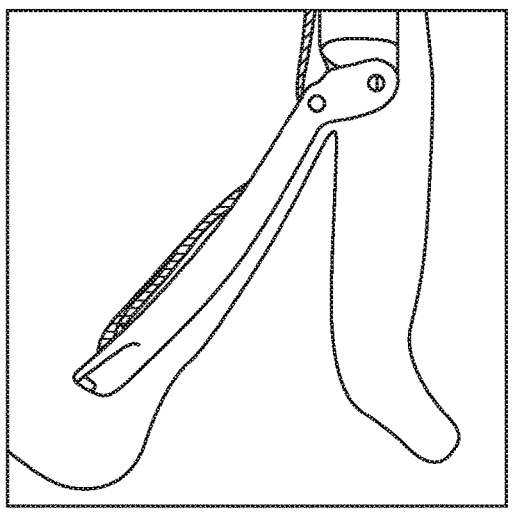
Figure 55E:
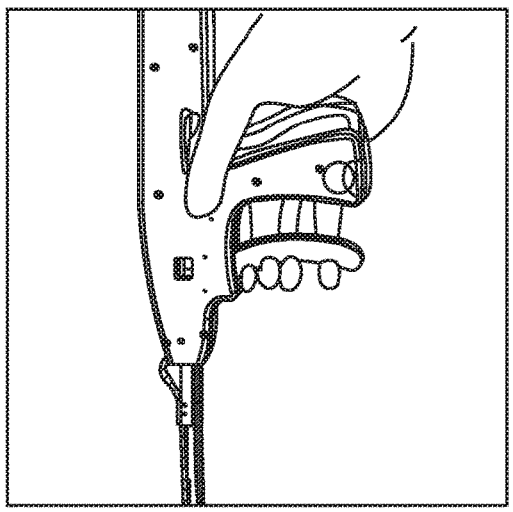
Figure 55A:
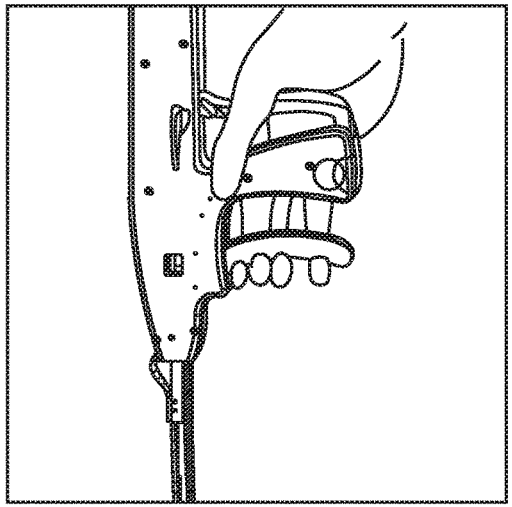
Figure 55D:
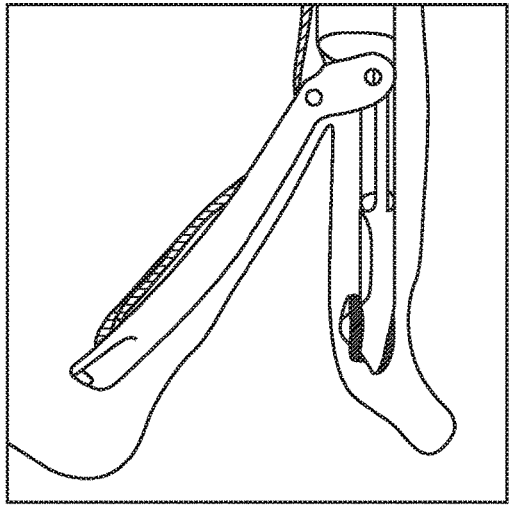

FIGS. 55B to 55D show positioning of the tissue passer around the target tissue. In positioning the device, the clamping trigger on the handle can be used to control the rotation of the upper jaw, as shown in FIG. 55A and 55B. Thus, the upper jaw can be positioned immediately adjacent to the tissue to be sutured, and the tissue can be clamped in the mouth of the device after using the handle to extend the lower jaw member by depressing a control (e.g., a lower jaw trigger control on the handle) as shown in FIG. 55C and 55D. The device may be positioned and repositioned until it is positioned as desired. In any of the methods described herein, imaging (e.g., arthroscopy) can be used to guide the procedure.

Figure 55I:
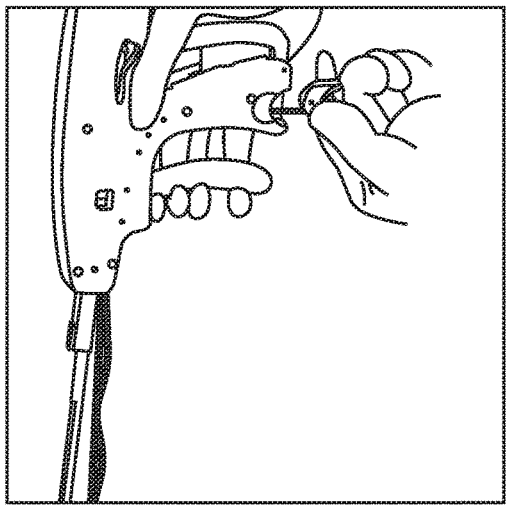
Figure 55L:
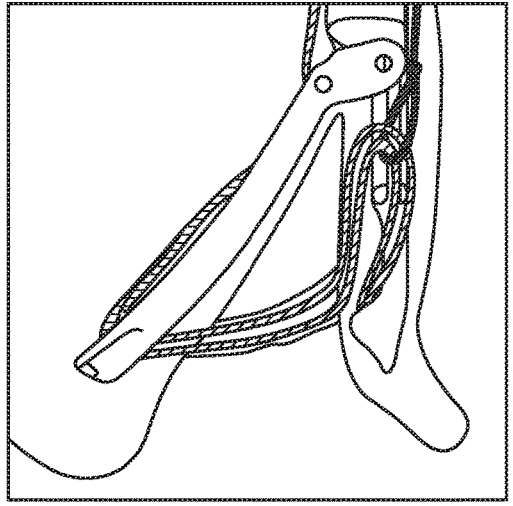
Figure 55H:
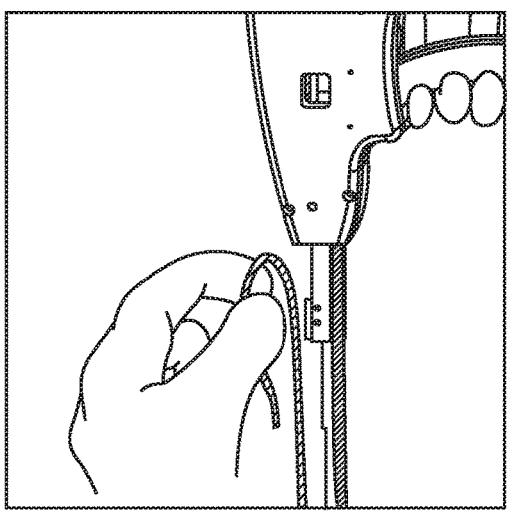
Figure 55K:
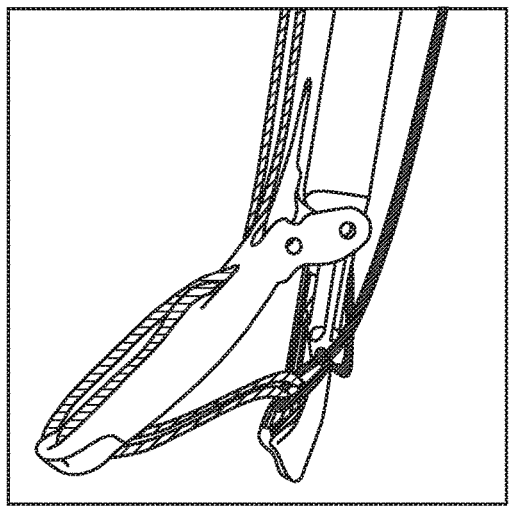
Figure 55G:
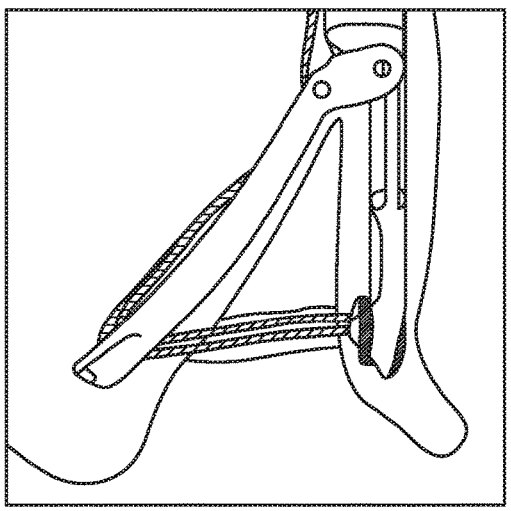
Figure 55J:
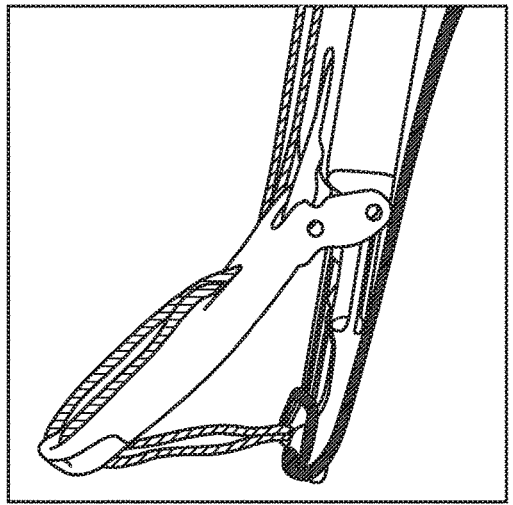
Figure 55N:
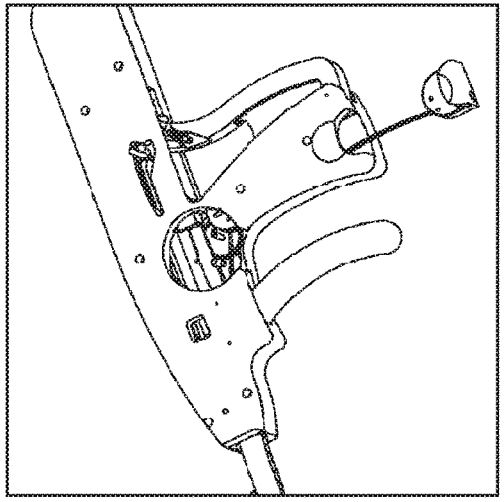

Once in position, the needle may be deployed, as shown in FIG. 55E. In this example, the lower jaw trigger is also configured to extend the tissue penetrator after the control has already been actuated to extend the lower jaw. The second actuation of the control results in the needle being extended in a sigmoidal path from the lower jaw, through the tissue, and to the upper jaw, where it can extend beyond the distal tip and pull back the suture to the first jaw, though the mouth of the suture snare. FIG. 55F illustrates a device such as the one schematically illustrated in FIGS. 55A-E, in which the tissue penetrator is pulling a loop of suture loaded in the upper jaw to the lower jaw. The suture is then pulled through the eye of the snare as shown in FIG. 55G. The tissue penetrator may continue to pull the suture, which can be removed from tension in the upper jaw as shown in FIG. 55H by uncoupling the suture from a tensioner (cleat) on the device. As shown in FIG. 55I, a rip cord pull 5511, may be present on the handle of the device, and may be pulled to tighten and/or withdraw the snare from the distal end of the device towards the proximal end. This is illustrated in FIGS. 55I (showing pulling of the snare/ripcord) and FIGS. 55J (before pulling snare/ripcord) and FIG. 55K (showing pulling of the snare/ripcord). The tissue penetrator may release the suture so that the end of the suture can be withdrawn proximally as the snare is withdrawn proximally. As the snare pulls the suture proximally, the suture may play out over the upper jaw, pulling the suture through the meniscus. The snare pulls the body of the suture outside of the knee, as shown in FIG. 55N.

Figure 55Q:
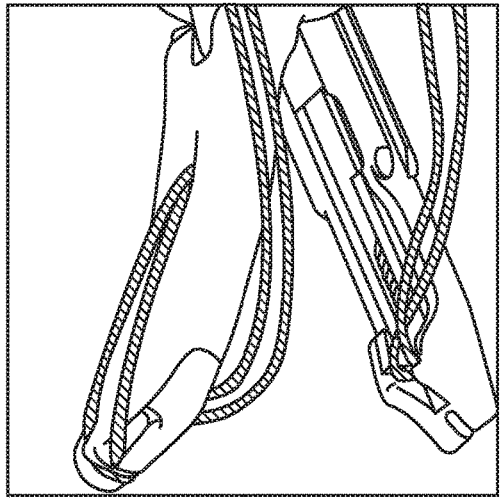
Figure 55O:
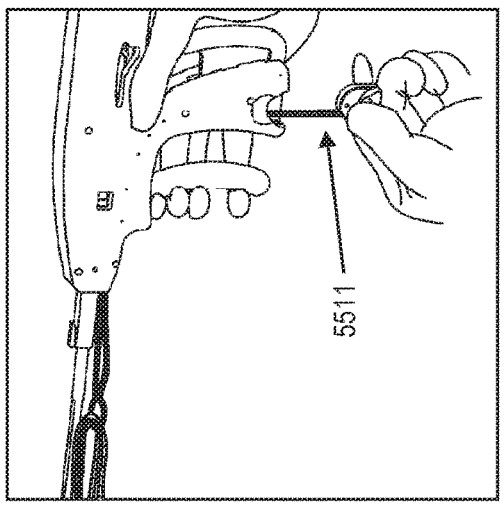
Figure 55R:
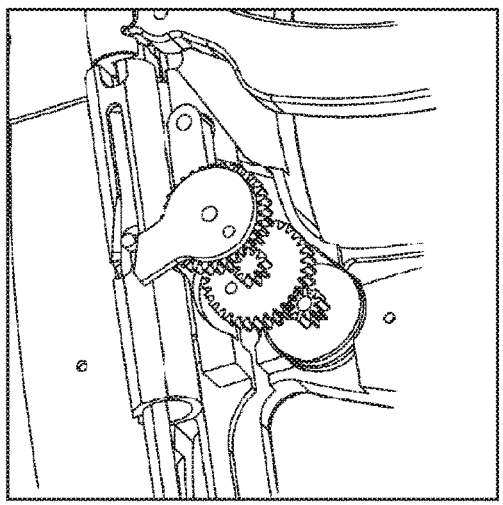
Figure 55M:
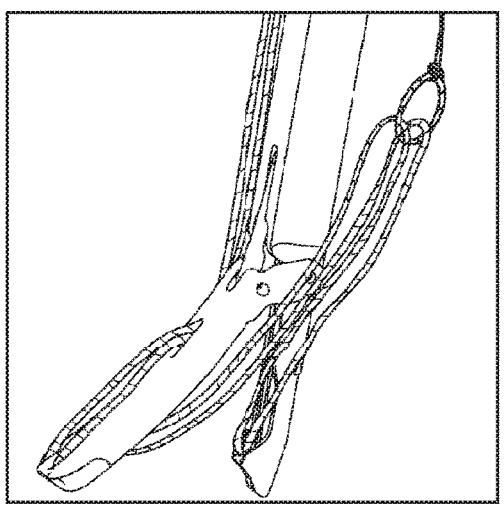
Figure 55P:
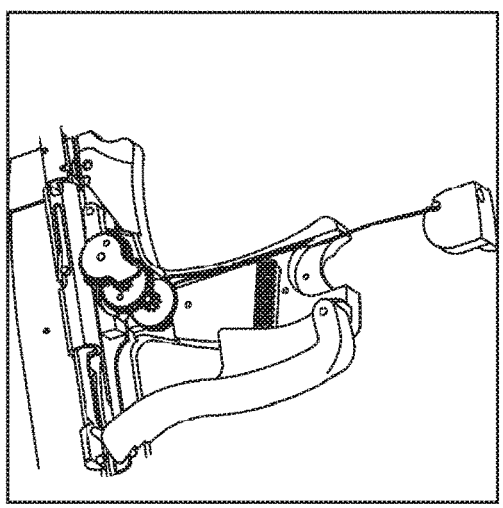
Figure 55U:
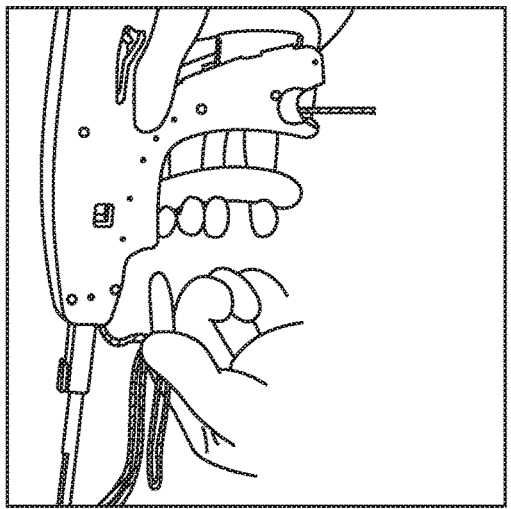
Figure 55X:
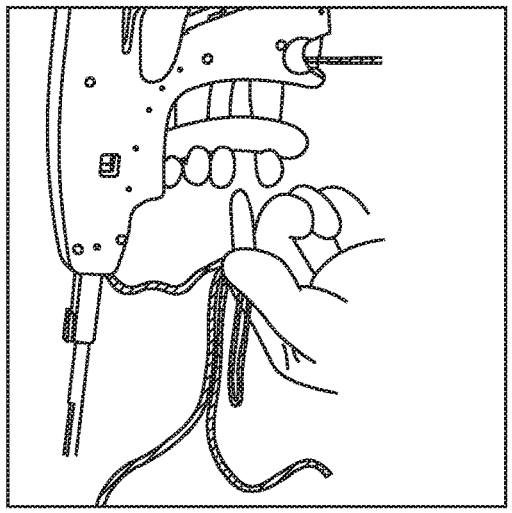
Figure 55T:
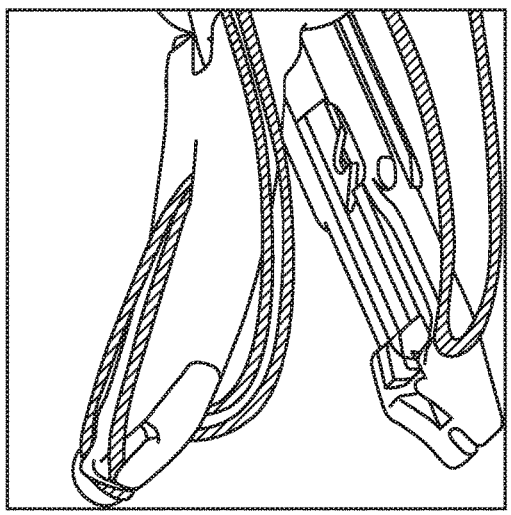
Figure 55W:
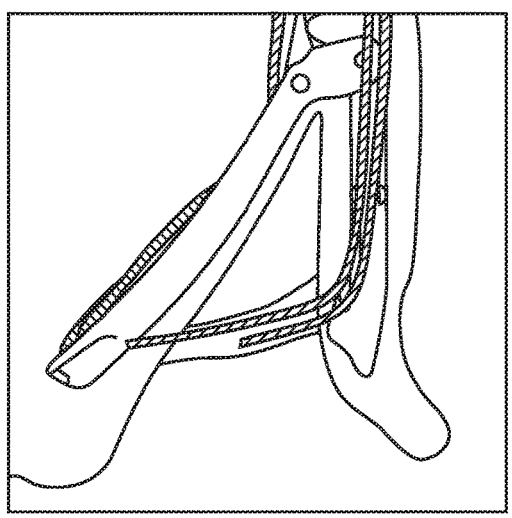
Figure 55S:
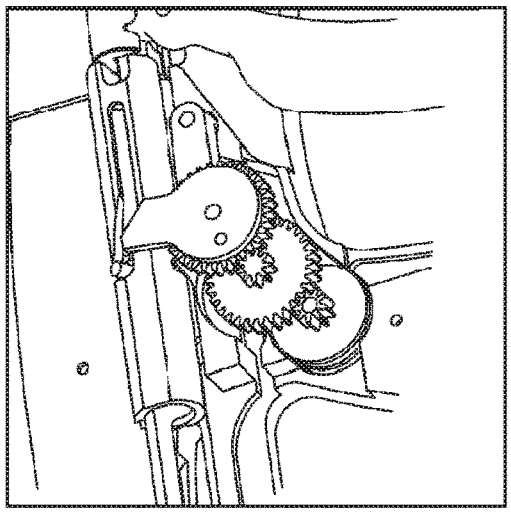
Figure 55V:
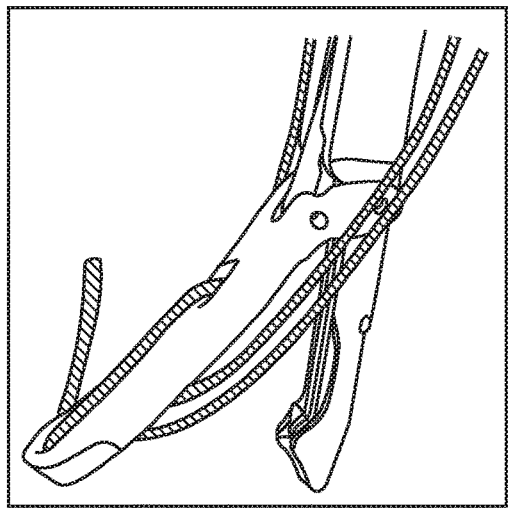
Figure 55A:
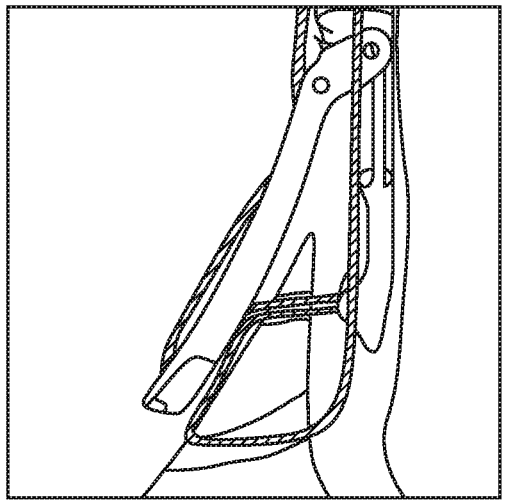
Figure 55D:
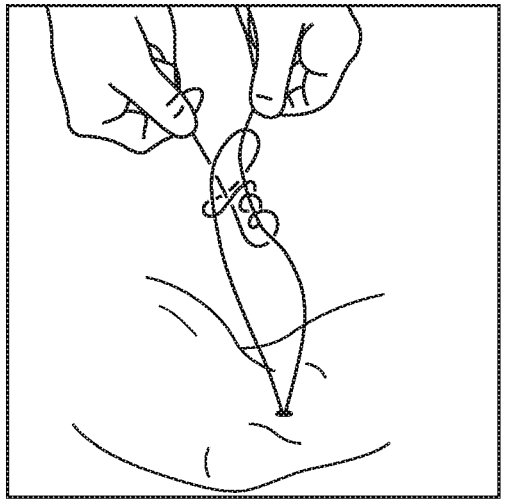

In some variations, the suture passer may monitor the pulling of the snare (e.g., ripcord), activating an internal mechanism that determines the timing of the suture's release from the lower jaw (e.g., tissue penetrator), as shown in FIG. 55O. After a predetermined time or distance of pulling the ripcord, the snare mechanism (shown in FIG. 55P) eventually releases the snare. This may be accomplished by gearing within the handle (FIG. 55Q). Prior to release, the suture may be held in the lower jaw with the tissue penetrator, as shown in FIG. 55R. Towards the end of the snare pulley mechanism, an internal gear may trigger the tissue penetrator to switch to a release position. A release window may be present in the lower jaw. The needle may retract to this window near the end of the snare mechanisms travel, as shown in FIGS. 55S-55T. The suture body that has been pulled out of the knee may then be grasped by the surgeon, as shown in FIG. 55U; the surgeon may continue to pull the suture end out of the knee. In some variations, the suture may be drawn from the knee until the end of the suture is beyond the upper jaw member, as shown in FIG. 55V and 55W. The passed end of the suture may be fully withdrawn, as shown in FIG. 55X. The suture (and particularly the portion of the suture in the upper jaw) may then be pulled to apply tension, as shown in FIG. 55Y. The end of the suture that was not withdrawn from the knee may be attached to a tensioning element (e.g., tensioner, cleat, etc.).

Figure 55Z:
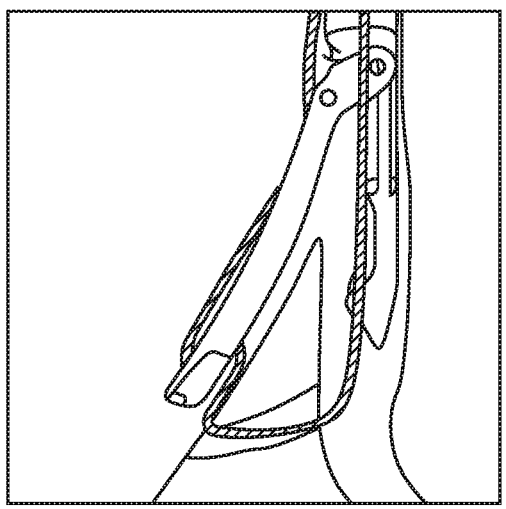
Figure 55C:
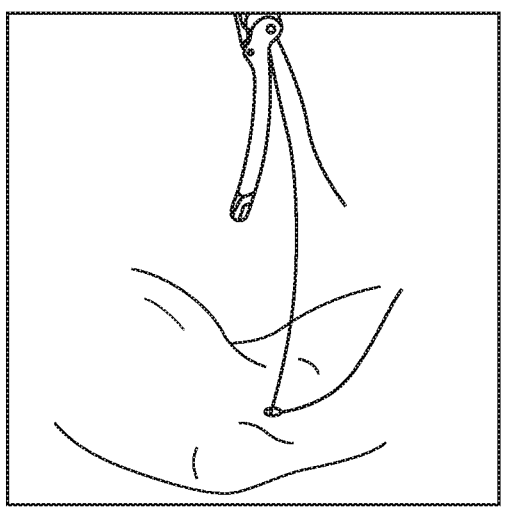
Figure 55Y:
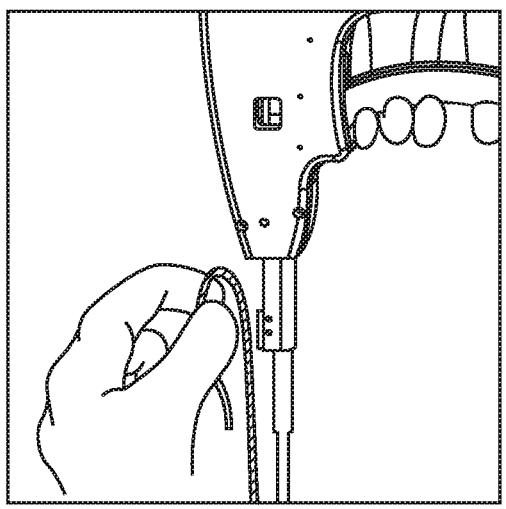
Figure 55B:
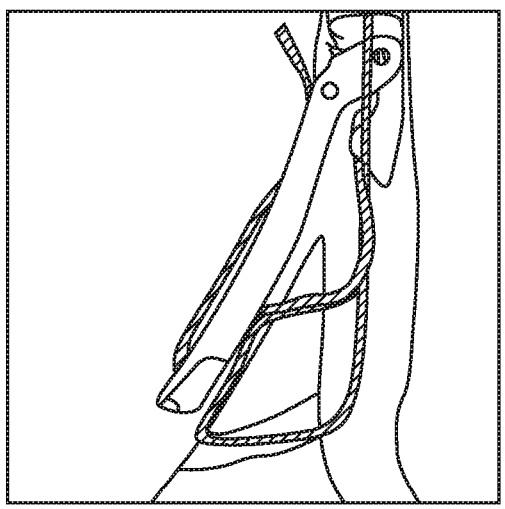

The device can then be repositioned around the tissue, as shown in FIG. 55Z, so that it is positioned in the second fire position. The tissue penetrator may then be extended across the tissue to engage the suture in the upper jaw member, then retracted back through the tissue so that the suture loop is again secured in the lower jaw member, as shown in FIG. 55AA. The device may then be retracted, leaving the loop of suture in place. For example, in FIG. 55BB, the lower jaw (with one end of the suture attached) may be retracted, and the entire device may be withdrawn from the knee, as shown in FIG. 55CC. Finally, the end of the suture may be removed from the device, and the suture may be tied off. The knot may be tied outside of the knee to complete the stitch, as shown in FIG. 55DD.

Although many of the variations of the devices illustrated above include internal deflection regions for directing the shape of the path taken by the tissue penetrator, the deflection regions may be external or partially external. For example, in some variation the tissue penetrator extends distally beneath the upper jaw, rather than entering into the upper jaw; a suture may be picked up and/or dropped off in the upper jaw from this external position.

Figure 56A:
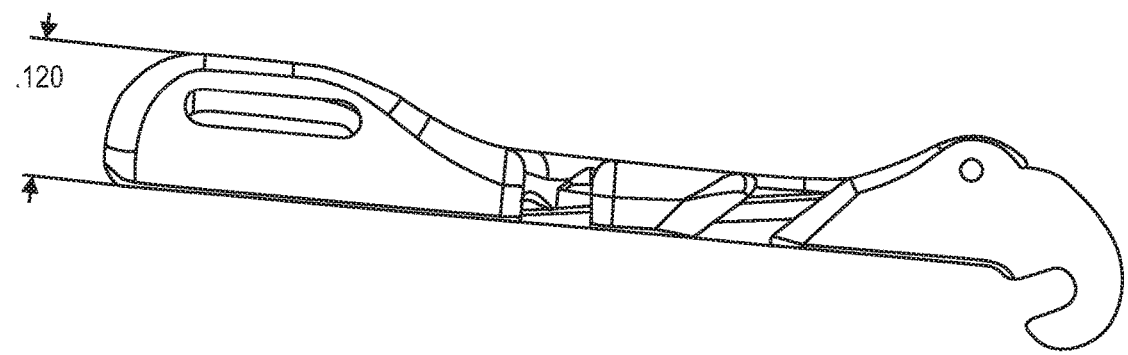
FIGS. 56A-56C illustrate variations of a first jaw (e.g., upper jaw) of a suture passer device having different thicknesses.
Figure 56B:
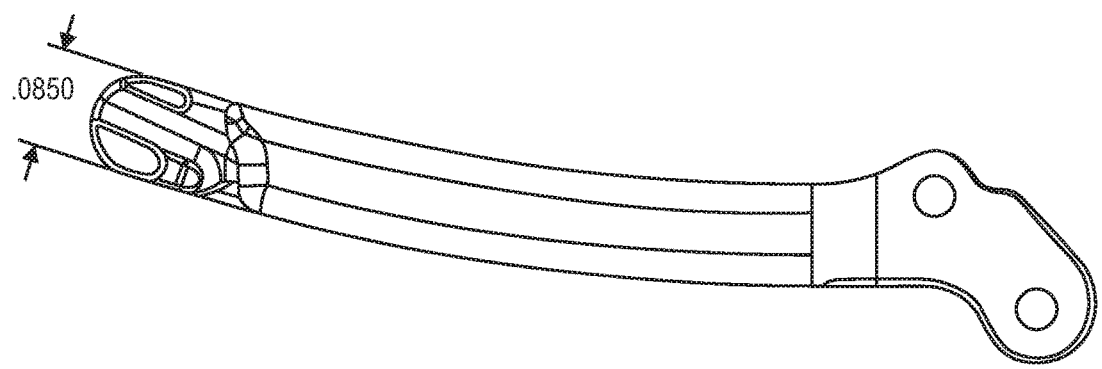
Figure 56C:
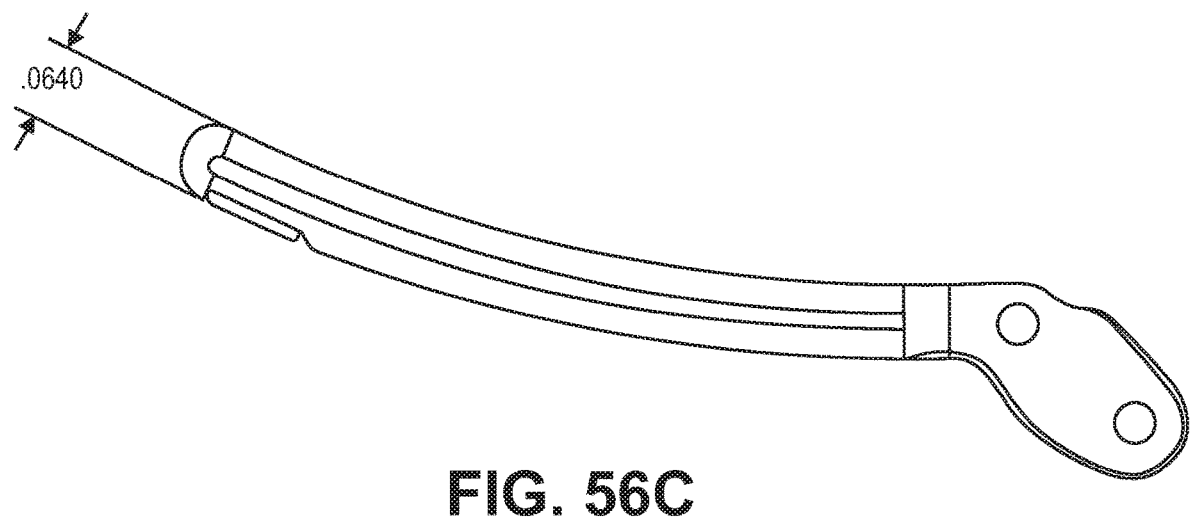

In general, the devices described herein may be sized and configured to easily insert to repair tissue into even difficult to access regions, including joint regions such as the knee, shoulder and hip. As mentioned above the upper and/or lower jaw may be relatively thin. For example, in some variations the upper jaw thickness, which may also be referred to as the height of the upper jaw, may be less than about 0.120 inches (e.g., less than 0.1 inch, less than 0.08 inches, less than 0.07 inches, less than 0.06 inches, etc.). In some variations the height or thickness of the upper jaw is between about 0.064"-0.120". FIGS. 56A-56C illustrate variations of the upper jaw having different heights or thicknesses. For example, in FIG. 56A, the upper jaw member has a maximum height of approximately 0.120 inches. This variation of the first (or upper) jaw member is similar to that shown in FIGS. 1-8. In this variation the upper jaw member includes a limiter that limits the extension of the tissue penetrator from the upper jaw. In FIG. 56B the upper jaw member has as maximum height of approximately 0.085 inches, and is curved. This variation is similar to that described above in FIGS. 16A-16C and 37A-37B. FIG. 56C shows another variation of an upper jaw member having a maximum height of approximately 0.064 inches. This variation is similar to that shown in FIGS. 40A-40B, 40D and 42A-42B. As shown, any of these variations may also be curved, and may be hinged and/or pivotally connected to an elongated member extending from a handle.

The width of the jaw member (upper and/or lower) may be greater than the height/thickness of the jaw member. In some variations the jaw member has a width that is more than twice its height (e.g., between about 0.4 and about 0.1 inches). The width may be less of a constraining dimension, as there may be sufficient space in the joint from side to side; the size constraint may be the space from top to bottom (height) in joints such as the knee.

Figure 57:
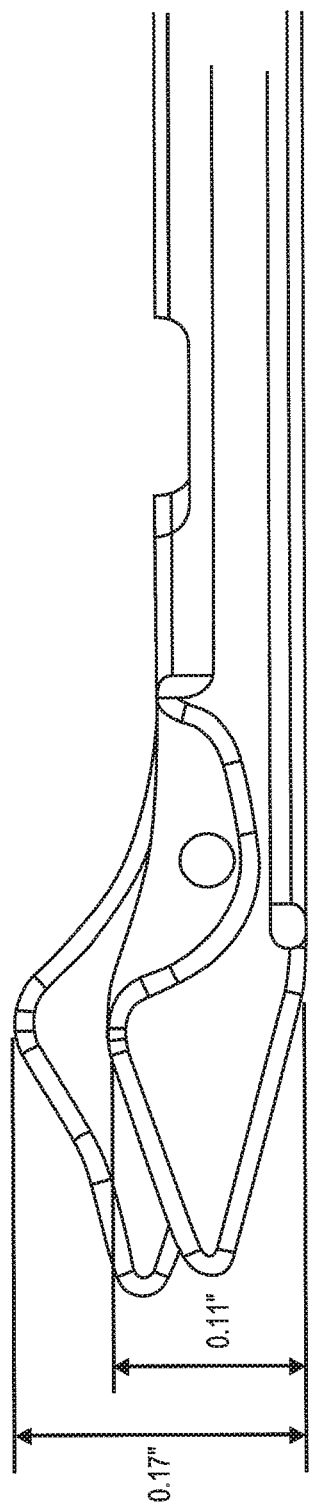
FIG. 57 illustrates two variations of second jaw (e.g., lower jaw) members of a suture passer having different thicknesses.

FIG. 57 shows a comparison between two variations of the lower (e.g., second) jaw members. In FIG. 57, one of the lower jaw members is shown having a height of about 0.17". For comparison, another variation of the lower jaw member having a height of approximately 0.11" is shown in front of the taller member. In general, the jaw member may have a height that is less than about 0.2", less than 0.18", less than about 0.17", less than about 0.15", less than about 0.13", less than about 0.11", less than about 0.10", etc. The lower jaw member may house the tissue penetrator and may include a deflection region for deflecting the tissue penetrator so that it exits the lower jaw member nearly perpendicularly from the proximal-to-distal elongate axis of the lower jaw member.

Figure 58:
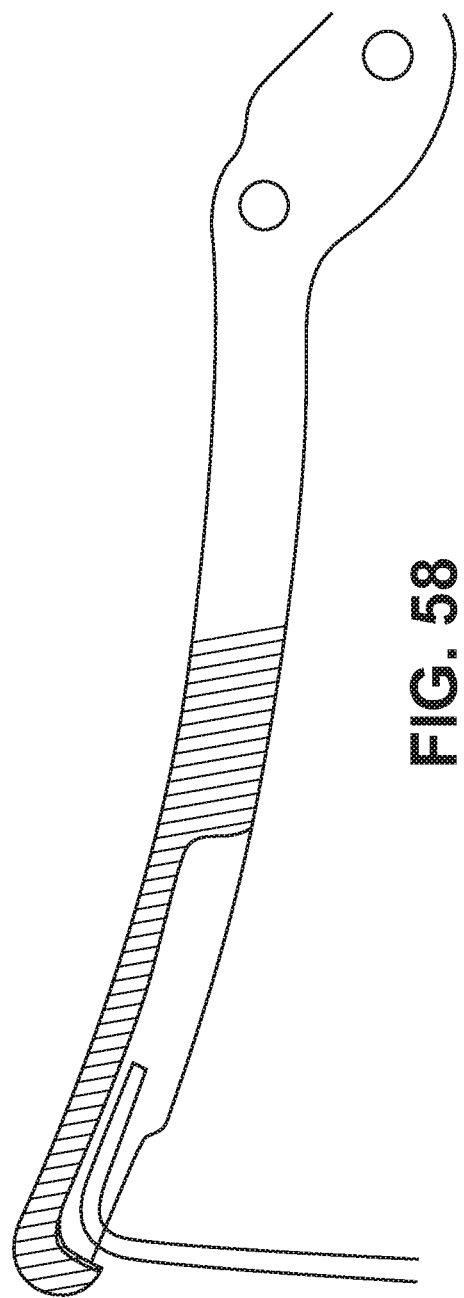
FIG. 58 shows a variation of a suture passer device in which the tissue penetrator is configured to extend proximally within the jaw member opposite from the jaw member housing the tissue penetrator.

Although many of the variations of suture passer devices described herein are configured so that the tissue penetrator extends distally from an opening in a jaw, any of the suture passers described herein may be configured so that the tissue penetrator extends proximally after extending between the upper and lower jaws. Thus, the deflection features on the upper jaw could be set to facilitate the needle heading in the proximal direction. For example, in some variations the tissue penetrator extends proximally within (or out of) the upper jaw member after extending across the opening between the jaws. In some variations the tissue penetrator extends along an internal channel within the opposite (upper) jaw member, as illustrated in FIG. 58. In this variation the upper jaw member includes a deflector that deflects the tissue penetrator proximally (towards the proximal handle direction). Thus a suture may be pushed or pulled while the tissue penetrator is given sufficient clearance to pass the suture. Suture passers moving in this manner may be referred to as having a "U" shaped (or 180°) pathway.

Figure 63B:
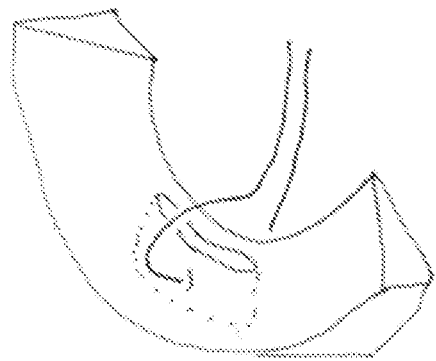
FIGS. 63A and 63B illustrate another example of a suture that may be formed arthroscopically ("hay bale stitch") to repair a torn meniscus having a horizontal cleavage tear.
Figure 63A:
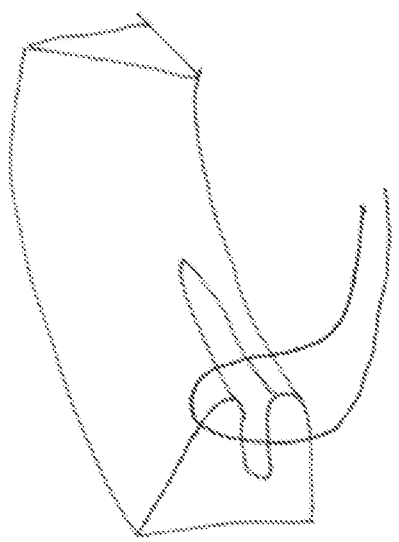

Other variations of suture patterns (stitches) that may be performed arthroscopically to repair a torn meniscus, and in particular, using the suture passers described herein, are also possible. For example, FIGS. 63A-63B illustrate a "hay bale" stitch that may be used to repair a torn meniscus, and in particular a meniscus that has a horizontal cleavage tear 6300. In a horizontal cleavage tear, the meniscus is divided up into two layers, an inferior ("bottom") region and a superior ("upper") region. The inferior portion extends radially further than the superior region because of the angle of the superior surface. In a hay bale type stitch, a single length of suture is passed through the meniscus a single time through both the inferior and superior regions, as shown in the sectional view of FIG. 63A. The suture may then be cinched so that the resulting loop of suture passes has a single length of suture that passes through the meniscus and the rest of the loop extends outside, around the apex of the meniscus. The un-tied loop is shown in FIG. 63B. To form this suture, the suture passer such as the ones described herein may be positioned with a lower jaw adjacent to the inferior surface and the upper jaw adjacent to the superior surface, and the suture may be passed (e.g., from the bottom to the top or from the top to the bottom) between the superior and inferior surfaces, then one end of the suture pulled out so that both ends of the suture length may be knotted together to form the complete loop.

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A minimally invasive method of repairing a meniscus within a patient's knee, the method comprising:
  inserting a suture passer through a cannula and into the patient's knee to minimally invasively approach the meniscus from an apex of the meniscus, so that a first jaw of the suture passer is on a superior surface of the meniscus and a second jaw of the suture passer is on an inferior surface of the meniscus, wherein the first jaw is pivotally attached to an elongate body of the suture passer and first positioned over the superior surface of the meniscus before the second jaw is axially extended under the inferior surface of the meniscus;
  passing a tissue penetrating member releasably holding a suture through the meniscus between the inferior surface and the superior surface of the meniscus;
  releasing the suture from the tissue penetrator by retracting the tissue penetrating member into one of the first or second jaw; and
  withdrawing the suture passer through the cannula with the tissue penetrating member retracted to form the suture into a loop around the apex, the inferior and the superior surfaces of the meniscus; and
  knotting the suture to close the loop.

2. The method of claim 1, wherein the suture is passed from the inferior surface to the superior surface of the meniscus.

3. The method of claim 1, wherein the suture is passed from the superior surface to the inferior surface of the meniscus.

\* \* \* \* \*